(12) United States Patent
Henderson, Jr. et al.

(10) Patent No.: US 12,011,016 B2
(45) Date of Patent: Jun. 18, 2024

(54) PROTEIN METHODS AND COMPOSITIONS

(71) Applicant: Impossible Foods Inc., Redwood City, CA (US)

(72) Inventors: Carl Allen Henderson, Jr., Brisbane, CA (US); Ratnayake Mudiyanselage Dunilka Nishani Ratnayake, San Mateo, CA (US); Ian Guiles Ronningen, San Francisco, CA (US); Laila Dafik, Belmont, CA (US)

(73) Assignee: Impossible Foods Inc., Redwood City, CA (US)

( * ) Notice: Subject to any disclaimer, the term of this patent is extended or adjusted under 35 U.S.C. 154(b) by 58 days.

(21) Appl. No.: 17/475,095

(22) Filed: Sep. 14, 2021

(65) Prior Publication Data

US 2022/0087286 A1 Mar. 24, 2022

Related U.S. Application Data

(60) Provisional application No. 63/078,230, filed on Sep. 14, 2020.

(51) Int. Cl.
| | |
|---|---|
| *A23J 3/20* | (2006.01) |
| *A23J 1/00* | (2006.01) |
| *A23J 1/18* | (2006.01) |
| *A23L 2/66* | (2006.01) |
| *A23L 33/195* | (2016.01) |

(Continued)

(52) U.S. Cl.
CPC ............... *A23J 3/20* (2013.01); *A23J 1/008* (2013.01); *A23J 1/18* (2013.01); *C07K 1/145* (2013.01); *C07K 1/34* (2013.01); *A23L 2/66* (2013.01); *A23L 33/195* (2016.08); *A23V 2002/00* (2013.01)

(58) Field of Classification Search
CPC ...... A23J 3/20; A23J 1/008; A23J 1/18; A23L 2/66; A23L 33/195; A23V 2002/00
See application file for complete search history.

(56) References Cited

U.S. PATENT DOCUMENTS

| | | | |
|---|---|---|---|
| 3,043,826 A | 7/1962 | Beaber et al. | |
| 3,821,080 A | 6/1974 | Kalina et al. | |
| 3,959,246 A | 5/1976 | Bickoff et al. | |

(Continued)

FOREIGN PATENT DOCUMENTS

| | | |
|---|---|---|
| CN | 103766573 | 5/2014 |
| CN | 108409827 | 8/2018 |

(Continued)

OTHER PUBLICATIONS

Anonymous, "Cytochrome c from equine heart", Sigma Product Information, Aug. 28, 2008, retrieved on May 17, 2021, retrieved from URL :https://www.sigmaaldri ch.com/content/dam/sigma-aldrich/docs/Sigma/Datasheet/3/c2867dat.pdf, 1 page.

(Continued)

*Primary Examiner* — Elizabeth Gwartney
*Assistant Examiner* — Andrew E Merriam
(74) *Attorney, Agent, or Firm* — Fish & Richardson P.C.

(57) ABSTRACT

This disclosure describes methods for purifying protein, and more particularly to methods for purifying protein that minimize the development of undesirable odors and flavors in the purified protein and increase protein yield.

27 Claims, 21 Drawing Sheets

Specification includes a Sequence Listing.

(51) Int. Cl.
  *C07K 1/14* (2006.01)
  *C07K 1/34* (2006.01)

(56) References Cited

U.S. PATENT DOCUMENTS

| | | | |
|---|---|---|---|
| 4,006,078 | A | 2/1977 | Bickoff et al. |
| 4,334,024 | A | 6/1982 | Johal |
| 4,340,676 | A | 7/1982 | Bourque |
| 4,427,580 | A | 1/1984 | Kinsella et al. |
| 4,588,691 | A | 5/1986 | Johal |
| 4,683,294 | A | 1/1987 | Van Wijnendaele et al. |
| 5,151,358 | A | 9/1992 | Heinsohn |
| 5,328,841 | A | 7/1994 | Lorch et al. |
| 5,407,810 | A | 4/1995 | Builder et al. |
| 5,760,189 | A | 6/1998 | Vicik et al. |
| 6,174,704 | B1 | 1/2001 | Chu et al. |
| 7,387,884 | B2 | 6/2008 | Suzuki et al. |
| 9,011,949 | B2 | 4/2015 | Brown et al. |
| 9,593,143 | B2 | 3/2017 | Colaco et al. |
| 9,700,067 | B2 | 7/2017 | Fraser et al. |
| 9,765,112 | B2 | 9/2017 | Oliver et al. |
| 10,039,306 | B2 | 8/2018 | Vrljic et al. |
| 10,087,434 | B2 | 10/2018 | Kale et al. |
| 10,093,913 | B2 | 10/2018 | Kale et al. |
| 10,287,568 | B2 | 5/2019 | Kale et al. |
| 11,051,532 | B2 | 7/2021 | Henerson, Jr. et al. |
| 2004/0101947 | A1 | 5/2004 | Engel et al. |
| 2004/0151817 | A1 | 8/2004 | Fukuda et al. |
| 2004/0166026 | A1 | 8/2004 | Bratcher et al. |
| 2004/0171813 | A1 | 9/2004 | Garger et al. |
| 2006/0025579 | A1 | 2/2006 | Riedl et al. |
| 2008/0182002 | A1 | 7/2008 | Staerk et al. |
| 2008/0187988 | A1 | 8/2008 | Warmington et al. |
| 2010/0304126 | A1 | 12/2010 | Wu et al. |
| 2012/0053328 | A1 | 3/2012 | Yan et al. |
| 2012/0164234 | A1 | 6/2012 | Kwiatkowski et al. |
| 2012/0252065 | A1 | 10/2012 | Rozenszain et al. |
| 2012/0292241 | A1 | 11/2012 | Bertanza et al. |
| 2015/0087532 | A1 | 3/2015 | Brown et al. |
| 2015/0289541 | A1 | 10/2015 | Brown et al. |
| 2015/0305361 | A1 | 10/2015 | Holz-Schietinger et al. |
| 2015/0335043 | A1 | 11/2015 | De Jong et al. |
| 2016/0340411 | A1 | 11/2016 | Fraser et al. |
| 2016/0360770 | A1 | 12/2016 | Sherlock et al. |
| 2017/0035076 | A1 | 2/2017 | Geistlinger et al. |
| 2017/0172169 | A1 | 6/2017 | Grzanich et al. |
| 2017/0188612 | A1 | 7/2017 | Varadan et al. |
| 2017/0298337 | A1 | 10/2017 | Kale et al. |
| 2017/0321203 | A1 | 11/2017 | Kale et al. |
| 2017/0321204 | A1 | 11/2017 | Kale et al. |
| 2018/0127764 | A1 | 5/2018 | Shankar et al. |
| 2020/0361986 | A1 | 11/2020 | Shultz et al. |
| 2020/0397021 | A1 | 12/2020 | Henderson |
| 2021/0307358 | A1 | 10/2021 | Henderson, Jr. et al. |
| 2023/0210150 | A1 | 7/2023 | Li et al. |

FOREIGN PATENT DOCUMENTS

| | | | | |
|---|---|---|---|---|
| EP | | 1197154 | 4/2002 | |
| EP | | 3670646 | 6/2020 | |
| GB | | 1556297 A | * 11/1979 | ............ A21D 2/267 |
| WO | WO 2001/019969 | | 3/2001 | |
| WO | WO 2010/046920 | | 4/2010 | |
| WO | WO 2011/078671 | | 6/2011 | |
| WO | WO 2016/054375 | | 4/2016 | |
| WO | WO 2018/102656 | | 6/2018 | |
| WO | WO 2018/102721 | | 6/2018 | |
| WO | WO 2020/127957 | | 6/2020 | |
| WO | WO 2021/174226 | | 9/2021 | |

OTHER PUBLICATIONS

Bansal-Mutalik et al, "Reverse micellar solutions aided permeabilization of baker's yeast," Process Biochemistry, Jan. 1, 2006, 41(1): 133-141.

Castro et al., Liquid-liquid equilibrium of water + PEG 8000 + magnesium sulfate or sodium sulfate aqueous two-phase systems at 35 oC: experimental determination and thermodynamic modeling, Braz. J. Chem. Eng., 2005, 22(3):463-470.

Degerli et al., "A novel concentration method for concentrating solutions of protein extracts based on dialysis techniques," Analytical Biochemistry, Oct. 2001, 297(2):192-194.

Ferreira et al., "β-Conglycinin (7S) and glycinin (11S) exert a hypocholesterolemic effect comparable to that of fenofibrate in rats fed a high-cholesterol diet," Journal of Functional Foods, 2(2010), pp. 275-283.

Gressent et al., "Characterization of a high-affinity binding site for the pea albumin 1b entomotoxin in the weevil Sitophilus," Eur J Biochem. Jun. 2003, 270(11):2429-35.

Guo et al., "Mini-review: In vitro Metabolic Engineering for Biomanufacturing of High-value Products", Computational and Structural Biotechnology Journal, 2017, vol. 15, 161-167.

International Preliminary Report on Patentability in International Application No. PCT/US2015/053492, dated Apr. 4, 2017, 7 pages.

International Search Report and Written Opinion in International Application No. PCT/US2015/053492, dated Feb. 5, 2016, 10 pages.

International Search Report on Patentability in International Appln. No. PCT/US2020/050774, date Jun. 9, 2021, 27 pages.

Lamsal et al., "Separation of Protein Fraction in Alfalfa Juice: Effects of Some Pre-Treatment Methods," Trans. ASAE 2003 46(3):715-720.

Reedy et al., "Development of a heme protein structure-electrochemical function database," Nucleic acids research, Oct. 11, 2007, 36:D307-D113.

Srinivas et al., "Extraction and purification of a plant peroxidase by aqueous two-phase extraction coupled with gel filtration," Process Biochemistry, Oct. 1999, 35(1/2):43-48.

Supplementary European Search Report in European Patent Application No. 15846579.9, dated Feb. 5, 2018, 6 pages.

Yamgata et al., "O-acetylserine and O-acetylhomoserine sulfhydrylase of yeast Further purification and characterization as a pyridoxal enzyme," The Journal of Biochemistry, Oct. 1, 1976, 80(4): 777-785.

Yang et al., "Antihypertensive properties of spinach leaf protein digests," J. Agric. Food Chem. 2004, 52:2223-2225.

CAS No. 137397-56-9, "3-[18-(2-carboxylatoethyl)-7-ethenyl-12-[(4E,8E)-1-hydroxy-5,9,13-trimethyltetradeca-4,8,12-trienyl]-3,8,13,17-tetramethylporphyrin-21,23-diid-2-yl]propanoate;hydron;iron(2+)" retrieved on Sep. 1, 2022, retrieved from <https://pubchem.ncbi.nlm.nih.gov/compound/6438400>, 12 pages.

CAS No. 17375-41-6, "Ferrous sulfate monohydrate," PubChem, retrieved on Aug. 31, 2022, retrieved from URL<https://pubchem.ncbi.nlm.nih.gov/compound/62712>, 26 pages.

CAS No. 207399-12-0, "Ferric citrate hydrate," PubChem, retrieved on Aug. 31, 2022, retrieved from URL<https://pubchem.ncbi.nlm.nih.gov/compound/51341966>, 19 pages.

CAS No. 22830-45-1, "Iron(II) gluconate hydrate," PubChem, retrieved on Sep. 1, 2022, retrieved from <https://pubchem.ncbi.nlm.nih.gov/compound/443752>, 10 pages.

CAS No. 699014-53-4, "iron;(2R,3S,4R,5R)-2,3,4,5,6-pentahydroxyhexanoic acid;hydrate," PubChem, retrieved on Sep. 1, 2022, retrieved from <https://pubchem.ncbi.nlm.nih.gov/compound/22836455>, 10 pages.

CAS No. 7782-63-0, "Ferrous sulfate heptahydrate," PubChem, retrieved on Sep. 1, 2022, retrieved from <https://pubchem.ncbi.nlm.nih.gov/compound/62662>, 35 pages.

CAS No. 10028-22-5, "Ferric sulfate," PubChem, retrieved on Aug. 31, 2022, retrieved from URL<https://pubchem.ncbi.nlm.nih.gov/compound/24826>, 47 pages.

CAS No. 14875-96-8, "Protoheme," retrieved on Sep. 1, 2022, retrieved from <https://pubchem.ncbi.nlm.nih.gov/compound/26945>, 22 pages.

CAS No. 15664-29-6, "Pheophorbide a," retrieved on Sep. 12, 2022, retrieved from <https://pubchem.ncbi.nlm.nih.gov/compound/253193>, 26 pages.

(56) References Cited

OTHER PUBLICATIONS

CAS No. 17099-81-9, "Ferric-EDTA," retrieved on Sep. 12, 2022, retrieved from <https://pubchem.ncbi.nlm.nih.gov/compound/28283>, 21 pages.
CAS No. 18535-39-2, "Heme a3," retrieved on Sep. 12, 2022, retrieved from <https://pubchem.ncbi.nlm.nih.gov/compound/5489981>, 14 pages.
CAS No. 26598-29-8, "Heme C," retrieved on Sep. 30, 2022, retrieved from <https://chem.nlm.nih.gov/chemidplus/rn/26598-29-8>, 2 pages.
CAS No. 69138-22-3, "Chlorophyllin ferrous-sodium complex," retrieved on Sep. 30, 2022, retrieved from <https://www.guidechem.com/cas/69138-22-3.html>, 2 pages.
CAS Nos. 2338-05-8, "Iron citrate," retrieved on Sep. 12, 2022, retrieved from <https://pubchem.ncbi.nlm.nih.gov/compound/4989393>, 25 pages.
CAS Nos. 299-29-6, "Ferrous gluconate hydrate," retrieved on Sep. 12, 2022, retrieved from <https://pubchem.ncbi.nlm.nih.gov/compound/16212939>, 36 pages.
CAS Nos. 3522-50-7, "Ferric citrate," retrieved on Sep. 12, 2022, retrieved from <https://pubchem.ncbi.nlm.nih.gov/compound/61300>, 58 pages.
CAS Nos. 7720-78-7, "Ferrous sulfate," retrieved on Sep. 12, 2022, retrieved from <https://pubchem.ncbi.nlm.nih.gov/compound/24393>, 64 pages.

Hemeprotein [online] "Heme Protein Database," retrieved on Aug. 30, 2022, retrieved from URL<http://hemeprotein.info/heme.php>, 1 page.
International Preliminary Report on Patentability in International Appln. No. PCT/US2021/020356, dated Sep. 9, 2022, 15 pages.
International Search Report and Written Opinion in International Appln. No. PCT/US2021/020356, dated Aug. 16, 2021, 23 pages.
Irwin et al., "Identification of Flavor-Active Volatiles in Soy Protein Isolate via Gas Chromatography Olfactometry," InChemistry, Texture, and Flavor of Soy 2010, 389-400.
Kao et al. "Volatile compounds produced during deodorization of soybean oil and their flavor significance," Journal of the American Oil Chemists' Society, Dec. 1998, 75(12):1103-1107.
Lei et al., "Compounds contributing to the odor of aqueous slurries of soy protein concentrate," Journal of food science, Nov. 2001, 66(9):1306-1310.
Ravi et al., "Rapid profiling of soybean aromatic compounds using electronic nose," Biosensors, May 24, 2019, 9(2): 13 pages.
Rickert et al., "Effect of extraction pH and temperature on isoflavone and saponin partitioning and profile during soy protein isolate production," Journal of food science, Oct. 2004, 69(8):C623-C631.
Roland et al. "Flavor aspects of pulse ingredients," Cereal Chemistry, Jan. 2017, 94(1):58-65.
Solina et al., "Volatile aroma components of soy protein isolate and acid-hydrolysed vegetable protein," Food chemistry, May 1, 2005, 90(4):861-873.

* cited by examiner

PROTEIN METHODS AND COMPOSITIONS

CROSS-REFERENCE TO RELATED APPLICATIONS

This application claims priority to U.S. Provisional Application No. 63/078,230, filed Sep. 14, 2020, which is incorporated herein by reference.

TECHNICAL FIELD

This invention relates to methods for purifying protein, and more particularly to methods for purifying protein that minimize the development of undesirable odors and flavors in the purified protein, enhance functionality and increase protein yield. This invention also relates to food products including purified protein.

BACKGROUND

The success of food products that mimic animal derived food products (e.g., cheese or meat) can be dependent on generating functional protein that can be manipulated and has low flavor so the source of the protein is not readily identifiable and does not provide unacceptable "off" flavors to the food product. Common protein purification methods typically include steps with chemicals that are not food-safe and/or that result in denatured protein. It would be useful to have a method of protein purification that is food-safe and results in minimal undesirable odors and flavors in the purified protein.

SUMMARY

This document provides protein compositions, and it also provides methods for purifying protein from microbial cells including eukaryotes, fungi, prokaryotes, and Archaea cells, using at least a pH of about 8.5 throughout the process, which results in a protein composition. This document also provides food products that include these protein compositions. In some embodiments, the methods described herein are food-safe, inexpensive, and scalable, while minimizing the development of undesirable odors and flavors in the purified protein and increasing protein yield. In some embodiments of methods of purifying protein provided herein in which the pH is less than 8.5 (e.g., 8.0 or less) during the purification process, increased off-flavors and/or off-odors can be present in the resulting protein composition and process yields can be reduced compared to otherwise corresponding methods of purifying protein in which the pH is greater than 8.5 (e.g., 9.0 or greater) during some or all of the purification process. In some embodiments, compositions described herein can be food-safe and inexpensive, with minimal undesirable odors and flavors. Total cellular protein, e.g., proteins that are isolated from throughout a cell or produced by it, including proteins from the cytoplasm, and nucleus and subcellular compartments (e.g., lysosomes, peroxisomes, mitochondria, endoplasmic reticulum, Golgi apparatus, periplasm, secretory vesicles, extracellular matrix, biofilm, chloroplast and nucleus) as applicable, can be purified using the methods described herein. In some embodiments, a protein composition as described herein can comprise total cellular protein, but the term "total" does not indicate that every cellular protein is present in the protein composition. In some embodiments, a protein composition as described herein can consist essentially of total cellular protein.

Furthermore, the protein in a protein composition can be functional. As described herein, functional proteins can have one or more of the following properties: non-denatured; capable of forming a gel upon heating (e.g., a suspension of about 25 to about 250 mg/mL (e.g., about 25 to about 50 mg/mL, about 25 to about 100 mg/mL, about 25 to about 150 mg/mL, about 25 to about 200 mg/mL, about 50 to about 250 mg/mL, about 100 to about 250 mg/mL, about 150 to about 250 mg/mL, or about 200 to about 250 mg/mL) at a pH of about 7.0) thermally transitions to a gel upon heating to about 65° C.); thermally denatures during incubation between about 50° C. and about 85° C., with greater than about 80% of the protein denaturing after about 20 minutes at about 85° C., as measured either by differential scanning calorimetry (DSC) or differential scanning fluorimetry (DSF); in a solution or suspension of purified protein at or above about 50 mg/mL (5% w/v), protein forms a freestanding gel (with, e.g., a 100 Pa storage modulus) when heated at or above about 85° C. for about 20 minutes; can denature and gel between about pH 5.5 and about pH 10.0; can denature and gel in solutions with ionic strength (I) below about 0.5M, when I is calculated based on the concentration of non-protein solutes; at a protein concentration of about 10 mg/mL, particle size distribution D10, D50 and D90 are less than about 0.1 µm, 1.0 µm and 5 µm, respectively; has enzymatic activity; has an emulsion activity index (EAI) of greater than or equal to about 50 m$^2$/g protein across a pH range of about 4.0 to about 8.0.

In some embodiments, a (w/v) suspension can refer to the amount of dry solids (in grams) per 100 mL of solution.

Non-limiting examples of functional proteins that can be present in a protein composition include proteins that have enzymatic activity such as, without limitation, cysteine synthase (Met17p, ED 2.5.1.47), cystathionine beta-synthase (Cys4p, EC 4.2.1.22), hexokinase, glucose oxidase, glutathione reductase, catalase, and lipase.

Enzymatic activity also can be described more generically and examples can include, for example amino acid catabolism (e.g., hydrogen sulfide ($H_2S$) present at less than about 0.1 ppm in the headspace when no L-cysteine (e.g., L-cysteine by itself, or provided in the form of a mixture of isomers) is added (e.g., to 5 mL of a 2% (w/v) suspension at pH 7.0), and $H_2S$ present at greater than or equal to about 0.2 ppm (e.g., greater than or equal to about 0.3 ppm) after (e.g., after about 24 hours at 25° C.) L-cysteine is added to 25 mM final concentration (e.g., to 5 mL of a 2% (w/v) suspension)), glucose catabolism (e.g., generation of pyruvate from glucose, generation of glucose-6-phosphate, generation of lactate, production of D-glucono-δ-lactone), lipid catabolism (e.g., lipid hydrolysis), reduction of glutathione disulfide, and decomposition of hydrogen peroxide. For example, enzymatic activity can be illustrated using a single-enzyme reaction (e.g., generation of glucose-6-phosphate from glucose by hexokinase) or a multi-enzyme reaction, e.g., transformation of a starting material to a final product by more than one enzyme (e.g., generation of pyruvate from glucose by the enzymes of glycolysis or generation of glutathione from glutamate, cysteine and glycine by the cellular glutathione biosynthesis pathway).

The protein composition can have food activity. As described herein, proteins with food activity can have one or more of the following properties (defined on a per-gram basis): capable of forming a gel; capable of emulsifying oil and water (oil-in water, water-in-oil); capable of emulsifying air and water (air-in-water).

In the description and Figures, the following abbreviations are used: CS (cell suspension); RN (cell wash); LY (lysate, e.g., obtained by bead milling, homogenizer, high shear mixer or microfluidizer); CN (centrate, e.g., supernatant of centrifugal spin to remove solids); MF (microfiltration, e.g., using a pore size of 0.2. 0.3, or 0.45 µm in diameter); DF (diafiltration, e.g., using pH 9.3+/−0.3 water); UF (ultrafiltration, e.g., using a molecular weight cutoff of 5, 10, 30, or 50 kDa); PZ (pasteurization, e.g., at 65° C. for 60 seconds); SD (spray drying, e.g., with an inlet temperature of 180° C., an outlet temperature of 80° C. and a feed of 0.27 LPM).

The term "about" is used with respect to a particular value to account for experimental variation when measuring the value.

In one aspect, this document includes a method for purifying protein from a cell (e.g., a plurality of cells), the method including lysing an aqueous suspension of the plurality of cells to obtain a cell lysate; clarifying the cell lysate, optionally in the presence of one or more flocculants, to obtain a clarified lysate; filtering the clarified lysate to obtain a filtered lysate; concentrating the filtered lysate to obtain a protein composition; and optionally pasteurizing the protein composition of protein to obtain a pasteurized protein composition, wherein the lysing, clarifying, and filtering steps, independently, are performed at a pH between about 8.5 and about 12.0.

In some embodiments of a protein composition or a food product described herein, the protein composition or food product contains less than 10% by weight animal products. In some embodiments of a protein composition or a food product described herein, the protein composition or food product contains less than 5% by weight animal products. In some embodiments, a protein composition or food product described herein contains less than 1% by weight animal products. In some embodiments, a protein composition or food product described herein contains no animal products.

In some embodiments of a protein composition or a food product described herein, the protein composition or food product contains less than 10% by weight animal-derived products. In some embodiments of a protein composition or a food product described herein, the protein composition or food product contains less than 5% by weight animal-derived products. In some embodiments, a protein composition or a food product described herein contains less than 1% by weight animal-derived products. In some embodiments, a protein composition or food product described herein contains no animal-derived products.

In some embodiments of a protein composition or a food product described herein, the protein composition or food product contains less than 10% by weight animal meat. In some embodiments of a protein composition or a food product described herein, the protein composition or food product contains less than 5% by weight animal meat. In some embodiments, a protein composition or food product described herein contains less than 1% by weight animal meat. In some embodiments, a protein composition or food product described herein contains no animal meat.

In some embodiments of a protein composition or a food product described herein, the protein composition or food product is free of or is substantially free of lactose, E. coli, whey, casein, animal fat, soy proteins, nut proteins, ovalbumins, gelatin, dairy products, animal products, animal-derived products, agar, carrageenan, tofu, cholesterol, or two or more thereof.

As used herein, the term "animal products" refers to a material obtained from or produced by the body of an animal (e.g., a mammal, a bird, a fish, an amphibian, a reptile, an insect, a mollusk, a crustacean, a coral, an arachnid, or a horseshoe crab). Examples include, without limitation, meat, fat, flesh, blood, milk, eggs, isinglass, rennet, fur, skin, hair, bone, fibers, cartilage, casein, gelatin, and honey. The term "no animal products" means that the composition does not contain any animal products.

As used herein, the term "animal-derived products" refers to a material or compound derived from the body of an animal (e.g., a mammal, a bird, a fish, an amphibian, a reptile, an insect, a mollusk, a crustacean, a coral, an arachnid, or a horseshoe crab). Examples include, without limitation, a material or compound derived from animal meat, fat, flesh, blood, milk, eggs, isinglass, rennet, fur, skin, hair, bone, fibers, cartilage, casein, gelatin, and honey. Further examples of animal-derived products include materials isolated from the body of an animal, including without limitation, hormones, amino acids, vitamins, organic acids, proteins, collagen, dyes, fatty acids, oils, glycerol, sugars, keratin, and nucleic acids isolated from the body of an animal. The term "no animal-derived products" means that the composition does not contain any animal products.

As used herein, the term "animal meat" refers to a flesh of an animal (e.g., a mammal, a bird, a fish, an amphibian, a reptile, an insect, a mollusk, a crustacean, a coral, an arachnid, or a horseshoe crab). Examples include without limitation, muscle and organs. The term "no animal meat" means that the composition does not contain any animal meat.

As used herein, the term "substantially free of" means less than 5.0% by weight, (e.g., less than 5.0% by weight, less than 4.0% by weight, less than 3.0% by weight, less than 2.5% by weight, less than 2.0% by weight, less than 1.5% by weight, less than 1.0% by weight, less than 0.5% by weight, less than 0.1% by weight or less than 0.01% by weight) of the referenced ingredient is present in a composition. For example, a dairy replica as disclosed herein in is substantially free of animal products when it contains less than 5.0% by weight (e.g., less than 4.0% by weight, less than 3.0% by weight, less than 2.5% by weight, less than 2.0% by weight, less than 1.5% by weight, less than 1.0% by weight, less than 0.5% by weight, less than 0.1% by weight, or less than 0.01% by weight) of animal products.

As used herein, the term "free of" means that none of the referenced ingredient is detectable in a composition. For example, a protein composition or food product disclosed herein in is free of animal products when it contains no detectable animal products.

As used herein a "bacteria-derived protein", "yeast-derived protein", "algae-derived protein", "fungus-derived protein", or "plant-derived protein" refers to the immediate production organism of the protein, and can mean any protein that is produced in a bacterium, a yeast, an algae, a fungus, or a plant, independently of whether the protein is natively expressed in the bacterium, yeast, algae, fungus, or plant, respectively.

The term "not natively expressed" can refer to a protein that is produced in an organism that does not produce said protein in nature. Non-limiting examples of a protein that is not natively expressed include an animal protein expressed in bacteria, a plant protein expressed in yeast, and an animal protein expressed in algae.

The term "pasteurized" can mean any process, treatment, or combination thereof, that is applied to food to reduce the most resistant microorganism(s) of public health significance to a level that is not likely to present a public health risk under normal conditions of distribution and storage.

The term "intact", as it pertains to cells, as used herein includes cells that are perforated, but not cells that are burst or lysed. In cells that have subcellular compartments, intact cells typically retain the subcellular compartments within the cellular membrane. Exemplary methods that result in the lysis of cells include mechanical lysis (e.g., bead beating, bead milling, grinding, or rotator-shaker homogenizers), cryopulverization, high pressure cell disruption (e.g., by French press, or microfluidizer), sonication, and nitrogen decompression. In some embodiments when intact cells are specified, none of mechanical lysis (e.g., bead beating, bead milling, grinding, or rotator-shaker homogenizers), cryopulverization, high pressure cell disruption (e.g., by French press, or microfluidizer), sonication, or nitrogen decompression were performed. In some embodiments, intact cells can be determined by particle size distribution. In some embodiments, the particle size distribution of intact cells (e.g., that have undergone a treatment, such as any of the treatments described herein), can be significantly unchanged compared to a suspension of single cells. For example, the particle size distribution median for intact yeast cells can be about 3 µm. In some embodiments, the particle size distribution of intact yeast cells can lack a peak smaller than about 3 µm, which can be indicative of cell fragments.

As used herein, "low flavor" with respect to a protein composition means that the protein composition has less flavor than the source of the protein composition (e.g., yeast, if a yeast protein composition is described). For example, less of one or more flavor compounds that give rise to a distinguishing flavor associated with the source of the protein. In some embodiments, a low flavor protein composition can have little flavor of its own. In some instances, a low flavor protein composition has less flavor than a known protein composition (e.g., a commercial soy protein isolate). Having less flavor can be determined, for example, by a trained human panelist, or, for example, by measurement of one or more volatile compounds commonly understood to impart flavor and/or aroma.

The term "flavor compound" as used herein refers to a compound that imparts to a protein composition as described herein a taste and/or aroma detectable, for example, by a trained human panelist. In some embodiments, a flavor compound can be a positive aspect, e.g., imparting a flavor that is expected in a use of the protein composition, e.g., a flavor compound suggestive of an animal meat flavor in a meat replica product. In some embodiments, a flavor compound can be a negative aspect, e.g., imparting a flavor that is not expected in a use of the protein composition, e.g., a flavor compound suggestive of soy in a meat replica product.

The term "aromaome" can mean the totality of aromas associated by the ordinary human observer with a particular food, ingredient, or cooking process. Non-limiting examples of aromaomes are a poultry aromaome, a chicken aromaome, a beef aromaome, a pork aromaome, a seafood aromaome, a game meat aromaome, a cinnamon aromaome, a chocolate aromaome, a deep frying aromaome, and a grilling aromaome.

In one aspect, this disclosure includes a method for purifying protein from a plurality of cells, the method including lysing an aqueous suspension of the plurality of cells to obtain a cell lysate; clarifying the cell lysate, optionally in the presence of one or more flocculants, to obtain a clarified lysate; filtering the clarified lysate to obtain a protein composition; and optionally pasteurizing the protein composition, to obtain a pasteurized protein composition, wherein steps a), b), c), and d) independently, are performed at a pH between about 8.5 and about 12.0.

In another aspect, this disclosure includes a method for purifying protein from a plurality of cells, the method including lysing an aqueous suspension of the plurality of cells to obtain a cell lysate; filtering the cell lysate to obtain a protein composition; and optionally pasteurizing the protein composition to obtain a pasteurized protein composition, wherein steps a), b), and c) independently, are performed at a pH between about 8.5 and about 12.0.

These and other embodiments can optionally include any of the following. Filtering can include microfiltration, ultrafiltration, diafiltration, or a combination thereof. A clarifying step can be performed by centrifugation to less than about 20% dry solids. A plurality of cells can include microbial cells. A method can further include washing an aqueous suspension of a plurality of cells at a pH between about 8.5 and about 12.0 before step a). A protein composition can include at least about 35%, on a dry weight basis, of compounds larger than 5 kDa. At least about 50% of the protein in a protein composition can fall between about 10 kDa and about 200 kDa.

In another aspect, this disclosure includes protein composition produced by a method comprising: lysing an aqueous suspension of a plurality of cells to obtain a cell lysate; filtering the cell lysate to obtain a protein composition; and optionally pasteurizing the protein composition to obtain a pasteurized protein composition, wherein steps a), b), and c) independently, are performed at a pH between about 8.5 and about 12.0.

This and other embodiments can optionally include any of the following. Filtering can include microfiltration, ultrafiltration, diafiltration, or a combination thereof. A process can further include washing an aqueous suspension of a plurality of cells at a pH between about 8.5 and about 12.0 before step a). At least about 50% of the protein in a protein composition can fall between about 10 kDa and about 200 kDa. A protein composition can have a buffering capacity of less than about 2.5 mmol NaOH per gram dry solids. Hydrogen sulfide ($H_2S$) can be detectable in an amount of less than about 0.1 ppm after about 24 hours at 25° C. when L-cysteine is not added to 5 mL of a 2% (w/v) suspension of a protein composition at pH 7.0. Hydrogen sulfide can be detectable an amount of at least about 0.2 ppm about 24 hours at 25° C. after 5 mL of a 2% (w/v) suspension of a protein composition is brought to about 25 mM final concentration of L-cysteine.

In some embodiments, provided herein are methods for purifying proteins from a plurality of cells having cell walls. In some embodiments, provided is a method for purifying proteins from a plurality of cells having cell walls, the method including: a) perforating the cell walls of the plurality of cells, b) separating an aqueous suspension of the plurality of cells to form a solids portion and a liquid portion, c) filtering the liquid portion to form a filtrate and a retentate, d) concentrating the retentate to form a protein composition, and e) optionally pasteurizing the protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, provided is a method for purifying proteins from a plurality of cells, the method including: a) treating an aqueous suspension of the plurality of cells with a base until the pH of the aqueous suspension is about 8.5 to about 12.0, b) separating the aqueous suspension of the plurality of cells to form a solids portion and a liquid portion, c) filtering the liquid portion to form a filtrate and a retentate, d) concentrating the retentate to form a protein composition, and e) optionally pasteurizing the protein composition, wherein each of a)-d), independently, are performed at a pH of about 8.5 and about 12.0, and/or wherein the method results in the liquid portion including at least about 10% by weight of the cytoplasmic proteins of the plurality of cells. In some embodiments, provided is a method for purifying proteins from a plurality of cells having cell walls, the method including: a) treating an aqueous suspension of the plurality of cells with a base until the pH of the aqueous suspension is about 8.5 to about 12.0, b) perforating the cell walls of the plurality of cells, c) separating the aqueous suspension of the plurality of cells to form a solids portion and a liquid portion, d) filtering the liquid portion to form a filtrate and a retentate, e) concentrating the retentate to form a protein composition, and f) optionally pasteurizing the protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for purifying proteins from a plurality of cells having cell walls, the method including: a) perforating the cell walls of the plurality of cells, b) treating an aqueous suspension of the plurality of cells with a base until the pH of the aqueous suspension is about 8.5 to about 12.0, c) separating the aqueous suspension of the plurality of cells to form a solids portion and a liquid portion, d) filtering the liquid portion to form a filtrate and a retentate, e) concentrating the retentate to form a protein composition, and f) optionally pasteurizing the protein composition, wherein each of a)-e), independently, are performed at a pH of about 8.5 and about 12.0, and/or wherein the method results in the liquid portion including at least about 50% by weight of the cytoplasmic proteins of the plurality of cells.

In some embodiments, provided herein are methods for purifying a plurality in proteins from a plurality of cells. In some embodiments, provided is a method for purifying proteins from a plurality of cells, the method including: a) heating the plurality of cells to a temperature of about 50° C. to about 85° C., b) separating an aqueous suspension of the plurality of cells to form a solids portion and a liquid portion, c) filtering the liquid portion to form a filtrate and a retentate, d) concentrating the retentate to form a protein composition, and e) optionally pasteurizing the protein composition, wherein each of a)-d), independently, are performed at a pH of about 8.5 and about 12.0, and/or wherein the method results in the liquid portion including at least about 50% by weight of the cytoplasmic proteins of the plurality of cells.

In some embodiments, provided herein are methods for preparing a cytosolic protein-enriched protein composition from a plurality of cells having cell walls. In some embodiments, provided is a method for preparing a cytosolic protein-enriched protein composition from a plurality of cells having cell walls, the method including: a) perforating the cell walls of the plurality of cells, b) separating an aqueous suspension of the plurality of cells to form a solids portion and a liquid portion, c) filtering the liquid portion to form a filtrate and a retentate, d) concentrating the retentate to form a cytosolic protein-enriched protein composition, and e) optionally pasteurizing the cytosolic protein-enriched protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, provided is a method for preparing a cytosolic protein-enriched protein composition from a plurality of cells, the method including: a) treating an aqueous suspension of the plurality of cells with a base until the pH of the aqueous suspension is about 8.5 to about 12.0, b) separating the aqueous suspension of the plurality of cells to form a solids portion and a liquid portion, c) filtering the liquid portion to form a filtrate and a retentate, d) concentrating the retentate to form a cytosolic protein-enriched protein composition, and e) optionally pasteurizing the cytosolic protein-enriched protein composition, wherein each of a)-d), independently, are performed at a pH of about 8.5 and about 12.0, and/or wherein the method results in the liquid portion including at least about 10% by weight of the cytoplasmic proteins of the plurality of cells. In some embodiments, provided is a method for preparing a cytosolic protein-enriched protein composition from a plurality of cells having cell walls, the method including: a) treating an aqueous suspension of the plurality of cells with a base until the pH of the aqueous suspension is about 8.5 to about 12.0, b) perforating the cell walls of the plurality of cells, c) separating the aqueous suspension of the plurality of cells to form a solids portion and a liquid portion, d) filtering the liquid portion to form a filtrate and a retentate, e) concentrating the retentate to form a cytosolic protein-enriched protein composition, and f) optionally pasteurizing the cytosolic protein-enriched protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for preparing a cytosolic protein-enriched protein composition from a plurality of cells having cell walls, the method including: a) perforating the cell walls of the plurality of cells, b) treating an aqueous suspension of the plurality of cells with a base until the pH of the aqueous suspension is about 8.5 to about 12.0, c) separating the aqueous suspension of the plurality of cells to form a solids portion and a liquid portion, d) filtering the liquid portion to form a filtrate and a retentate, e) concentrating the retentate to form a cytosolic protein-enriched protein composition, and f) optionally pasteurizing the cytosolic protein-enriched protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for preparing a cytosolic protein-enriched protein composition from a plurality of cells, the method including: a) heating the plurality of cells to a temperature of about 50° C. to about 85° C., b) separating an aqueous suspension of the plurality of cells to form a solids portion and a liquid portion, c) filtering the liquid portion to form a filtrate and a retentate, d) concentrating the retentate to form a cytosolic protein-enriched protein composition, and e) optionally pasteurizing the cytosolic protein-enriched protein composition, wherein each of a)-d), independently, are performed at a pH of about 8.5 and about 12.0, and/or wherein the method results in the liquid portion including at least about 50% by weight of the cytoplasmic proteins of the plurality of cells.

In some embodiments, provided herein are methods for preparing a membrane-bound and/or subcellular compartment protein-enriched protein composition from a plurality of cells having cell walls. In some embodiments, provided is a method for preparing a membrane-bound and/or subcellular compartment protein-enriched protein composition from a plurality of cells having cell walls, the method including: a) perforating the cell walls of the plurality of cells, b) separating an aqueous suspension of the plurality of cells to form a solids portion and a liquid portion, c) extracting protein from the solids portion to form a membrane-bound and/or subcellular compartment protein-enriched protein composition, and d) optionally pasteurizing the membrane-bound and/or subcellular compartment protein-enriched protein composition, wherein each of a)-b), independently, are performed at a pH of about 8.5 and about 12.0, and/or wherein the method results in the liquid portion including at least about 50% by weight of the cytoplasmic proteins of the plurality of cells. In some embodiments, provided is a method for preparing a membrane-bound and/or subcellular compartment protein-enriched protein composition from a plurality of cells, the method including: a) treating an aqueous suspension of the plurality of cells with a base until the pH of the aqueous suspension is about 8.5 to about 12.0, b) separating the aqueous suspension of the plurality of cells to form a solids portion and a liquid portion, c) extracting protein from the solids portion to form a membrane-bound and/or subcellular compartment protein-enriched protein composition, and d) optionally pasteurizing the membrane-bound and/or subcellular compartment protein-enriched protein composition, wherein each of a)-b), independently, are performed at a pH of about 8.5 and about 12.0, and/or wherein the method results in the liquid portion including at least about 10% by weight of the cytoplasmic proteins of the plurality of cells. In some embodiments, provided is a method for preparing a membrane-bound and/or subcellular compartment protein-enriched protein composition from a plurality of cells having cell walls, the method including: a) treating an aqueous suspension of the plurality of cells with a base until the pH of the aqueous suspension is about 8.5 to about 12.0, b) perforating the cell walls of the plurality of cells, c) separating the aqueous suspension of the plurality of cells to form a solids portion and a liquid portion, d) extracting protein from the solids portion to form a membrane-bound and/or subcellular compartment protein-enriched protein composition, and e) optionally pasteurizing the membrane-bound and/or subcellular compartment protein-enriched protein composition, wherein each of a)-c), independently, are performed at a pH of about 8.5 and about 12.0, and/or wherein the method results in the liquid portion including at least about 50% by weight of the cytoplasmic proteins of the plurality of cells. In some embodiments, provided is a method for preparing a membrane-bound and/or subcellular compartment protein-enriched protein composition from a plurality of cells having cell walls, the method including: a) perforating the cell walls of the plurality of cells, b) treating an aqueous suspension of the plurality of cells with a base until the pH of the aqueous suspension is about 8.5 to about 12.0, c) separating the aqueous suspension of the plurality of cells to form a solids portion and a liquid portion, d) extracting protein from the solids portion to form a membrane-bound and/or subcellular compartment protein-enriched protein composition, and e) optionally pasteurizing the membrane-bound and/or subcellular compartment protein-enriched protein composition, wherein each of a)-c), independently, are performed at a pH of about 8.5 and about 12.0, and/or wherein the method results in the liquid portion including at least about 50% by weight of the cytoplasmic proteins of the plurality of cells. In some embodiments, provided is a method for preparing a membrane-bound and/or subcellular compartment protein-enriched protein composition from a plurality of cells, the method including: a) heating the plurality of cells to a temperature of about 50° C. to about 85° C., b) separating an aqueous suspension of the plurality of cells to form a solids portion and a liquid portion, d) extracting protein from the solids portion to form a membrane-bound and/or subcellular compartment protein-enriched protein composition, and e) optionally pasteurizing the membrane-bound and/or subcellular compartment protein-enriched protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, the extracting protein from the solids portion comprises mechanical lysis of the solids portion.

In some embodiments, provided herein are methods for purifying a soluble protein from a plurality of cells having cell walls. In some embodiments, provided is a method for purifying a soluble protein from a plurality of cells having cell walls, the method including: a) perforating the cell walls of the plurality of cells, b) separating an aqueous suspension of the plurality of cells to form a solids portion and a liquid portion, c) filtering the liquid portion to form a filtrate and a retentate, d) concentrating the retentate to form a protein composition including the soluble protein, and e) optionally pasteurizing the protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, provided is a method for purifying a soluble protein from a plurality of cells, the method including: a) treating an aqueous suspension of the plurality of cells expressing the soluble protein with a base until the pH of the aqueous suspension is about 8.5 to about 12.0, b) separating the aqueous suspension of the plurality of cells to form a solids portion and a liquid portion, c) filtering the liquid portion to form a filtrate and a retentate, d) concentrating the retentate to form a protein composition including the soluble protein, and e) optionally pasteurizing the protein composition, wherein each of a)-d), independently, are performed at a pH of about 8.5 and about 12.0, and/or wherein the method results in the liquid portion including at least about 10% by weight of the cytoplasmic proteins of the plurality of cells. In some embodiments, provided is a method for purifying a soluble protein from a plurality of cells having cell walls, the method including: a) treating an aqueous suspension of the plurality of cells expressing the soluble protein with a base until the pH of the aqueous suspension is about 8.5 to about 12.0, b) perforating the cell walls of the plurality of cells, c) separating the aqueous suspension of the plurality of cells to form a solids portion and a liquid portion, d) filtering the liquid portion to form a filtrate and a retentate, e) concentrating the retentate to form a protein composition including the soluble protein, and f) optionally pasteurizing the protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for purifying a soluble protein from a plurality of cells having cell walls, the method including: a) perforating the cell walls of the plurality of cells, b) treating an aqueous suspension of the plurality of cells with a base until the pH of the aqueous suspension is about 8.5 to about 12.0, c) separating the aqueous suspension of the plurality of cells to form a solids portion and a liquid portion, d) filtering the liquid portion to form a filtrate and a retentate, e) concentrating the retentate to form a protein composition including the soluble protein, and f) optionally pasteurizing the protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for purifying a soluble protein from a plurality of cells, the method including: a) heating the plurality of cells expressing the soluble protein to a temperature of about 50° C. to about 85° C., b) separating an aqueous suspension of the plurality of cells to form a solids portion and a liquid portion, c) filtering the liquid portion to form a filtrate and a retentate, d) concentrating the retentate to form a protein composition including the soluble protein, and e) optionally pasteurizing the protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, the soluble protein is a heme-containing protein. In some embodiments, the method comprises treating the plurality of cells with about 5 mM to about 500 mM reducing equivalents of includes reductant. In some embodiments, treatment with the reductant comprises treatment with about 20 mM to about 80 mM reducing equivalents of the reductant. In some embodiments, the reductant is selected from the group consisting of cysteine, glutathione, bisulfite, and a combination thereof. In some embodiments, the reductant is a food safe reductant. In some embodiments, the soluble protein has a melting point, and method further comprises, before a), heating the plurality of cells to a temperature of about 10° C. or about 5° C. below the melting point of the soluble protein. In some embodiments, the soluble protein has a melting point of at least about 60° C. In some embodiments, the soluble protein is heterologous to the plurality of cells.

In some embodiments, provided herein are methods of treating a plurality of cells (e.g., a plurality of cells having cell walls). In some embodiments, provided is a method for treating a plurality of cells having cell walls, the method including: perforating the cell walls of the plurality of cells, wherein treatment of a supernatant of the plurality of cells with a mannosidase yields less than about 30 μg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells, the method including: treating an aqueous suspension of the plurality of cells with a base until the pH of the aqueous suspension is about 8.5 to about 12.0, wherein treatment of a supernatant of the plurality of cells with a mannosidase yields less than about 30 μg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells having cell walls, the method including: a) treating an aqueous suspension of the plurality of cells with a base until the pH of the aqueous suspension is about 8.5 to about 12.0, b) perforating the cell walls of the plurality of cells, wherein treatment of a supernatant of the plurality of cells with a mannosidase yields less than about 30 μg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells having cell walls, the method including: a) perforating the cell walls of the plurality of cells, b) treating an aqueous suspension of the plurality of cells with a base until the pH of the aqueous suspension is about 8.5 to about 12.0, wherein treatment of a supernatant of the plurality of cells with a mannosidase yields less than about 30 μg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells, the method including: heating the plurality of cells to a temperature of about 50° C. to about 85° C., wherein treatment of a supernatant of the plurality of cells with a mannosidase yields less than about 30 μg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells having cell walls, the method including: perforating the cell walls of the plurality of cells, wherein less than about 200 μg/mL beta glucan is detectable in a soluble phase, wherein the soluble phase is prepared using a 10% (w/v) suspension of the plurality of cells, after being incubated at 50° C. for 10 minutes at pH 12.0. In some embodiments, provided is a method for treating a plurality of cells, the method including: treating an aqueous suspension of the plurality of cells with a base until the pH of the aqueous suspension is about 8.5 to about 12.0, wherein less than about 200 μg/mL beta glucan is detectable in a soluble phase, wherein the soluble phase is prepared using a 10% (w/v) suspension of the plurality of cells, after being incubated at 50° C. for 10 minutes at pH 12.0. In some embodiments, provided is a method for treating a plurality of cells having cell walls, the method including: a) treating an aqueous suspension of the plurality of cells with a base until the pH of the aqueous suspension is about 8.5 to about 12.0, b) perforating the cell walls of the plurality of cells, wherein less than about 200 μg/mL beta glucan is detectable in a soluble phase, wherein the soluble phase is prepared using a 10% (w/v) suspension of the plurality of cells, after being incubated at 50° C. for 10 minutes at pH 12.0. In some embodiments, provided is a method for treating a plurality of cells having cell walls, the method including: a) perforating the cell walls of the plurality of cells, b) treating an aqueous suspension of the plurality of cells with a base until the pH of the aqueous suspension is about 8.5 to about 12.0, wherein less than about 200 μg/mL beta glucan is detectable in a soluble phase, wherein the soluble phase is prepared using a 10% (w/v) suspension of the plurality of cells, after being incubated at 50° C. for 10 minutes at pH 12.0. In some embodiments, provided is a method for treating a plurality of cells, the method including: heating the plurality of cells to a temperature of about 50° C. to about 85° C., wherein less than about 200 μg/mL beta glucan is detectable in a soluble phase, wherein the soluble phase is prepared using a 10% (w/v) suspension of the plurality of cells, after being incubated at 50° C. for 10 minutes at pH 12.0.

Also provided herein are compositions of cells, such as those that have been treated as described herein. In some embodiments, provided is a composition including: a plurality of cells, wherein treatment of a supernatant of the plurality of cells with a mannosidase yields less than about 30 μg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a composition including: a plurality of cells, wherein less than about 200 μg/mL beta glucan is detectable in a soluble phase, wherein the soluble phase is prepared using a 10% (w/v) suspension of the plurality of cells, after being incubated at 50° C. for 10 minutes at pH 12.0.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and drawings, and from the claims. The word "comprising" in the claims may be replaced by "consisting essentially of" or with "consisting of," according to standard practice in patent law.

DETAILED DESCRIPTION

Figure 1:
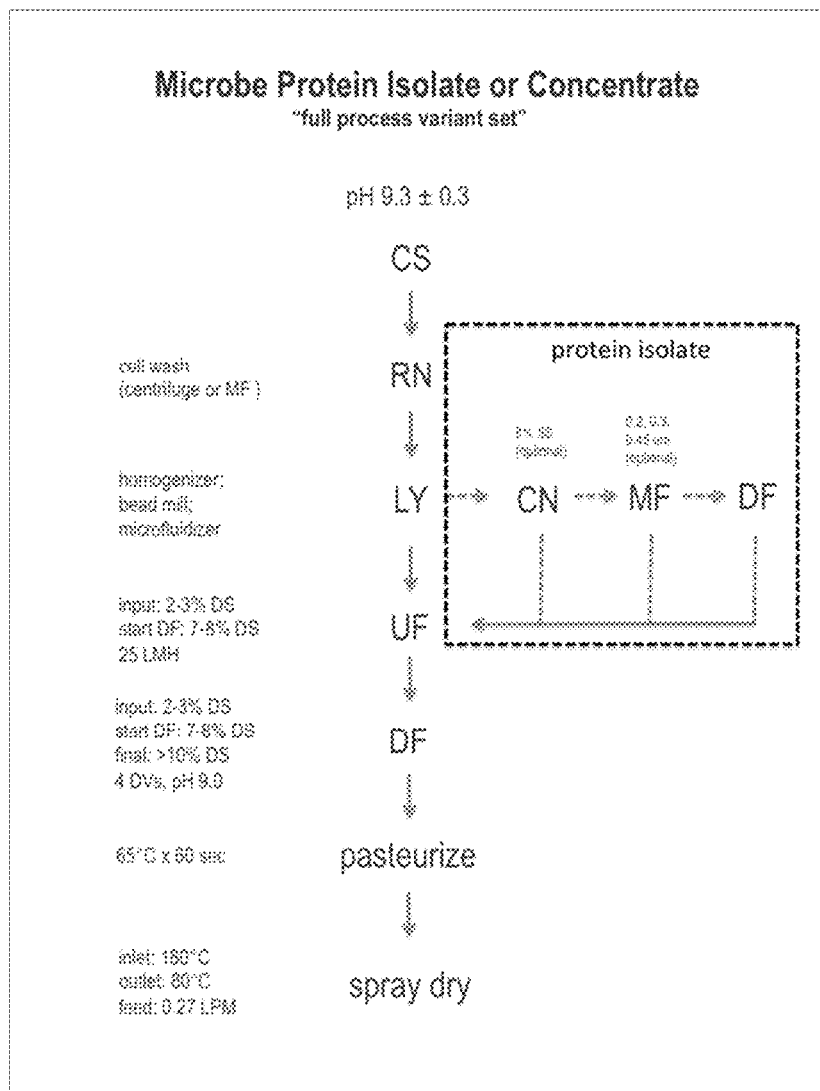
FIG. 1 is a schematic of exemplary process variants for isolation and concentration of protein.

Proteins (e.g., in their undenatured state) can contribute to the success of food replica products, such as meat and dairy replica products. Existing commercial protein extraction processes however, can result in denaturation of such proteins. Further, many proteins that might have functionality in food replica products have associated colors or aromas, which can detract from or inhibit their application. Without wishing to be bound by any particular theory, it is believed that maintaining a high pH (e.g., about 8.5 to about 12.0) throughout the purification process can aid in obtaining a low-flavor and/or low-color protein composition.

In general, this document provides protein compositions as well as methods and materials for purifying total cellular protein from cells resulting in protein compositions that can be used, for example, in food replicas, e.g., meat and dairy replica products or substitutes. In some embodiments, the methods provided herein result in a low-flavor protein composition that can be used in any number of food products. In some embodiments, the methods provided herein result in a low-color protein composition that can be used in any number of food products (e.g., having decreased yellow color that results in greater red color perception in a meat replica). In some embodiments, the methods provided herein result in a protein composition with food activity, such as gelling or emulsion stabilization.

Also provided herein are methods that increase the speed and/or efficiency of protein purification. For example, by perforating cells instead of lysing them, subcellular components, cell wall components, and/or nucleic acids can, in some embodiments, be easily separated from cytosolic protein. In some embodiments, the retained subcellular components, cell wall components, and/or nucleic acids can also be a source of valuable products, such as nucleic acid flavorant compounds GMP and IMP. As another example, methods provided herein can aid in the purification of an abundant protein (e.g., a recombinantly produced protein), particularly when the abundant protein is not normally secreted by the production cell. As yet another example, some treatments, e.g., reduction, alkaline exhaustion, and/or upfront pasteurization, can increase protein recovery in most process variants, including variants that include and those that exclude mechanical lysis.

Methods for Producing Protein Compositions

In some embodiments, a protein composition can be purified using any of the methods described herein). Suitable cells from which proteins can be extracted include, without limitation, cells from fungi, algae, prokaryotes, and Archea. In some embodiments, suitable cells may be naturally found in single-celled organisms (including yeasts) or in multicellular organisms (including Ascomycota and Basidiomycota). In some embodiments, a protein composition can be purified from one or more fungal species from, for example, the genera *Saccharomyces, Pichia, Candida, Hansenula, Torulopsis, Kluyveromyces, Yarrowia, Aspergillus, Trichoderma*, or *Fusarium*. For example, a protein composition can be purified from *Saccharomyces cerevisiae, Pichia pastoris, Candida boidinii, Hansenula polymorpha, Kluyveromyces lactis, Yarrowia lipolytica*, or *Fusarium venenatum* cells. In some embodiments, a protein composition can be purified from one or more archaeal or bacterial species from, for example, the genera *Bacillus, Escherichia, Lactobacillus, Corynebacterium, Pseudomonas*, or *Methanococcus*. For example, a protein composition can be purified from *E. coli, Bacillus subtilis, Lactobacillus lactis, Corynebacterium glutamicum, Pseudomonas fluorescens*, or *Methanococcus maripaludis*. In some embodiments, a protein composition can be purified from one or more algal species from, for example, the genera *Chlorella, Cyanobacteria, Chlamydomonas, Euglenid*, or *Spirulina*. For example, a protein composition can be purified from *Chlorella protothecoides, Arthrospira platensis, Euglena gracilis*, or *Nostoc flagelliforme*.

In some embodiments, one or more proteins in a protein composition described herein can have functional activity as a biocatalyst, as a food processing aid, an enzyme, as a flavor enhancer, a therapeutic, or a nutraceutical.

In some embodiments, a protein composition or a protein purified from a microbe can include one or more heterologous proteins (e.g., from a species different from the organism used to purify a protein or protein composition such as, for example, a protein from a eukaryote, an animal, a plant, an algae, a thermophile, a yeast, a bacteria, a protist or an archea). In some embodiments, the heterologous protein has functional activity as a biocatalyst, as a food processing aid, an enzyme, as a flavor enhancer, a therapeutic, a sweetener, a pharmaceutical, or a nutraceutical.

In some embodiments, an aqueous solution can include a buffer. The buffer can be any food-grade buffer (e.g., a buffer that includes sodium phosphate, potassium phosphate, calcium phosphate, sodium acetate, potassium acetate, sodium citrate, calcium citrate, sodium bicarbonate, sodium lactate, potassium lactate, sodium malate, potassium malate, sodium gluconate, and/or potassium gluconate) at a concentration of about 2 mM to about 200 mM (e.g., about 2 mM to about 10 mM, about 10 mM to about 20 mM, about 10 mM to about 30 mM, about 20 mM to about 30 mM, about 30 mM to about 40 mM, about 40 mM to about 50 mM, about 50 mM to about 100 mM, or about 100 mM to about 200 mM), and a pH of about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0).

In some embodiments of the methods described herein, a plurality of cells (e.g., microbial cells) can be suspended in an aqueous solution. In some embodiments, the plurality of cells can be washed.

A plurality of cells can be lysed at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0) to obtain a cell lysate. As described herein, maintaining a high pH during lysis can help to improve lysis (e.g., protein yield) and/or clarification. Without limitation, an aqueous suspension or a cell lysate can have from about 2% to about 25% dry solids (i.e., the mass remaining after removing all water). For example, an aqueous suspension or a cell lysate can have from about 2% to about 5%, about 5% to about 10%, about 10% to about 15%, about 15% to about 20%, about 20% to about 25%, about 5% to about 25%, about 10% to about 25%, about 15% to about 20%, about 2%, 5%, 7.5%, 10%, 12.5%, 15%, 17.5%, 20%, 22.5%, or 25% dry solids. In some embodiments, lysis can be biochemical such as enzymatic cell wall degradation or the lysis can be chemical, e.g., surfactant-based lysis, chaotropic-based lysis, or organic solvent-based lysis. Additionally or alternatively, lysis also can be mechanical using, for example, sonication, bead milling, osmotic lysis, homogenization, manual grinding, or by subjecting the cells to freeze-thaw cycles. Lysis can be performed at a temperature between about 4° C. and about 15° C. (e.g., about 4° C. to about 12° C., about 5° C. to about 10° C., about 4° C., 5° C., 6° C., 7° C., 8° C., 9° C., 10° C., 11° C., 12° C., 13° C., 14° C. or 15° C.).

Figure 2:
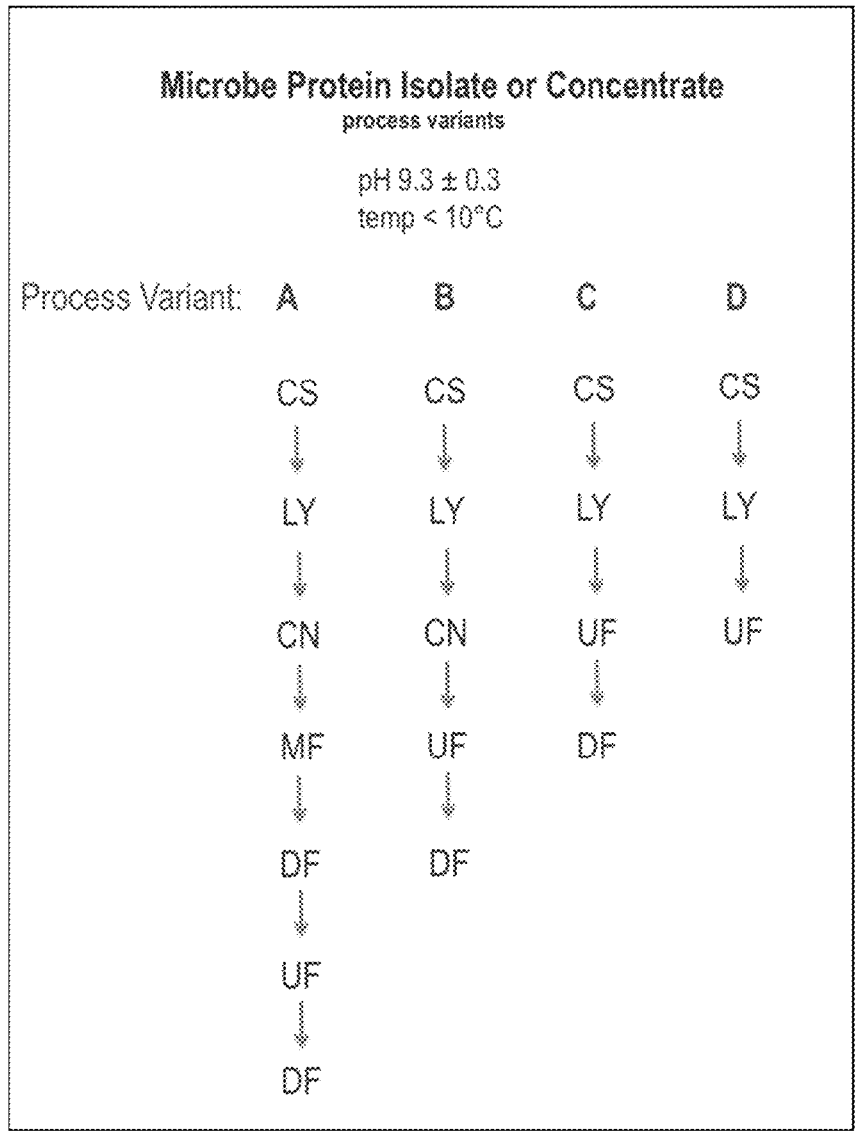
FIG. 2 is a schematic of exemplary process variants for isolation and concentration of protein. All steps may be followed by pasteurization (PZ) and/or spray drying (SD). Process conditions in all: pH 9.3+/−0.3; temperature<10° C.
Figure 3:
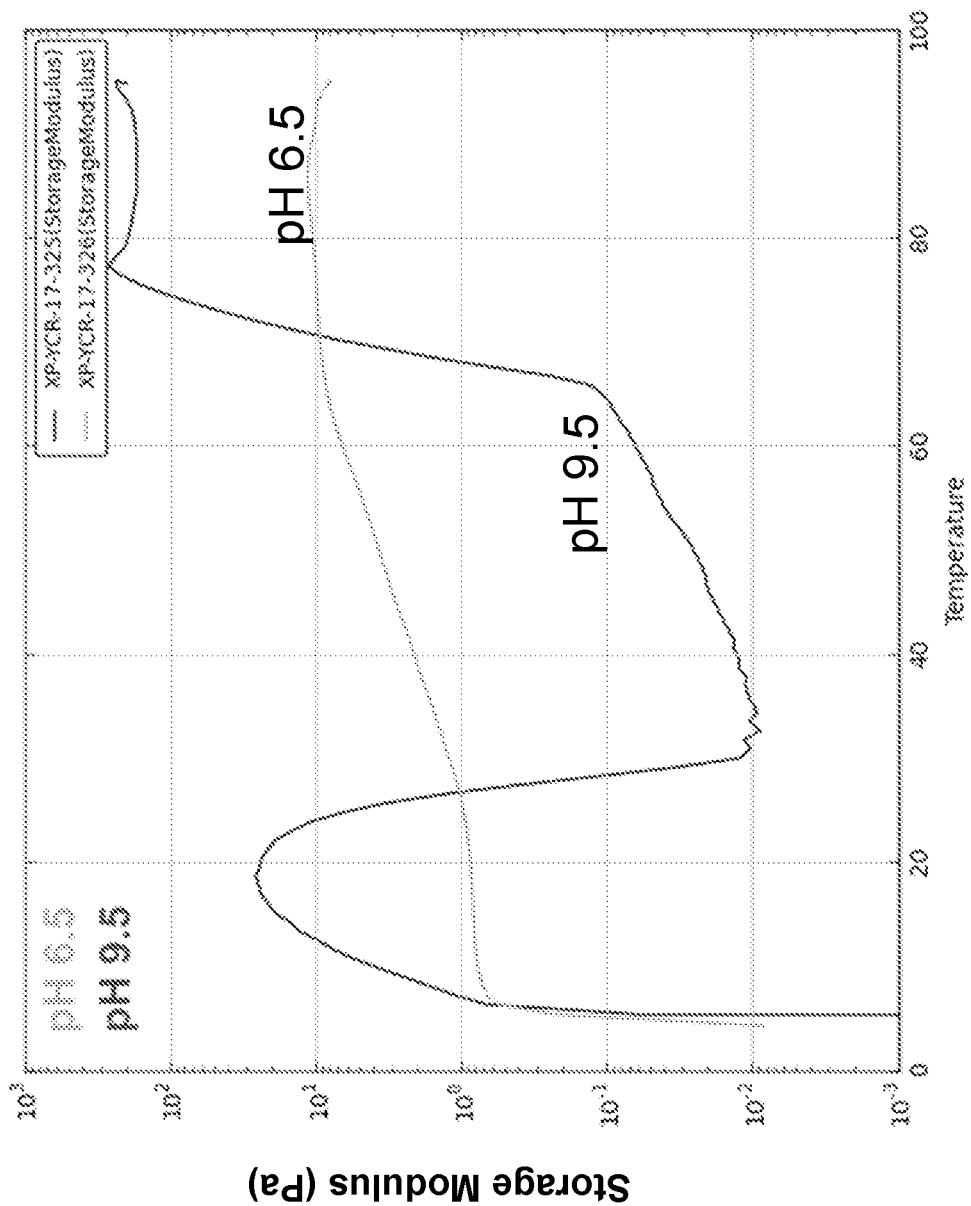
FIG. 3 is a plot showing that the product of high pH process creates firmer gels when heated. Process Variant A (see FIG. 2) was conducted at pH 6.5 or at pH 9.5. Rheology of the resulting material was measured using a hybrid rheometer. Vertical axis shows storage modulus (Pa) in log scale. Horizontal axis shows incubation temperature.
Figure 4:
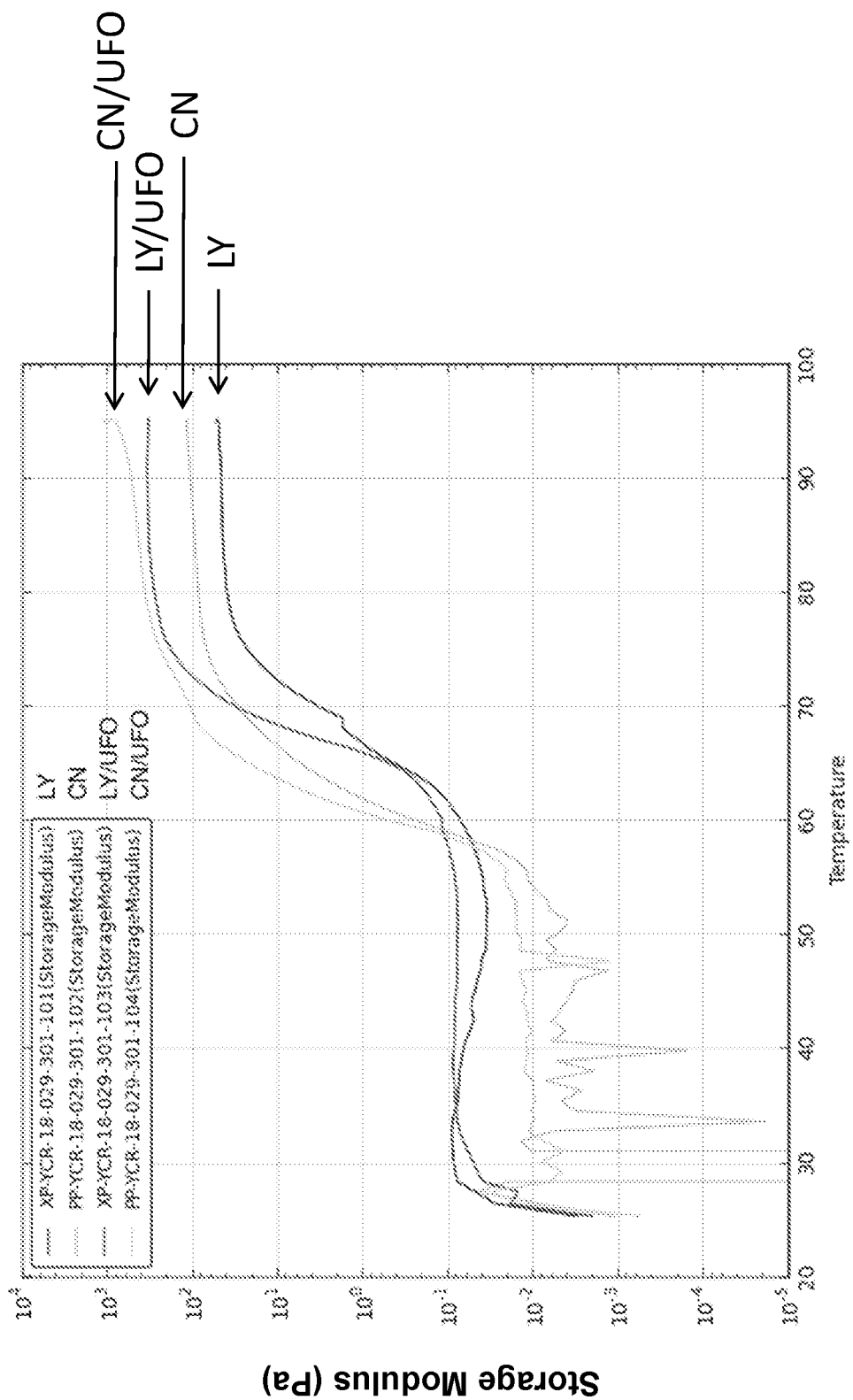
FIG. 4 is a plot showing that removing small molecules from microbial protein isolates and concentrates increased gel firmness by >5×; the effect was independent of solids removal. Process Variants B and C (see FIG. 2) were conducted at pH 9.3. In-process samples were taken of centrate ("CN") or lysate ("LY") and the final product of respective process B ("CN/UFO") or process C ("LY/UFO"). Each sample was freeze dried, then suspended to 10% (w/v) in MILLI-Q® water. Suspensions were assayed at pH 7.5. Rheology of the resulting material was measured using a hybrid rheometer. Vertical axis shows storage modulus (Pa) in log scale. Horizontal axis shows incubation temperature.
Figure 5:
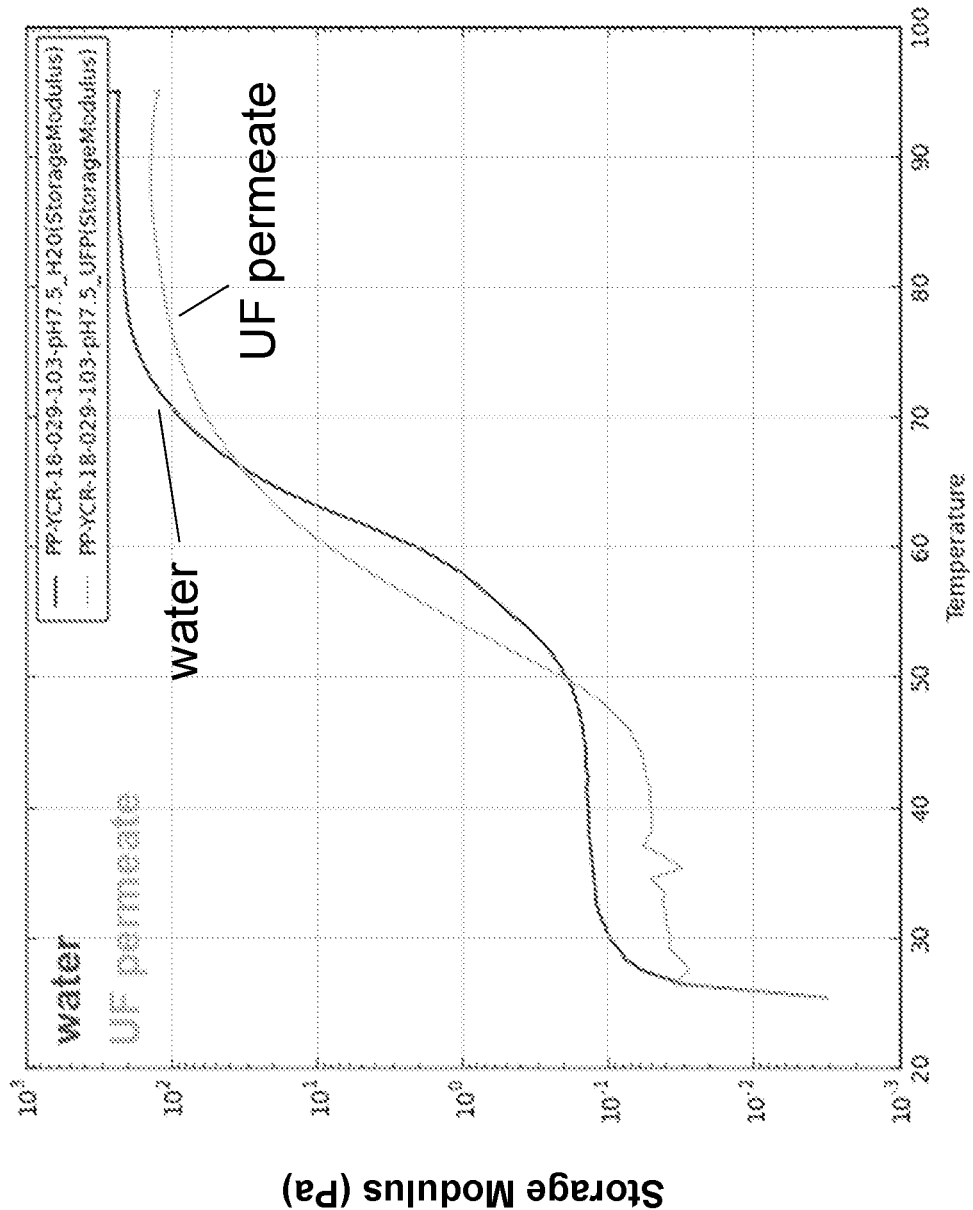
FIG. 5 is a plot showing that reconstituting protein isolates and concentrates with native small molecules reduces gel firmness by >2×. Process Variant C (see FIG. 2) was conducted at pH 9.3. The final material was freeze dried, then resuspended to 10% (w/v) in either MILLI-Q® water or in the initial UF permeate taken as an in-process sample. Suspensions were assayed at pH 7.5. Rheology of the resulting material was measured using a hybrid rheometer. Vertical axis shows storage modulus (Pa) in log scale. Horizontal axis shows incubation temperature.

Purification of a cell lysate can include one or more steps of, for example, centrifugation, clarification, precipitation, microfiltration, ultrafiltration, diafiltration (e.g., using a microfiltration or ultrafiltration membrane), pasteurization, and/or spray drying. FIG. 1 illustrates some exemplary schematics of different purification schemes that may be employed. FIG. 2 illustrates four particular purification schemes. In some embodiments, a protein composition can be a clarified lysate. In some embodiments, a protein composition can be a filtered (e.g., using one or more filtration steps) lysate, whether or not the lysate has been clarified. A protein composition can be used, e.g., in foods and food replica products.

A cell lysate can be optionally clarified by removing bulk solids, forming a clarified lysate. A variety of techniques can be used to clarify a cell lysate. For example, the cell lysate can be clarified by centrifugation, gravity settling, or by adding diatomaceous earth. During clarification, in some embodiments, the pH is maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). The cell lysate can be clarified to a dry solids content of less than 20%, e.g., less than 17%, 15%, 12%, 10%, 9%, 8%, 7%, 6%, or 5% dry solids.

One or more flocculants can optionally be added to a final concentration of about 0.1 to about 10 g/L to help improve the solids removal during a clarification step. Non-limiting examples of flocculants include alkylamine-epichlorohydrin, polydimethyldiallylammonium chloride, a polyamine (e.g., MAGNAFLOC®, SUPERFLOC®, or TRAM-FLOC®, from BASF, Florham Park, NJ), poly-ε-lysine, lime, hydrated lime, ferric chloride, ferric sulfate, ferrous sulfate, aluminum sulfate, sodium aluminate, aluminium chloride, magnesium carbonate hydroxide, calcium carbonate, calcium hydroxide, an activated silicate, a guar gum, a starch, a tannin, sodium alginate, polyaluminum sulfate, polyaluminum hydroxy chloride, BIO-FLOCK®, and a synthetic polyelectrolyte (e.g., ZETAG®). In some embodiments, one or more flocculants are added. In some embodiments, a clarification step is performed without adding one or more flocculants.

In some embodiments, a cell lysate can be optionally diluted using, for example, water or an aqueous solution of salts or buffers, prior to solids removal, while maintaining the pH between about pH 8.5 and 12.0. For example, a cell lysate can be diluted 1:1 with water. In some embodiments, one or more flocculants are added to a cell lysate and the cell lysate is diluted before clarification. In some embodiments, a cell lysate is diluted before clarification, and the clarification step proceeds without adding one or more flocculants. In some embodiments, one or more flocculants are added to a cell lysate and the cell lysate is not diluted before clarification. In some embodiments, a clarification step is performed without adding one or more flocculants to a cell lysate and without diluting the cell lysate.

In some embodiments, a cell lysate (e.g., a cell lysate that has not undergone a clarification step, such as a clarification step as described herein) can be filtered to obtain a filtered lysate. A filtration step can further reduce the amount of particulates. During filtration, in some embodiments, the pH is maintained between a pH of about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During filtration, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.). A cell lysate or clarified lysate can be filtered using microfiltration, ultrafiltration, and/or diafiltration. Microfiltration can use a membrane with a pore size of about 0.2 μm to about 2.0 μm (e.g., about 0.2 to about 0.3 μm, about 0.3 to about 0.5 μm, about 0.5 to about 0.7 μm, about 0.7 to about 0.9 μm, about 0.9 to about 1.1 μm, about 1.0 to about 1.2 μm, about 1.2 to about 1.4 μm, about 1.4 to about 1.6 μm, about 1.6 to about 1.8 μm, or about 1.8 to about 2.0 μm). Ultrafiltration can use a membrane with a molecular weight cutoff of about 5 kDa to about 70 kDa (e.g., about 5 kDa to about 10 kDa, about 10 kDa to about 30 kDa, or about 30 kDa to about 50 kDa, about 20 kDa to about 40 kDa, about 40 to about 60 kDa, or about 50 kDa to about 70 kDa).

In some embodiments, a clarified lysate can be filtered to obtain a filtered lysate. In some embodiments, a filtration step can reduce the amount of particulates. During filtration, in some embodiments, the pH is maintained between a pH of about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During filtration, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.). A clarified lysate can be filtered using microfiltration, ultrafiltration, and/or diafiltration. Microfiltration can use a membrane with a pore size of about 0.2 μm to about 2.0 μm (e.g., about 0.2 to about 0.3 μm, about 0.3 to about 0.5 μm, about 0.5 to about 0.7 μm, about 0.7 to about 0.9 μm, about 0.9 to about 1.1 μm, about 1.0 to about 1.2 μm, about 1.2 to about 1.4 μm, about 1.4 to about 1.6 μm, about 1.6 to about 1.8 μm, or about 1.8 to about 2.0 μm). Ultrafiltration can use a membrane with a molecular weight cutoff of about 5 kDa to about 70 kDa (e.g., about 5 kDa to about 10 kDa, about 10 kDa to about 30 kDa, about 30 kDa to about 50 kDa, about 20 to about 40 kDa, about 40 kDa to about 60 kDa, or about 50 to about 70 kDa).

In some embodiments, a filtered lysate can be subjected to one or more additional filtration steps to obtain another filtered lysate. A filtered lysate can be filtered using microfiltration, ultrafiltration, and/or diafiltration. Microfiltration can use a membrane with a pore size of about 0.2 µm to about 2.0 µm (e.g., about 0.2 to about 0.3 µm, about 0.3 to about 0.5 µm, about 0.5 to about 0.7 µm, about 0.7 to about 0.9 µm, about 0.9 to about 1.1 µm, about 1.0 to about 1.2 µm, about 1.2 to about 1.4 µm, about 1.4 to about 1.6 µm, about 1.6 to about 1.8 µm, or about 1.8 to about 2.0 µm). Ultrafiltration can use a membrane with a molecular weight cutoff of about 5 kDa to about 70 kDa (e.g., about 5 kDa to about 10 kDa, about 10 kDa to about 30 kDa, about 30 kDa to about 50 kDa, about 20 kDa to about 40 kDa, about 40 kDa to about 60 kDa, or about 50 kDa to about 70 kDa). For example, a filtered lysate can be further filtered by forcing the solution (e.g., using increased pressure or centrifugation) through a semi-permeable membrane having, for example, a molecular weight cutoff of about 5 kDa to about 50 kDa (e.g., about 5 kDa to about 10 kDa, about 10 kDa to about 30 kDa, or about 30 kDa to about 50 kDa). In some embodiments, a filtered lysate can be diafiltered on a microfiltration membrane. In some embodiments, a filtered lysate can be diafiltered on an ultrafiltration membrane. In some embodiments, filtered lysate (e.g., cell lysate or clarified lysate filtered by microfiltration and/or ultrafiltration) can be concentrated to at least about 10% dry solids (e.g., at least about 15% or 20% dry solids) then diafiltered at constant volume for at least one diavolume (DV) (e.g., at least 2, 3, 4, 5, 6, 7, 8, 9, 10, 15, or 20 diavolumes). In some embodiments, filtered lysate (e.g., cell lysate or clarified lysate filtered by microfiltration and/or ultrafiltration) can be diluted (e.g., using water or an aqueous solution of salts or buffers, while maintaining the pH between about pH 8.5 and 12.0) to about 5% dry solids (e.g., about 6%, 7%, 8% or 9% dry solids) then diafiltered at constant volume for at least one diavolume (e.g., at least 2, 3, 4, 5, 6, 7, 8, 9, 10, 15, or 20 diavolumes). In some embodiments, filtered lysate (e.g., cell lysate or clarified lysate filtered by microfiltration and/or ultrafiltration) can be diluted (e.g., using water or an aqueous solution of salts or buffers, while maintaining the pH between about pH 8.5 and 12.0) to about 3% dry solids (e.g., about 2% or about 4% dry solids) then diafiltered to concentration the filtered lysate to about 15% dry solids (e.g., about 13%, 14%, 16%, or 17% dry solids). During the additional filtration step or steps, in some embodiments, the pH is maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During additional filtration step or steps, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.).

A cell lysate can be concentrated (e.g., through filtering methods as described for removing components smaller than the desired protein such as ultrafiltration, optionally with diafiltration). During the concentration, the pH can be maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During the concentration, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.). A cell lysate can be concentrated to a protein content of about 2 mg/mL to about 250 mg/mL (e.g., 10 mg/mL to 225 mg/mL, 15 mg/mL to 200 mg/mL, 25 mg/mL to about 225 mg/mL, 50 mg/mL to 200 mg/mL, or 50 mg/mL to 150 mg/mL). Concentration can occur concurrently with a filtration step. Concentration can occur separately from a filtration step.

A clarified lysate can be concentrated (e.g., through filtering methods as described for removing components smaller than the desired protein such as ultrafiltration, optionally with diafiltration). During the concentration, the pH can be maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During the concentration, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.). A clarified lysate can be concentrated to a protein content of about 2 mg/mL to about 250 mg/mL (e.g., 10 mg/mL to 225 mg/mL, 15 mg/mL to 200 mg/mL, 25 mg/mL to about 225 mg/mL, 50 mg/mL to 200 mg/mL, or 50 mg/mL to 150 mg/mL). Concentration can occur concurrently with a filtration step. Concentration can occur separately from a filtration step.

A filtered lysate can be concentrated (e.g., through filtering methods as described for removing components smaller than the desired protein such as ultrafiltration, optionally with diafiltration). During the concentration, the pH can be maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During the concentration, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.). A filtered lysate can be concentrated to a protein content of about 2 mg/mL to about 250 mg/mL (e.g., 10 mg/mL to 225 mg/mL, 15 mg/mL to 200 mg/mL, 25 mg/mL to about 225 mg/mL, 50 mg/mL to 200 mg/mL, or 50 mg/mL to 150 mg/mL). Concentration can occur concurrently with a filtration step. Concentration can occur separately from a filtration step.

In some embodiments, a plurality of cells (e.g., a washed plurality of cells and/or an aqueous suspension of cells) can undergo one or more treatments, e.g., before purification of proteins from the cells. Treatments can include, for example, perforation of cell walls, alkaline exhaustion, and/or pasteurization. These treatments can be performed in any combination or in any order (see, e.g., FIG. 9A for some exemplary treatment protocols starting with perforation or alkaline exhaustion).

Without wishing to be bound by any particular theory, it is believed that these treatments (alone or in any combination) can result in a more efficient and/or shorter duration purification protocol. For example, these treatments (alone or in any combination) can, in some cases, result in the release of a cytoplasmic protein of interest (e.g., a recombinantly produced protein) as if it had been secreted, and optionally in an unmodified form (e.g., without a secretion signal). As another example, the treatments described herein typically do not require osmotic stabilization of cell walls. With respect to speed, it has been surprisingly found that the combination of treatment with a reductant, alkaline exhaustion, and pasteurization results in the release of about 100% of a target cytoplasmic protein (LegH) in about 15-20 minutes, as compared to a commercial spheroplasting kit that results in about 70% release in more than 30 minutes. In some embodiments, the treatments described herein are scalable. In some embodiments, the treatments described herein are food-safe. Another potential benefit of these treatments is selective enrichment of certain species in solid and liquid portions; for example, the treatments described herein can, in some embodiments, result in one or more of the following after a separation of a liquid portion and a solid portion (e.g., via centrifugation): the enrichment of cytosolic proteins (and, in some embodiments, non-membrane-bound cell wall proteins, as without wishing to be bound by any particular theory, these proteins are often attached to the cell wall via disulfide bonds) in a liquid portion (and/or depletion of cytosolic proteins from a solid portion); the enrichment of cytosolic small molecules (and/or, in some embodiments, non-membrane-bound cell wall small molecules) (and/or depletion of cytosolic small molecules from a solid portion); the enrichment of membrane-bound cell wall proteins and/or subcellular compartment proteins in a solid portion (and/or depletion of membrane-bound cell wall proteins and/or subcellular compartment proteins in a liquid portion); the enrichment of non-cytosolic small molecules in a solid portion (and/or depletion of non-cytosolic small molecules in a liquid portion); the enrichment of nucleic acids (e.g., sources of flavor precursors IMP and GMP) in a solid portion (and/or depletion of nucleic acids in a liquid portion); the enrichment of cell wall components in a solid portion (and/or depletion of cell wall components in a liquid portion); or the enrichment of lipids/fats in solid portion (and/or depletion of lipids/fats in a liquid portion) (e.g., as compared to a method comprising significant lysis (e.g., mechanical lysis) of cells).

In general, when one or more of these treatments is performed, lysis of the cells is not necessary (but the treatment(s) may increase the yield if a lysis step is performed as compared to a lysis step lacking the treatment(s)). In some embodiments, when one or more of these treatments if performed, the method does not comprise mechanical lysis (e.g., bead beating, bead milling, grinding, or rotator-shaker homogenizers), cryopulverization, high pressure cell disruption (e.g., by French press, or microfluidizer), sonication, nitrogen decompression, or a combination thereof. Again without wishing to be bound by any theory, it is believed that when cells remain intact, some typical contaminants of protein purification, such as cell wall materials, subcellular compartments, and nucleic acids, are retained in the cells to a greater degree than if lysis is performed.

Perforation of the cell walls of a plurality of cells (having cell walls) can be performed using any appropriate method. Typically, perforation of cell walls results in intact cells rather than lysis of the cells. Non-limiting examples of methods of perforation include treatment with a reductant, treatment with an enzyme, electroporation, or a combination thereof.

In some embodiments, perforation of the cell walls comprises treatment with a reductant. Without wishing to be bound by any particular theory, it is believed that treatment with a reductant can promote the weakening of cell walls, the release of cytoplasmic contents, drive flocculation, promote solids removal, protect cytoplasmic targets from oxidation during a purification process, and/or stabilize redox-sensitive proteins to thermal processing (e.g., pasteurization). In some embodiments, a reductant can be a food-safe reductant. In some embodiments, a reductant can be selected from the group consisting of cysteine, glutathione, bisulfate, and a combination thereof. In some embodiments, treatment with a reductant comprises treatment with about 5 mM to about 500 mM (e.g., about 5 mM to about 20 mM, about 5 mM to about 50 mM, about 5 mM to about 100 mM, about 5 mM to about 200 mM, about 5 mM to about 300 mM, about 5 mM to about 400 mM, about 10 mM to about 20 mM, about 10 mM to about 50 mM, about 10 mM to about 100 mM, about 10 mM to about 200 mM, about 10 mM to about 300 mM, about 10 mM to about 400 mM, about 10 mM to about 500 mM, about 20 mM to about 500 mM, about 50 mM to about 500 mM, about 100 mM to about 500 mM, about 200 mM to about 500 mM, about 300 mM to about 500 mM, about 400 mM to about 500 mM, about 20 mM to about 80 mM, about 30 mM to about 70 mM, about 40 mM to about 60 mM, about 80 mM to about 120 mM, about 90 mM to about 110 mM, about 50 mM, or about 100 mM) reducing equivalents of the reductant. As used herein a "reducing equivalent" is the number of reducing units present on a reductant molecule. For example, cysteine has a single sulfhydryl group and represents a single reducing equivalent. As another example, dithiothreitol (DTT) has two sulfhydryl groups and represents two reducing equivalents. In most cases, a reducing equivalent can refer to the transfer of two electrons, but single electron reductions are also known. During the perforation of the cell walls, in some embodiments, the pH is maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During the perforation of the cell walls, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.).

In some embodiments, a plurality of cells can be subject to alkaline exhaustion. As used herein, "alkaline exhaustion" refers to treating cells with base until the pH of the aqueous suspension is about 8.5 to about 12.0, for example, for a period of time (e.g., at least about 3 minutes, at least about 5 minutes, or at least about 10 minutes). Without wishing to be bound by any particular theory, it is believed that cells (e.g., fungal cells (e.g., yeast cells)) respond to an alkaline environment by acidification of the environment; however, cells have a limited ability to adjust the pH of the environment, and eventually, further adjustment will not be possible. Again without wishing to be bound by any particular theory, it is believed that alkaline exhaustion of the cells can minimize pH drops through a purification process, and that such pH drops can precipitate and/or inactivate protein. Another potential benefit of alkaline exhaustion, without wishing to be bound by any particular theory, is the weakening of cell walls and an increase protein release efficiency (e.g., either with perforation or with a lysis step). During the alkaline exhaustion, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.).

In some embodiments, a plurality of cells can be pasteurized (e.g., before any filtration steps, also called herein "up-front pasteurization" or "PZ1"). For example, in some embodiments, a plurality of cells can be heated to about 50° C. to about 85° C. (e.g., about 50° C. to about 55° C., about 50° C. to about 60° C., about 50° C. to about 65° C., about 50° C. to about 70° C., about 50° C. to about 75° C., about 50° C. to about 80° C., about 55° C. to about 85° C., about 60° C. to about 85° C., about 65° C. to about 85° C., about 70° C. to about 85° C., about 75° C. to about 85° C., about 80° C. to about 85° C.). Without wishing to be bound by any particular theory, it is believed that pasteurization can have one or more benefits, such as an increase in the release of protein from cells, minimal impact on particle size, promotion of solids removal (e.g., versus mechanical lysis), killing of the production organism (e.g., for bioburden reduction), and/or chemical reduction of intracellular protein. During pasteurization, in some embodiments, the pH is maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0).

These treatments can be practiced alone, or combined in any order. For example, some methods described herein can include a step of perforating cell walls, an alkaline exhaustion step, or a pasteurization step, and neither of the other two. In some embodiments, methods described herein can include a step of perforating cell walls followed by an alkaline exhaustion step or a pasteurization step, optionally then followed by a pasteurization step or alkaline exhaustion step, respectively. In some embodiments, methods described herein can include an alkaline exhaustion step followed by a step of perforating cell walls or a pasteurization step, optionally then followed by a pasteurization step or a step of perforating cell walls, respectively. In some embodiments, methods described herein can include a pasteurization step followed by a step of perforating cell walls or an alkaline exhaustion step, optionally then followed by an alkaline exhaustion step or a step of perforating cell walls, respectively.

Without being bound by any particular theory, it is believed that using one or more of the treatments provided herein results in at least partial alteration of cell walls, while the cells remain generally intact. For example, in some embodiments, when a 10% (w/v) suspension of a plurality of cells treated with any one or more of the treatments provided herein is incubated for about 10 minutes at about 50° C. and pH 10.5, then is centrifuged to remove solids, and the supernatant is treated with a mannosidase (e.g., alpha mannosidase), less than about 50 µg/mL (e.g., less than about 40 µg/mL, less than about 30 µg/mL, less than about 20 µg/mL, less than about 15 µg/mL, or less than about 10 µg/mL) of mannose is detected. As another example, in some embodiments, when a 10% (w/v) suspension of a plurality of cells treated with any one or more of the treatments provided herein is incubated at about 50° C. and pH 12.0, less than about 400 µg/mL (e.g., less than about 300 µg/mL, less than about 200 µg/mL, less than about 150 µg/mL, less than about 100 µg/mL, or less than about 50 µg/mL) beta glucan is detectable in the soluble phase of the plurality of cells.

Accordingly, in some embodiments, provided herein are compositions produced by using any one or more of the treatments provided herein. In some embodiments, provided herein is a composition comprising a plurality of cells, wherein treatment of a supernatant of the plurality of cells with a mannosidase (e.g., alpha-mannosidase) yields less than about 50 µg/mL less than about 50 µg/mL (e.g., less than about 40 µg/mL, less than about 30 µg/mL, less than about 20 µg/mL, less than about 15 µg/mL, or less than about 10 µg/mL) detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided herein is a composition comprising a plurality of cells, wherein less than about 400 µg/mL (e.g., less than about 300 µg/mL, less than about 200 µg/mL, less than about 150 µg/mL, less than about 100 µg/mL, or less than about 50 µg/mL) beta glucan is detectable in a soluble phase, wherein the soluble phase is prepared using a 10% (w/v) suspension of the plurality of cells, after being incubated at 50° C. for 10 minutes at pH 12.0. In some embodiments, the composition further comprises a reductant. In some embodiments, the reductant is present in the composition in an amount of about 5 mM to about 500 mM (e.g., about 5 mM to about 20 mM, about 5 mM to about 50 mM, about 5 mM to about 100 mM, about 5 mM to about 200 mM, about 5 mM to about 300 mM, about 5 mM to about 400 mM, about 10 mM to about 20 mM, about 10 mM to about 50 mM, about 10 mM to about 100 mM, about 10 mM to about 200 mM, about 10 mM to about 300 mM, about 10 mM to about 400 mM, about 10 mM to about 500 mM, about 20 mM to about 500 mM, about 50 mM to about 500 mM, about 100 mM to about 500 mM, about 200 mM to about 500 mM, about 300 mM to about 500 mM, about 400 mM to about 500 mM, about 20 mM to about 80 mM, about 30 mM to about 70 mM, about 40 mM to about 60 mM, about 80 mM to about 120 mM, about 90 mM to about 110 mM, about 50 mM, or about 100 mM) reducing equivalents of the reductant. In some embodiments, the reductant is selected from the group consisting of cysteine, glutathione, bisulfate, and a combination thereof. In some embodiments, the reductant is a food safe reductant. In some embodiments, at least about 25% by weight of the cells of the plurality of cells are intact. In some embodiments, at least about 50% by weight of the cells of the plurality of cells are intact. In some embodiments, at least about 75% by weight of the cells of the plurality of cells are intact. In some embodiments, the plurality of cells has a particle size distribution median of about 2 µm to about 4 µm (e.g., about 3 µm).

In some embodiments, provided herein are methods of treating a plurality of cells (e.g., a plurality of cells having cell walls). In some embodiments, provided is a method for treating a plurality of cells having cell walls, the method including: perforating the cell walls of the plurality of cells, wherein treatment of a supernatant of the plurality of cells with a mannosidase (e.g., alpha-mannosidase) yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells, the method including: treating an aqueous suspension of the plurality of cells with a base until the pH of the aqueous suspension is about 8.5 to about 12.0, wherein treatment of a supernatant of the plurality of cells with mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells having cell walls, the method including: a) treating an aqueous suspension of the plurality of cells with a base until the pH of the aqueous suspension is about 8.5 to about 12.0, b) perforating the cell walls of the plurality of cells, wherein treatment of a supernatant of the plurality of cells with mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells having cell walls, the method including: a) perforating the cell walls of the plurality of cells, b) treating an aqueous suspension of the plurality of cells with a base until the pH of the aqueous suspension is about 8.5 to about 12.0, wherein treatment of a supernatant of the plurality of cells with mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells, the method including: heating the plurality of cells to a temperature of about 50° C. to about 85° C., wherein treatment of a supernatant of the plurality of cells with mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a method for treating a plurality of cells having cell walls, the method including: perforating the cell walls of the plurality of cells, wherein less than about 200 µg/mL beta glucan is detectable in a soluble phase, wherein the soluble phase is prepared using a 10% (w/v) suspension of the plurality of cells, after being incubated at 50° C. for 10 minutes at pH 12.0. In some embodiments, provided is a method for treating a plurality of cells, the method including: treating an aqueous suspension of the plurality of cells with a base until the pH of the aqueous suspension is about 8.5 to about 12.0, wherein less than about 200 µg/mL beta glucan is detectable in a soluble phase, wherein the soluble phase is prepared using a 10% (w/v) suspension of the plurality of cells, after being incubated at 50° C. for 10 minutes at pH 12.0. In some embodiments, provided is a method for treating a plurality of cells having cell walls, the method including: a) treating an aqueous suspension of the plurality of cells with a base until the pH of the aqueous suspension is about 8.5 to about 12.0, b) perforating the cell walls of the plurality of cells, wherein less than about 200 µg/mL beta glucan is detectable in a soluble phase, wherein the soluble phase is prepared using a 10% (w/v) suspension of the plurality of cells, after being incubated at 50° C. for 10 minutes at pH 12.0. In some embodiments, provided is a method for treating a plurality of cells having cell walls, the method including: a) perforating the cell walls of the plurality of cells, b) treating an aqueous suspension of the plurality of cells with a base until the pH of the aqueous suspension is about 8.5 to about 12.0, wherein less than about 200 µg/mL beta glucan is detectable in a soluble phase, wherein the soluble phase is prepared using a 10% (w/v) suspension of the plurality of cells, after being incubated at 50° C. for 10 minutes at pH 12.0. In some embodiments, provided is a method for treating a plurality of cells, the method including: heating the plurality of cells to a temperature of about 50° C. to about 85° C., wherein less than about 200 µg/mL beta glucan is detectable in a soluble phase, wherein the soluble phase is prepared using a 10% (w/v) suspension of the plurality of cells, after being incubated at 50° C. for 10 minutes at pH 12.0.

Also provided herein are compositions of cells, such as those that have been treated as described herein. In some embodiments, provided is a composition including: a plurality of cells, wherein treatment of a supernatant of the plurality of cells with a mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids. In some embodiments, provided is a composition including: a plurality of cells, wherein less than about 200 µg/mL beta glucan is detectable in a soluble phase, wherein the soluble phase is prepared using a 10% (w/v) suspension of the plurality of cells, after being incubated at 50° C. for 10 minutes at pH 12.0.

These treatments can be followed with any of the steps described herein, including but not limited to, lysis, phase separation, filtering, concentration, pasteurization, and/or drying. In some embodiments, these treatments are not followed by a lysis step, as one or more treatments can result in the release of cytosolic proteins.

Figure 9A:
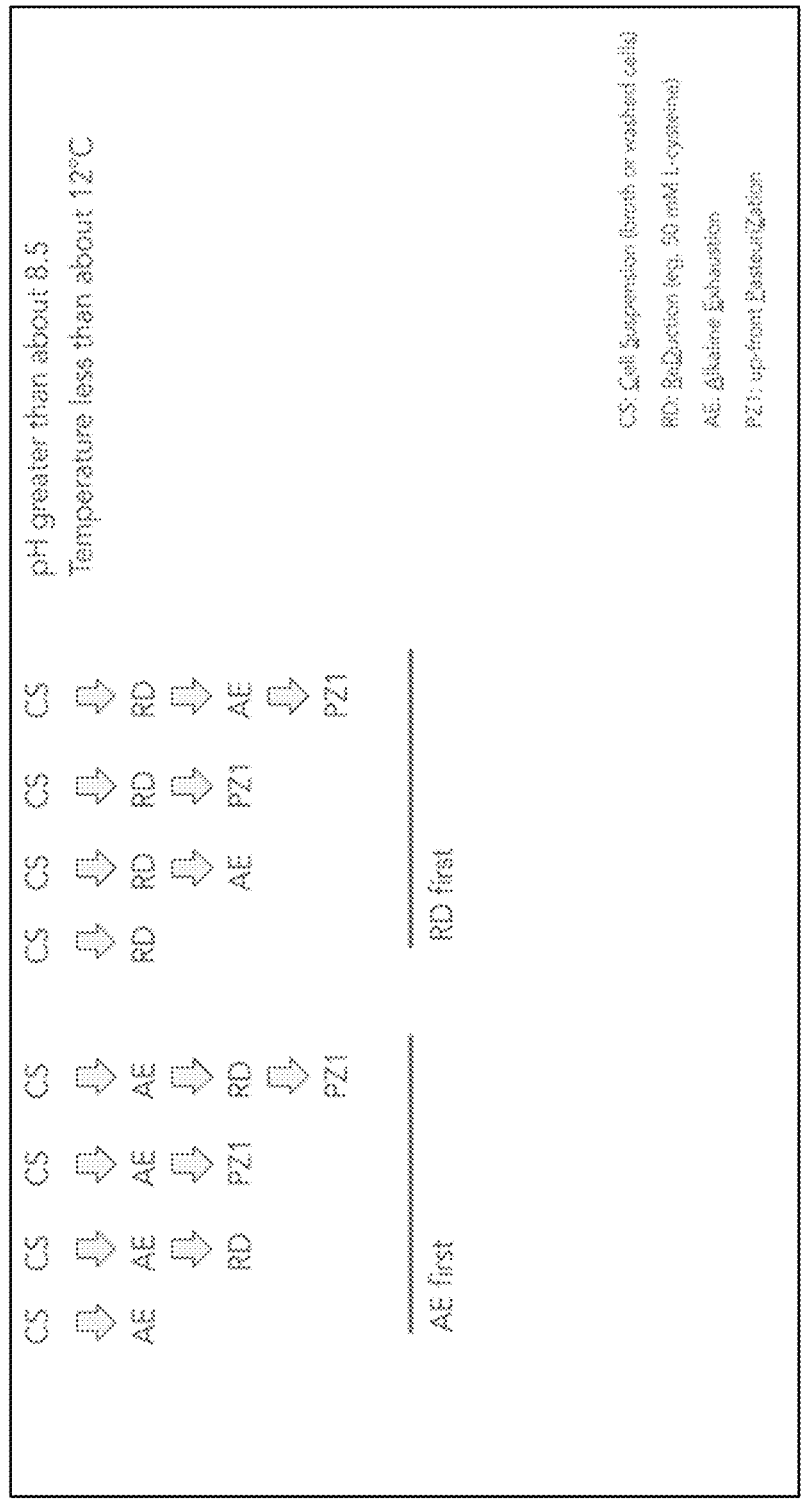
FIG. 9A is a schematic of exemplary process variants for treatment of cell suspensions, including either alkaline exhaustion ("AE") or reduction ("RD") as initial steps.
Figure 9B:
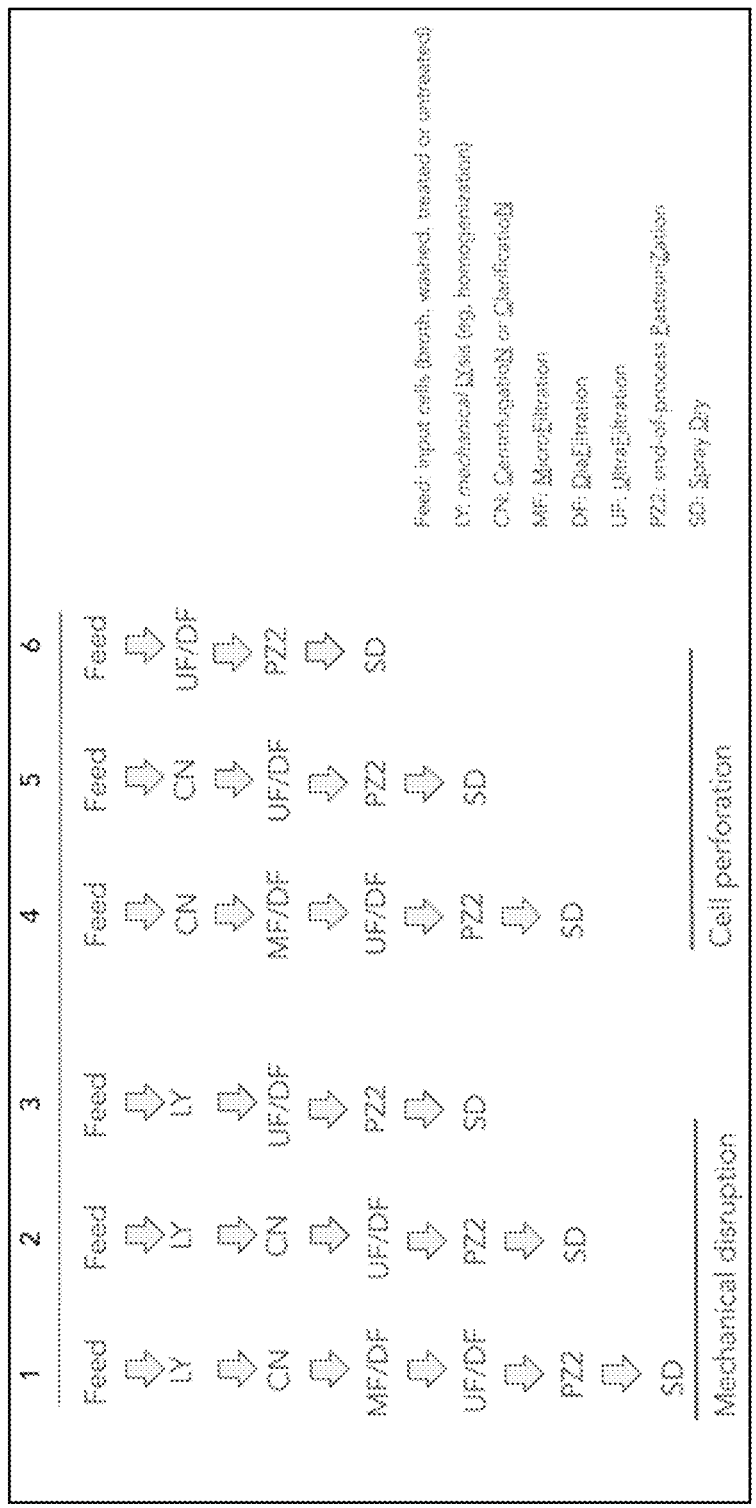
FIG. 9B is a schematic of exemplary process variants for isolation and concentration of protein, optionally including any of the products of the processes of FIG. 9 as the "Feed".

Subsequent purification steps after one of the above treatments can include one or more steps of, for example, centrifugation, phase separation, precipitation, microfiltration, ultrafiltration, diafiltration (e.g., using a microfiltration or ultrafiltration membrane), pasteurization, and/or spray drying. FIG. 9B illustrates some exemplary subsequent purification steps that can be performed on a plurality of cells (e.g., an aqueous suspension of cells treated with any one or more of the treatments described herein). A protein composition can be used, e.g., in foods and food replica products.

After treatment, an aqueous suspension of a plurality of cells can be subject to a separation step to separate a solid portion from a liquid portion (analogous to the clarification described hereinabove). For example, the phase separation can be achieved by centrifugation, depth filtration, gravity settling, microfiltration, or a combination thereof. In some embodiments, centrifugation comprises centrifugation at a force of at least 3 k×g (e.g., at least about 5 k×g, at least about 10 k×g, at least about 20 k×g, or at least about 40 k×g). During separation, in some embodiments, the pH is maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). The separation can be performed to a dry solids content of less than 20%, e.g., less than 17%, 15%, 12%, 10%, 9%, 8%, 7%, 6%, or 5% dry solids in the liquid portion. During the separation, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.).

One or more flocculants can optionally be added to a final concentration of about 0.1 to about 10 g/L to help improve the solids removal during a separation step. In some embodiments, one or more flocculants are added. In some embodiments, a separation step is performed without adding one or more flocculants.

In some embodiments, an aqueous suspension of a plurality of cells can be optionally diluted using, for example, water or an aqueous solution of salts or buffers, prior to a separation step, while maintaining the pH between about pH 8.5 and 12.0. For example, a cell lysate can be diluted 1:1 with water. In some embodiments, one or more flocculants are added to an aqueous suspension of a plurality of cells and the aqueous suspension of the plurality of cells is diluted before separation of a solid portion and a liquid portion. In some embodiments, an aqueous suspension of a plurality of cells is diluted before separation, and the separation step proceeds without adding one or more flocculants. In some embodiments, one or more flocculants are added to an aqueous suspension of a plurality of cells and the aqueous suspension of the plurality of cells is not diluted before separation. In some embodiments, a separation step is performed without adding one or more flocculants to the aqueous suspension of the plurality of cells and without diluting the aqueous suspension of the plurality of cells.

As noted herein, methods described herein can, in some embodiments, result in efficient separation of cellular components (e.g., proteins and/or nucleic acids) from different cellular locations to either the liquid portion or the solids portion. For example, in some embodiments, the liquid portion can include at least 30% (e.g., at least about 40%, at least about 50%, at least about 60%, at least about 70%, at least about 80%, or at least about 90%) by weight of the cytoplasmic proteins of the plurality of cells. In some embodiments, the liquid portion can include at least about 30% (e.g., at least about 40%, at least about 50%, at least about 60%, at least about 70%, at least about 80%, or at least about 90%) by weight of the hexokinase (e.g., as an indicator of cytosolic protein content) of the plurality of cells. In some embodiments, the liquid portion can include at least about 30% (e.g., at least about 40%, at least about 50%, at least about 60%, at least about 70%, at least about 80%, or at least about 90%) by weight of the non-membrane-bound cell wall proteins of the plurality of cells. In some embodiments, the protein in the liquid portion can include less than about 40% (e.g., less than about 35%, less than about 33%, less than about 30%, less than about 25%, less than about 20%, less than about 15% or less than about 10%) by weight of membrane-bound and subcellular compartment protein. In some embodiments, dry solids from the liquid portion (e.g., resuspended in buffer or water) can have an $A_{260}/A_{280}$ ratio of less than about 1.5, typically after desalting (e.g., by a standard nucleic acid miniprep kit with no nuclease treatment). In some embodiments, dry solids from the solid portion (e.g., resuspended in buffer or water) can have an A260/A280 ratio of greater than about 1.5, typically after desalting (e.g., by a standard nucleic acid miniprep kit with no nuclease treatment). In some embodiments, the solids portion can include at least about 30% (e.g., at least about 40%, at least about 50%, at least about 60%, at least about 70%, at least about 80%, or at least about 90%) by weight of the membrane-bound and/or subcellular compartment protein of the plurality of cells. In some embodiments, the solids portion can include at least about 30% (e.g., at least about 40%, at least about 50%, at least about 60%, at least about 70%, at least about 80%, or at least about 90%) by weight of total histone protein of the plurality of cells. In some embodiments, the solids portion can include at least about 30% (e.g., at least about 40%, at least about 50%, at least about 60%, at least about 70%, at least about 80%, or at least about 90%) by weight of ferrochelatase protein (e.g., as an indicator of mitochondrial protein content) of the plurality of cells.

In some embodiments, the methods described herein can result in a significant portion of intact cells (e.g., that will end up in a solids portion). For example, methods described herein can result in at least about 20% (e.g., at least about 25%, at least about 30%, at least about 40%, at least about 50%, at least about 60%, at least about 70%, at least about 75%, or at least about 80%) by weight of the cells of the plurality of cells remaining intact. In some embodiments, the intact cells can have a particle size distribution median of about 2 μm to about 4 μm (e.g., 3 μm).

Following a step of separating the liquid portion from the solid portion, the liquid portion can be filtered (for example, in the generation of a protein composition, in the generation of cytosolic-protein enriched protein composition, or in the purification of a soluble protein) to form a filtrate and a retentate. A liquid portion can be filtered using microfiltration, ultrafiltration, and/or diafiltration. Microfiltration can use a membrane with a pore size of about 0.2 μm to about 2.0 μm (e.g., about 0.2 to about 0.3 μm, about 0.3 to about 0.5 μm, about 0.5 to about 0.7 μm, about 0.7 to about 0.9 μm, about 0.9 to about 1.1 μm, about 1.0 to about 1.2 μm, about 1.2 to about 1.4 μm, about 1.4 to about 1.6 μm, about 1.6 to about 1.8 μm, or about 1.8 to about 2.0 μm). Ultrafiltration can use a membrane with a molecular weight cutoff of about 5 kDa to about 70 kDa (e.g., about 5 kDa to about 10 kDa, about 10 kDa to about 30 kDa, or about 30 kDa to about 50 kDa, about 20 kDa to about 40 kDa, about 40 to about 60 kDa, or about 50 kDa to about 70 kDa). Ultrafiltration can use a membrane with a molecular weight cutoff of about 5 kDa to about 70 kDa (e.g., about 5 kDa to about 10 kDa, about 10 kDa to about 30 kDa, about 30 kDa to about 50 kDa, about 20 kDa to about 40 kDa, about 40 kDa to about 60 kDa, or about 50 kDa to about 70 kDa). In some embodiments, a liquid portion can be filtered by forcing the solution (e.g., using increased pressure or centrifugation) through a semi-permeable membrane having, for example, a molecular weight cutoff of about 5 kDa to about 50 kDa (e.g., about 5 kDa to about 10 kDa, about 10 kDa to about 30 kDa, or about 30 kDa to about 50 kDa). In some embodiments, a liquid portion can be diafiltered on a microfiltration membrane. In some embodiments, a liquid portion can be diafiltered on an ultrafiltration membrane. In some embodiments, a liquid portion can be concentrated to at least about 10% dry solids (e.g., at least about 15% or 20% dry solids) then diafiltered at constant volume for at least one diavolume (DV) (e.g., at least 2, 3, 4, 5, 6, 7, 8, 9, 10, 15, or 20 diavolumes). In some embodiments, a liquid portion can be diluted (e.g., using water or an aqueous solution of salts or buffers, while maintaining the pH between about pH 8.5 and 12.0) to about 5% dry solids (e.g., about 6%, 7%, 8% or 9% dry solids) then diafiltered at constant volume for at least one diavolume (e.g., at least 2, 3, 4, 5, 6, 7, 8, 9, 10, 15, or 20 diavolumes). In some embodiments, a liquid portion can be diluted (e.g., using water or an aqueous solution of salts or buffers, while maintaining the pH between about pH 8.5 and 12.0) to about 3% dry solids (e.g., about 2% or about 4% dry solids) then diafiltered to about 15% dry solids (e.g., about 13%, 14%, 16%, or 17% dry solids). During the filtration step or steps, in some embodiments, the pH is maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During the filtration step or steps, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.).

A retentate can be concentrated (e.g., through filtering methods as described for removing components smaller than the desired protein size such as ultrafiltration, optionally with diafiltration) to form a protein composition. During the concentration, the pH can be maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). A retentate can be concentrated to a protein content of about 2 mg/mL to about 250 mg/mL (e.g., 10 mg/mL to 225 mg/mL, 15 mg/mL to 200 mg/mL, 25 mg/mL to about 225 mg/mL, 50 mg/mL to 200 mg/mL, or 50 mg/mL to 150 mg/mL) in the protein concentration. Concentration can occur concurrently with a filtration step. Concentration can occur separately from a filtration step. During the concentration, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.).

In some embodiments, provided herein are methods for purifying proteins from a plurality of cells having cell walls. In some embodiments, provided is a method for purifying proteins from a plurality of cells having cell walls, the method including: a) perforating the cell walls of the plurality of cells, b) separating an aqueous suspension of the plurality of cells to form a solids portion and a liquid portion, c) filtering the liquid portion to form a filtrate and a retentate, d) concentrating the retentate to form a protein composition, and e) optionally pasteurizing the protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, provided is a method for purifying proteins from a plurality of cells, the method including: a) treating an aqueous suspension of the plurality of cells with a base until the pH of the aqueous suspension is about 8.5 to about 12.0, b) separating the aqueous suspension of the plurality of cells to form a solids portion and a liquid portion, c) filtering the liquid portion to form a filtrate and a retentate, d) concentrating the retentate to form a protein composition, and e) optionally pasteurizing the protein composition, wherein each of a)-d), independently, are performed at a pH of about 8.5 and about 12.0, and/or wherein the method results in the liquid portion including at least about 10% by weight of the cytoplasmic proteins of the plurality of cells. In some embodiments, provided is a method for purifying proteins from a plurality of cells having cell walls, the method including: a) treating an aqueous suspension of the plurality of cells with a base until the pH of the aqueous suspension is about 8.5 to about 12.0, b) perforating the cell walls of the plurality of cells, c) separating the aqueous suspension of the plurality of cells to form a solids portion and a liquid portion, d) filtering the liquid portion to form a filtrate and a retentate, e) concentrating the retentate to form a protein composition, and f) optionally pasteurizing the protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for purifying proteins from a plurality of cells having cell walls, the method including: a) perforating the cell walls of the plurality of cells, b) treating an aqueous suspension of the plurality of cells with a base until the pH of the aqueous suspension is about 8.5 to about 12.0, c) separating the aqueous suspension of the plurality of cells to form a solids portion and a liquid portion, d) filtering the liquid portion to form a filtrate and a retentate, e) concentrating the retentate to form a protein composition, and f) optionally pasteurizing the protein composition, wherein each of a)-e), independently, are performed at a pH of about 8.5 and about 12.0, and/or wherein the method results in the liquid portion including at least about 50% by weight of the cytoplasmic proteins of the plurality of cells.

In some embodiments, provided herein are methods for purifying a plurality of proteins from a plurality of cells. In some embodiments, provided is a method for purifying proteins from a plurality of cells, the method including: a) heating the plurality of cells to a temperature of about 50° C. to about 85° C., b) separating an aqueous suspension of the plurality of cells to form a solids portion and a liquid portion, c) filtering the liquid portion to form a filtrate and a retentate, d) concentrating the retentate to form a protein composition, and e) optionally pasteurizing the protein composition, wherein each of a)-d), independently, are performed at a pH of about 8.5 and about 12.0, and/or wherein the method results in the liquid portion including at least about 50% by weight of the cytoplasmic proteins of the plurality of cells.

In some embodiments, provided herein are methods for preparing a cytosolic protein-enriched protein composition from a plurality of cells having cell walls. In some embodiments, provided is a method for preparing a cytosolic protein-enriched protein composition from a plurality of cells having cell walls, the method including: a) perforating the cell walls of the plurality of cells, b) separating an aqueous suspension of the plurality of cells to form a solids portion and a liquid portion, c) filtering the liquid portion to form a filtrate and a retentate, d) concentrating the retentate to form a cytosolic protein-enriched protein composition, and e) optionally pasteurizing the cytosolic protein-enriched protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, provided is a method for preparing a cytosolic protein-enriched protein composition from a plurality of cells, the method including: a) treating an aqueous suspension of the plurality of cells with a base until the pH of the aqueous suspension is about 8.5 to about 12.0, b) separating the aqueous suspension of the plurality of cells to form a solids portion and a liquid portion, c) filtering the liquid portion to form a filtrate and a retentate, d) concentrating the retentate to form a cytosolic protein-enriched protein composition, and e) optionally pasteurizing the cytosolic protein-enriched protein composition, wherein each of a)-d), independently, are performed at a pH of about 8.5 and about 12.0, and/or wherein the method results in the liquid portion including at least about 10% by weight of the cytoplasmic proteins of the plurality of cells. In some embodiments, provided is a method for preparing a cytosolic protein-enriched protein composition from a plurality of cells having cell walls, the method including: a) treating an aqueous suspension of the plurality of cells with a base until the pH of the aqueous suspension is about 8.5 to about 12.0, b) perforating the cell walls of the plurality of cells, c) separating the aqueous suspension of the plurality of cells to form a solids portion and a liquid portion, d) filtering the liquid portion to form a filtrate and a retentate, e) concentrating the retentate to form a cytosolic protein-enriched protein composition, and f) optionally pasteurizing the cytosolic protein-enriched protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for preparing a cytosolic protein-enriched protein composition from a plurality of cells having cell walls, the method including: a) perforating the cell walls of the plurality of cells, b) treating an aqueous suspension of the plurality of cells with a base until the pH of the aqueous suspension is about 8.5 to about 12.0, c) separating the aqueous suspension of the plurality of cells to form a solids portion and a liquid portion, d) filtering the liquid portion to form a filtrate and a retentate, e) concentrating the retentate to form a cytosolic protein-enriched protein composition, and f) optionally pasteurizing the cytosolic protein-enriched protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for preparing a cytosolic protein-enriched protein composition from a plurality of cells, the method including: a) heating the plurality of cells to a temperature of about 50° C. to about 85° C., b) separating an aqueous suspension of the plurality of cells to form a solids portion and a liquid portion, c) filtering the liquid portion to form a filtrate and a retentate, d) concentrating the retentate to form a cytosolic protein-enriched protein composition, and e) optionally pasteurizing the cytosolic protein-enriched protein composition, wherein each of a)-d), independently, are performed at a pH of about 8.5 and about 12.0, and/or wherein the method results in the liquid portion including at least about 50% by weight of the cytoplasmic proteins of the plurality of cells.

In some embodiments, provided herein are methods for preparing a membrane-bound and/or subcellular compartment protein-enriched protein composition from a plurality of cells having cell walls. In some embodiments, provided is a method for preparing a membrane-bound and/or subcellular compartment protein-enriched protein composition from a plurality of cells having cell walls, the method including: a) perforating the cell walls of the plurality of cells, b) separating an aqueous suspension of the plurality of cells to form a solids portion and a liquid portion, c) extracting protein from the solids portion to form a membrane-bound and/or subcellular compartment protein-enriched protein composition, and d) optionally pasteurizing the membrane-bound and/or subcellular compartment protein-enriched protein composition, wherein each of a)-b), independently, are performed at a pH of about 8.5 and about 12.0, and/or wherein the method results in the liquid portion including at least about 50% by weight of the cytoplasmic proteins of the plurality of cells. In some embodiments, provided is a method for preparing a membrane-bound and/or subcellular compartment protein-enriched protein composition from a plurality of cells, the method including: a) treating an aqueous suspension of the plurality of cells with a base until the pH of the aqueous suspension is about 8.5 to about 12.0, b) separating the aqueous suspension of the plurality of cells to form a solids portion and a liquid portion, c) extracting protein from the solids portion to form a membrane-bound and/or subcellular compartment protein-enriched protein composition, and d) optionally pasteurizing the membrane-bound and/or subcellular compartment protein-enriched protein composition, wherein each of a)-b), independently, are performed at a pH of about 8.5 and about 12.0, and/or wherein the method results in the liquid portion including at least about 10% by weight of the cytoplasmic proteins of the plurality of cells. In some embodiments, provided is a method for preparing a membrane-bound and/or subcellular compartment protein-enriched protein composition from a plurality of cells having cell walls, the method including: a) treating an aqueous suspension of the plurality of cells with a base until the pH of the aqueous suspension is about 8.5 to about 12.0, b) perforating the cell walls of the plurality of cells, c) separating the aqueous suspension of the plurality of cells to form a solids portion and a liquid portion, d) extracting protein from the solids portion to form a membrane-bound and/or subcellular compartment protein-enriched protein composition, and e) optionally pasteurizing the membrane-bound and/or subcellular compartment protein-enriched protein composition, wherein each of a)-c), independently, are performed at a pH of about 8.5 and about 12.0, and/or wherein the method results in the liquid portion including at least about 50% by weight of the cytoplasmic proteins of the plurality of cells. In some embodiments, provided is a method for preparing a membrane-bound and/or subcellular compartment protein-enriched protein composition from a plurality of cells having cell walls, the method including: a) perforating the cell walls of the plurality of cells, b) treating an aqueous suspension of the plurality of cells with a base until the pH of the aqueous suspension is about 8.5 to about 12.0, c) separating the aqueous suspension of the plurality of cells to form a solids portion and a liquid portion, d) extracting protein from the solids portion to form a membrane-bound and/or subcellular compartment protein-enriched protein composition, and e) optionally pasteurizing the membrane-bound and/or subcellular compartment protein-enriched protein composition, wherein each of a)-c), independently, are performed at a pH of about 8.5 and about 12.0, and/or wherein the method results in the liquid portion including at least about 50% by weight of the cytoplasmic proteins of the plurality of cells. In some embodiments, provided is a method for preparing a membrane-bound and/or subcellular compartment protein-enriched protein composition from a plurality of cells, the method including: a) heating the plurality of cells to a temperature of about 50° C. to about 85° C., b) separating an aqueous suspension of the plurality of cells to form a solids portion and a liquid portion, d) extracting protein from the solids portion to form a membrane-bound and/or subcellular compartment protein-enriched protein composition, and e) optionally pasteurizing the membrane-bound and/or subcellular compartment protein-enriched protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, the extracting protein from the solids portion comprises mechanical lysis of the solids portion.

In some embodiments, provided herein are methods for purifying a soluble protein from a plurality of cells having cell walls. In some embodiments, provided is a method for purifying a soluble protein from a plurality of cells having cell walls, the method including: a) perforating the cell walls of the plurality of cells, b) separating an aqueous suspension of the plurality of cells to form a solids portion and a liquid portion, c) filtering the liquid portion to form a filtrate and a retentate, d) concentrating the retentate to form a protein composition including the soluble protein, and e) optionally pasteurizing the protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, provided is a method for purifying a soluble protein from a plurality of cells, the method including: a) treating an aqueous suspension of the plurality of cells expressing the soluble protein with a base until the pH of the aqueous suspension is about 8.5 to about 12.0, b) separating the aqueous suspension of the plurality of cells to form a solids portion and a liquid portion, c) filtering the liquid portion to form a filtrate and a retentate, d) concentrating the retentate to form a protein composition including the soluble protein, and e) optionally pasteurizing the protein composition, wherein each of a)-d), independently, are performed at a pH of about 8.5 and about 12.0, and/or wherein the method results in the liquid portion including at least about 10% by weight of the cytoplasmic proteins of the plurality of cells. In some embodiments, provided is a method for purifying a soluble protein from a plurality of cells having cell walls, the method including: a) treating an aqueous suspension of the plurality of cells expressing the soluble protein with a base until the pH of the aqueous suspension is about 8.5 to about 12.0, b) perforating the cell walls of the plurality of cells, c) separating the aqueous suspension of the plurality of cells to form a solids portion and a liquid portion, d) filtering the liquid portion to form a filtrate and a retentate, e) concentrating the retentate to form a protein composition including the soluble protein, and f) optionally pasteurizing the protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for purifying a soluble protein from a plurality of cells having cell walls, the method including: a) perforating the cell walls of the plurality of cells, b) treating an aqueous suspension of the plurality of cells with a base until the pH of the aqueous suspension is about 8.5 to about 12.0, c) separating the aqueous suspension of the plurality of cells to form a solids portion and a liquid portion, d) filtering the liquid portion to form a filtrate and a retentate, e) concentrating the retentate to form a protein composition including the soluble protein, and f) optionally pasteurizing the protein composition, wherein each of a)-e), independently, are performed at a pH of about 8.5 and about 12.0, and/or wherein the method results in the liquid portion including at least about 50% by weight of the cytoplasmic proteins of the plurality of cells. In some embodiments, provided is a method for purifying a soluble protein from a plurality of cells, the method including: a) heating the plurality of cells expressing the soluble protein to a temperature of about 50° C. to about 85° C., b) separating an aqueous suspension of the plurality of cells to form a solids portion and a liquid portion, c) filtering the liquid portion to form a filtrate and a retentate, d) concentrating the retentate to form a protein composition including the soluble protein, and e) optionally pasteurizing the protein composition, wherein each of a)-d), independently, are performed at a pH of about 8.5 and about 12.0, and/or wherein the method results in the liquid portion including at least about 50% by weight of the cytoplasmic proteins of the plurality of cells. In some embodiments, the soluble protein is a heme-containing protein. In some embodiments, the method comprises treating the plurality of cells with about 5 mM to about 500 mM reducing equivalents of includes reductant. In some embodiments, treatment with the reductant comprises treatment with about 20 mM to about 80 mM reducing equivalents of the reductant. In some embodiments, the reductant is selected from the group consisting of cysteine, glutathione, bisulfate, and a combination thereof. In some embodiments, the reductant is a food safe reductant. In some embodiments, the soluble protein has a melting point, and method further comprises, before a), heating the plurality of cells to a temperature of about 10° C. or about 5° C. below the melting point of the soluble protein. In some embodiments, the soluble protein has a melting point of at least about 50° C. (e.g., at least about 55° C., at least about 60° C. at least about 65° C., at least about 70° C., or at least about 75° C.). In some embodiments, the soluble protein is heterologous to the plurality of cells. In some embodiments, one or more components (e.g., membrane-bound protein, subcellular compartment protein, cell wall materials, lipids, nucleic acids) of the solids portion can be of interest. In some such embodiments, the component can be extracted from the solids portion, for example, by suspending the solids portion in water or aqueous buffer, then mechanically disrupting the solids portion. In some embodiments, these methods can be used to generate a membrane-bound and/or subcellular compartment-enriched (e.g., mitochondrial protein-enriched, nuclear protein-enriched, and/or endoplasmic reticulum protein-enriched) protein composition. During the extraction, the pH can be maintained at a pH between about 8.5 to about 12.0 (e.g., about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at 9.0, at 9.5, at 10.0, at 10.5, at 11.0, at 11.5, or at 12.0). During the extraction, in some embodiments, the temperature is maintained below about 12° C. (e.g., below about 10° C., below about 8° C., or below about 6° C.), or between about 4° C. and about 12° C. (e.g., between about 4° C. and about 10° C., about 4° C. and about 8° C., about 4° C. and about 6° C., about 6° C. and about 12° C., about 8° C. and about 12° C., or about 10° C. and about 12° C.). In some embodiments, any of the methods described herein can be used to purify a protein of interest. In some embodiments, the protein of interest is expressed abundantly in the plurality of cells. In some embodiments, the protein of interest is expressed recombinantly in the plurality of cells. In some embodiments, the protein of interest is heterologous to the plurality of cells. In some embodiments, the protein of interest is a soluble protein. In some embodiments, the protein of interest is a heme-containing protein (e.g., any of the heme-containing proteins described herein). A protein of interest can make up any suitable portion of a protein composition as described herein. For example, in some embodiments, a protein of interest can make up at least about 30% (e.g., at least about 40%, at least about 50%, at least about 60%, at least about 70%, at least about 80%, or at least 90%) by dry weight of the protein in the protein composition.

In some embodiments, the protein of interest is a cytosolic protein. In some such embodiments, the methods described herein can result in the enrichment of the protein of interest in the liquid portion. For example, it was surprisingly found that treatment of an aqueous suspension of a plurality of cells with alkaline exhaustion and upfront pasteurization resulted in a relative abundance of a target protein (LegH) of about 0.9 in the liquid portion and about 0.53 in the solids portion (see, e.g., FIG. 12C). In some embodiments, the methods described herein comprise heating the plurality of cells to a temperature of about 10° C. to about 5° C. below the melting point of the protein of interest. Without being bound by any particular theory, it is believed that such a heating step can result in the unfolding and/or aggregation of proteins with melting points below the melting point of the protein of interest, thus enriching the protein of interest in the liquid portion. In some embodiments, the methods described herein comprising heating the plurality of cells to about 60° C.

In some embodiments, the protein of interest is a subcellular compartment (e.g., mitochondrial, nuclear, and/or endoplasmic reticulum) protein. In some embodiments, the protein of interest is a membrane-bound protein. In some such embodiments, the methods described herein can result in the enrichment of the protein of interest in the solids portion.

A protein composition also can be pasteurized. For example, a protein composition can be pasteurized using heat treatment, high temperature short time pasteurization, pulsed electric field, high pressure pasteurization, UV irradiation, gamma irradiation, or microfiltration. In some embodiments, one or more antimicrobials (e.g., polylysine) can be added during or after pasteurization.

In some embodiments, a protein composition, whether pasteurized or not, can be dried, e.g., spray dried or freeze dried or the like under mild conditions to ensure that the protein is not denatured.

In some embodiments, steps in any of the methods described herein can be performed independently at a pH of 8.5 to 12. For example, a lysing step can be performed at a pH of about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at about 9.0, at about 9.5, at about 10.0, at about 10.5, at about 11.0, at about 11.5, or at about 12.0, while a clarifying and/or filtering steps can each be independently performed at a pH different from the pH of the lysing step, so long as the different pH of the clarifying and/or filtering steps is above 8.5. As another example, a clarifying step can be performed at a pH of about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at about 9.0, at about 9.5, at about 10.0, at about 10.5, at about 11.0, at about 11.5, or at about 12.0, while the lysing and/or filtering steps can each be independently performed at a pH different from the pH of the clarifying step, so long as the different pH of the lysing and/or filtering steps is above 8.5. As another example, a filtering step can be performed at a pH of about 8.5 to about 9.0, about 9.0 to about 10.0, about 9.0 to about 11.0, about 10.0 to about 11.0, about 11.0 to about 12.0, about 9.5 to about 10.5, about 9.5 to about 11.5, about 10.5 to about 11.5, at about 9.0, at about 9.5, at about 10.0, at about 10.5, at about 11.0, at about 11.5, or at about 12.0, while the lysing and/or clarifying steps can each be independently performed at a pH different from the pH of the filtering step, so long as the different pH of the lysing and/or clarifying steps is above 8.5.

Without being bound by any particular theory, carrying out steps as disclosed herein at a pH of about 8.5 to about 12.0 can have multiple benefits, for example: stabilization (e.g., thermal stabilization) of one or more target proteins (e.g., particularly if the isoelectric point of the protein is below pH 8.5); stabilization of redox-sensitive proteins; increase in membrane flux during filtration; promotion of solids separation; efficacy at or below 10° C., and use of food safe and widely available reagents.

Also provided herein is a protein composition produced by any of the methods described herein. Also provided herein is a use of a protein composition produced by any of the methods described herein in a food, a beverage, or a supplement. In some embodiments, a food can be a meat replica.

In some aspects, protein compositions are also provided herein.

In some embodiments, a protein composition provided herein (e.g., where one or more purification steps (e.g., two or more, three or more, or all of the purification steps) were carried out between about pH 8.5 and about 12.0), can comprise at least 35% (e.g. at least 40%, 50%, 55%, 60%, 65%, 70%, 75%, 80%, 85%, 90%, 95%, or 99%) on a dry weight basis of molecules larger than 500 Da (e.g., 1 kDa, 2 kDa, 3 kDa, 5 kDa, 10 kDa, 30 kDa, or 50 kDa). A person of ordinary skill in the art can determine the total amount of large molecules (e.g., molecules larger than 500 Da, 1 kDa, 2 kDa, 3 kDa, 5 kDa, 10 kDa, 30 kDa, or 50 kDa), or the amount of a particular large molecule in a sample, using any of a variety of known methods, e.g., liquid chromatography-mass spectrometry (LCMS). A person of ordinary skill in the art can determine the total amount of small molecules (e.g., molecules smaller than 30 kDa, 20 kDa, 10 kDa, 5 kDa, 3 kDa, 2 kDa, 1 kDa, or 500 Da), or the amount of a particular small molecule in a sample, using any of a variety of known methods, e.g., liquid chromatography-mass spectrometry (LCMS). In some embodiments, a reduction in small molecules (e.g., molecules smaller than 30 kDa, 20 kDa, 10 kDa, 5 kDa, 3 kDa, 1 kDa, or 500 Da) can occur concurrently with a filtration step, e.g., diafiltration.

It will be appreciated that the choice of filter (e.g., membrane material, pore size) and filtration method (e.g., microfiltration, ultrafiltration, or diafiltration) can affect or even dictate whether a desired component will be in the retentate or the filtrate of a given filtration step. For example, in some embodiments, if a large molecule is a desired component, ultrafiltration can be selected as the filtration method, and the desired component can be part of the retentate. In some embodiments, ultrafiltration can be combined with diafiltration.

In some embodiments, a protein composition provided herein (e.g., where one or more purification steps (e.g., two or more, three or more, or all of the purification steps) were carried out between about pH 8.5 and about 12.0), can have a reduced the amount of or none of one or more small molecules that can contribute buffering capacity compared to purified protein wherein the same purification step or steps were not carried out about pH 8.5 and about 12.0. Ingredient buffering capacity can contribute to pH drift, which can promote off-flavor development, as well as potentially impacting product assembly and formulation. For example, a protein composition can have a buffering capacity of less than about 3.0 mmol NaOH per gram dry solids (e.g., less than about 2.9, 2.8, 2.7, 2.6, 2.5, 2.4, 2.3, 2.2, 2.1, 2.0, 1.9, 1.8. 1.7, 1.6, 1.5, 1.4, 1.3, 1.2, 1.1, 1.0, 0.5, or 0.1 mmol NaOH per gram dry solids). In some embodiments, diafiltration (at, e.g., pH 9.3±0.3) can lower the buffering capacity (e.g., from about 3.6 mmol NaOH per gram dry solids) to less than about 3.0 mmol NaOH per gram dry solids (e.g., less than about 2.9, 2.8, 2.7, 2.6, 2.5, 2.4, 2.3, 2.2, 2.1, 2.0, 1.9, 1.8. 1.7, 1.6, 1.5, 1.4, 1.3, 1.2, 1.1, 1.0, 0.5, or 0.1 mmol NaOH per gram dry solids). The buffer capacity can be determined by pH titration of a 2% (w/v) suspension or solution, measuring the mmol of NaOH that would be required to adjust the suspension or solution from pH 3.0 to pH 12.0.

In some embodiments, a protein composition provided herein (e.g., where one or more purification steps (e.g., two or more, three or more, or all of the purification steps) were carried out between about pH 8.5 and about 12.0), can form a gel with a higher storage modulus compared to purified protein where the same purification step or steps were not carried out about pH 8.5 and about 12.0. For example, in some embodiments, a gel can be formed from a protein composition with a concentration of about 25 to about 250 mg/mL (e.g., about 25 to about 50 mg/mL, about 25 to about 100 mg/mL, about 25 to about 150 mg/mL, about 25 to about 200 mg/mL, about 50 to about 250 mg/mL, about 100 to about 250 mg/mL, about 150 to about 250 mg/mL, or about 200 to about 250 mg/mL) at a pH of about 7.0. In some embodiments, a gel formed from a protein composition provided herein (e.g., where one or more purification steps (e.g., two or more, three or more, or all of the purification steps) were carried out between about pH 8.5 and about 12.0) at a 10% (w/v) suspension can have storage modulus greater than a similar gel where the same purification step or steps were not carried out about pH 8.5 and about 12.0. In some embodiments, the storage modulus of a gel formed from a protein composition provided herein (e.g., where one or more purification steps (e.g., two or more, three or more, or all of the purification steps) were carried out between about pH 8.5 and about 12.0) at a 10% (w/v) suspension can have a storage modulus of at least about 100 Pa at about 95° C. In some embodiments, the storage modulus of a gel at about 95° C. formed from a protein composition where one or more purification steps (e.g., two or more, three or more, or all of the purification steps) were carried out between about pH 8.5 and about 12.0 at a 10% (w/v) suspension can have a storage modulus at least about 10-fold (e.g., 15-fold or 20-fold) greater than the storage modulus of a similar gel, where one or more purification steps (e.g., two or more, three or more, or all of the purification steps) were not carried out between about pH 8.5 and about 12.0. In some embodiments, the storage modulus of a pasteurized (e.g., at 65° C. for 30 seconds) gel at about 95° C. formed from a protein composition where one or more purification steps (e.g., two or more, three or more, or all of the purification steps) were carried out between about pH 8.5 and about 12.0 at a 10% (w/v) suspension can have a storage modulus at least about 2-fold (e.g., 3-fold, 4-fold, or 5-fold) greater than the storage modulus of a similar gel, where one or more purification steps (e.g., two or more, three or more, or all of the purification steps) were not carried out between about pH 8.5 and about 12.0.

In some embodiments, a protein composition provided herein (e.g., where one or more purification steps (e.g., two or more, three or more, or all of the purification steps) were carried out between about pH 8.5 and about 12.0), can be a low-flavor protein composition.

In some embodiments, a protein composition, where one or more purification steps (e.g., two or more, three or more, or all of the purification steps) were carried out between about pH 8.5 and about 12.0, can have less (e.g., a smaller absolute amount or a smaller concentration) (e.g., at least 5-fold less, at least 10-fold less, at least 20-fold less, or at least 50-fold less) esters, as compared to a similar method wherein each step was carried out at a pH of about 6.5.

In some embodiments, a protein composition, where one or more purification steps (e.g., two or more, three or more, or all of the purification steps) were carried out between about pH 8.5 and about 12.0, can have less (e.g., a smaller absolute amount or a smaller concentration) of one or more flavor compounds that can contribute to off-odors or off-flavors (e.g., cysteine; 1-hexanol; 2-butylfuran; 2-methyl-2-pentenal; 3-octanone; ethyl-acetate; 2-ethyl-furan; 2-pentyl-furan; pyrazine; 1-decanol; acetophenone; 1-nonanol; 2,5-dimethyl-pyrazine; dodecanal; benzeneacetaldehyde; nonanal; butyrolactone; octanal; 2-decanone; hexanal; 2-nonanone; benzaldehyde; heptanal; 2-octanone; furfural; 2-heptanone; pentanal; 3-methyl butanal; 3-methylbutanoic acid) than a protein composition obtained by purification method in which one or more purification steps (e.g., two or more, three or more, or all of the purification steps) were not carried out between about pH 8.5 and about 12.0. In some embodiments, a protein composition, where one or more purification steps (e.g., two or more, three or more, or all of the purification steps) were carried out between about pH 8.5 and about 12.0, can have a reduction of at least about 1.05-fold (e.g., at least about 2.0-fold, at least about 2.5-fold, at least about 3-fold, at least about 4-fold, at least about 5-fold, or at least about 10-fold) in one or more small molecules that can contribute to off-odors or off-flavors (e.g., cysteine; 1-hexanol; 2-butylfuran; 2-methyl-2-pentenal; 3-octanone; ethyl-acetate; 2-ethyl-furan; 2-pentyl-furan; pyrazine; 1-decanol; acetophenone; 1-nonanol; 2,5-dimethyl-pyrazine; dodecanal; benzeneacetaldehyde; nonanal; butyrolactone; octanal; 2-decanone; hexanal; 2-nonanone; benzaldehyde; heptanal; 2-octanone; furfural; 2-heptanone; pentanal; 3-methyl butanal; 3-methylbutanoic acid) compared to purified protein wherein the same purification step or steps were not carried out about pH 8.5 and 12.0. In some embodiments, a fold-reduction can be calculated by dividing the amount of a small molecule in a protein composition where one or more steps (e.g., two or more, three or more, or all of the purification steps) were not carried out between about pH 8.5 and about 12.0 by the amount of the same small molecule where the same purification step or steps were carried out between about pH 8.5 and about 12.0. A person of ordinary skill in the art can determine the amount of a particular small molecule in a sample, using, e.g., GCMS.

In some embodiments, a protein composition provided herein (e.g., where one or more purification steps (e.g., two or more, three or more, or all of the purification steps) were carried out between about pH 8.5 and about 12.0), includes one or more small molecules that contribute to off-odors or off-flavors (e.g., cysteine, 1-hexanol; 2-butylfuran; 2-methyl-2-pentenal; 3-octanone; ethyl-acetate; 2-ethyl-furan; 2-pentyl-furan; pyrazine; 1-decanol; acetophenone; 1-nonanol; 2,5-dimethyl-pyrazine; dodecanal; benzeneacetaldehyde; nonanal; butyrolactone; octanal; 2-decanone;

hexanal; 2-nonanone; benzaldehyde; heptanal; 2-octanone; furfural; 2-heptanone; pentanal; 3-methyl butanal; 3-methylbutanoic acid) in an amount below a level detectable by a panelist. A person of ordinary skill in the art can determine the amount of a particular small molecule in a sample, using, e.g., GCMS.

In some embodiments, a protein composition provided herein (e.g., where one or more purification steps (e.g., two or more, three or more, or all of the purification steps) were carried out between about pH 8.5 and about 12.0), has no detectable level of one or more small molecules that contribute to off-odors or off-flavors (e.g., cysteine, 1-hexanol; 2-butylfuran; 2-methyl-2-pentenal; 3-octanone; ethyl-acetate; 2-ethyl-furan; 2-pentyl-furan; pyrazine; 1-decanol; acetophenone; 1-nonanol; 2,5-dimethyl-pyrazine; dodecanal; benzeneacetaldehyde; nonanal; butyrolactone; octanal; 2-decanone; hexanal; 2-nonanone; benzaldehyde; heptanal; 2-octanone; furfural; 2-heptanone; pentanal; 3-methyl butanal; 3-methylbutanoic acid).

In some embodiments, at least about 50% (e.g., at least about 60%, 70%, 80%, or 90%) of polypeptides in a protein composition fall between about 10 kDa and about 200 kDa when measured by reducing and denaturing gel electrophoresis (e.g., SDS-PAGE) and densitometry after detection in a manner common to the art (e.g., Coomassie Brilliant Blue G-250, Coomassie Brilliant Blue R-250, or silver nitrate).

In some embodiments, one or more proteins in a protein composition as described herein is functional (as described above). Typically, a protein composition as described herein includes a plurality of functional proteins. A protein composition can have any appropriate additional properties. In some embodiments, the protein composition can stabilize an oil-in-water emulsion. In some embodiments, the protein composition can stabilize a water-in-oil emulsion. In some embodiments, the protein composition can stabilize an air-in-water emulsion (e.g., a foam).

In some embodiments, a protein composition can be used in a variety of food products, including, for example, protein supplements (e.g., protein powders), meal replacements, or baked goods, or to replace all or a portion of an animal protein (e.g., from cows, pigs, poultry, lamb, or fish) in a food product that mimics an animal derived food product (e.g., a cheese replica, an egg replica or meat replica such as a ground meat replica). Accordingly, also provided herein is a food, beverage, or supplement including any of the protein compositions described herein. In some embodiments, a food can be a meat replica.

Protein compositions as described herein can have any appropriate components.

In some embodiments, the protein content of a protein composition as described herein can include at least about 30% (e.g., at least about 40%, at least about 50%, at least about 60%, at least about 70%, at least about 80%, or at least about 90%) by dry weight of cytosolic protein.

In some embodiments, the protein content of a protein composition as described herein can include at least about 30% (e.g., at least about 40%, at least about 50%, at least about 60%, at least about 70%, at least about 80%, or at least about 90%) by dry weight of a combination of cytosolic protein and non-membrane-bound cell wall proteins.

In some embodiments, the protein content of a protein composition as described herein can include a protein of interest (e.g., any of the proteins of interest described herein). In some embodiments, a protein composition can include at least about 30% (e.g., at least about 40%, at least about 50%, at least about 60%, at least about 70%, at least about 80%, or at least about 90%) by dry weight of a protein of interest.

In some embodiments, a plurality of functional proteins can include at least 10 (e.g., at least 20, at least 30, at least 40, at least 50, at least 75, or at least 100) different functional proteins.

In some embodiments, a protein composition can include one or more proteins selected from the group consisting of AOX1 and AOX2.

In some embodiments, a protein composition can include one or more proteins, identified by GI number, selected from the group consisting of: 254568470, 254567507, 254570367, 254568544, 254573764, 254566601, 254566257, 254567798, 254570575, 254571387, 254571425, 254568572, 254571679, 254569858, 254573010, 254564691, 254571699, 254572585, 254566127, 254570667, 254572870, 254573696, 254565205, 254569186, 254572668, 254571899, 254569222, 254572359, 254573464, 254572163, 254570957, 254573014, 254570673, 254566987, 254567581, 254564747, 254568562, 254566731, 254565437, 254564519, 254571763, 254566729, 254569372, 254571423, 254565451, 254565973, 254573008, 254574310, 254564587, 254568946, 254569478, 254566861, 254565513, 254572906, 254572796, 254573092, 254567233, 254565959, 254570383, 254570885, 254565519, 254574530, 254573558, 254569654, 254573466, 254571991, 254568780, 254565859, 254568564, 254570088, 254564995, 254573142, 254571407, 254569976, 254570771, 254565455, 254565551, 254574244, 254567716, 254572952, 254568654, 254570661, 254566481, 254565045, 254567189, 254570098, 254566883, 254569212, 254574528, 254565655, 254568196, 254572782, 254570305, 254572856, 254568894, 254564809, 254569780, 254565263, 254567287, 254567754, 254565279, 254567471, 254564667, 254568442, 254571893, 254573996, 254572005, 254572033, 254567027, 254569734, 254566559, 254570993, 254566611, 254566089, 254567714, 254571057, 254573908, 254572676, 254570100, 254567055, 254565475, 254567834, 254567872, 254566327, 254574366, 254568036, 254567738, 254565307, 254570727, 254566301, 254565783, 254567173, 254568492, 254565493, 254571145, 254565699, 254567029, 254573198, 254568642, 254568302, 254574036, 254569716, 254571157, 254571485, 254567788, 254573482, 254566631, 254571293, 254569576, 254572962, 254565129, 254569094, 254570112, 254566447, 254570515, 254568944, 254573180, 254573098, 254570969, 254569500, 254564507, 254569714, 254570072, 254573324, 254568444, 254569156, 254568334, 254568304, 254566885, 254571359, 254574464, 254569852, 254569144, 254573818, 254573050, 254572992, 254571587, 254573470, 254565991, 254566975, 254570022, 254569102, 254574442, 254569298, 254572501, 254569162, 254565713, 254565211, 254572377, 254571575, 254574030, 254572872, 254565431, 254569400, 254572599, 254565725, 254569842, 254570271, 254573426, 254574502, 254569568, 254572822, 254568950, 254572257, 254569700, 254573726, 254574210, 254567569, 254569896, 254571915, 254568132, 254567191, 254566971, 254567243, 254566843, 254568386, 254571131, 254572628, 254567025, 254569344, 254571043, 254572958, 254569782, 254566517, 254566423, 254573664, 254566489, 254566607, 254569916, 254571179, 254565207, 254566497, 254566087, 254571791, 254569898, 254567938, 254566619, 254566141, 254568702, 254569082, 254569470, 254565589, 254572159, 254573164, 254573328, 254570166, 254570561, and 254574100. A GI number can be searched 254565545, 254570535, 254564705, 254570393, in in the PubMed protein database found at ncbi.nlm.nih-254566769, 254565063, 254567203, 254573714, .gov/protein, e.g., to retrieve the name and/or sequence of 254571903, 254571639, 254564825, 254569512, the corresponding protein.
254569682, 254574296, 254574080, 254564849,
254570719, 254568186, 254572093, 254573284, In some embodiments, a protein composition can include one or more proteins selected from a Pfam family selected
254571919, 254570821, 254565769, 254573468, from the group consisting of Pf00044, Pf02800, Pf02826,
254571883, 254570633, 254570315, 254570527, Pf00009, Pf03143, Pf03144, Pf00113, Pf03952, Pf00107,
254567583, 254573420, 254569866, 254569290, Pf08240, Pf00012, Pf06723, Pf00162, Pf00183, Pf02518,
254569438, 254574316, 254566267, 254570897, Pf00009, Pf00679, Pf03144, Pf03764, Pf00205, Pf02775,
254569696, 254566847, 254572974, 254569386, Pf02776, Pf00006, Pf00306, Pf02874, Pf01249, Pf00240,
254568682, 254565735, 254574242, 254568876, Pf01020, Pf11976, Pf00240, Pf01599, Pf11976, Pf00006,
254566225, 254566479, 254569106, 254566881, Pf00306, Pf02874, Pf00153, Pf00189, Pf07650, Pf00012,
254569226, 254565085, 254569736, 254572157, Pf06723, Pf01929, Pf00400, Pf00012, Pf06723, Pf00297,
254565157, 254573986, 254569320, 254570679, Pf01015, Pf01116, Pf00224, Pf02887, Pf03328, Pf00005,
254572211, 254566063, 254568616, 254564917, Pf03193, Pf00300, Pf00416, Pf01287, Pf01294, Pf00121,
254564915, 254568842, 254573376, 254566487, Pf00012, Pf06723, Pf01251, Pf00022, Pf00318, Pf00327,
254565875, 254568412, 254564663, 254565961, Pf00238, Pf00411, Pf01090, Pf00687, Pf00573, Pf00177,
254569890, 254566293, 254568216, 254572836, Pf00828, Pf01459, Pf00270, Pf00271, Pf00298, Pf03946,
254570523, 254568506, 254572347, 254567662, Pf01201, Pf00572, Pf00276, Pf00428, Pf00466, Pf00827,
254567720, 254574020, 254571733, 254571747, Pf00923, Pf01781, Pf01248, Pf00118, Pf00043, Pf00647,
254569894, 254571377, 254566013, 254569558, Pf00900, Pf01479, Pf08071, Pf00333, Pf03719, Pf01450,
254565617, 254566191, 254571955, 254565721, Pf07991, Pf01280, Pf01780, Pf00181, Pf03947, Pf03501,
254567996, 254566897, 254574140, 254571035, Pf00312, Pf08069, Pf00338, Pf00380, Pf00132, Pf00483,
254570359, 254566893, 254568298, 254566101, Pf12804, Pf00366, Pf00347, Pf00410, Pf00334, Pf00160,
254565989, 254568566, 254571457, 254571393, Pf01248, Pf00237, Pf00393, Pf03446, Pf00213, Pf00347,
254571161, 254564537, 254571649, 254570979, Pf00080, Pf01248, Pf01198, Pf00838, Pf01200, Pf00122,
254566595, 254566417, 254569072, 254570669, Pf00690, Pf00702, Pf08282, Pf12710, Pf00252, Pf00163,
254569122, 254567253, 254573448, 254571343, Pf01479, Pf00833, Pf01092, Pf01667, Pf00107, Pf08240,
254572333, 254566649, 254571369, 254573496, Pf01092, Pf01775, Pf01159, Pf01667, Pf01849, Pf00125,
254572133, 254573886, 254569410, 254570411, Pf02969, Pf00675, Pf05193, Pf00153, Pf00244, Pf00208,
254565705, 254573462, 254568908, 254572495, Pf02812, Pf01158, Pf00330, Pf00694, Pf00125, Pf00808,
254569552, 254566933, 254568102, 254569702, Pf02284, Pf00281, Pf00673, Pf00438, Pf02772, Pf02773,
254569846, 254574136, 254569390, 254567273, Pf00670, Pf02826, Pf05221, Pf00428, Pf00578, Pf08534,
254572371, 254569354, 254572053, 254568006, Pf10417, Pf01247, Pf02953, Pf09598, Pf04969, Pf01246,
254565653, 254570487, 254573510, 254564923, Pf00202, Pf01212, Pf00349, Pf03727, Pf01776, Pf03332,
254568606, 254572503, 254569166, 254572145, Pf08282, Pf00253, Pf00155, Pf00012, Pf06723, Pf01717,
254572531, 254568464, 254570723, 254570485, Pf08267, Pf00166, Pf00085, Pf00056, Pf02866, Pf00076,
254567349, 254565049, 254574132, 254564979, Pf00658, Pf00285, Pf00406, Pf05191, Pf00456, Pf02779,
254564629, 254572309, 254565163, 254573160, Pf02780, Pf00861, Pf00349, Pf03727, Pf00025, Pf00071,
254573452, 254565165, 254573834, 254574102, Pf01926, Pf04670, Pf08477, Pf05873, Pf00342, Pf00831,
254568996, 254573756, 254572015, 254568992, Pf00203, Pf01282, Pf00515, Pf07719, Pf01215, Pf01159,
254572535, 254566143, 254572321, 254568056, Pf05405, Pf00180, Pf02297, Pf00108, Pf00109, Pf02803,
254573266, 254566351, 254571007, 254571463, Pf01488, Pf03435, Pf05368, Pf02953, Pf00076, Pf00012,
254570629, 254573948, 254572884, 254567375, Pf06723, Pf00828, Pf00070, Pf01262, Pf02852, Pf07992,
254567467, 254567928, 254572307, 254567700, Pf12831, Pf00793, Pf11022, Pf00389, Pf00670, Pf02826,
254571783, 254573676, 254567900, 254568714, Pf05221, Pf00085, Pf02114, Pf01063, Pf01209, Pf02353,
254564921, 254564599, 254573602, 254573662, Pf08241, Pf08242, Pf08498, Pf12847, Pf03297, Pf00719,
254570521, 254572814, 254571619, 254566321, Pf00254, Pf00226, Pf00684, Pf01556, Pf00164, Pf00125,
254568896, 254566743, 254572553, 254565607, Pf00627, Pf01849, Pf00736, Pf01283, Pf01157, Pf00009,
254565035, 254565403, 254573760, 254566097, Pf03143, Pf03144, Pf05680, Pf00180, Pf04911, Pf00180,
254564603, 254572956, 254564565, 254572834, Pf01926, Pf06071, Pf00270, Pf00271, Pf00310, Pf00733,
254566317, 254564665, 254573056, 254568582, Pf00266, Pf01243, Pf10590, Pf00231, Pf00025, Pf00071,
254564717, 254572724, 254565955, 254568718, Pf00503, Pf01926, Pf04670, Pf08477, Pf09439, Pf01588,
254573174, 254566999, 254569742, 254573508, Pf01253, Pf00675, Pf02136, Pf00036, Pf00006, Pf00306,
254565095, 254569494, 254573046, 254568148, Pf02874, Pf00410, Pf01655, Pf00085, Pf01546, Pf00270,
254574028, 254569828, 254566605, 254569010, Pf00271, Pf04851, Pf00025, Pf00071, Pf00503, Pf01926,
254568244, 254564675, 254569952, 254574158, Pf08477, Pf09439, Pf00254, Pf00006, Pf00306, Pf02874,
254567143, 254566779, 254574118, 254573866, Pf04568, Pf00956, Pf00180, Pf00133, Pf01406, Pf08264,
254570090, 254569428, 254573178, 254574370, Pf09334, Pf00004, Pf00910, Pf01078, Pf02359, Pf02933,
254569876, 254571543, 254570799, 254569038, Pf05496, Pf05673, Pf06068, Pf07724, Pf07728, Pf00676,
254570373, 254567774, 254571247, 254574144, Pf12718, Pf01808, Pf02142, Pf02167, Pf11578, Pf00091,
254571313, 254570649, 254565795, 254572920, Pf03953, Pf01873, Pf02020, Pf00702, Pf01030, Pf00226,
254568600, 254571879, 254567231, 254567553, Pf00083, Pf07690, Pf00587, Pf02403, Pf02779, Pf02780, Pf01798, Pf08060, Pf08156, Pf00365, Pf00106, Pf01073, Pf01370, Pf07993, Pf08659, Pf00034, Pf00155, Pf01041, Pf01053, Pf00549, Pf01071, Pf08442, Pf00501, Pf11930, Pf03114, Pf10455, Pf01199, Pf00106, Pf00109, Pf01648, Pf02801, Pf00291, Pf00571, Pf01118, Pf02774, Pf08718, Pf01154, Pf08540, Pf00070, Pf07992, Pf00081, Pf02777, Pf00152, Pf01336, Pf01798, Pf08060, Pf08156, Pf10642, Pf00289, Pf00364, Pf00682, Pf02436, Pf02785, Pf02786, Pf07478, Pf00180, Pf09229, Pf01704, Pf00076, Pf00887, Pf00698, Pf01575, Pf03060, Pf08354, Pf05047, Pf00155, Pf01347, Pf00549, Pf02629, Pf00076, Pf08662, Pf00018, Pf00241, Pf07653, Pf00070, Pf01946, Pf07992, Pf01269, Pf00133, Pf08264, Pf09334, Pf00117, Pf00958, Pf02540, Pf03054, Pf06508, Pf07722, Pf02550, Pf00479, Pf02781, Pf00005, Pf03193, Pf12848, Pf00155, Pf00266, Pf01041, Pf01053, Pf01212, Pf02347, Pf03841, Pf00009, Pf03144, Pf09173, Pf00118, Pf01907, Pf00155, Pf00464, Pf04718, Pf00733, Pf00764, Pf03054, Pf06508, Pf10791, Pf00926, Pf04669, Pf01459, Pf00294, Pf01192, Pf04281, Pf00638, Pf01873, Pf01399, Pf00587, Pf02824, Pf03129, Pf07973, Pf01920, Pf00743, Pf07992, Pf00255, Pf00578, Pf08534, Pf03134, Pf02271, Pf00120, Pf03951, Pf00310, Pf01380, Pf09280, Pf01634, Pf08029, Pf09084, Pf00682, Pf00501, Pf00176, Pf00270, Pf00271, Pf00437, Pf00625, Pf00910, Pf05729, Pf00198, Pf00364, Pf02817, Pf00171, Pf00705, Pf02144, Pf02747, Pf01652, Pf00241, Pf00171, Pf03198, Pf07983, Pf03198, Pf07983, Pf04627, Pf01042, Pf00152, Pf01336, Pf00682, Pf08502, Pf01912, Pf00578, Pf08534, Pf10417, Pf00226, Pf01556, Pf01399, Pf09440, Pf00262, Pf00118, Pf00750, Pf03485, Pf05746, Pf00111, Pf00384, Pf09326, Pf10588, Pf01248, Pf00085, Pf00462, Pf00676, Pf02779, Pf00009, Pf00071, Pf02421, Pf08477, Pf05091, Pf00133, Pf08264, Pf09334, Pf10458, Pf01472, Pf01509, Pf08068, Pf00118, Pf01111, Pf00160, Pf00152, Pf01336, Pf00899, Pf02134, Pf09358, Pf10585, Pf00682, Pf04111, Pf00175, Pf00970, Pf08030, Pf03435, Pf00575, Pf07541, Pf00332, Pf01257, Pf00742, Pf03447, Pf01262, Pf05222, Pf00832, Pf12710, Pf01266, Pf01411, Pf02272, Pf07973, Pf00013, Pf01991, Pf06505, Pf00587, Pf03129, Pf01398, Pf11976, Pf09796, Pf00025, Pf00071, Pf04670, Pf08477, Pf01176, Pf00043, Pf00749, Pf03950, Pf02374, Pf06244, Pf02939, Pf00160, Pf00515, Pf07719, Pf00793, Pf00709, Pf00235, Pf02115, Pf00881, Pf11885, Pf02823, Pf00291, Pf10276, Pf00004, Pf00158, Pf06414, Pf07724, Pf07726, Pf07728, Pf01433, Pf00155, Pf00076, Pf00118, Pf01194, Pf00317, Pf02867, Pf03477, Pf03483, Pf03484, Pf00076, Pf12353, Pf02453, Pf05262, Pf00578, Pf08534, Pf01238, Pf01564, Pf01218, Pf00227, Pf10584, Pf00240, Pf00627, Pf11976, Pf00153, Pf00009, Pf00025, Pf00071, Pf04670, Pf08477, Pf09439, Pf00350, Pf01031, Pf02212, Pf00535, Pf00890, Pf02910, Pf00583, Pf00403, Pf12223, Pf02854, Pf12152, Pf00152, Pf00587, Pf01409, Pf00004, Pf01057, Pf01078, Pf06068, Pf07724, Pf07726, Pf07728, Pf00155, Pf00464, Pf01381, Pf08523, Pf12844, Pf00156, Pf00735, Pf01926, Pf03193, Pf00004, Pf01057, Pf01078, Pf05673, Pf06068, Pf07726, Pf07728, Pf00290, Pf00291, Pf01208, Pf01466, Pf03931, Pf08327, Pf09229, Pf00107, Pf08240, Pf03223, Pf12757, Pf09731, Pf00557, Pf01753, Pf02936, Pf01793, Pf00155, Pf00202, Pf00155, Pf00687, Pf00091, Pf03953, Pf08597, Pf00118, Pf00586, Pf01071, Pf02222, Pf02655, Pf02769, Pf02843, Pf02844, Pf08442, Pf00118, Pf00343, Pf03130, Pf00332, Pf00270, Pf00271, Pf00004, Pf05496, Pf06068, Pf06414, Pf01145, Pf00579, Pf00266, Pf01212, Pf01965, Pf00815, Pf01502, Pf01503, Pf00149, Pf00542, Pf00156, Pf03098, Pf00400, Pf03604, Pf00248, Pf00365, Pf04145, Pf00400, Pf00329, Pf01086, Pf00004, Pf00158, Pf02861, Pf07724, Pf07728, Pf10431, Pf00205, Pf02775, Pf02776, Pf00043, Pf02798, Pf01546, Pf00227, Pf10584, Pf00156, Pf00310, Pf00118, Pf01012, Pf01145, Pf00481, Pf00248, Pf00206, Pf01397, Pf01602, Pf08752, Pf00227, Pf10584, Pf00491, Pf00300, Pf05739, Pf00004, Pf03796, Pf06068, Pf00107, Pf08240, Pf00298, Pf03946, Pf01399, Pf04135, Pf00637, Pf03463, Pf03464, Pf03465, Pf02330, Pf08662, Pf01512, Pf10531, Pf10589, Pf10785, Pf12853, Pf00735, Pf03193, Pf04548, Pf00635, Pf00650, Pf03765, Pf02656, Pf04758, Pf00731, Pf02222, Pf02655, Pf07478, Pf00118, Pf00275, Pf00465, Pf01202, Pf01487, Pf01488, Pf01761, Pf08501, Pf07957, Pf04280, Pf01399, Pf08375, Pf05383, Pf00076, Pf05383, Pf00636, Pf01641, Pf03678, Pf00125, Pf00364, Pf02817, Pf00462, Pf00227, Pf10584, Pf00291, Pf00585, Pf01263, Pf01399, Pf05470, Pf00459, Pf01576, Pf05911, Pf12128, Pf12757, Pf01398, Pf00009, Pf01926, Pf03029, Pf08597, Pf11987, Pf00390, and Pf03949.

In some embodiments, a protein composition can include one or more proteins selected from the group consisting of Adh1, Adh2, Cit2, Eno1, Eno2, Fba1, Hxk1, Hxk2, Icl1, Pdb1, Pdc1, Pfk1, Pgi1, Pgk1, Pyc1, Tal1, Tdh2, Tdh3, Tpi1, Efb1, Eft1, Eft2, Prt1, Rpa0, Tif1,2, Yef3, Hsc82, Hsp60, Hsp82, Hsp104, Kar2, Ssa1, Ssa2, Ssb1, Ssb2, Ssc1, Sse1, Sti1, Ade1, Ade3, Ade5,7, Arg4, Gdh1, Gln1, His4, Ilv5, Lys9, Meth, Pro2, Ser1, Trp5, Act1, Adk1, Ald6, Atp2, Bmh1, Bmh2, Cdc19, Cdc48, Cdc60, Erg20, Gpp1, Gsp1, Ipp1, Lcb1, Mol1, Pab1, Pma1, Psa1, Rnr4, Sam1, Sam2, Sod1, Uba1, YKL056, YLR109, and YMR116.

In some embodiments, a protein composition can include one or more proteins selected from the group consisting of cspB, cspD, rp1L, rp1U, hag, rpsN, rp1D, and yweA.

In some embodiments, a protein composition can include one or more proteins selected from the group consisting of hup, ptsH, dpsA, tuf, gapB, rp1×, malE, and yhjA.

In some embodiments, a protein composition can include one or more proteins selected from the group consisting of uspA, tufa, yqiA, rp1E, 1pp, rp1Y, gatB, and rp1L.

In some embodiments, a protein composition can include one or more proteins, identified by SwissProt accession number, selected from the group consisting of P00575, P06958, P00577, P02996, P04475, P02349, P06139, P09373, P02990, P17547, P22257, P06959, P06977, P11665, P14178, P02997, P00957, P00350, P07813, P23843, P00956, P08324, P08839, P02995, P07650, P03815, P09831, P05055, P00882, P00961, P07118, P09743, P10413, P60422, P02934, P00391, P30148, P04079, P36683, P12283, P06711, P00477, P02351, P0A8N3, P08177, P39184, P02384, P02354, P00968, P06981, P0A6T1, P07395, P08200, P27302, P62593, P03002, P09097, P11604, P16659, P15639, P00824, P02359, P00574, P60438, P00962, P62399, P15254, P07015, P26427, P23721, P00959, P00864, P02352, P03003, P39171, P62707, P39170, P15046, P02392, P17242, P00452, P14926, P00561, P25739, P00490, P02356, P76116, P04805, P00822, P00509, P23304, P07651, P32132, P30136, P17169, P21889, P08398, P61175, P00955, P08202, P08936, P29132, P06996, P04790, P04825, P03948, P02418, P09156, P15288, P32176, P00448, P33136, P08328, P02390, P17963, P22783, P02925, P60723, P02408, P08859, P09169, P13029, P16174, P25716, P04384, P21202, P02999, P30850, P33602, P35340, P05082, P08837, P37797, P02410, P22259, P07459, P10408, P22523, P02358, P09376, P45523, P00353, P06612, P33195, P08312, P24182, P12758, P17579, P00579, P07460, P61889, P25715, P60624, P09625, P23861, P22992, P33633, P07012, P17288, P27430, P60240, P02413, P37689, P32168, P00951, P08330, P18391, P21155, P07016, P13519, P21170, P06998, P02369, P02928, P02361, P11454, P06982, P02420, P77241, P31120, P36546, Q46829, P00954, P39172, P02426, P31216, P45577, P60906, P06138, P19673, P09372, P21513, P10177, P09151, P00891, P60785, P76177, P36938, P61517, P28691, P11457, P02428, P02419, P02416, P46837, P33599, P37747, P00913, P02931, P09546, P06971, P11096, P09157, P00934, P23480, P00960, P77482, P21346, P77349, P02364, P25665, P33138, P02375, P11875, P37095, P39435, P27827, P00479, P27248, P21599, P30867, P02363, P0A8N5, P22106, P04425, P37901, P02411, P02409, P39174, P02432, P39173, P10377, P25532, P31554, P02378, P24249, P30859, P03020, P37191, P37759, P23839, P77645, P33998, P76268, P02930, P24199, P02342, P14177, P07672, P23847, P63020, P08374, P08204, P27298, P02366, P24991, P05380, P17315, P21167, P21165, P23869, P31224, P17114, P76558, P15877, P19935, P07176, P61714, P10378, P24237, P60651, P77395, P17117, P24167, P06715, P37744, P02421, P25553, P24171, P05053, P03026, P08957, P00393, P02430, P27290, P02370, P04287, P23851, P00963, P17577, P39179, P10344, P09832, P07638, P76344, P00946, P38469, P10344, P05838, P75780, P23844, P31979, P00886, P11285, P07912, P25520, P00907, P02422, P18197, P26616, P07671, P52697, P02341, P39311, P33221, P39168, P00837, P22767, P19675, P05793, P62620, P02373, P45390, P00582, P77146, P30958, P24233, P05640, P16921, P07006, P30017, P00496, P31223, P36541, P02372, P76372, P31550, P39182, P11668, P21499, P77718, P10444, P19245, P02371, P08178, P18843, P45578, P21888, P22786, P02367, P23893, P23882, P11648, P51001, P02379, P10121, P05020, P24231, P02427, P60757, P15002, P31663, P19494, P08193, P37051, P02424, P13036, P02429, P00274, P15640, P02414, P36997, P0A6A6, P07004, P02435, P32164, P77310, P27252, P13652, P52643, P02436, P15277, P77804, P31057, P30139, P11028, P80063, P21774, P08622, P04951, P02374, P15716, P03017, P37648, P00923, P04422, P11557, P16456, P07906, P09159, P15048, Q46856, P39377, P14374, P06128, P29464, P60716, P00453, P37192, P76492, P45464, P23887, P00495, P45803, P33363, P30849, P04036, P18274, P28635, P77774, P46853, P25521, P14175, P36658, P39287, P78258, P77348, P30746, P29209, P24186, P26650, P23865, P05459, P15040, P30125, P25528, P30856, P36996, P08186, P02901, P33398, P39831, P18400, P23836, P20752, P29015, P04693, P00859, P02339, P36979, P60560, P0A6T3, P23858, P05825, P09424, P00831, P39330, P15047, P76153, P23853, P04816, P33598, P02998, P27251, P25714, P21892, P37754, P37329, P28909, P37187, P21590, P28302, P09029, P02937, P55741, P25662, P15039, P23863, P27851, P00370, P23932, P02905, P07019, P76002, P75876, P37688, P03025, P78083, P52065, P39406, P77258, P30744, P61316, P77254, P24253, P39811, P07005, P11026, P40874, P36540, P00478, P02437, P75789, P36766, P03844, P37010, P26428, P37190, P24250, P77438, P06984, P27434, P37749, P10384, Q57261, P15770, P00501, P24247, P77734, P12996, P42641, Q47130, P60546, P06129, P24223, P75838, P43675, P28694, P75902, P09375, P76403, P76658, P25529, P25516, P15034, P09200, P10902, P06995, P00547, P29210, P00583, P06613, P0A6W9, P75802, P28904, P31803, P25661, P27511, P30126, P00470, P30177, P17952, P10443, P37665, P36671, P76351, P36950, P09028, P00832, P06999, P23331, P07862, P09170, P40120, P80449, P77486, P14189, P06992, P05054, P75864, P09158, P61949, P62768, P07024, P23929, P75844, P07913, P37666, P00373, P04982, P03842, P76536, P07014, P13035, P36559, P76055, P36539, P09030, P21504, P36767, P39169, P08756, P42617, P32661, P37765, P23827, P04381, P52054, P20082, P09147, P06988, P76367, P46143, P05797, P77150, P06983, P25397, P18133, P75790, P16244, P08956, P37634, P43329, P24229, P06968, P75743, P28242, P18783, P27291, P30138, P45467, P06975, P46885, P39199, P10440, P25745, P40681, P25437, P33648, P37760, P75805, P00894, P77695, P00510, P31222, P09830, P31059, P05826, P76258, P76569, P18198, P46880, P30977, P07001, P45391, P13024, P13009, P33635, P24176, P31142, P17112, P60752, Q93K97, P11458, P08331, P37620, Q46828, P13000, P26615, P33644, P02917, P33918, P25888, P19934, P77338, P13685, P28225, P09997, P40718, P27828, P23830, P08188, P03812, P52647, P37667, Q46918, P00482, P18401, P32052, P03841, P62623, P46889, P27190, P37026, P11666, P39164, P46130, P30860, P37188, P76576, P33921, P31221, P37687, P12281, P76506, P25894, P00893, P03843, P25663, P45571, P77552, P52635, P30137, P76494, P39099, P24201, P20083, P46132, P76034, P39315, P09323, P37163, P07011, P31465, P39321, P05194, P77225, P32691, P37902, P09371, P77484, P23486, P39290, P76008, P32165, P19677, P76270, P45396, P75950, P77247, P75915, P32175, P05828, Q59384, P27306, P05848, P45748, P31133, P39396, P06986, P05796, P10740, P33570, P46473, P28690, P32130, P17993, P39177, P31664, P23911, P43671, P30848, P21338, Q46920, P77392, P61320, P23003, P39202, P45533, P15042, P30010, P02943, P32126, P26282, P46186, P38521, P09053, P00642, P25907, P00562, P17580, P09152, P17994, P76277, P76504, P75947, P37096, P37066, P52049, P02914, Q46933, P22333, P29217, P07020, P15298, P03807, P37631, P33597, P37347, P08367, P07002, P28304, P52061, P39356, P37308, Q46871, P15302, P00363, P75914, Q46948, P22563, P37345, P11056, P05791, P33601, P28633, P08373, P42550, P17113, P77202, P31218, P37175, P32157, P29679, P24178, P29680, P75736, P22188, P45389, P76290, P55139, P21645, P17448, P55253, P37440, P36564, P24245, P76370, P36995, P45799, P33636, P32105, Q46837, P23909, P78067, P21169, P08390, P30748, P16680, P36680, P41407, P76110, P23930, P28692, P16095, P03018, P15977, P21829, P09148, P05021, P23483, P31658, P45847, P39286, P46860, P40191, P37350, 065938, P32680, P12008, P27303, P03817, P46930, P21507, P77499, P76550, P52083, P37346, P33016, P09551, P24251, P25519, P11721, P27292, P00928, P17445, P43672, P33650, P24218, P07604, P39335, P28637, P29745, 069415, P71295, P11603, P76272, P32099, P77455, P45426, P15484, P15028, P08323, P00550, P02918, P30870, P76503, P24183, P36672, P23874, P03818, P02978, P33349, P75783, P33916, Q46863, P27848, P23199, P25533, P36768, P19641, P76423, P18393, P27841, P03019, P45580, P08660, P61887, P39401, P23894, P23884, P33643, P19674, P00811, P08179, P40717, P07085, P18390, P75849, P33031, P37189, P39323, P22938, P10346, P37647, P23089, P76187, P24285, P75823, P37745, P76426, P28861, Q46872, P75958, P02924, P60340, Q47622, P32174, P03033, P32703, P43781, P75949, P15050, P37349, P76316, P25738, P11288, P24203, P10957, P76015, P08203, P37354, P27838, P17109, P34086, P76141, P31220, P27550, P51024, P46131, P28248, P31680, P37606, Q46893, Q46868, P08244, P16528, P20099, P39903, P07003, P77293, P45756, P24213, P21516, P37692, P75745, P32695, P37194, P27829, P76495, P45529, P52124, P75968, P00844, P11027, P52084, P33220, P33362, P77605, P22255, P00926, P26648, P30854, P33129, P32050, P15272, P06149, P32177, P75957, P11349, P77674, P32678, P76036, P30858, P12610, P23870, P36879, P37904, P39347, P18196, P17443, P36929, P31546, P26646, P03004, P31828, P05792, P30178, P33353, P29011, P30855, Q00191, P77561, P76496, P77252, P32721, P08338, P18775, P37330, P33940, P76422, P07676, Q46841, P45535, P30846, P06964, P23282, P39833, P33226, P76017, P52052, P45471, P03021, P23917, P11880, P60472, P36565, P77624, P07762, P28689, P06716, P22256, P45802, Q52280, P75913, P46474, P19635, P09391, P15038, P22997, Q57154, P08577, P75874, P76146, P24181, P22763, P27850, P77239, P37005, Q46814, P37626, P77562, P39835, P76256, P77500, P24205, P06712, P09454, P11257, P75793, P42908, P31475, P76014. A SwissProt accession number can be searched for in the UniProt protein database found at uniprot.org, e.g., to retrieve the name and/or sequence of the corresponding protein.

In some embodiments, a protein composition can include a heme-containing protein. In some embodiments, a protein composition can include one or more proteins selected from the group consisting of an androglobin, a cytoglobin, a globin E, a globin X, a globin Y, a hemoglobin, a leghemoglobin, a flavohemoglobin, Hell's gate globin I, a myoglobin, an erythrocruorin, a beta hemoglobin, an alpha hemoglobin, a protoglobin, a cyanoglobin, a cytoglobin, a histoglobin, a neuroglobins, a chlorocruorin, a truncated hemoglobin (e.g., HbN or HbO), a truncated 2/2 globin, a hemoglobin 3 (e.g., Glb3), a cytochrome, or a peroxidase.

In some embodiments, a protein composition can include carbohydrate polymers (e.g., beta-glucan, glycogen, xanthan, xylinan, gellan, curdlan, agarose, dextran, pullulan, teichoic acids, peptidoglycan (e.g., murein) or nucleic acid polymers (e.g., ribosomal RNA (rRNA), transfer RNA (tRNA), messenger RNA (mRNA), or genomic DNA), or other biopolymers.

In some embodiments, a protein composition can include a heterologously expressed protein. In some embodiments, a heterologously expressed protein may be from a species different from the host cell, for example from a eukaryote, an animal, a plant, an algae, a thermophile, a yeast, a bacteria, a protist or an archea. In some embodiments, a heterologously expressed protein can be any of the proteins described herein. In some embodiments, a heterologously expressed protein can be a heme-containing protein. In some embodiments, a heterologous protein has functional activity as a biocatalyst, as a food processing aid, an enzyme, as a flavor enhancer, a therapeutic, a sweetener, a pharmaceutical, a nutraceutical.

As described herein, maintaining a pH between 8.5 and 12.0 during a purification process can result in a protein composition having minimal off-flavors or off-odors such that the source of the protein (e.g., the microbe from which the protein was purified) is not readily identifiable. In some embodiments, such a protein composition provides minimal off-flavors or off-odors to a food product of which it is a part or to which it is added. In some embodiments, off-flavor and off-odor generation can be assessed using trained human panelists. The evaluations can involve eyeing, feeling, chewing, and/or tasting of the protein or a food product made with the protein, to judge appearance, color, integrity, texture, flavor, and mouth feel, etc. Panelists can be served samples under different colored lights (e.g., red or under white light). Samples can be assigned random three digit numbers and rotated in ballot position to prevent bias. Panelists can be asked to correctly pair two different sample replicate sets (e.g., A1, A2 vs. B1, B2) in a sample-blinded "tetrad" format. Panelists can be asked to correctly pair two different sample replicate sets (e.g., A1, A2, A3 vs. B1, B2, B3) in a sample-blinded "hexad" format. Sensory judgments can be scaled for "acceptance" or "likeability" or use special terminology. For example, letter scales (A for excellent, B for good, C for poor) or number scales can be used (1=dislike, 2=fair, 3=good; 4=very good; 5=excellent). A scale can be used to rate the overall acceptability or quality of the tested product or specific quality attributes such as beefiness, texture, and flavor. Panelists can be trained using specific sensory references (e.g., "toasted grain" against a commercially available cereal, or "fermented dairy" against a commercially available yogurt). Panelists can be given opportunity to comment on each sample and encouraged to rinse their mouths with water between samples.

In some embodiments, a protein composition described herein or a food product made with such proteins can be assessed based upon olfactometer readings. In various embodiments, the olfactometer can be used to assess odor concentration and odor thresholds, odor suprathresholds with comparison to a reference gas, hedonic scale scores to determine the degree of appreciation, or relative intensity of odors. In some embodiments, an olfactometer allows the training and automatic evaluation of expert panels.

In some embodiments, a protein composition can be used as a biocatalyst. For example, the substrate of an enzyme present in a protein composition can be added to the composition and, after incubation, the product of the enzymatic reaction can be isolated. In some embodiments, multiple substrates and cofactors may be added to support the production of one or more products of interest. In some embodiments, the products of the reaction can a pharmaceutical, a pharmaceutical intermediate, a flavor compound, a cofactor, a modified sugar, an amino acid, a monomer or any other compound of interest.

In some embodiments, a protein composition can be used for in vitro transcription and translation of proteins. In some embodiments, a protein composition can be used for in vitro translation of proteins. Addition of template DNA, energy system and amino acids can lead to production of the target protein (see for example recent reviews such as Mini-review: In vitro Metabolic Engineering for Biomanufacturing of High-value Products Computational and Structural Biotechnology Journal, 2017, Volume 15, 161-167). In some embodiments, a protein composition can be used to incorporate unnatural amino acids into proteins using in vitro translation.

In some embodiments, a protein composition (e.g., produced by a method described herein) can comprise total cellular protein. In some embodiments, a protein composition (e.g., produced by a method described herein) can comprise a plurality of proteins. For example, a protein composition can comprise 5 or more (e.g., 10, 15, 20, 30, 40, 50, 100, 200, 300, 400, or 500) different proteins. In some embodiments, at least 25% (e.g., at least 30%, 40%, 50%, 60%, 70%, 80%, or 90%) of the protein in a protein composition is functional, as described herein.

Food Products

Any of the protein compositions described herein can be used as or in one or more food products. Protein compositions as described herein can be used in a variety of food products, including, for example, protein supplements (e.g., protein powders or shakes), meal replacements, or baked goods, or to replace all or a portion of an animal protein (e.g., from cows, pigs, poultry, lamb, or fish) in a food product that mimics an animal derived food product (e.g., a dairy replica (e.g., a milk replica, a cheese replica), an egg replica (e.g., an albumen replica, an egg yolk replica, a whole egg replica, or a scrambled egg replica) or meat replica such as a beef replica, a chicken replica, a pork replica, a fish replica, a lamb replica, any of which can be in the form of a ground meat replica, a whole cut replica (e.g., a roast replica, steak replica, a breast replica, wing replica, a thigh replica, a filet replica, or a chop replica), an organ replica, or a sausage replica. In some embodiments, a protein composition can be used as a meat extender.

In some embodiments, a protein composition as described herein can have minimal off-flavors or off-odors such that the source of the protein (i.e., the microbe from which the protein was purified) is not readily identifiable and provide minimal off-flavors or off-odors to the food product. In some embodiments, off-flavor and off-odor generation can be assessed using trained human panelists. The evaluations can involve eyeing, feeling, chewing, and/or tasting of the protein or a food product made with the protein, to judge appearance, color, integrity, texture, flavor, and mouth feel, etc. Panelists can be served samples under different colored lights (e.g., red or under white light). Samples can be assigned random three digit numbers and rotated in ballot position to prevent bias. Sensory judgments can be scaled for "acceptance" or "likeability" or use special terminology. For example, letter scales (A for excellent, B for good, C for poor) or number scales can be used (1=dislike, 2=fair, 3=good; 4=very good; 5=excellent). A scale can be used to rate the overall acceptability or quality of the tested product or specific quality attributes such as beefiness, texture, and flavor. Panelists can be given opportunity to comment on each sample and encouraged to rinse their mouths with water between samples.

In some embodiments, a protein composition described herein or a food product made with such proteins can be assessed based upon olfactometer readings. In various embodiments, the olfactometer can be used to assess odor concentration and odor thresholds, odor suprathresholds with comparison to a reference gas, hedonic scale scores to determine the degree of appreciation, or relative intensity of odors. In some embodiments, an olfactometer allows the training and automatic evaluation of expert panels.

In some embodiments, a protein composition described herein can comprise least about 35% (e.g. at least about 40%, 50%, 55%, 60%, 65%, 70%, 75%, 80%, 85%, 90%, 95%, or 99%) by dry weight molecules larger than about 500 Da (e.g., about 1 kDa, 2 kDa, 3 kDa, 5 kDa, 10 kDa, 30 kDa, or 50 kDa). In some embodiments, a protein composition described herein can comprise least about 35% (e.g. at least 40%, 50%, 55%, 60%, 65%, 70%, 75%, 80%, 85%, 90%, 95%, or 99%) by dry weight molecules between about 500 Da (e.g., about 1 kDa, 2 kDa, 3 kDa, 5 kDa, 10 kDa, 30 kDa, or 50 kDa) and about 200 kDa (e.g., 300 kDa, 400 kDa, or 500 kDa). In some embodiments, at least about 35% (e.g. at least 40%, 50%, 55%, 60%, 65%, 70%, 75%, 80%, 85%, 90%, 95%, or 99%) of the polypeptides (also called proteins) in a protein composition described herein can fall between about 500 Da (e.g., about 1 kDa, 2 kDa, 3 kDa, 5 kDa, 10 kDa, 30 kDa, or 50 kDa) and about 200 kDa (e.g., 300 kDa, 400 kDa, or 500 kDa). In some embodiments, a protein composition described herein can exclude one or more small molecules that contribute to off-odors or off-flavors (e.g., a protein composition can comprise no cysteine, 1-hexanol; 2-butylfuran; 2-methyl-2-pentenal; 3-octanone; ethyl-acetate; 2-ethyl-furan; 2-pentyl-furan; pyrazine; 1-decanol; acetophenone; 1-nonanol; 2,5-dimethyl-pyrazine; dodecanal; benzeneacetaldehyde; nonanal; butyrolactone; octanal; 2-decanone; hexanal; 2-nonanone; benzaldehyde; heptanal; 2-octanone; furfural; 2-heptanone; pentanal; 3-methyl butanal; 3-methylbutanoic acid). A person of ordinary skill in the art can determine the total amount of small molecules or the amount of a particular small molecule in a sample, using, e.g., GCMS.

In some embodiments, a protein composition described herein can comprise a molecule that contribute to off-odors or off-flavors (e.g., cysteine, 1-hexanol; 2-butylfuran; 2-methyl-2-pentenal; 3-octanone; ethyl-acetate; 2-ethyl-furan; 2-pentyl-furan; pyrazine; 1-decanol; acetophenone; 1-nonanol; 2,5-dimethyl-pyrazine; dodecanal; benzeneacetaldehyde; nonanal; butyrolactone; octanal; 2-decanone; hexanal; 2-nonanone; benzaldehyde; heptanal; 2-octanone; furfural; 2-heptanone; pentanal; 3-methyl butanal; 3-methylbutanoic acid). A person of ordinary skill in the art can determine the amount of a particular small molecule in a sample, using, e.g., GCMS.

In some embodiments, a protein composition described herein can have a buffering capacity of less than about 3.0 mmol NaOH per gram dry solids (e.g., less than about 2.9, 2.8, 2.7, 2.6, 2.5, 2.4, 2.3, 2.2, 2.1, 2.0, 1.9, 1.8. 1.7, 1.6, 1.5, 1.4, 1.3, 1.2, 1.1, 1.0, 0.5, or 0.1 mmol NaOH per gram dry solids). The buffer capacity can be determined by pH titration of a 2% (w/v) suspension or solution, measuring the mmol of NaOH that would be required to adjust the suspension or solution from pH 3.0 to pH 12.0.

In some embodiments, a protein composition described herein can be in the form of a solution. In some embodiments, a protein composition can be in the form of a solid (e.g., a solution that has been freeze-dried or spray-dried). In some embodiments, a protein composition described herein can be pasteurized. For example, a protein composition can be pasteurized by heat treatment, high temperature short time pasteurization, pulsed electric field, high pressure pasteurization, UV irradiation, gamma irradiation, or microfiltration. In some embodiments, one or more antimicrobials (e.g., polylysine) can be included in a protein composition described herein.

In some embodiments, a protein composition described herein can be used as a biocatalyst. For example, the substrate of an enzyme present in a protein composition described herein can be added to the composition and after incubation the product of the enzymatic reaction can be isolated. In some embodiments, multiple substrates and cofactors may be added to support the production of one or more products of interest. In some embodiments, the products of the reaction can a pharmaceutical, a pharmaceutical intermediate, a flavor compound, a cofactor, a modified sugar, an amino acid, a monomer or any other compound of interest.

In some embodiments, a protein composition can be used for in vitro transcription and translation of proteins. In some embodiments, a protein composition can be used for in vitro translation of proteins. Addition of the template DNA, energy system and amino acids leads to production of the target protein (see for example recent reviews such as Mini-review: In vitro Metabolic Engineering for Biomanufacturing of High-value Products Computational and Structural Biotechnology Journal, 2017, Volume 15, 161-167). In some embodiments, a protein composition can be used to incorporate unnatural amino acids into proteins using in vitro translation.

Also provided herein are food products (sometimes also called "foods"), beverages, and/or supplements including any of the protein compositions described herein. Also provided herein are uses of any of the protein compositions provided herein in a food product, a beverage, or a supplement. Food products containing any of protein compositions described herein can be used as a base for formulating a variety of additional food products, including meat replicas, soup bases, stew bases, snack foods, bouillon powders, bouillon cubes, flavor packets, or frozen food products. Meat replicas (sometimes also called "meat substitutes") can be formulated, for example, as hot dogs, burgers, ground meat, sausages, steaks, filets, organs (such as liver, heart, tongue, kidney, sweetmeats, etc.) roasts, breasts, thighs, wings, meatballs, meatloaf, bacon, strips, fingers, nuggets, cutlets, or cubes.

Exemplary food products are described in U.S. Pat. Nos. 10,039,306, 9,700,067, and 9,011,949; U.S. Patent Application Publication Nos. US20150305361A1, US20170172169A1, US20150289541A1, and US20170188612A1, each of which is incorporated by reference in its entirety.

In some embodiments, a food product can be a protein supplement. For example, in some embodiments, a protein composition as disclosed herein can be part of a protein powder, which can be used in protein shakes, smoothies, baking, and the like.

In some embodiments, a food product can include a muscle replica. In some embodiments, a food product can be a meat substitute. In some embodiments, a food product can include an adipose replica. In some embodiments, a food product can include a muscle replica and an adipose replica. In some embodiments, a food product that includes a muscle replica and an adipose replica can also be called a meat replica.

In some embodiments, a food product can be a dairy replica. In some embodiments, a food product can be a cheese replica. In some embodiments, a food product can be a milk replica. In some embodiments, a milk replica can be used to make a cheese replica.

In some embodiments, a food product can be an egg replica. In some embodiments, a food product can be a whole egg replica (e.g., with a yolk replica partitioned from an albumen replica). In some embodiments, a food product can be an egg yolk replica. In some embodiments, a food product can be an albumen replica. In some embodiments, a food product can be a scrambled egg replica (e.g., a mixture of an egg yolk replica and an albumen replica).

A food product can include one or more proteins (e.g., a protein composition as described herein, a commercially available protein, a protein purified by any method known in the art, or a combination thereof). In some embodiments, a food product can include any of the protein compositions as described herein. In some embodiments, a food product can include any of the protein compositions as described herein in addition to a commercially available protein (e.g., soy protein concentrate, soy protein isolate, casein, whey, wheat gluten, pea vicilin, or pea legumin). In some embodiments, a food product can include any of the protein compositions as described herein, in addition to one or more proteins purified by any method known in the art.

One or more proteins (e.g., a protein composition as described herein, a commercially available protein, a protein purified by any method known in the art, or a combination thereof) can be present in an amount of about 0.1% to about 100% by weight (e.g., about 0.1% to about 1%, about 1% to about 5%, about 5% to about 10%, about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100% about 10% to about 30%, about 30% to about 50%, about 50% to about 70%, about 70% to about 90%, about 0.1% to about 20%, about 20% to about 40%, about 40% to about 60%, about 60% to about 80%, about 80% to about 100%, about 0.1% to about 33%, about 33% to about 66%, about 66% to about 100, about 0.1% to about 50%, or about 50% to about 100%) of a food product (e.g., a meat replica, a beef-like food product, a chicken-like food product, a pork-like food product, a fish-like food product, a beef food product, a chicken food product, a pork food product, or a fish food product).

Figure 8:
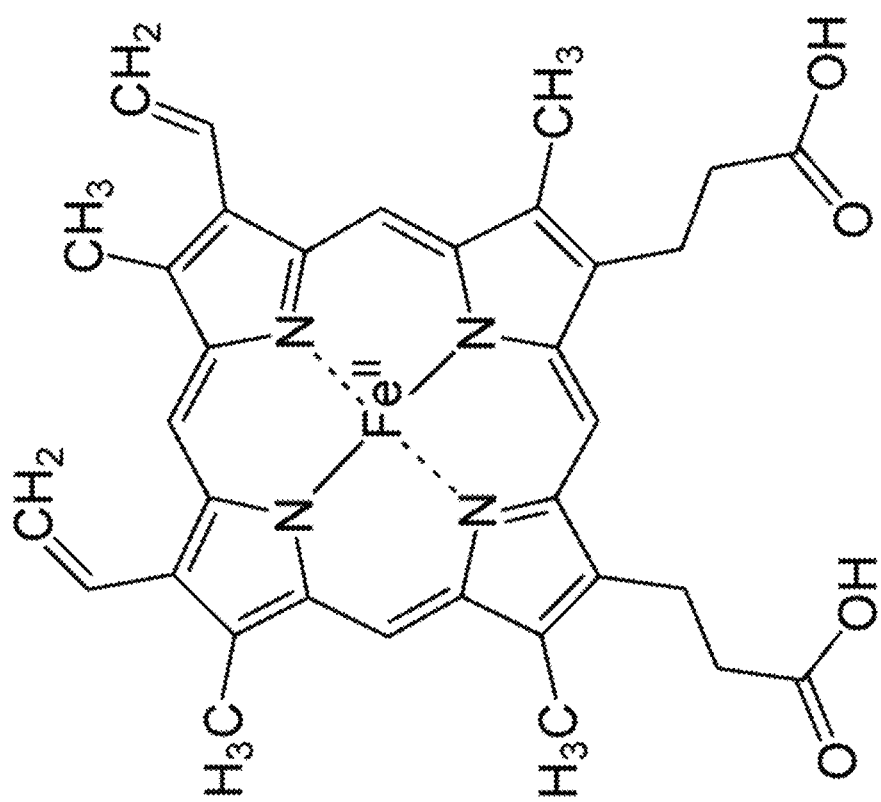
FIG. 8 is a structure of Heme B.

Any of the food products described herein can include an iron complex (e.g., ferrous chlorophyllin (e.g., CAS No. 69138-22-3), iron pheophorbide (e.g., CAS No. 15664-29-6), an iron salt (e.g. iron sulfate (e.g., any of CAS Nos. 7720-78-7, 17375-41-6, 7782-63-0, or 10028-22-5) iron gluconate (e.g., any of CAS Nos. 299-29-6, 22830-45-1, or 699014-53-4), iron citrate (e.g., any of CAS Nos. 3522-50-7, 2338-05-8, or 207399-12-0), ferric EDTA (e.g., CAS No. 17099-81-9) or a heme moiety such as a heme (e.g., heme A (e.g., CAS No. 18535-39-2), heme B (e.g. CAS No. 14875-96-8), heme C (e.g., CAS No. 26598-29-8), heme 0 (e.g., CAS No. 137397-56-9), heme I, heme M, heme D, heme S) or a heme-containing protein). For example, a structure of heme B is shown in FIG. 8.

In some embodiments, the heme moiety is a heme non-covalently or covalently bound to a protein or polypeptide as a heme-containing protein. In some embodiments, the protein or polypeptide is a globin. In some embodiments, the globin is selected from the group consisting of an androglobin, a cytoglobin, a globin E, a globin X, a globin Y, a hemoglobin, a myoglobin, a leghemoglobin, an erythrocruorin, a beta hemoglobin, an alpha hemoglobin, a protoglobin, a cyanoglobin, a cytoglobin, a histoglobin, a neuroglobins, a chlorocruorin, a truncated hemoglobin, a truncated 2/µglobin, and a hemoglobin 3. In some embodiments, the protein or polypeptide is a non-animal protein or polypeptide. In some embodiments, the protein or polypeptide is a plant, fungal, algal, archaeal, or bacterial protein. In some embodiments, the protein or polypeptide is not natively expressed in plant, fungal, algal, archaeal, or bacterial cells. In some embodiments, the protein or polypeptide comprises an amino acid sequence having at least 50% sequence identity (e.g., at least 60%, 70%, 80%, 90%, or 95% sequence identity) to a polypeptide set forth in SEQ ID NOs. 1-27.

Heme-containing proteins that can be used in any of the food products described herein can be from mammals (e.g., farms animals such as cows, goats, sheep, pigs, ox, or rabbits), birds, plants, algae, fungi (e.g., yeast or filamentous fungi), ciliates, or bacteria. For example, a heme-containing protein can be from a mammal such as a farm animal (e.g., a cow, goat, sheep, pig, ox, or rabbit) or a bird such as a turkey or chicken. Heme-containing proteins can be from a plant such as *Nicotiana tabacum* or *Nicotiana sylvestris* (tobacco); *Zea mays* (corn), *Arabidopsis thaliana*, a legume such as *Glycine max* (soybean), *Cicer arietinum* (garbanzo or chick pea), *Pisum sativum* (pea) varieties such as garden peas or sugar snap peas, *Phaseolus vulgaris* varieties of common beans such as green beans, black beans, navy beans, northern beans, or pinto beans, *Vigna unguiculata* varieties (cow peas), *Vigna radiata* (Mung beans), *Lupinus albus* (lupin), or *Medicago sativa* (alfalfa); *Brassica napus* (canola); *Triticum* sps. (wheat, including wheat berries, and spelt); *Gossypium hirsutum* (cotton); *Oryza sativa* (rice); *Zizania* sps. (wild rice); *Helianthus annuus* (sunflower); *Beta vulgaris* (sugarbeet); *Pennisetum glaucum* (pearl millet); *Chenopodium* sp. (quinoa); *Sesamum* sp. (sesame); *Linum usitatissimum* (flax); or *Hordeum vulgare* (barley). Heme-containing proteins can be isolated from fungi such as *Saccharomyces cerevisiae, Pichia pastoris, Magnaporthe oryzae, Fusarium graminearum, Aspergillus oryzae, Trichoderma reesei, Myceliopthera thermophile, Kluyvera lactis,* or *Fusarium oxysporum*. Heme-containing proteins can be isolated from bacteria such as *Escherichia coli, Bacillus subtilis, Bacillus licheniformis, Bacillus megaterium, Synechocistis* sp., *Aquifex aeolicus, Methylacidiphilum infernorum,* or thermophilic bacteria such as *Thermophilus*. The sequences and structure of numerous heme-containing proteins are known. See for example, Reedy, et al., Nucleic Acids Research, 2008, Vol. 36, Database issue D307-D313 and the Heme Protein Database available on the world wide web at hemeprotein.info/heme.php.

For example, a non-symbiotic hemoglobin can be from a plant selected from the group consisting of soybean, sprouted soybean, alfalfa, golden flax, black bean, black eyed pea, northern, garbanzo, moong bean, cowpeas, pinto beans, pod peas, quinoa, sesame, sunflower, wheat berries, spelt, barley, wild rice, or rice.

Any of the heme-containing proteins described herein that can be used for producing food products can have at least 70% (e.g., at least 75%, 80%, 85%, 90%, 95%, 97%, 98%, 99%, or 100%) sequence identity to the amino acid sequence of the corresponding wild-type heme-containing protein or fragments thereof that contain a heme-binding motif. For example, a heme-containing protein can have at least 70% sequence identity to an amino acid sequence, including a non-symbiotic hemoglobin such as that from *Vigna radiata* (SEQ ID NO:1), *Hordeum vulgare* (SEQ ID NO:5), *Zea mays* (SEQ ID NO:13), *Oryza sativa* subsp. *japonica* (rice) (SEQ ID NO:14), or *Arabidopsis thaliana* (SEQ ID NO:15), a Hell's gate globin I such as that from *Methylacidiphilum infernorum* (SEQ ID NO:2), a flavohemoprotein such as that from *Aquifex aeolicus* (SEQ ID NO:3), a leghemoglobin such as that from *Glycine max* (SEQ ID NO:4), *Pisum sativum* (SEQ ID NO:16), or *Vigna unguiculata* (SEQ ID NO:17), a heme-dependent peroxidase such as from *Magnaporthe oryzae,* (SEQ ID NO:6) or *Fusarium oxysporum* (SEQ ID NO:7), a cytochrome c peroxidase from *Fusarium graminearum* (SEQ ID NO:8), a truncated hemoglobin from *Chlamydomonas moewusii* (SEQ ID NO:9), *Tetrahymena pyriformis* (SEQ ID NO:10, group I truncated), *Paramecium caudatum* (SEQ ID NO:11, group I truncated), a hemoglobin from *Aspergillus niger* (SEQ ID NO:12), or a mammalian myoglobin protein such as the *Bos taurus* (SEQ ID NO:18) myoglobin, *Sus scrofa* (SEQ ID NO:19) myoglobin, *Equus caballus* (SEQ ID NO:20) myoglobin, a heme-protein from *Nicotiana benthamiana* (SEQ ID NO:21), *Bacillus subtilis* (SEQ ID NO:22), *Corynebacterium glutamicum* (SEQ ID NO:23), *Synechocystis* PCC6803 (SEQ ID NO:24), *Synechococcus* sp. PCC 7335 (SEQ ID NO:25), *Nostoc commune* (SEQ ID NO:26), or *Bacillus megaterium* (SEQ ID NO: 27).

The percent identity between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., fr.com/blast/) or the U.S. government's National Center for Biotechnology Information web site (ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length polypeptide amino acid sequence followed by multiplying the resulting value by 100. It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

In some embodiments, heme-containing proteins can be extracted from a production organism (e.g., extracted from animal tissue, or plant, fungal, algal, or bacterial biomass, or from the culture supernatant for secreted proteins) or from a combination of production organisms (e.g., multiple plant species). Leghemoglobin is readily available as an unused by-product of commodity legume crops (e.g., soybean, alfalfa, or pea). The amount of leghemoglobin in the roots of these crops in the United States exceeds the myoglobin content of all the red meat consumed in the United States.

In some embodiments, extracts of heme-containing proteins include one or more non-heme-containing proteins from the source material (e.g., other animal, plant, fungal, algal, or bacterial proteins) or from a combination of source materials (e.g., different animal, plant, fungi, algae, or bacteria). For example, a heme-containing protein can be part of a protein composition as described herein.

In some embodiments, heme-containing proteins can be provided in a food product in a form that is not part of a protein composition as described herein. In some embodiments, heme-containing proteins can be purified by any method known in the art.

Proteins can be separated on the basis of their molecular weight, for example, by size exclusion chromatography, ultrafiltration through membranes, or density centrifugation. In some embodiments, the proteins can be separated based on their surface charge, for example, by isoelectric precipitation, anion exchange chromatography, or cation exchange chromatography. Proteins also can be separated on the basis of their solubility, for example, by ammonium sulfate precipitation, isoelectric precipitation, surfactants, detergents or solvent extraction. Proteins also can be separated by their affinity to another molecule, using, for example, hydrophobic interaction chromatography, reactive dyes, or hydroxyapatite. Affinity chromatography also can include using antibodies having specific binding affinity for the protein (e.g., the heme-containing protein), nickel NTA for His-tagged recombinant proteins, lectins to bind to sugar moieties on a glycoprotein, or other molecules which specifically binds the protein.

Heme-containing proteins also can be recombinantly produced using polypeptide expression techniques (e.g., heterologous expression techniques using bacterial cells, insect cells, fungal cells such as yeast, plant cells such as tobacco, soybean, or *Arabidopsis*, or mammalian cells). In some cases, standard polypeptide synthesis techniques (e.g., liquid-phase polypeptide synthesis techniques or solid-phase polypeptide synthesis techniques) can be used to produce heme-containing proteins synthetically. In some cases, in vitro transcription-translation techniques can be used to produce heme-containing proteins.

In some embodiments, a heme-containing protein is part of a total cellular protein composition as described herein.

A heme-containing protein can be present in a food product (e.g., a dairy replica, a cheese replica, an egg replica, a meat replica, a beef-like food product, a chicken-like food product, a pork-like food product, a fish-like food product, a beef food product, a chicken food product, a pork food product, or a fish food product) in an amount of about 0.005% to about 5% (wt heme-containing protein/wt food product) (e.g., about 0.005% to about 0.01%, about 0.01% to about 0.1%, about 0.1% to about 0.5%, about 0.5% to about 1%, about 1% to about 2%, about 2% to about 3%, about 3% to about 4%, about 4% to about 5%, about 1% to about 3%, about 3% to about 5%, or about 1% to about 5% (wt/wt)). In some embodiments, a heme-containing protein can be a non-animal heme-containing protein. In some embodiments, a heme-containing protein can be an algal, bacterial, fungal, plant, or Archaeal heme-containing protein.

A heme can be present in a food product (e.g., a dairy replica, a cheese replica, an egg replica, a meat replica, a beef-like food product, a chicken-like food product, a pork-like food product, a fish-like food product, a beef food product, a chicken food product, a pork food product, or a fish food product) in an amount of about 0.00005% to about 2% (wt heme/wt food product) (e.g., about 0.00005% to about 0.0001%, about 0.0001% to about 0.0005%, about 0.0005% to about 0.001%, about 0.001% to about 0.005%, about 0.005% to about 0.01%, about 0.01% to about 0.05%, about 0.05% to about 0.1%, about 0.1% to about 0.5%, about 0.5% to about 1%, about 0.1% to about 0.2%, about 0.2% to about 0.4%, about 0.4% to about 0.6%, about 0.6% to about 0.8%, about 0.8% to about 1%, about 1% to about 2%, about 1.0% to about 1.2%, about 1.2% to about 1.4%, about 1.4% to about 1.6%, about 1.6% to about 1.8%, or about 1.8% to about 2.0% (wt/wt)).

Food products described herein can be free of or substantially free of some types of animal products (e.g., animal heme-containing proteins, or all animal products).

In some embodiments, a food product can be substantially soy-free, substantially wheat-free, substantially yeast-free, substantially MSG-free, substantially free of protein hydrolysis products, soy-free, wheat-free, yeast-free, MSG-free, and/or free of protein hydrolysis products, and can taste meaty, highly savory, and without off odors or flavors.

In some embodiments, a food product can include one or more flavor precursors. Suitable flavor precursors include sugars, sugar alcohols, sugar derivatives, oils (e.g., vegetable oils), free fatty acids, alpha-hydroxy acids, dicarboxylic acids, amino acids and derivatives thereof, nucleosides, nucleotides, vitamins, peptides, protein hydrolysates, extracts, phospholipids, lecithin, and organic molecules. Non-limiting examples of such flavor precursors are provided in Table 1.

TABLE 1

| Flavor Precursor Molecules |
|---|
| Sugars, sugar alcohols, sugar acids, and sugar derivatives: glucose, fructose, ribose, sucrose, arabinose, glucose-6-phosphate, fructose-6-phosphate, fructose 1,6-diphosphate, inositol, maltose, molasses, maltodextrin, glycogen, galactose, lactose, ribitol, gluconic acid, glucuronic acid, amylose, amylopectin, glycerol and/or xylose |
| Oils: coconut oil, mango oil, sunflower oil, cottonseed oil, safflower oil, rice bran oil, cocoa butter, palm fruit oil, palm oil, soybean oil, canola oil, corn oil, sesame oil, walnut oil, flaxseed, jojoba oil, castor, grapeseed oil, peanut oil, olive oil, algal oil, and/or oil from bacteria or fungi |
| Free fatty acids: caprylic acid, capric acid, lauric acid, myristic acid, palmitic acid, palmitoleic acid, stearic, oleic acid, linoleic acid, alpha linolenic acid, gamma linolenic acid, arachidic acid, arachidonic acid, behenic acid, and/or erucic acid |
| Amino acids and derivatives thereof: cysteine, cystine, a cysteine sulfoxide, allicin, selenocysteine, methionine, ergothioneine, isoleucine, leucine, lysine, phenylalanine, threonine, tryptophan, 5-hydroxytryptophan, valine, arginine, histidine, alanine, asparagine, aspartate, glutamate, glutamine, glycine, proline, serine, and/or tyrosine |
| Nucleosides and Nucleotides: inosine, inosine monophosphate (IMP), guanosine, guanosine monophosphate (GMP), adenosine, and/or adenosine monophosphate (AMP) |

TABLE 1-continued

Flavor Precursor Molecules

Vitamins: thiamine, vitamin C, Vitamin D, Vitamin B6, and/or Vitamin E
Misc: phospholipid, lecithin, pyrazine, creatine, carnitine, and/or pyrophosphate
Acids: acetic acid, alpha hydroxy acids such as lactic acid or glycolic acid, tricarboxylic acids such as citric acid, dicarboxylic acids such as succinic acid and/or tartaric acid
Peptides and protein hydrolysates: glutathione, carnosine, anserine, vegetable protein hydrolysates, soy protein hydrolysates, yeast protein hydrolysates, algal protein hydrolysates, and/or meat protein hydrolysates
Extracts: a malt extract, a yeast extract, and/or a peptone

---

Food products described herein can be packaged in various ways, including being sealed within individual packets or shakers, such that the composition can be sprinkled or spread on top of a food product before or during cooking.

Food products described herein can include additional ingredients including food-grade oils such as canola, corn, sunflower, soybean, olive or coconut oil, seasoning agents such as edible salts (e.g., sodium or potassium chloride) or herbs (e.g., rosemary, thyme, basil, sage, or mint), flavoring agents, proteins (e.g., soy protein isolate, wheat glutin, pea vicilin, and/or pea legumin), protein concentrates (e.g., soy protein concentrate), emulsifiers (e.g., lecithin), gelling agents (e.g., k-carrageenan or gelatin), fibers (e.g., bamboo filer or inulin), or minerals (e.g., iodine, zinc, and/or calcium).

Food products described herein also can include a natural coloring agent such as turmeric or beet juice, or an artificial coloring agent such as azo dyes, triphenylmethanes, xanthenes, quinines, indigoids, titanium dioxide, red #3, red #40, blue #1, or yellow #5.

Food products described herein also can include meat shelf life extenders such as carbon monoxide, nitrites, sodium metabisulfite, Bombal, vitamin E, rosemary extract, green tea extract, catechins and other anti-oxidants.

In some embodiments, a food product including a heme, a flavor precursor, or a combination thereof, when cooked, can result in the increased production of one or more (e.g., 2, 3, 4, 5, 6, 7, 8, 9, 10, or more) volatile compounds associated with a meat-like aroma. Non-limiting examples of volatile compounds associated with a meat-like aroma are presented in the attached Appendix 1, each of which has been associated with meat aroma, such as the aroma of beef, chicken, or pork, as supported by the listed references. In some embodiments, cooking any of the food products as described herein can result in increased production of one or more (e.g., 2, 3, 4, 5, 6, 7, 8, 9, 10, 12, 14, 16, 18, 20 or more) volatile compounds selected from the group consisting of (E)-2-decenal, (E)-2-heptenal, (E)-2-nonenal, (E)-2-octen-1-ol, (E)-2-octenal, (E)-3-penten-2-one, (E,E)-2,4-hexadienal, 1-(2-furanyl)-ethanone, 1-(acetyloxy)-2-propanone, 1-heptanol, 1-hexanol, 1-octanol, 1-penten-3-one, 1-undecanol, 2,3-dimethyl-pyrazine, 2,3-hexanedione, 2,4-dimethyl-thiazole, 2,5-dimethyl-pyrazine, 2,6-dimethylpyrazine, 2-acetyl-1-pyrroline, 2-acetylthiazole, 2-butanol, 2-butanone, 2-butenal, 2-heptanone, 2-hydroxy-benzaldehyde, 2-methyl-2(E)-butenal, 2-methyl-3-furanthiol, 2-methyl-butanal, 2-methyl-propanal, 2-methyl-thiazole, 2-n-butyl furan, 2-pentyl-furan, 2-propenal, 2-undecanone, 3-ethyl-pyridine, 3-methyl-2-butenal, 3-methyl-3-buten-2-one, 3-methyl-butanal, 3-methyl-hexane, 3-methyl-thiophene, 4-pentenal, 5-methyl-2-thiophenecarboxaldehyde, 6-methyl-5-hepten-2-one, acetaldehyde, acetone, acetophenone, benzaldehyde, benzeneacetaldehyde, bis(2-methyl-3-furyl)disulfide, dimethyl disulfide, dimethyl trisulfide, dodecanal, E-2-undecenal, ethyl-pyrazine, furan, furfural, heptanal, hexanal, methional, methyl-thiirane, propyl mercaptan, pyrazine, pyridine, tetradecane, tetrahydro-2H-pyran-2-one, and trimethyl-pyrazine.

Food products described herein can include a lipid (also called a fat) component. Lipids can be isolated and/or purified and can be in the form of triglycerides, monoglycerides, diglycerides, free fatty acids, sphingosides, glycolipids, phospholipids, or oils, or assemblies of such lipids (e.g., membranes, lecithin, lysolecithin, or fat droplets containing a small amount of lipid in a bulk water phase). In some embodiments, lipid sources are oils obtained from non-animal sources (e.g., oils obtained from plants, algae, fungi such as yeast or filamentous fungi, seaweed, bacteria, or Archae), including genetically engineered bacteria, algae, archaea or fungi. Non-limiting examples of plant oils include corn oil, olive oil, soy oil, peanut oil, walnut oil, almond oil, sesame oil, cottonseed oil, rapeseed oil, canola oil, safflower oil, sunflower oil, flax seed oil, palm oil, palm kernel oil, coconut oil, babassu oil, shea butter, mango butter, cocoa butter, wheat germ oil, or rice bran oil; or margarine. Oils can be hydrogenated (e.g., a hydrogenated vegetable oil) or non-hydrogenated.

In some embodiments, a lipid can be triglycerides, monoglycerides, diglycerides, free fatty acids, sphingosides, glycolipids, lecithin, lysolecithin, phospholipids such as phosphatidic acids, lysophosphatidic acids, phosphatidyl cholines, phosphatidyl inositols, phosphatidyl ethanolamines, or phosphatidyl serines; sphingolipids such as sphingomyelins or ceramides; sterols such as stigmasterol, sitosterol, campesterol, brassicasterol, sitostanol, campestanol, ergosterol, zymosterol, fecosterol, dinosterol, lanosterol, cholesterol, or episterol; lipid amides, such as N-palmitoyl proline, N-stearoyl glycine, N-palmitoyl glycine, N-arachidonoyl glycine, N-palmitoyl taurine, N-arachidonoyl histidine, or anandamide; free fatty acids such as palmitoleic acid, palmitic acid, myristic acid, lauric acid, myristoleic acid, caproic acid, capric acid, caprylic acid, pelargonic acid, undecanoic acid, linoleic acid (C18:2), eicosanoic acid (C22:0), arachidonic acid (C20:4), eicosapentanoic acid (C20:5), docosapentaenoic acid (C22:5), docosahexanoic acid (C22:6), erucic acid (C22:1), conjugated linoleic acid, linolenic acid (C18:3), oleic acid (C18:1), elaidic acid (trans isomer of oleic acid), trans-vaccenic acid (C18:1 trans 11), or conjugated oleic acid; or esters of such fatty acids, including monoacylglyceride esters, diacylglyceride esters, and triacylglyceride esters of such fatty acids.

Lipids can comprise phospholipids, lipid amides, sterols, or neutral lipids. The phospholipids can comprise a plurality of amphipathic molecules comprising fatty acids, glycerol and polar groups. In some embodiments, the polar groups are, for example, choline, ethanolamine, serine, phosphate, glycerol-3-phosphate, inositol or inositol phosphates. In some embodiments, lipids are, for example, sphingolipids, ceramides, sphingomyelins, cerebrosides, gangliosides, ether lipids, plasmalogens or pegylated lipids.

In some embodiments, a fat can be present in an amount of about 0.1% to about 95% by weight (e.g., about 0.1% to about 1%, about 1% to about 5%, about 5% to about 10%, about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 95% about 10% to about 30%, about 30% to about 50%, about 50% to about 70%, about 70% to about 90%, about 0.1% to about 20%, about 20% to about 40%, about 40% to about 60%, about 60% to about 80%, about 80% to about 95%, about 0.1% to about 33%, about 33% to about 66%, about 66% to about 95%, about 0.1% to about 50%, or about 50% to about 95%) of a food product (e.g., a meat replica, a beef-like food product, a chicken-like food product, a pork-like food product, a fish-like food product, a beef food product, a chicken food product, a pork food product, or a fish food product).

In some embodiments, a fat can be present in a food product in the form of an adipose replica.

A food product can include a binding agent or a carbohydrate-based gel. In some embodiments, a carbohydrate-based gel can be included in a binding agent. A binding agent can be about 2% to about 10% by weight of a food product. A binding agent can include one or more proteins that have been chemically or enzymatically modified to improve their textural and/or flavor properties, or to modify their denaturation and gelling temperatures. A carbohydrate based gel can contain methylcellulose, hydroxypropylmethyl cellulose, guar gum, locust bean gum, xanthan gum, agar, pectin, carrageenan, konjac, alginate, chemically-modified agarose, or a mixture thereof. A binding agent can include egg albumin or collagen.

The disclosure provides, in certain embodiments, methods for determining the suitability for a consumable to qualify as a replica of a food product, for example, by determining whether an animal or human can distinguish the consumable from a predicate food product, e.g., a particular meat. One method to determine whether the consumable is comparable to a food product (e.g. meat) is to a) define the properties of meat and b) determine whether the consumable has similar properties.

Properties that can be tested or used to compare or describe a food product include mechanical properties such as hardness, cohesiveness, brittleness, chewiness, gumminess, viscosity, elasticity, and adhesiveness. Properties of food products that can be tested also include geometric properties such as particle size and shape, and particle shape and orientation. The three dimensional organization of particles may also be tested. Additional properties can include moisture content and fat content. These properties can be described using terms such as "soft," "firm" or "hard" describe hardness; "crumbly," "crunchy," "brittle," "chewy," "tender," "tough," "short," "mealy," "pasty," or "gummy," to describe cohesiveness; "thin" or "viscous" to describe viscosity; "plastic" or "elastic" to describe elasticity; "sticky," "tacky" or "gooey" to describe adhesiveness; "gritty," "grainy" or "course" to describe particle shape and size; "fibrous," "cellular" or "crystalline" to describe particle shape and orientation, "dry," "moist," "wet," or "watery" to describe moisture content; or "oily" or "greasy" to describe fat content. Accordingly, in some embodiments, a group of people can be asked to rate a certain reference food product, for instance ground beef, according to properties which describe the reference food product. A food product described herein can be rated by the same people to determine equivalence.

Flavor of a food product of the disclosure can also be assessed. Flavors can be rated according to similarity to reference foods, e.g., "eggy," "fishy," "buttery," "chocolaty," "fruity", "peppery," "baconlike," "creamy," "milky," "or "beefy." Flavors can be rated according to the seven basic tastes, i.e., sweet, sour, bitter, salty, umami (savory), pungent (or piquant), and metallic. Flavors can be described according to the similarity to an experience caused by a chemical, e.g., diacetyl (buttery), 3-hydroxy-2 butanone (buttery), nona-2E-enal (fatty), 1-octene-3-ol (mushroom), hexanoic acid (sweaty), 4-hydroxy-5-methyl furanone (HMF, meaty), pyrazines (nutty), bis(2-methyl-3-furyl) disulfide (roast meat), decanone (musty/fruity), isoamyl acetate (banana), benzaldehyde (bitter almond), cinnamic aldehyde (cinnamon), ethyl propionate (fruity), methyl anthranilate (grape), limonene (orange), ethyl decadienoate (pear), allyl hexanoate (pineapple), ethyl maltol (sugar, cotton candy), ethylvanillin (vanilla), butanoic acid (rancid), 12-methyltridecanal (beefy), or methyl salicylate (wintergreen). These ratings can be used as an indication of the properties of the reference food product. A food product of the present disclosure can then be compared to a reference food product to determine how similar the food product is to the reference food product. In some embodiments, the properties of a food product of the disclosure are then altered to make the food product of the disclosure more similar to the reference food product. Accordingly, in some embodiments, a food product of the disclosure is rated similar to a reference food product according to human evaluation. In some embodiments, a food product of the disclosure is indistinguishable from the reference food product to a human.

In some embodiments, subjects asked to identify the food product of the disclosure can identify it as a form of a reference food product, or as a particular reference food product, e.g., a subject will identify a food product of the disclosure as meat. For example, in some embodiments, a human can identify a food product of the disclosure as having properties equivalent to meat. In some embodiments, one or more properties of the food product of the disclosure are equivalent to the corresponding properties of meat according to a human's perception. Such properties include the properties that can be tested. In some embodiments, a human identifies a food product of the present disclosure as more meat like than any meat replicas found in the art.

Experiments can demonstrate that a food product of the disclosure is acceptable to consumers. A panel can be used to screen a variety of consumables described herein. A number of human panelists can test multiple food product samples, namely, natural meats vs. the food products described herein, or a meat substitute vs. a consumable composition described herein. Variables such as fat content can be standardized, for example to 20% fat using lean and fat meat mixes. Fat content can be determined using the Babcock for meat method (S. S. Nielson, Introduction to the Chemical Analysis of Foods (Jones & Bartlett Publishers, Boston, 1994)). Mixtures of ground beef and food products of the invention prepared according to the procedure described herein can be formulated.

Panelists can be served samples (e.g., in booths), under red lights or under white light, in an open consumer panel. Samples can be assigned random three-digit numbers and rotated in ballot position to prevent bias. Panelists can be asked to evaluate samples for tenderness, juiciness, texture, flavor, and overall acceptability using a hedonic scale from 1=dislike extremely, to 9=like extremely, with a median of 5=neither like nor dislike. Panelists can be encouraged to rinse their mouths with water between samples, and given opportunity to comment on each sample.

The results of this experiment can indicate significant differences or similarities between the traditional meats and the food products of the disclosure.

These results can demonstrate that the food products described herein are judged as acceptably equivalent to real meat products. Additionally, these results can demonstrate that food products described herein are preferred by panelists over other commercially available meat substitutes. Thus, in some embodiments, the present disclosure provides for food products that are similar to traditional meats and are more meat like than previously known meat alternatives.

Food products of the disclosure can also have similar physical characteristics as food products, e.g., traditional meat. In one embodiment, the force required to pierce a 1 inch thick structure (e.g., a patty) made of a food product of the disclosure with a fixed diameter steel rod is not significantly different than the force required to pierce a 1 inch thick similar food product structure (e.g., a ground beef patty) with a similar fixed diameter steel rod. Accordingly, the disclosure provides for food products with similar physical strength characteristics to meat. In another embodiment, the force required to tear a sample of a food product of the disclosure with a cross-sectional area of 100 mm$^2$ is not significantly different than the force required to tear a sample of animal tissue (muscle, fat or connective tissue) with a cross-sectional area 100 mm$^2$ measured the same way. Force can be measured using, for example, TA.XT Plus Texture Analyzer (Textrue Technologies Corp.). Accordingly, the disclosure provides for food products with similar physical strength characteristics to meat.

Food products described herein can have a similar cook loss characteristic as a food product, e.g., meat. For example, a food product of the disclosure can have a similar fat and protein content to ground beef and have the same reduction in size when cooked as real ground beef. Similarities in size loss profiles can be achieved for various compositions of food products described herein matched to various meats. The cook loss characteristics of a food product described herein also can be engineered to be superior to food products. For example, a food product described herein can be produced that has less loss during cooking but achieves similar tastes and texture qualities as the cooked products. One way this can be achieved is by altering the proportions of lipids based on melting temperatures in a food product of the disclosure. Another way this can be achieved is by altering the protein composition of a food product by controlling the concentration of protein or by the mechanism by which a tissue replica is formed.

In some embodiments, a food product of the disclosure is compared to a reference food product (e.g., an animal based food product (e.g., meat)) based upon olfactometer readings. In some embodiments, an olfactometer can be used to assess odor concentration and odor thresholds, or odor suprathresholds with comparison to a reference gas, hedonic scale scores to determine the degree of appreciation, or relative intensity of odors. In some embodiments, an olfactometer allows the training and automatic evaluation of expert panels. So in some embodiments, a food product of the disclosure is a food product that causes similar or identical olfactometer readings to a reference food product. In some embodiments, the differences are sufficiently small to be below the detection threshold of human perception.

Gas chromatography-mass spectrometry (GCMS) is a method that combines the features of gas-liquid chromatography and mass spectrometry to separate and identify different substances within a test sample. GCMS can, in some embodiments, be used to evaluate the properties of a food product of the disclosure. For example, volatile chemicals can be isolated from the head space around meat. These chemicals can be identified using GCMS. A profile of the volatile chemicals in the headspace around meat can be thereby created. In some embodiments, each peak of the GCMS can be further evaluated. For instance, a human could rate the experience of smelling the chemical responsible for a certain peak. This information could be used to further refine the profile. GCMS could then be used to evaluate the properties of the consumable. The GCMS profile can be used to refine the consumable.

Characteristic flavor and fragrance components are mostly produced during the cooking process by chemical reactions molecules including amino acids, fats and sugars which are found in plants as well as meat. Therefore, in some embodiments, a food product of the disclosure is tested for similarity to meat during or after cooking. In some embodiments human ratings, human evaluation, olfactometer readings, or GCMS measurements, or combinations thereof, are used to create an olfactory map of a reference food product (e.g., cooked meat). Similarly, an olfactory map of a food product of the disclosure, for instance a meat replica, can be created. These maps can be compared to assess how similar the cooked consumable is to meat. In some embodiments, an olfactory map of a food product of the disclosure during or after cooking is similar to or indistinguishable from that of cooked or cooking meat. In some embodiments, the similarity is sufficient to be beyond the detection threshold of human perception. In some embodiments, a food product of the disclosure can be created so its characteristics are similar to a reference food product after cooking, but the uncooked food product of the disclosure can have properties that are different from the reference food product prior to cooking.

In some embodiments, a food product can be a dairy replica (also called a non-dairy product).

In one aspect, the disclosure provides a non-dairy cheese source that can be used as a starting material for preparing a non-dairy cheese. The term "non-dairy cheese source" refers to an emulsion comprising proteins (e.g., including a protein composition as described herein, a commercially available protein, or a protein purified by any method known in the art, or a combination thereof) and fats, wherein said proteins and fats are prepared from a non-dairy source.

In some embodiments, a non-dairy cheese source can be a milk replica (also called a non-dairy milk). In some embodiments, a milk replica can be used to make a cheese replica (also called a non-dairy cheese).

In some embodiments, a non-dairy milk is an emulsion comprising one or more proteins (e.g., a protein composition as described herein, a commercially available protein, a protein purified by any method known in the art, or a combination thereof) and one or more fats. In some embodiments, the proteins are contained in a protein solution. The solution can comprise EDTA (0-0.1M), NaCl (0-1M), KCl (0-1M), NaSO$_4$ (0-0.2M), potassium phosphate (0-1M), sodium citrate (0-1M), sodium carbonate (0-1M), sucrose (0-50%), Urea (0-2M) or any combination thereof. The solution can have a pH of 3 to 11. In some embodiments, the one or more proteins accounts for 0.1%, 0.2%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or more of the protein content of said protein solution. In some embodiments, the one or more proteins accounts for 0.1-5%, 1-10%, 5-20%, 10-40%, 30-60%, 40-80%, 50-90%, 60-95%, or 70-100% of the protein content of said protein solution. In some embodiments, the total protein content of the protein solution is about 0.1%, 0.2%, 0.3%, 0.4%, 0.5%, 0.75%, 1%, 1.5%, 2%, 5%, 7.5%, 10%, 12.5%, 15%, 17.5%, 20%, or more than 20% weight/volume. In some embodiments, the total protein content of the protein solution is 0.1-5%, 1-10%, 5-20%, or more than 20% weight/volume.

In some embodiments, the proteins are concentrated using any methods known in the art. The proteins may be concentrated 2-fold, five-fold, 10-fold, or up to 100 fold. The proteins may be concentrated to a final concentration of 0.001-1%, 0.05-2%, 0.1-5%, 1-10%, 2-15%, 4-20%, or more than 20%. Exemplary methods include, e.g., ultrafiltration (or tangential flow filtration), lyophilisation, spray drying, or thin film evaporation.

In some embodiments, fats used in preparing the emulsion can be from a variety of sources. In some embodiments, the sources can be non-animal sources (e.g., oils obtained from plants, algae, fungi such as yeast or filamentous fungi, seaweed, bacteria, Archae), including genetically engineered bacteria, algae, archaea or fungi. The oils can be hydrogenated (e.g., a hydrogenated vegetable oil) or non-hydrogenated. Non-limiting examples of plant oils include corn oil, olive oil, soy oil, peanut oil, walnut oil, almond oil, sesame oil, cottonseed oil, rapeseed oil, canola oil, safflower oil, sunflower oil, flax seed oil, palm oil, palm kernel oil, coconut oil, babassu oil, shea butter, mango butter, cocoa butter, wheat germ oil, or rice bran oil; or margarine.

In some embodiments, a fat can be triglycerides, monoglycerides, diglycerides, sphingosides, glycolipids, lecithin, lysolecithin, phospholipids such as phosphatidic acids, lysophosphatidic acids, phosphatidyl cholines, phosphatidyl inositols, phosphatidyl ethanolamines, or phosphatidyl serines; sphingolipids such as sphingomyelins or ceramides; sterols such as stigmasterol, sitosterol, campesterol, brassicasterol, sitostanol, campestanol, ergosterol, zymosterol, fecosterol, dinosterol, lanosterol, cholesterol, or episterol; free fatty acids such as palmitoleic acid, palmitic acid, myristic acid, lauric acid, myristoleic acid, caproic acid, capric acid, caprylic acid, pelargonic acid, undecanoic acid, linoleic acid (C18:2), eicosanoic acid (C22:0), arachidonic acid (C20:4), eicosapentanoic acid (C20:5), docosapentaenoic acid (C22:5), docosahexanoic acid (C22:6), erucic acid (C22:1), conjugated linoleic acid, linolenic acid (C18:3), oleic acid (C18:1), elaidic acid (trans isomer of oleic acid), trans-vaccenic acid (C18:1 trans 11), or conjugated oleic acid; or esters of such fatty acids, including monoacylglyceride esters, diacylglyceride esters, and triacylglyceride esters of such fatty acids.

A fat can comprise phospholipids, sterols or lipids. Phospholipids can comprise a plurality of amphipathic molecules comprising fatty acids (e.g., see above), glycerol and polar groups. In some embodiments, the polar groups are, for example, choline, ethanolamine, serine, phosphate, glycerol-3-phosphate, inositol or inositol phosphates. In some embodiments, the lipids are, for example, sphingolipids, ceramides, sphingomyelins, cerebrosides, gangliosides, ether lipids, plasmalogens or pegylated lipids.

In some embodiments, an emulsion is prepared by preparing a solution comprising the one or more proteins, admixing said solution with one or more fats, thereby creating said emulsion. The ratio of protein solution to fats can be about 1:10, 1:5, 1:4, 1:3, 1:2, 1:1, 2:1, 3:1, 4:1, 5:1, or 10:1. The ratio of protein solution to fats can be about 10:1-1:2, 1:4-2:1, 1:1-4:1, or 2:1-10:1. The emulsion can be used as a non-dairy milk for the preparation of a non-dairy cheese. By way of example only, 0%-50% fat can be added to a protein solution by weight/weight or weight/volume.

Flavor compounds can be generated by microbes in the non-animal derived material used for producing many different non-dairy products described herein, including cheese replicas. The methods of flavoring generally include contacting a non-dairy milk or protein solution with one or more microbes, and preparing a cultured non-dairy product from the non-dairy milk. Microbes such as bacteria, yeast, or mold can be used to create a product with a desired flavor profile or be used as a component of the flavor in a product, as bacteria can create desirable flavors (e.g., buttery, creamy, dairy, or cheesy) in a neutral, planty, or beany product.

Exemplary non-dairy milks are described herein. Any of the non-dairy cheese milks or combinations thereof may be contacted with one or more microbes (e.g., a controlled amount of bacteria) to control the flavor of a resulting cultured non-dairy product such as a cheese replica. In some embodiments, the microbes can be selected from bacteria, yeast, or molds. In some embodiments, the bacteria can comprise mesophilic and/or thermophilic bacteria. In some embodiments, the bacteria can comprise bacteria from a commercial starter. Exemplary commercial starters are described herein.

Flavor production in the replicas can be controlled by the use of one or more microbes e.g., one or more bacteria, yeast, or molds, including but not limited to flavor production in the replicas can be controlled by the use of one or more microbes e.g., one or more bacteria, yeast, or molds, including but not limited to *Lactococcus* species such as *Lactococcus lactis lactis* (LLL, used alone or as a component of commercial mix MA11), *Lactococcus lactis cremoris* (LLC, used alone or as a component of commercial mix MA11), or *Lactococcus lactis biovar diacetylactis* (LLBD, often used as commercial culture MD88), a *Lactobacillus* species such as *Lactobacillus delbrueckii lactis*, *Lactobacillus delbrueckii bulgaricus*, *Lactobacillus helveticus*, *Lactobacillus plantarum*, *Lactobacillus casei*, or *Lactobacillus rhamnosus*, a *Leuconostocaceae* species such as *Leuconostoc mesenteroides cremoris* (LM), a *Streptococcus* species such as *Streptococcus thermophiles* (ST, often used as commercial culture TA61) a *Pediococcus* species such as *Pediococcus pentosaceus*, a *Clostridium* species such as *Clostridium butyricum*, a *Staphylococcus* species such as *Staphylococcus xylosus* (SX), a *Brevibacterium* species such as *Brevibacterium linens*, a *Propioniibacteria* species, a *Penicillium* species such as *Penicillium candidum*, *Penicillium camemberti*, or *Penicillium roqueforti*, a *Debaryomyces* species such as *Debaryomyces hansenii*, a *Geotrichum* species such as *Geotrichum candidum*, a *Corynebacteria* species, a *Verticillium* species such as *Verticillium lecanii*, a *Kluyveromyces* species such as *Kluyveromyces lactis*, a *Saccharomyces* species such as *Saccharomyces cerevisiae*, a *Candida* species such as *Candida jefer* or *Candida utilis*, a *Rhodosporidum* species such as *Rhodosporidum infirmominiatum*, a *Micrococcus* species, a *Halomonas* species, a *Psychrobacter* species. In some embodiments, lactic acid bacteria such as *Lactobacillus, Leuconostoc, Pediococcus, Lactococcus,* or *Streptococcus* are used. In some embodiments, the bacteria do not comprise *Lactobaccilius acidophilus* strains. In some embodiments, a yeast such as *Saccharomyces cerevisiae, Kluveromyces lactis* and/or *Debaromyces hansenii* can be used. In some embodiments, a mold can be *Penicillium candidum, Penicillium camemberti, Penicillium roqueforti, Geotrichum candidum*, or a combination thereof.

In some embodiments, one or more of the follow microbes are used: *Pediococcus pentosaceus, Clostridium butyricum, Lactobacillus delbrueckii lactis, Lactobacillus delbrueckii bulgaricus, Lactobacillus helveticus, Lactobacillus plantarum, Lactobacillus casei, Lactobacillus rhamnosus, Staphylococcus xylosus*, and *Brevibacterium linens*.

In some embodiments, a non-dairy cheese source can be cultured with one or more microbes (e.g., bacteria, yeast, or mold alone), or in combination with two or more microbes (e.g., two different bacteria, two different yeast, two different molds, a bacteria and a yeast, a bacteria and a mold, or a yeast and a mold). When two or more microbes are used, the microbes can be co-cultured or sequentially cultured, i.e., one microbe can be cultured for a length of time before adding another microbe. Particular good combinations for flavor generation in replicas are pre-culturing with SX, followed by either TA61 or MD88, or MD88 co-cultured with MA11.

Growth conditions of microbes also can control flavor generation in replicas. The temperature of microbes growth ranging from 4° C. to 45° C. can control the amount and type of flavor compounds produced in replicas. The amount of aeration by shaking (e.g., 0 to 300 rpm) can change the flavor productions of many different bacteria in non-dairy media. Greater aeration during culturing by either SX, TA61, or MD88 can generate more desired cheese and buttery compounds. Aeration can also decrease some undesired flavor compounds. Desired cheese compounds such as 2-heptanone can increase when SX, MD88, or TA61 are cultured with aeration. MD88's production of hexanoic methyl ester in cheese replicas can also be modulated by aeration. An increase in aeration of SX during culturing in soymilk can increase 3-methyl and 2-methyl butanoic acid production and can decrease the amounts of undesirable aroma compounds such as 2-ethyl furan or 2-pentyl furan in cheese replicas.

The amount of time the one or more microbes is cultured also can modulate the amount and types of flavor compounds. In some embodiments, culturing can range from 1 hour to multiple days. In some embodiments, one or more microbes and the non-dairy milk are incubated together for a length of time ranging from 1 min-60 minutes, 0.5-5 hours, 3-10 hours, 6-15 hours, 10-20 hours, or more than 20 hours. In some embodiments, most buttery compounds are created within the first 10 hours, while additional cheese compounds can be formed in 24-48 hours or more hours. Butyrolactone, a creamy, milky note compound can be created in non-dairy media (e.g., a non-dairy cheese source or a milk replica) by MD88 and MA11 only after 20 hours of culturing in soymilk.

In some embodiments, the one or more microbes also can be added at different inoculums, e.g., $10^2$-$10^9$ cfu/mL or even greater. The phase of growth (i.e, stationary phase versus exponential phase) and the cell density of the bacterial culture can affect the flavor compound profile of the medium. Higher inocula of a starter culture can protect the replica from unwanted microbial contamination (e.g., bacterial contamination). Therefore, an inoculum of $10^6$-$10^9$ cfu/mL is usually used.

Flavor production by the one or more microbes also can be modulated by directing the metabolic pathways, e.g., by modulating their nitrogen source, carbon source, additional available nutrients, and growth conditions.

In some embodiments, the one or more microbes, the non-dairy cheese source, and the one or more optional components that can be used to alter flavor (e.g., sugars, fats, carbohydrates, vitamins, organic acids, nucleotides, or food products) are incubated together for a sufficient period of time to achieve a desired pH. The pH can range from pH 3-5, 4-6, or 4.3-5.7. The desired pH can be pH 6 or lower, pH 5 or lower, or pH 4 or lower. Culturing the material by bacteria in some cases decreases the pH to 6.5, 6, 5.5, 5, 4.5, 4, or 3.5, while in other cases, flavors are generated with no change in pH. Culturing with *Lactococcus, Lactobacillus, Leuconostoc, Pediococcus* and/or *Streptococcus* generally results in a decrease in pH with most starting material, while culturing with *Staphylococcus, Brevibacterium*, and/or *Clostridium* generally has little or no effect on the pH.

In some embodiments, one or more enzymes can be used alone or in combination any one the culturing methods and additives described to help modulate the flavor, texture, and/or melting profile, comprising contacting a non-dairy cheese source with one or more enzymes. In some embodiments, the one or more enzymes can be added before solidification, after solidification but before the whey is drained, or after whey is drained. Surprisingly, adding trace amounts of one or more enzymes (e.g., proteases, lipases, and/or amylases) can enhance the texture, flavor, and/or meltability of the resulting non-dairy cheese replica, as determined by blind taste test or by the detection of volatile odorants by, e.g., GCMS. Using such enzymes can also impact flavor production by microbial cultures (e.g., when soymilk is pre-treated with amylases, TA61 produces much more diacetyl).

In some embodiments, the enzyme is aspartic protease.

In specific embodiments, the protease is papain, bromelain, AO protease, figin, rennet, protease type XXI from *Streptomyces griseus*, a protease from *Bacillus licheniformis*, a protease from *Aspergillus oryzae*, a protease from *Bacillus amyloliquefaciens*, a protease from *Aspergillus saitoi*, a thermolysin from *Bacillus thermoproteolyticus rokko*, Subtilisin A, protease type X, or a fungal protease type XIII In some embodiments, the enzyme is a lipase.

The added enzyme can account for 0.00001-0.005%, 0.001-0.01%, 0.01-0.1%, 0.05-1%, 0.1-2%, or 0.5-5% of the non-dairy cheese source by weight or volume. In some embodiments, the added enzyme can account for 0.00001-0.1% of the non-dairy cheese source by weight or volume.

In some embodiments, the protease is papain. In some embodiments, 0.001-0.01% of papain is added to the non-dairy cheese source. In some embodiments, a protein solution with added protease is solidified by a heat/cool method. In some embodiments, addition of papain improves the softness and creaminess of the resulting cheese replica.

A method can comprise adding one or more fats to the non-dairy cheese source to create an emulsion.

By way of example only, some non-dairy cheese replicas can be prepared by adding 0%-50% fat to a non-dairy cheese source to create an emulsion, then solidifying the emulsion by protein denaturation, e.g., by heating. In some embodiments, one or more fats are added before solidifying, or after solidifying. In some embodiments, the one or more fats are added after solidifying and after draining the whey. By way of other example only, some cheese replicas made from protein denaturation have 0% to 50% fat added after solidification by denaturation, or 0% to 50% fat added after draining the whey. In some embodiments, after formation of a gel, either by protein denaturation or crosslinking, whey can be drained to increase the total fat in the cheese replica, further draining and aging the cheese can reduce the moisture content to increase the total fat of the cheese replica.

In some embodiments, the addition of 5-20% unsaturated fats to enzyme crosslinked gels can increase the firmness of the gel.

In some embodiments, addition of saturated fats from 5%-50% can increase the firmness of the cheese replicas.

In another aspect, the disclosure provides cheese replicas and methods of making the same. In some embodiments, the method comprises solidifying a non-dairy cheese source (e.g., a non-dairy milk) (e.g., by forming a gel). In some embodiments, the non-dairy milk is capable of retaining a shape after said solidifying. There are many ways in which the non-dairy cheese source can be solidified, including using enzymes, heat denature, forming cold gels, forming coacervate, liquid separation, acids, change in ionic strength, high pressure processing, solvents, chaotropic agents, or disulfide bond reducers as described in this section.

Enzymes (or chemicals) can be used to crosslink non-animal (e.g., plant based) proteins or non-dairy cheese sources, with or without emulsified fats or oils, sugars, and cultures. The resulting cross-linked cheese replicas can have bacteria cultures added or not, and the timing of addition can be either before or after the crosslinking step. In some embodiments, solidifying involves a process of cross-linking components (e.g., polypeptides, also referred to as proteins herein) in the non-dairy cheese source. In some embodiments, cross-linking comprises contacting the non-dairy cheese source with a cross-linking enzyme, thereby creating crosslinks between polypeptide chains. In some embodiments, a crosslinking enzyme can be a transglutaminase, tyrosinase, lipoxygenase, protein disulfide reductase, protein disulfide isomerase, sulfhydryl oxidase, peroxidase, hexose oxidase, lysyl oxidase, or amine oxidase.

In some embodiments, the cross-linking enzyme is a transglutaminase. Transglutaminases are a family of enzymes that catalyze the formation of a covalent bond between a free amine and the gamma-carboxyl group of glutamine thereby linking proteins together. For example, transglutaminases catalyze crosslinking of e.g., lysine in a protein or peptide and the gamma-carboxamide group of a protein- or peptide-glutamine residue. The covalent bonds formed by transglutaminase can exhibit high resistance to proteolytic degradation.

Many types of transglutaminase can be used in various embodiments of the invention. Acceptable transglutaminases for crosslinking include, but are not limited to, *Streptoverticillium mobaraense* transglutaminase, an enzyme that is similar to a transglutaminase from *Streptoverticillium mobaraense*, other microbial transglutaminases, transglutaminases produced by genetically engineered bacteria, fungi or algae, Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6), TGM Z (TGM7), or a lysyl oxidase.

The timing of adding the cultures, the type of cultures, and amount of cultures can change the pH of the emulsion, and therefore the activity of transglutaminase and the final texture of the cheese. In addition, changing the pH of the solution with the addition of acid or base, and overall buffering capacity of the emulsion can alter the crosslinking ability and the final texture of the cheese-replica.

In some embodiments, the present invention provides for a composition comprising a non-dairy milk and a *Streptoverticillium mobaraense* transglutaminase, an enzyme is similar to a transglutaminase from *Streptoverticillium mobaraense*, other microbial transglutaminases, transglutaminases produced by genetically engineered bacteria, fungi or algae, Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6) and/or TGM Z (TGM7). In some embodiments the enzyme used for cross-linking is not Factor XIII (fibrin-stabilizing factor), Keratinocyte transglutaminase (TGM1), Tissue transglutaminase (TGM2), Epidermal transglutaminase (TGM3), Prostate transglutaminase (TGM4), TGM X (TGM5), TGM Y (TGM6), TGM Z (TGM7), or lysyl oxidase.

Transglutaminases can be produced by *Streptoverticillium mobaraense* fermentation in commercial quantities or extracted from animal tissues. Additionally, a transglutaminase (TGM) of the present disclosure can be isolated from bacteria or fungi, expressed in bacteria or fungi from a synthetic or cloned gene. In some particular embodiments, a transglutaminase is obtained from a commercial source, for example in the form of Activa™ from Ajinomoto Food Ingredients LLC.

In some embodiments, a transglutaminase is added at an amount between 0.0000001-0.001%, 0.0001-0.1%, 0.001-0.05%, 0.1-2%, 0.5-4%, or greater than 4% by weight/volume. In some embodiments, a transglutaminase is added at amounts greater than 0.1% and up to 10%.

In some embodiments, cross-linking by a transglutaminase can be done at temperatures ranging from 10-30° C., 20-60° C., 30-70° C., or 50-100° C. Transglutaminase cross-linking can occur for 10 minutes-24 hours.

In some embodiments, between 0.1 and 20 units (U) of transglutaminase is added per 1 mL of non-dairy milk. In some embodiments about 0.1, 0.5, 1, 1.5, 2, 2.5, 3, 5, 7, 10, 15, or 20 U of transglutaminase is added per 1 mL of non-dairy milk. In some embodiments after the transglutaminase is added, a heated incubation occurs, for example in a 100° F. water bath. The heated incubation can be at a temperature optimized for the enzyme function. In some embodiments the temperature is about 65, 70, 75, 80, 85, 90, 95, 100, 105, 110, 115, 120 or 125° F. In some embodiments, enzymatic cross-linking does not comprise contacting the non-dairy cheese source with glutaminase and transglutaminase. Transglutaminase crosslinking has been done at room temperature, and up to 65° C., for 10 minutes to 24 hours.

In some embodiments, solidifying comprises inducing protein denaturation. In some embodiments, denaturation is induced by heating the mixture, followed by cooling the mixture. In some embodiments, denaturation is induced by heating the mixture to a temperature between 30-35, 32-40, 37-45, 40-50, 45-55, 50-60, 55-65, 60-70, 65-75, 70-80, 75-85, 80-95, 90-100° C., or above 100° C. In some embodiments, denaturation is induced by heating the mixture for about 10-20, 15-30, 25-40, 30-50, 40-70 seconds or about 1-3, 2-5, 3-8, or 5-20 minutes. In some embodiments, the mixture is allowed to cool after heating. For example, proteins (e.g., a protein composition as disclosed herein, a commercially available protein, a protein purified by any method known in the art, purified or fractionated plant proteins such as from peas, moong, soy, RuBisCO, or a combination thereof), preferably at concentrations>1%, can be homogenized with oils (such as canola oil, sunflower oil, palm oil or oil bodies from seeds such as sunflower) at 0.1-60% concentration. The emulsion can be subjected to a heat-cool cycle wherein it is heated to a temperature of 45-100° C. for 5-60 minutes and then cooled to less than 30°

C. (e.g., 20-25° C.). The resulting gel can be incubated at a temperature≤30° C., preferably for 2-16 hours and then drained through cheesecloth. The drained curds are ready to be shaped and aged or processed further by heating or pressing.

Acids, change in ionic strength, high pressure processing, solvents, chaotropic agents, or disulfide bond reducers can be used to denature the proteins in the non-dairy cheese source. In some embodiments, urea is added to the non-dairy cheese source to form curds.

In some embodiments, solidifying results in the formation of solid curds and whey (resulting liquid that remains after curd is formed). In some embodiments, the curds are separated from the whey.

In some embodiments, solidifying comprises a combination of two or more methods. For example, solidifying can include crosslinking proteins and denaturation by heating followed by cooling. For example, a cold set gel can be cross-linked with transglutaminase to yield firmer gels or combined with other proteins such as soy, pea-legumins, pea-albumins, crude protein fraction from chick peas and lentils or materials (for example, fats or pea protein coacervates) to increase firmness and/or meltability.

In another aspect, the disclosure provides methods for flavoring cultured non-dairy products, including sour cream, crème fraiche, yogurt, or cheese replicas. In some embodiments, the method comprises comparing a flavor note profile of a test non-dairy product with one or more flavor additives and/or one or more individual microbial strains described herein to a flavor note profile of a control non-dairy product without the additives and/or individual microbial strain. The texture and flavor profile of a non-dairy product (e.g. cheese replica) can be ascertained by any method known in the art or described herein. Exemplary methods of ascertaining flavor and texture can be by a taste test, e.g., a blind taste test, or using gas chromatography-mass spectrometry (GCMS).

GCMS is a method that combines the features of gas-liquid chromatography and mass spectrometry to identify different substances within a test sample. GCMS can, in some embodiments, be used to evaluate the properties of a dairy cheese and a cheese replica. For example volatile chemicals can be detected from the head space around a dairy cheese or a cheese replica. These chemicals can be identified using GCMS. A profile of the volatile chemicals in the headspace around cheese is thereby created. In some embodiments, each peak of the GCMS can be further evaluated. For instance, a human could rate the experience of smelling the chemical responsible for a certain peak. This information could be used to further refine the profile. GCMS could then be used to evaluate the properties of the cheese replicas. The GCMS could be used to refine the cheese replica. In some embodiments the cheese replica has a GCMS profile similar to that of dairy cheese. In some embodiments the cheese replica has a GCMS profile identical to that of dairy cheese.

A flavor profile of a dairy replica can be characterized by the presence and/or intensity of one or more flavor notes. Exemplary flavor notes include, but are not limited to butteriness, fruitiness, nuttiness, dairy, milky, cheesy, fatty, fruity, pineapple, waxy, buttery, tonka, dark fruit, citrus, sour, banana-like, sweet, bitter, musty, floral, goaty, sweaty, woody, earthly, mushroom, malty, spicy, pear, green, balsamic, pungent, oily, rose, fatty, butterscotch, orange, pine, carnation, melon, pineapple, vanilla, garlic, herbaceous, woody, cinnamon, rue, yogurt, peach, vanilla, hawthorn, and herbaceous. The flavor notes may be associated with the release of one or more volatile compounds. The flavor profile can be characterized by the absence or reduction in the intensity of one or more flavor notes. Exemplary flavor notes include: planty, beany, soy, green, vegetable, nutty, dirty, and sour.

Exemplary volatile compounds include, e.g., gamma-nonanoic lactone, gamma-undecalactone, gamma-decalactone, delta-tetradecalactone, S-methyl thiopropionate, delta-tridecalactone, delta-tetradecalactone, δ-tetradecalactone, butyl butyryllactate, 2,3-hexandione, methyl hexanoate, butyrolactone, propanoic acid, 2-methyl propanoic acid, methyl isobutyl ketone, gamma octalactone, delta octalactone, gamma nonalactone, 5-hydroxy-4-octanone, 2-ethyl-1-hexanol, octane, ethanol, 2,3-butanedione, 2 heptanone, 1-butanol, acetoin, butanoic acid, nonanal, acetic acid, 1,3 butanediol, methyl-3-buten-1-ol, methanol, hexanol, dimethyl-benzene, ethyl-benzene, indole, limonene, toluene, acetophenone, pentan-2,3-dione, 2-pentanone, 2-heptanone, 2-nonanone, acetone, butanone, 2-methylpropionic acid, butanoic acid, 2-methylbutanoic acid, 3-methylbutanoic acid, pentanoic acid, 4-methylpentanoic acid, hexanoic acid, octanoic acid, decanoic acid, undecanoic acid, dodecanoic acid, tetradecanoic acid, hexadecanoic acid, octadecanoic acid, oleic acid, linoleic acid, linolenic acid, propanol, butanol, pentanol, hexanol, heptanol, octanol, propan-2-ol, butan-2-ol, pentan-2-ol, hexan-2-ol, heptan-2-ol, nonan-2-ol, undecan-2-ol, octen-3-ol, octa-1,5-dien-3-ol, 3-methyl-2-cyclohexenol, 2-methylpropanol, 2-methylbutanol, 3-methylbutanol, 3-methylpentanol, phenylmethanol, 2-phenylethanol, 2-phenyl-ethan-2-ol, propan-2-one, butan-2-one, pentan-2-one, hexan-2-one, heptan-2-one, octan-2-one, nonan-2-one, decan-2-one, undecan-2-one, dodecan-2-one, tridecan-2-one, pentadeca-2-one, pentan-3-one, octan-3-one, 3-methylpentan-2-one, 4-methylpentan-2-one, methylhexan-2-one, hydroxypropan-2-one, hept-5-en-2-one, 4-methylpent-3-en-2-one, octen-3-one, octa-1,5-dien-3-one, nonen-2-one, undecen-2-one, methylfuryl ketone, phenylpropan-2-one, propiophenone, methyl butanoate, methyl hexanoate, methyl octanoate, methyl decanoate, methyl tetradecanoate, methyl hexadecanoate, methyl cinnamate, ethyl formate, ethyl acetate, ethyl propanoate, ethyl butanoate, ethyl hexanoate, ethyl octanoate, ethyl decanoate, ethyl dodecanoate, ethyl tetradecanoate, ethyl-3-methyl butanoate, propyl acetate, propyl butanoate, butyl formate, butyl acetate, amyl acetate, isoamyl formate, isoamyl acetate, isoamyl propanoate, isoamyl butanoate, diethyl phthalate, dimethyl phthalate, 2-phenylethyl acetate, 2-phenylethyl propanoate, 2-phenylethyl butanoate, 3-methylthiopropanol, methanethiol, hydrogen sulfide, dimethyl disulfide, dimethyl trisulfide, dimethyl tetrasulfide, methylethyl disulfide, diethyl disulfide, 2,4-dithiapentane, methional, 3-methylthio-2,4-dithiapentane, 2,4,5-trithiahexane, 1,1-bis-methylmercaptodisulfide, methanethiol acetate, methyl thiopropanoate, methyl thiobenzoate, thiophen-2-aldehyde, methylindole, p-ethylphenol, p-cresol, acetaldehyde, butanal, 2-methylbutanal, 3-methylbutanal, 2-methylpropanal, hexanal, heptanal, nonanal, 2-methylbuten-2-al, benzaldehyde, 3-methylheptyl acetate, 1-butanol, 1-butanol, 3-methyl, 1-heptanol, formic acid, 1-hexanol-2, ethyl, 1-octanol, 2-butanone, 2-hepten-1-ol, 2-hexanone, heptanal, 2-octen-1-ol, 1-octen-3-ol, 2-pentanone, 2,3-butanedione, 3-buten-1-ol, 5-Hepten-2-one, octane, ethanol, 2,3-butanedione, 2 heptanone, 1-butanol, butanoic acid, nonanal, acetic acid, 1,3 butanediol, methyl-3-buten phenylethyl alcohol, toluene, 1-pentanol, 3-octene-1-ol, 2 octene-1-ol, 2-undecanone, 1-octanol, Benzaldehyde, 1-heptanol, 2-heptanone, 4-methyl-2-nonanone, 2-methyl-2-nonanol, 1-hexanol, 2-methyl 2-propanol, Ethanol, 3 methyl 1-butanol, 1-hexanol, 2-methyl 2-nonanol, 2-nonanone, 2-heptanone, 4-methyl, 1-heptanol, 1-octanol, 2 octene-1-ol, 3-octene-1-ol, 1-octanol, 1-heptanol, 2-heptanone, 4-methyl-2-nonanone, 2-dodecanol, 2-dodecanone, 3-decene 1-ol acetate, benzyl alcohol, phenylethyl alcohol, 2-methoxy 4-vinylphenol, 3-decene 1-ol acetate, 2-dodecanone, 2-dodecanol, or 2-methoxy 4-vinylphenol.

In some embodiments, improved flavors are due to the decreased levels of volatile flavor compounds, such as, e.g., 1-hexanol; 2-butylfuran; 2-methyl-2-pentenal; 3-octanone; ethyl-acetate; 2-ethyl-furan; 2-pentyl-furan; pyrazine; 1-decanol; acetophenone; 1-nonanol; 2,5-dimethyl-pyrazine; dodecanal; benzeneacetaldehyde; nonanal; butyrolactone; octanal; 2-decanone; hexanal; 2-nonanone; benzaldehyde; heptanal; 2-octanone; furfural; 2-heptanone; pentanal; 3-methyl butanal; 3-methylbutanoic acid.

In some embodiments, the method further comprises preparing a cultured non-dairy product such as a cheese replica, yogurt, sour cream, or crème fraiche with a controlled flavor profile, by the controlled addition of defined combinations of flavor additives, described herein, to the non-dairy e source at any time point of the replica making process. Exemplary additives and specific combinations are described herein.

EXEMPLARY EMBODIMENTS

Embodiment 1 is a method for purifying protein from a plurality of cells, the method comprising:
  a) lysing an aqueous suspension of the plurality of cells to obtain a cell lysate;
  b) clarifying the cell lysate, optionally in the presence of one or more flocculants, to obtain a clarified lysate;
  c) filtering the clarified lysate to obtain a filtered lysate;
  d) concentrating the filtered lysate to obtain a protein composition; and
  e) optionally pasteurizing the protein composition of protein to obtain a pasteurized protein composition,
  wherein steps a), b), c), and d) independently, are performed at a pH between about 8.5 and about 12.0.

Embodiment 2 is a method for purifying protein from a plurality of cells, the method comprising:
  a) lysing an aqueous suspension of the plurality of cells to obtain a cell lysate;
  b) clarifying the cell lysate, optionally in the presence of one or more flocculants, to obtain a clarified lysate;
  c) concentrating the clarified lysate to obtain a protein composition; and
  d) optionally pasteurizing the protein composition to obtain a pasteurized protein composition,
  wherein steps a), b), c), and d) independently, are performed at a pH between about 8.5 and about 12.0.

Embodiment 3 is a method for purifying protein from a plurality of cells, the method comprising:
  a) lysing an aqueous suspension of the plurality of cells to obtain a cell lysate;
  b) clarifying the cell lysate, optionally in the presence of one or more flocculants, to obtain a clarified lysate;
  c) filtering the clarified lysate to obtain a protein composition; and
  d) optionally pasteurizing the protein composition, to obtain a pasteurized protein composition wherein steps a), b), c), and d) independently, are performed at a pH between about 8.5 and about 12.0.

Embodiment 4 is a method for purifying protein from a plurality of cells, the method comprising:
  a) lysing an aqueous suspension of the plurality of cells to obtain a cell lysate;
  b) clarifying the cell lysate, optionally in the presence of one or more flocculants, to obtain a clarified lysate;
  c) filtering the clarified lysate using microfiltration to obtain a first filtered lysate;
  d) filtering the first filtered lysate using diafiltration to obtain a second filtered lysate;
  e) filtering the second filtered lysate using ultrafiltration to obtain a third filtered lysate;
  f) filtering the third filtered lysate using diafiltration to obtain a protein composition; and
  g) optionally pasteurizing the protein composition to obtain a pasteurized protein composition,
  wherein steps a), b), c), d), e), f), and g) independently, are performed at a pH between about 8.5 and about 12.0.

Embodiment 5 is a method for purifying protein from a plurality of cells, the method comprising:
  a) lysing an aqueous suspension of the plurality of cells to obtain a cell lysate;
  b) clarifying the cell lysate, optionally in the presence of one or more flocculants, to obtain a clarified lysate;
  c) filtering the clarified lysate using microfiltration to obtain a first filtered lysate;
  d) filtering the first filtered lysate using diafiltration to obtain a protein composition; and
  e) optionally pasteurizing the protein composition to obtain a pasteurized protein composition,
  wherein steps a), b), c), d), and e) independently, are performed at a pH between about 8.5 and about 12.0.

Embodiment 6 is the method of any one of embodiments 1-5, wherein filtering comprises microfiltration.

Embodiment 7 is the method of any one of embodiments 1-6, wherein filtering comprises ultrafiltration.

Embodiment 8 is the method of any one of embodiments 1-7, wherein filtering comprises diafiltration Embodiment 9 is the method of embodiment 8, where diafiltration is performed for at least two diavolumes.

Embodiment 10 is the method of any one of embodiments 1-9, wherein the plurality of cells comprises microbial cells.

Embodiment 11 is the method of any one of embodiments 1-10, wherein the plurality of cells comprises fungal cells.

Embodiment 12 is the method of embodiment 11, wherein the fungal cells are selected from the group consisting of *Saccharomyces, Pichia, Candida, Hansenula, Torulopsis, Kluyveromyces, Yarrowia*, and *Fusarium* cells.

Embodiment 13 is the method of embodiment 11, wherein the fungal cells are selected from the group consisting of *Saccharomyces cerevisiae, Pichia pastoris, Candida boidinii, Hansenula polymorpha, Kluyveromyces lactis, Yarrowia lipolytica*, and *Fusarium venenatum*.

Embodiment 14 is the method of any one of embodiments 1-13, wherein the plurality of cells comprises bacterial cells.

Embodiment 15 is the method of embodiment 14, wherein the bacterial cells are selected from the group consisting of *Bacillus, Escherichia, Lactobacillus, Corynebacterium, Pseudomonas*, and *Methanococcus*.

Embodiment 16 is the method of embodiment 14, wherein the bacterial cells are selected from the group consisting of *Escherichia coli, Bacillus subtilis, Lactobacillus lactis, Corynebacterium glutamicum, Pseudomonas fluorescens*, and *Methanococcus maripaludis*.

Embodiment 17 is the method of any one of embodiments 1-16, wherein the aqueous suspension of the plurality of cells comprises from about 2% to about 25% dry solids.

Embodiment 18 is the method of any one of embodiments 1-17, further comprising washing the aqueous suspension of the plurality of cells at a pH between about 8.5 and about 12.0 before step a).

Embodiment 19 is the method of any one of embodiments 1-18, wherein the lysing step is performed at a temperature between about 4° C. and about 15° C.

Embodiment 20 is the method of any one of embodiments 1-19, wherein the lysing step is performed biochemically.

Embodiment 21 is the method of any one of embodiments 1-20, wherein the lysing step is performed chemically.

Embodiment 22 is the method of any one of embodiments 1-21, wherein the lysing step is performed mechanically.

Embodiment 23 is the method of any one of embodiments 1-22, wherein the lysing step is performed a pH between about 9.0 and about 12.0.

Embodiment 24 is the method of embodiment 22, wherein the lysing step is performed at a pH between about 9.0 and about 10.0.

Embodiment 25 is the method of embodiment 22, wherein the lysing step is performed at a pH between about 10.0 and about 11.0.

Embodiment 26 is the method of embodiment 22, wherein the lysing step is performed at a pH between about 11.0 and about 12.0.

Embodiment 27 is the method of any one of embodiments 1-26 wherein the clarifying step is performed, optionally in the presence of one or more flocculants, at a pH between about 9.0 and about 12.0.

Embodiment 28 is the method of embodiment 27, wherein the clarifying step is performed at a pH between about 9.0 and about 10.0.

Embodiment 29 is the method of embodiment 27, wherein the clarifying step is performed at a pH between about 10.0 and about 11.0.

Embodiment 30 is the method of embodiment 27, wherein the clarifying step is performed at a pH between about 11.0 and about 12.0.

Embodiment 31 is the method of any one of embodiments 1-30, wherein clarifying step is performed by centrifugation to less than about 20% dry solids.

Embodiment 32 is the method of any one of embodiments 1-31, wherein the clarifying step is performed by gravity settling to less than about 20% dry solids.

Embodiment 33 is the method of any one of embodiments 1-32, wherein the clarifying step is performed by diatomaceous earth filtration to less than about 20% dry solids.

Embodiment 34 is the method of any one of embodiments 1-33, wherein the lysate is diluted 1:1 with water or aqueous solution of salt or buffer before clarifying, wherein the pH is between about 8.5 and about 12.0.

Embodiment 35 is the method of any one of embodiments 1-34, wherein the cell lysate from step a) is clarified in the presence of one or more flocculants.

Embodiment 36 is the method of embodiment 35, wherein the one or more flocculants comprise one or more of alkylamine epichlorohydrin, polydimethyldiallylammonium chloride, a polyamine, lime, hydrated lime, ferric chloride, ferric sulfate, ferrous sulfate, aluminum sulfate, sodium aluminate, aluminum chloride, magnesium carbonate hydroxide, calcium carbonate, calcium hydroxide, an activated silicate, a guar gum, a starch, a tannin, sodium alginate, polyaluminum sulfate, polyaluminum hydroxy chloride, BIO-FLOCK®, and a synthetic polyelectrolyte.

Embodiment 37 is the method of embodiment 36, wherein the one or more flocculants are selected from the group consisting of alkylamine epichlorohydrin, polydimethyldiallylammonium chloride, a polyamine, lime, hydrated lime, ferric chloride, ferric sulfate, ferrous sulfate, aluminum sulfate, sodium aluminate, aluminum chloride, magnesium carbonate hydroxide, calcium carbonate, calcium hydroxide, an activated silicate, a guar gum, a starch, a tannin, sodium alginate, polyaluminum sulfate, polyaluminum hydroxy chloride, BIO-FLOCK®, and a synthetic polyelectrolyte.

Embodiment 38 is the method of any one of embodiments 1-37, wherein the protein composition has a protein content of about 2 mg/mL to about 250 mg/mL.

Embodiment 39 is the method of any one of embodiments 1-38, wherein the protein composition exhibits one or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 $m^2$/g protein across about pH 4.0 to about pH 8.0.

Embodiment 40 is the method of any one of embodiments 1-38, wherein the protein composition exhibits two or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 41 is the method of any one of embodiments 1-38, wherein the protein composition exhibits three or more characteristics selected from the group consisting of: H$_2$S is detectable in an amount of less than about 0.1 ppm when L-cysteine is not added to the protein composition, and H$_2$S is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 42 is the method of any one of embodiments 1-38, wherein the protein composition exhibits four or more characteristics selected from the group consisting of: H$_2$S is detectable in an amount of less than about 0.1 ppm when L-cysteine is not added to the protein composition, and H$_2$S is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 43 is the method of any one of embodiments 1-38, wherein the protein composition exhibits five or more characteristics selected from the group consisting of: H$_2$S is detectable in an amount of less than about 0.1 ppm when L-cysteine is not added to the protein composition, and H$_2$S is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 44 is the method of any one of embodiments 1-38, wherein the protein composition exhibits six or more characteristics selected from the group consisting of: H$_2$S is detectable in an amount of less than about 0.1 ppm when L-cysteine is not added to the protein composition, and H$_2$S is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 45 is the method of any one of embodiments 1-38, wherein the protein composition exhibits seven or more characteristics selected from the group consisting of: H$_2$S is detectable in an amount of less than about 0.1 ppm when L-cysteine is not added to the protein composition, and H$_2$S is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 46 is the method of any one of embodiments 1-38, wherein the protein composition exhibits the characteristics:

H$_2$S is detectable in an amount of less than about 0.1 ppm when L-cysteine is not added to the protein composition, and H$_2$S is detectable in an amount of at least about 0.2 ppm in the headspace about 24 hours at 25° C. after about 25 mM L-cysteine is added to the protein composition, the protein composition forms a gel upon heating to 65° C., the protein composition has a particle size distribution D10, D50, and D90 of less than 0.1 μm, 1.0 μm and 5 μm, respectively, the protein composition is least about 80% denatured after about 20 minutes at about 85° C., the protein composition forms a gel with a storage modulus of at least about 100 Pa when heated at or above about 85° C. for about 20 minutes, wherein the protein composition forms a gel between about pH 5.5 and about pH 10.0, the protein composition forms a gel in solutions with ionic strength below about 0.5 M, wherein the ionic strength is calculated based on the concentration of non-protein solutes, and the protein composition has an emulsion activity index of greater than or equal to about 50 $m^2$/g protein across about pH 4.0 to about pH 8.0.

Embodiment 47 is the method of any one of embodiments 1-45, wherein the protein composition comprises at least about 35%, on a dry weight basis, of compounds larger than 5 kDa.

Embodiment 48 is the method of any one of embodiments 1-45, wherein the protein composition comprises at least about 40%, on a dry weight basis, of compounds larger than 5 kDa.

Embodiment 49 is the method of any one of embodiments 1-45, wherein the protein composition comprises at least about 50%, on a dry weight basis, of compounds larger than 5 kDa.

Embodiment 50 is the method of any one of embodiments 1-45, wherein the protein composition comprises at least about 60%, on a dry weight basis, of compounds larger than 5 kDa.

Embodiment 51 is the method of any one of embodiments 1-45, wherein the protein composition comprises at least about 70%, on a dry weight basis, of compounds larger than 5 kDa.

Embodiment 52 is the method of any one of embodiments 47-51, wherein the compounds larger than 5 kDa are compounds larger than 10 kDa.

Embodiment 53 is the method of any one of embodiments 47-51, wherein the compounds larger than 5 kDa are compounds larger than 15 kDa.

Embodiment 54 is the method of any one of embodiments 47-51, wherein the compounds larger than 5 kDa are compounds larger than 20 kDa.

Embodiment 55 is the method of any one of embodiments 47-51, wherein the compounds larger than 5 kDa are compounds larger than 25 kDa.

Embodiment 56 is the method of any one of embodiments 1-55, further comprising drying the protein composition.

Embodiment 57 is the method of embodiment 56, wherein the protein composition is spray dried.

Embodiment 58 is the method of embodiment 56, wherein the protein composition is freeze dried.

Embodiment 59 is the method of any one of embodiments 1-55, further comprising pasteurizing the protein composition to obtain a pasteurized protein composition.

Embodiment 60 is the method of embodiment 59, wherein the protein composition is pasteurized by microfiltration.

Embodiment 61 is the method of embodiment 59, wherein the protein composition is pasteurized by high-temperature short time pasteurization.

Embodiment 62 is the method of embodiment 59, wherein the protein composition is pasteurized by adding one or more antimicrobials.

Embodiment 63 is the method of any one of embodiments 59-62, further comprising drying the pasteurized protein composition.

Embodiment 64 is the method of embodiment 63, wherein the pasteurized protein composition is spray dried.

Embodiment 65 is the method of embodiment 63, wherein the pasteurized protein composition is freeze dried.

Embodiment 66 is the method of any one of embodiments 1-65, wherein the amount of one or more volatile compounds is reduced by at least about 1.05-fold compared to a corresponding method in which one or more of the lysing, clarifying, or filtering steps are not performed at a pH between about 8.5 and about 12.0, wherein the volatile compound is selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment 67 is the method of any one of embodiments 1-66, wherein the protein composition does not comprise one or more compounds selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment 68 is the method of any one of embodiments 1-67, wherein at least about 50% of the protein in the protein composition falls between about 10 kDa and about 200 kDa.

Embodiment 69 is the method of any one of embodiments 1-3, wherein filtering the clarified lysate comprises microfiltering the clarified lysate using a filter having an average pore diameter from 0.2-2.0 μm and/or diafiltering the clarified lysate to produce the filtered lysate.

Embodiment 70 is the method of embodiment 69, wherein the diafiltering comprises using an ultrafiltration membrane system.

Embodiment 71 is the method of any one of embodiments 1-2, wherein the filtered lysate from step c), before concentrating, is further filtered.

Embodiment 72 is the method of embodiment 71, wherein the filtered lysate is ultrafiltered using a membrane having from about 10 kDa to about 30 kDa molecular weight cutoff.

Embodiment 73 is a method for purifying protein from a plurality of cells, the method comprising:
a) lysing an aqueous suspension of the plurality of cells to obtain a cell lysate;
b) filtering the cell lysate to obtain a protein composition; and
c) optionally pasteurizing the protein composition to obtain a pasteurized protein composition, wherein steps a), b), and c) independently, are performed at a pH between about 8.5 and about 12.0.

Embodiment 74 is a method for purifying protein from a plurality of cells, the method comprising:
a) lysing an aqueous suspension of the plurality of cells to obtain a cell lysate;
b) filtering the cell lysate using microfiltration obtain a first filtered lysate;
c) filtering the first filtered lysate using diafiltration to obtain a protein composition; and
d) optionally pasteurizing the protein composition to obtain a pasteurized protein composition,
wherein steps a), b), c), and d) independently, are performed at a pH between about 8.5 and about 12.0.

Embodiment 75 is a method for purifying protein from a plurality of cells, the method comprising:
a) lysing an aqueous suspension of the plurality of cells to obtain a cell lysate;
b) filtering the cell lysate using microfiltration to obtain a protein composition; and
c) optionally pasteurizing the protein composition to obtain a pasteurized protein composition,
wherein steps a), b), and c) independently, are performed at a pH between about 8.5 and about 12.0.

Embodiment 76 is the method of any one of embodiments 73-75, wherein filtering comprises microfiltration.

Embodiment 77 is the method of any one of embodiments 73-76, wherein filtering comprises ultrafiltration.

Embodiment 78 is the method of any one of embodiments 73-77, wherein filtering comprises diafiltration.

Embodiment 79 is the method of embodiment 78, where diafiltration is performed for at least two diavolumes.

Embodiment 80 is the method of any one of embodiments 73-79, wherein the plurality of cells comprises microbial cells.

Embodiment 81 is the method of any one of embodiments 73-80, wherein the plurality of cells comprises fungal cells.

Embodiment 82 is the method of embodiment 81, wherein the fungal cells are selected from the group consisting of *Saccharomyces*, *Pichia*, *Candida*, *Hansenula*, *Torulopsis*, *Kluyveromyces*, *Yarrowia*, and *Fasarium* cells.

Embodiment 83 is the method of embodiment 81, wherein the fungal cells are selected from the group consisting of *Saccharomyces cerevisiae*, *Pichia pastoris*, *Candida boidinii*, *Hansenula polymorpha*, *Kluyveromyces lactis*, *Yarrowia lipolytica*, and *Fusarium venenatum*.

Embodiment 84 is the method of any one of embodiments 73-83, wherein the plurality of cells comprises bacterial cells.

Embodiment 85 is the method of embodiment 84, wherein the bacterial cells are selected from the group consisting of *Bacillus*, *Escherichia*, *Lactobacillus*, *Corynebacterium*, *Pseudomonas*, and *Methanococcus*.

Embodiment 86 is the method of embodiment 84, wherein the bacterial cells are selected from the group consisting of *Escherichia coli*, *Bacillus subtilis*, *Lactobacillus lactis*, *Corynebacterium glutamicum*, *Pseudomonas fluorescens*, and *Methanococcus maripaludis*.

Embodiment 87 is the method of any one of embodiments 73-86, wherein the aqueous suspension of the plurality of cells comprises from about 2% to about 25% dry solids.

Embodiment 88 is the method of any one of embodiments 73-87, further comprising washing the aqueous suspension of the plurality of cells at a pH between about 8.5 and about 12.0 before step a).

Embodiment 89 is the method of any one of embodiments 73-88, wherein the lysing step is performed at a temperature between about 4° C. and about 15° C.

Embodiment 90 is the method of any one of embodiments 73-89, wherein the lysing step is performed biochemically.

Embodiment 91 is the method of any one of embodiments 73-90, wherein the lysing step is performed chemically.

Embodiment 92 is the method of any one of embodiments 73-91, wherein the lysing step is performed mechanically.

Embodiment 93 is the method of any one of embodiments 73-92, wherein the lysing step is performed at a pH between about 9.0 and about 12.0.

Embodiment 94 is the method of embodiment 93, wherein the lysing step is performed at a pH between about 9.0 and about 10.0.

Embodiment 95 is the method of embodiment 93, wherein the lysing step is performed at a pH between about 10.0 and about 11.0.

Embodiment 96 is the method of embodiment 93, wherein the lysing step is performed at a pH between about 11.0 and about 12.0.

Embodiment 97 is the method of any one of embodiments 73-96, wherein the lysate is diluted 1:1 with water or aqueous solution of salt or buffer before filtering, wherein the pH is between about 8.5 and about 12.0.

Embodiment 98 is the method of any one of embodiments 73-97, wherein the protein composition has a protein content of about 2 mg/mL to about 250 mg/mL.

Embodiment 99 is the method of any one of embodiments 73-98, wherein the protein composition exhibits one or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 $m^2$/g protein across about pH 4.0 to about pH 8.0.

Embodiment 100 is the method of any one of embodiments 73-98, wherein the protein composition exhibits two or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 101 is the method of any one of embodiments 73-98, wherein the protein composition exhibits three or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 102 is the method of any one of embodiments 73-98, wherein the protein composition exhibits four or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 103 is the method of any one of embodiments 73-98, wherein the protein composition exhibits five or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 104 is the method of any one of embodiments 73-98, wherein the protein composition exhibits six or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 105 is the method of any one of embodiments 73-98, wherein the protein composition exhibits seven or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 106 is the method of any one of embodiments 73-98, wherein the protein composition exhibits the characteristics:
  H₂S is detectable in an amount of less than about 0.1 ppm when L-cysteine is not added to the protein composition, and H₂S is detectable in an amount of at least about 0.2 ppm in the headspace about 24 hours at 25° C. after about 25 mM L-cysteine is added to the protein composition,
  the protein composition forms a gel upon heating to 65° C.,
  the protein composition has a particle size distribution D10, D50, and D90 of less than 0.1 µm, 1.0 µm and 5 µm, respectively,
  the protein composition is least about 80% denatured after about 20 minutes at about 85° C.,
  the protein composition forms a gel with a storage modulus of at least about 100 Pa when heated at or above about 85° C. for about 20 minutes, wherein the protein composition forms a gel between about pH 5.5 and about pH 10.0,
  the protein composition forms a gel in solutions with ionic strength below about 0.5 M, wherein the ionic strength is calculated based on the concentration of non-protein solutes, and
  the protein composition has an emulsion activity index of greater than or equal to about 50 m²/g protein across about pH 4.0 to about pH 8.0.

Embodiment 107 is the method of any one of embodiments 73-106, wherein the protein composition comprises at least about 35%, on a dry weight basis, of compounds larger than 5 kDa.

Embodiment 108 is the method of any one of embodiments 73-106, wherein the protein composition comprises at least about 40%, on a dry weight basis, of compounds larger than 5 kDa.

Embodiment 109 is the method of any one of embodiments 73-106, wherein the protein composition comprises at least about 50%, on a dry weight basis, of compounds larger than 5 kDa.

Embodiment 110 is the method of any one of embodiments 73-106, wherein the protein composition comprises at least about 60%, on a dry weight basis, of compounds larger than 5 kDa.

Embodiment 111 is the method of any one of embodiments 73-106, wherein the protein composition comprises at least about 70%, on a dry weight basis, of compounds larger than 5 kDa.

Embodiment 112 is the method of any one of embodiments 107-111, wherein the compounds larger than 5 kDa are compounds larger than 10 kDa.

Embodiment 113 is the method of any one of embodiments 107-111, wherein the compounds larger than 5 kDa are compounds larger than 15 kDa.

Embodiment 114 is the method of any one of embodiments 107-111, wherein the compounds larger than 5 kDa are compounds larger than 20 kDa.

Embodiment 115 is the method of any one of embodiments 107-111, wherein the compounds larger than 5 kDa are compounds larger than 25 kDa.

Embodiment 116 is the method of any one of embodiments 73-115, further comprising drying the protein composition.

Embodiment 117 is the method of embodiment 116, wherein the protein composition is spray dried.

Embodiment 118 is the method of embodiment 116, wherein the protein composition is freeze dried.

Embodiment 119 is the method of any one of embodiments 73-115, further comprising pasteurizing the protein composition to obtain a pasteurized protein composition.

Embodiment 120 is the method of embodiment 119, wherein the protein composition is pasteurized by microfiltration.

Embodiment 121 is the method of embodiment 119, wherein protein composition is pasteurized by high-temperature short time pasteurization.

Embodiment 122 is the method of embodiment 119, wherein the protein composition is pasteurized by adding one or more antimicrobials.

Embodiment 123 is the method of any one of embodiments 119-122, further comprising drying the pasteurized protein composition.

Embodiment 124 is the method of embodiment 123, wherein the pasteurized protein composition is spray dried.

Embodiment 125 is the method of embodiment 123, wherein the pasteurized protein composition is freeze dried.

Embodiment 126 is the method of any one of embodiments 73-125, wherein the amount of one or more volatile compounds is reduced by at least about 1.05-fold compared to a corresponding method in which one or more of the lysing or filtering steps are not performed at a pH between about 8.5 and about 12.0, wherein the volatile compound is selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment 127 is the method of any one of embodiments 73-126, wherein the protein composition does not comprise one or more compounds selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment 128 is the method of any one of embodiments 73-127, wherein at least about 50% of the protein in the protein composition falls between about 10 kDa and about 200 kDa.

Embodiment 129 is a protein composition comprising:
  a plurality of functional proteins,
    wherein the protein composition comprises at least about 35%, on a dry weight basis, compounds larger than 5 kDa.

Embodiment 130 is a protein composition comprising:
  a plurality of functional proteins,
    wherein the protein composition has a buffering capacity of less than about 2.5 mmol NaOH per gram dry solids.

Embodiment 131 is a protein composition comprising:
a plurality of functional proteins,
wherein heating a 10% (w/v) suspension of the protein composition to at least about 95° C. results in a gel with a storage modulus of at least about 100 Pa.

Embodiment 132 is the protein composition of any one of embodiments 129-131, wherein $H_2S$ is detectable in an amount of less than about 0.1 ppm in the headspace after about 24 hours at 25° C. when L-cysteine is not added to 5 mL of a 2% (w/v) suspension of the protein composition at pH 7.0.

Embodiment 133 is the protein composition of any one of embodiments 129-132, wherein $H_2S$ is detectable an amount of at least about 0.2 ppm in the headspace about 24 hours at 25° C. after about 25 mM L-cysteine is added to 5 mL of a 2% (w/v) suspension of the protein composition at pH 7.0.

Embodiment 134 is a protein composition comprising:
a plurality of functional proteins,
wherein $H_2S$ is detectable in an amount of less than about 0.1 ppm in the
headspace after about 24 hours at 25° C. when L-cysteine is not added to 5 mL of a 2% (w/v) suspension of the protein composition at pH 7.0.

Embodiment 135 is the protein composition of embodiment 134, wherein $H_2S$ is detectable in an amount of at least about 0.2 ppm in the headspace about 24 hours at 25° C. after about 25 mM L-cysteine is added to 5 mL of a 2% (w/v) suspension of the protein composition at pH 7.0.

Embodiment 136 is the protein composition of any one of embodiments 129-127, wherein the protein composition comprises at least about 35%, on a dry weight basis, of compounds larger than 5 kDa.

Embodiment 137 is the protein composition of any one of embodiments 129-136, wherein the protein composition transitions to a gel upon heating to 65° C.

Embodiment 138 is the protein composition of any one of embodiments 129-137, wherein the protein composition is at least about 80% denatured after about 20 minutes at about 85° C.

Embodiment 139 is the protein composition of any one of embodiments 129-138, wherein the protein composition forms a gel with a storage modulus of at least about 100 Pa when heated at or above about 85° C. for about 20 minutes.

Embodiment 140 is the protein composition of any one of embodiments 129-139, wherein the protein composition can form a gel between about pH 5.5 and about pH 10.0.

Embodiment 141 is the protein composition of any one of embodiments 129-140, wherein the protein composition can form a gel in solutions with ionic strength below about 0.5 M, wherein the ionic strength is calculated based on the concentration of non-protein solutes.

Embodiment 142 is the protein composition of any one of embodiments 129-141, wherein the protein composition has a particle size distribution D10 of less than about 0.1 μm.

Embodiment 143 is the protein composition of any one of embodiments 129-142, wherein the protein composition has a particle size distribution D50 of less than about 1.0 μm.

Embodiment 144 is the protein composition of any one of embodiments 129-143, wherein the protein composition has a particle size distribution D90 of less than about 5 μm.

Embodiment 145 is the protein composition of any one of embodiments 129-144, wherein the protein composition has an emulsion activity index of greater than or equal to about 50 $m^2$/g protein across about pH 4.0 to about pH 8.0.

Embodiment 146 is the protein composition of any one of embodiments 129 or 131-145, wherein the protein composition has a buffering capacity of less than about 2.5 mmol NaOH per gram dry solids Embodiment 147 is the protein composition of any one of embodiments 129-146, wherein the protein composition displays activity in one or more multi-step metabolic pathways.

Embodiment 148 is the protein composition of any one of embodiments 129-147, wherein the plurality of functional proteins comprises at least 10 different functional proteins.

Embodiment 149 is the protein composition of any one of embodiments 129-148, wherein the plurality of functional proteins comprises at least 20 different functional proteins.

Embodiment 150 is the protein composition of any one of embodiments 129-149, wherein the plurality of functional proteins comprises at least 50 different functional proteins.

Embodiment 151 is the protein composition of any one of embodiments 129-150, wherein the plurality of functional proteins comprises functional microbial proteins.

Embodiment 152 is the protein composition of any one of embodiments 129-151, wherein the plurality of functional proteins comprises functional fungal proteins.

Embodiment 153 is the protein composition of any one of embodiments 129-152, wherein the plurality of functional proteins comprises functional bacterial proteins.

Embodiment 154 is the protein composition of any one of embodiments 129-153, wherein the plurality of functional proteins comprises functional proteins from *Saccharomyces, Pichia, Candida, Hansenula, Torulopsis, Kluyveromyces, Yarrowia, Aspergillus, Trichoderma*, or *Fusarium*.

Embodiment 155 is the protein composition of any one of embodiments 129-154, wherein the plurality of functional proteins comprises functional proteins from *Saccharomyces cerevisiae, Pichia pastoris, Candida boidinii, Hansenula polymorpha, Kluyveromyces lactis, Yarrowia lipolytica*, or *Fusarium venenatum*.

Embodiment 156 is the protein composition of any one of embodiments 129-155, wherein the plurality of functional proteins comprises functional proteins from *Bacillus, Escherichia, Lactobacillus, Corynebacterium, Pseudomonas*, or *Methanococcus*.

Embodiment 157 is the protein composition of any one of embodiments 129-156, wherein the plurality of functional proteins comprises functional proteins from *E. coli, Bacillus subtilis, Lactobacillus lactis, Corynebacterium glutamicum, Pseudomonas fluorescens*, or *Methanococcus maripaludis*.

Embodiment 158 is the protein composition of any one of embodiments 129-157, wherein the plurality of functional proteins comprises one or more heterologous functional proteins.

Embodiment 159 is the protein composition of any one of embodiments 129 or 136-158, wherein the protein composition comprises at least about 40%, on a dry weight basis, of compounds larger than 5 kDa.

Embodiment 160 is the protein composition of any one of embodiments 129 or 136-158, wherein the protein composition comprises at least about 50%, on a dry weight basis, of compounds larger than 5 kDa.

Embodiment 161 is the protein composition of any one of embodiments 129 or 136-158, wherein the protein composition comprises at least about 60%, on a dry weight basis, of compounds larger than 5 kDa.

Embodiment 162 is the protein composition of any one of embodiments 129 or 136-158, wherein the protein composition comprises at least about 70%, on a dry weight basis, of compounds larger than 5 kDa.

Embodiment 163 is the protein composition of any one of embodiments 129 or 136-158, wherein the protein composition comprises at least about 80%, on a dry weight basis, of compounds larger than 5 kDa.

Embodiment 164 is the protein composition of any one of embodiments 129 or 136-163, wherein the compounds larger than 5 kDa are compounds larger than 10 kDa.

Embodiment 165 is the protein composition of any one of embodiments 129 or 136-163, wherein the compounds larger than 5 kDa are compounds larger than 15 kDa.

Embodiment 166 is the protein composition of any one of embodiments 129 or 136-163, wherein the compounds larger than 5 kDa are compounds larger than 20 kDa.

Embodiment 167 is the protein composition of any one of embodiments 129 or 136-163, wherein the compounds larger than 5 kDa are compounds larger than 25 kDa.

Embodiment 168 is the protein composition of any one of embodiments 129-167, wherein the protein composition does not comprise one or more compounds selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment169 is the protein composition of any one of embodiments 129-168, wherein at least about 50% of the protein in the protein composition falls between about 10 kDa and about 200 kDa.

Embodiment 170 is a *Saccharomyces cerevisiae* protein composition comprising:
  a plurality of functional *Saccharomyces cerevisiae* proteins,
  wherein the *Saccharomyces cerevisiae* protein composition comprises at least about 35%, on a dry weight basis, compounds larger than 5 kDa, and
  wherein the *Saccharomyces cerevisiae* protein composition exhibits two or more characteristics selected from the group consisting of: $H_2S$ is detectable in an amount of less than about 0.1 ppm when L-cysteine is not added to the *Saccharomyces cerevisiae* protein composition, and $H_2S$ is detectable in an amount of at least about 0.2 ppm in the headspace about 24 hours at 25° C. after about 25 mM L-cysteine is added to the *Saccharomyces cerevisiae* protein composition; the *Saccharomyces cerevisiae* protein composition forms a gel upon heating to 65° C.; the *Saccharomyces cerevisiae* protein composition has a particle size distribution D10, D50, and D90 of less than 0.1 µm, 1.0 µm and 5 µm, respectively; the *Saccharomyces cerevisiae* protein composition is least about 80% denatured after about 20 minutes at about 85° C.; the *Saccharomyces cerevisiae* protein composition forms a gel with a storage modulus of at least about 100 Pa when heated at or above about 85° C. for about 20 minutes; the *Saccharomyces cerevisiae* protein composition forms a gel between about pH 5.5 and about pH 10.0; the *Saccharomyces cerevisiae* protein composition forms a gel in solutions with ionic strength below about 0.5 M, wherein the ionic strength is calculated based on the concentration of non-protein solutes; and the *Saccharomyces cerevisiae* protein composition has an emulsion activity index of greater than or equal to about 50 $m^2/g$ protein across about pH 4.0 to about pH 8.0.

Embodiment 171 is the *Saccharomyces cerevisiae* protein composition of embodiment 170, wherein the *Saccharomyces cerevisiae* protein composition exhibits three or more characteristics selected from the group consisting of: $H_2S$ is detectable in an amount of less than about 0.1 ppm when L-cysteine is not added to the *Saccharomyces cerevisiae* protein composition, and $H_2S$ is detectable in an amount of at least about 0.2 ppm in the headspace about 24 hours at 25° C. after about 25 mM L-cysteine is added to the *Saccharomyces cerevisiae* protein composition; the *Saccharomyces cerevisiae* protein composition forms a gel upon heating to 65° C.; the *Saccharomyces cerevisiae* protein composition has a particle size distribution D10, D50, and D90 of less than 0.1 µm, 1.0 µm and 5 µm, respectively; the *Saccharomyces cerevisiae* protein composition is least about 80% denatured after about 20 minutes at about 85° C.; the *Saccharomyces cerevisiae* protein composition forms a gel with a storage modulus of at least about 100 Pa when heated at or above about 85° C. for about 20 minutes; the *Saccharomyces cerevisiae* protein composition forms a gel between about pH 5.5 and about pH 10.0; the *Saccharomyces cerevisiae* protein composition forms a gel in solutions with ionic strength below about 0.5 M, wherein the ionic strength is calculated based on the concentration of non-protein solutes; and the *Saccharomyces cerevisiae* protein composition has an emulsion activity index of greater than or equal to about 50 $m^2/g$ protein across about pH 4.0 to about pH 8.0.

Embodiment 172 is the *Saccharomyces cerevisiae* protein composition of embodiment 170, wherein the *Saccharomyces cerevisiae* protein composition exhibits four or more characteristics selected from the group consisting of: $H_2S$ is detectable in an amount of less than about 0.1 ppm when L-cysteine is not added to the *Saccharomyces cerevisiae* protein composition, and $H_2S$ is detectable in an amount of at least about 0.2 ppm in the headspace about 24 hours at 25° C. after about 25 mM L-cysteine is added to the *Saccharomyces cerevisiae* protein composition; the *Saccharomyces cerevisiae* protein composition forms a gel upon heating to 65° C.; the *Saccharomyces cerevisiae* protein composition has a particle size distribution D10, D50, and D90 of less than 0.1 µm, 1.0 µm and 5 µm, respectively; the *Saccharomyces cerevisiae* protein composition is least about 80% denatured after about 20 minutes at about 85° C.; the *Saccharomyces cerevisiae* protein composition forms a gel with a storage modulus of at least about 100 Pa when heated at or above about 85° C. for about 20 minutes; the *Saccharomyces cerevisiae* protein composition forms a gel between about pH 5.5 and about pH 10.0; the *Saccharomyces cerevisiae* protein composition forms a gel in solutions with ionic strength below about 0.5 M, wherein the ionic strength is calculated based on the concentration of non-protein solutes; and the *Saccharomyces cerevisiae* protein composition has an emulsion activity index of greater than or equal to about 50 m$^2$/g protein across about pH 4.0 to about pH 8.0.

Embodiment 173 is the *Saccharomyces cerevisiae* protein composition of embodiment 170, wherein the *Saccharomyces cerevisiae* protein composition exhibits five or more characteristics selected from the group consisting of: H$_2$S is detectable in an amount of less than about 0.1 ppm when L-cysteine is not added to the *Saccharomyces cerevisiae* protein composition, and H$_2$S is detectable in an amount of at least about 0.2 ppm in the headspace about 24 hours at 25° C. after about 25 mM L-cysteine is added to the *Saccharomyces cerevisiae* protein composition; the *Saccharomyces cerevisiae* protein composition forms a gel upon heating to 65° C.; the *Saccharomyces cerevisiae* protein composition has a particle size distribution D10, D50, and D90 of less than 0.1 μm, 1.0 μm and 5 μm, respectively; the *Saccharomyces cerevisiae* protein composition is least about 80% denatured after about 20 minutes at about 85° C.; the *Saccharomyces cerevisiae* protein composition forms a gel with a storage modulus of at least about 100 Pa when heated at or above about 85° C. for about 20 minutes; the *Saccharomyces cerevisiae* protein composition forms a gel between about pH 5.5 and about pH 10.0; the *Saccharomyces cerevisiae* protein composition forms a gel in solutions with ionic strength below about 0.5 M, wherein the ionic strength is calculated based on the concentration of non-protein solutes; and the *Saccharomyces cerevisiae* protein composition has an emulsion activity index of greater than or equal to about 50 m$^2$/g protein across about pH 4.0 to about pH 8.0.

Embodiment 174 is the *Saccharomyces cerevisiae* protein composition of embodiment 170, wherein the *Saccharomyces cerevisiae* protein composition exhibits six or more characteristics selected from the group consisting of: H$_2$S is detectable in an amount of less than about 0.1 ppm when L-cysteine is not added to the *Saccharomyces cerevisiae* protein composition, and H$_2$S is detectable in an amount of at least about 0.2 ppm in the headspace about 24 hours at 25° C. after about 25 mM L-cysteine is added to the *Saccharomyces cerevisiae* protein composition; the *Saccharomyces cerevisiae* protein composition forms a gel upon heating to 65° C.; the *Saccharomyces cerevisiae* protein composition has a particle size distribution D10, D50, and D90 of less than 0.1 μm, 1.0 μm and 5 μm, respectively; the *Saccharomyces cerevisiae* protein composition is least about 80% denatured after about 20 minutes at about 85° C.; the *Saccharomyces cerevisiae* protein composition forms a gel with a storage modulus of at least about 100 Pa when heated at or above about 85° C. for about 20 minutes; the *Saccharomyces cerevisiae* protein composition forms a gel between about pH 5.5 and about pH 10.0; the *Saccharomyces cerevisiae* protein composition forms a gel in solutions with ionic strength below about 0.5 M, wherein the ionic strength is calculated based on the concentration of non-protein solutes; and the *Saccharomyces cerevisiae* protein composition has an emulsion activity index of greater than or equal to about 50 m$^2$/g protein across about pH 4.0 to about pH 8.0.

Embodiment 175 is the *Saccharomyces cerevisiae* protein composition of embodiment 170, wherein the *Saccharomyces cerevisiae* protein composition exhibits seven or more characteristics selected from the group consisting of: H$_2$S is detectable in an amount of less than about 0.1 ppm when L-cysteine is not added to the *Saccharomyces cerevisiae* protein composition, and H$_2$S is detectable in an amount of at least about 0.2 ppm in the headspace about 24 hours at 25° C. after about 25 mM L-cysteine is added to the *Saccharomyces cerevisiae* protein composition; the *Saccharomyces cerevisiae* protein composition forms a gel upon heating to 65° C.; the *Saccharomyces cerevisiae* protein composition has a particle size distribution D10, D50, and D90 of less than 0.1 μm, 1.0 μm and 5 μm, respectively; the *Saccharomyces cerevisiae* protein composition is least about 80% denatured after about 20 minutes at about 85° C.; the *Saccharomyces cerevisiae* protein composition forms a gel with a storage modulus of at least about 100 Pa when heated at or above about 85° C. for about 20 minutes; the *Saccharomyces cerevisiae* protein composition forms a gel between about pH 5.5 and about pH 10.0; the *Saccharomyces cerevisiae* protein composition forms a gel in solutions with ionic strength below about 0.5 M, wherein the ionic strength is calculated based on the concentration of non-protein solutes; and the *Saccharomyces cerevisiae* protein composition has an emulsion activity index of greater than or equal to about 50 m$^2$/g protein across about pH 4.0 to about pH 8.0.

Embodiment 176 is the *Saccharomyces cerevisiae* protein composition of embodiment 170, wherein the *Saccharomyces cerevisiae* protein composition exhibits the characteristics:

H$_2$S is detectable in an amount of less than about 0.1 ppm when L-cysteine is not added to the *Saccharomyces cerevisiae* protein composition, and H$_2$S is detectable in an amount of at least about 0.2 ppm in the headspace about 24 hours at 25° C. after about 25 mM L-cysteine is added to the *Saccharomyces cerevisiae* protein composition, wherein the *Saccharomyces cerevisiae* protein composition forms a gel upon heating to 65° C., wherein the *Saccharomyces cerevisiae* protein composition has a particle size distribution D10, D50, and D90 of less than 0.1 μm, 1.0 μm and 5 μm, respectively, wherein the *Saccharomyces cerevisiae* protein composition is least about 80% denatured after about 20 minutes at about 85° C., wherein the *Saccharomyces cerevisiae* protein composition forms a gel with a storage modulus of at least about 100 Pa when heated at or above about 85° C. for about 20 minutes, wherein the *Saccharomyces cerevisiae* protein composition forms a gel between about pH 5.5 and about pH 10.0, wherein the *Saccharomyces cerevisiae* protein composition forms a gel in solutions with ionic strength below about 0.5 M, wherein the ionic strength is calculated based on the concentration of non-protein solutes, and wherein the *Saccharomyces cerevisiae* protein composition has an emulsion activity index of greater than or equal to about 50 m$^2$/g protein across about pH 4.0 to about pH 8.0.

Embodiment 177 is the *Saccharomyces cerevisiae* protein composition of any one of embodiments 170-176, wherein the protein composition comprises at least about 40%, on a dry weight basis, of compounds larger than 5 kDa.

Embodiment 178 is the *Saccharomyces cerevisiae* protein composition of any one of embodiments 170-176, wherein the protein composition comprises at least about 50%, on a dry weight basis, of compounds larger than 5 kDa.

Embodiment 179 is the *Saccharomyces cerevisiae* protein composition of any one of embodiments 170-176, wherein the protein composition comprises at least about 60%, on a dry weight basis, of compounds larger than 5 kDa.

Embodiment 180 is the *Saccharomyces cerevisiae* protein composition of any one of embodiments 170-176, wherein the protein composition comprises at least about 70%, on a dry weight basis, of compounds larger than 5 kDa.

Embodiment 181 is the *Saccharomyces cerevisiae* protein composition of any one of embodiments 170-176, wherein the protein composition comprises at least about 80%, on a dry weight basis, of compounds larger than 5 kDa.

Embodiment 182 is the *Saccharomyces cerevisiae* protein composition of any one of embodiments 170-181, wherein the compounds larger than 5 kDa are compounds larger than 10 kDa.

Embodiment 183 is the *Saccharomyces cerevisiae* protein composition of any one of embodiments 170-181, wherein the compounds larger than 5 kDa are compounds larger than 15 kDa.

Embodiment 184 is the *Saccharomyces cerevisiae* protein composition of any one of embodiments 170-181, wherein the compounds larger than 5 kDa are compounds larger than 20 kDa.

Embodiment 185 is the *Saccharomyces cerevisiae* protein composition of any one of embodiments 170-181, wherein the compounds larger than 5 kDa are compounds larger than 25 kDa.

Embodiment 186 is the *Saccharomyces cerevisiae* protein composition of any one of embodiments 170-185, wherein the protein composition does not comprise one or more compounds selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment 187 is the *Saccharomyces cerevisiae* protein composition of any one of embodiments 170-186, wherein at least about 50% of the protein in the protein composition falls between about 10 kDa and about 200 kDa.

Embodiment 188 is a *Pichia pastoris* protein composition comprising:
  a plurality of functional *Pichia pastoris* proteins,
  wherein the *Pichia pastoris* protein composition comprises at least about 35%, on a dry weight basis, compounds larger than 5 kDa, and
  wherein the *Pichia pastoris* protein composition exhibits two or more characteristics selected from the group consisting of: $H_2S$ is detectable in an amount of less than about 0.1 ppm when L-cysteine is not added to the *Pichia pastoris* protein composition, and $H_2S$ is detectable in an amount of at least about 0.2 ppm in the headspace about 24 hours at 25° C. after about 25 mM L-cysteine is added to the *Pichia pastoris* protein composition; the *Pichia pastoris* protein composition forms a gel upon heating to 65° C.; the *Pichia pastoris* protein composition has a particle size distribution D10, D50, and D90 of less than 0.1 µm, 1.0 µm and 5 µm, respectively; the *Pichia pastoris* protein composition is least about 80% denatured after about 20 minutes at about 85° C.; the *Pichia pastoris* protein composition forms a gel with a storage modulus of at least about 100 Pa when heated at or above about 85° C. for about 20 minutes; the *Pichia pastoris* protein composition forms a gel between about pH 5.5 and about pH 10.0; the *Pichia pastoris* protein composition forms a gel in solutions with ionic strength below about 0.5 M, wherein the ionic strength is calculated based on the concentration of non-protein solutes; and the *Pichia pastoris* protein composition has an emulsion activity index of greater than or equal to about 50 $m^2/g$ protein across about pH 4.0 to about pH 8.0.

Embodiment 189 is the *Pichia pastoris* protein composition of embodiment 188, wherein the *Pichia pastoris* protein composition exhibits three or more characteristics selected from the group consisting of: $H_2S$ is detectable in an amount of less than about 0.1 ppm when L-cysteine is not added to the *Pichia pastoris* protein composition, and $H_2S$ is detectable in an amount of at least about 0.2 ppm in the headspace about 24 hours at 25° C. after about 25 mM L-cysteine is added to the *Pichia pastoris* protein composition; the *Pichia pastoris* protein composition forms a gel upon heating to 65° C.; the *Pichia pastoris* protein composition has a particle size distribution D10, D50, and D90 of less than 0.1 µm, 1.0 µm and 5 µm, respectively; the *Pichia pastoris* protein composition is least about 80% denatured after about 20 minutes at about 85° C.; the *Pichia pastoris* protein composition forms a gel with a storage modulus of at least about 100 Pa when heated at or above about 85° C. for about 20 minutes; the *Pichia pastoris* protein composition forms a gel between about pH 5.5 and about pH 10.0; the *Pichia pastoris* protein composition forms a gel in solutions with ionic strength below about 0.5 M, wherein the ionic strength is calculated based on the concentration of non-protein solutes; and the *Pichia pastoris* protein composition has an emulsion activity index of greater than or equal to about 50 $m^2/g$ protein across about pH 4.0 to about pH 8.0.

Embodiment 190 is the *Pichia pastoris* protein composition of embodiment 188, wherein the *Pichia pastoris* protein composition exhibits four or more characteristics selected from the group consisting of: $H_2S$ is detectable in an amount of less than about 0.1 ppm when L-cysteine is not added to the *Pichia pastoris* protein composition, and $H_2S$ is detectable in an amount of at least about 0.2 ppm in the headspace about 24 hours at 25° C. after about 25 mM L-cysteine is added to the *Pichia pastoris* protein composition; the *Pichia pastoris* protein composition forms a gel upon heating to 65° C.; the *Pichia pastoris* protein composition has a particle size distribution D10, D50, and D90 of less than 0.1 µm, 1.0 µm and 5 µm, respectively; the *Pichia pastoris* protein composition is least about 80% denatured after about 20 minutes at about 85° C.;

the *Pichia pastoris* protein composition forms a gel with a storage modulus of at least about 100 Pa when heated at or above about 85° C. for about 20 minutes; the *Pichia pastoris* protein composition forms a gel between about pH 5.5 and about pH 10.0; the *Pichia pastoris* protein composition forms a gel in solutions with ionic strength below about 0.5 M, wherein the ionic strength is calculated based on the concentration of non-protein solutes; and the *Pichia pastoris* protein composition has an emulsion activity index of greater than or equal to about 50 m²/g protein across about pH 4.0 to about pH 8.0.

Embodiment 191 is the *Pichia pastoris* protein composition of embodiment 188, wherein the *Pichia pastoris* protein composition exhibits five or more characteristics selected from the group consisting of: H₂S is detectable in an amount of less than about 0.1 ppm when L-cysteine is not added to the *Pichia pastoris* protein composition, and H₂S is detectable in an amount of at least about 0.2 ppm in the headspace about 24 hours at 25° C. after about 25 mM L-cysteine is added to the *Pichia pastoris* protein composition; the *Pichia pastoris* protein composition forms a gel upon heating to 65° C.; the *Pichia pastoris* protein composition has a particle size distribution D10, D50, and D90 of less than 0.1 µm, 1.0 µm and 5 µm, respectively; the *Pichia pastoris* protein composition is least about 80% denatured after about 20 minutes at about 85° C.; the *Pichia pastoris* protein composition forms a gel with a storage modulus of at least about 100 Pa when heated at or above about 85° C. for about 20 minutes; the *Pichia pastoris* protein composition forms a gel between about pH 5.5 and about pH 10.0; the *Pichia pastoris* protein composition forms a gel in solutions with ionic strength below about 0.5 M, wherein the ionic strength is calculated based on the concentration of non-protein solutes; and the *Pichia pastoris* protein composition has an emulsion activity index of greater than or equal to about 50 m²/g protein across about pH 4.0 to about pH 8.0.

Embodiment 192 is the *Pichia pastoris* protein composition of embodiment 188, wherein the *Pichia pastoris* protein composition exhibits six or more characteristics selected from the group consisting of: H₂S is detectable in an amount of less than about 0.1 ppm when L-cysteine is not added to the *Pichia pastoris* protein composition, and H₂S is detectable in an amount of at least about 0.2 ppm in the headspace about 24 hours at 25° C. after about 25 mM L-cysteine is added to the *Pichia pastoris* protein composition; the *Pichia pastoris* protein composition forms a gel upon heating to 65° C.; the *Pichia pastoris* protein composition has a particle size distribution D10, D50, and D90 of less than 0.1 µm, 1.0 µm and 5 µm, respectively; the *Pichia pastoris* protein composition is least about 80% denatured after about 20 minutes at about 85° C.; the *Pichia pastoris* protein composition forms a gel with a storage modulus of at least about 100 Pa when heated at or above about 85° C. for about 20 minutes; the *Pichia pastoris* protein composition forms a gel between about pH 5.5 and about pH 10.0; the *Pichia pastoris* protein composition forms a gel in solutions with ionic strength below about 0.5 M, wherein the ionic strength is calculated based on the concentration of non-protein solutes; and the *Pichia pastoris* protein composition has an emulsion activity index of greater than or equal to about 50 m²/g protein across about pH 4.0 to about pH 8.0.

Embodiment 193 is the *Pichia pastoris* protein composition of embodiment 188, wherein the *Pichia pastoris* protein composition exhibits seven or more characteristics selected from the group consisting of: H₂S is detectable in an amount of less than about 0.1 ppm when L-cysteine is not added to the *Pichia pastoris* protein composition, and H₂S is detectable in an amount of at least about 0.2 ppm in the headspace about 24 hours at 25° C. after about 25 mM L-cysteine is added to the *Pichia pastoris* protein composition; the *Pichia pastoris* protein composition forms a gel upon heating to 65° C.; the *Pichia pastoris* protein composition has a particle size distribution D10, D50, and D90 of less than 0.1 µm, 1.0 µm and 5 µm, respectively; the *Pichia pastoris* protein composition is least about 80% denatured after about 20 minutes at about 85° C.; the *Pichia pastoris* protein composition forms a gel with a storage modulus of at least about 100 Pa when heated at or above about 85° C. for about 20 minutes; the *Pichia pastoris* protein composition forms a gel between about pH 5.5 and about pH 10.0; the *Pichia pastoris* protein composition forms a gel in solutions with ionic strength below about 0.5 M, wherein the ionic strength is calculated based on the concentration of non-protein solutes; and the *Pichia pastoris* protein composition has an emulsion activity index of greater than or equal to about 50 m²/g protein across about pH 4.0 to about pH 8.0.

Embodiment 194 is the *Pichia pastoris* protein composition of embodiment 188, wherein the *Pichia pastoris* protein composition exhibits the characteristics:

H₂S is detectable in an amount of less than about 0.1 ppm when L-cysteine is not added to the *Pichia pastoris* protein composition, and H₂S is detectable in an amount of at least about 0.2 ppm in the headspace about 24 hours at 25° C. after about 25 mM L-cysteine is added to the *Pichia pastoris* protein composition, wherein the *Pichia pastoris* protein composition forms a gel upon heating to 65° C., wherein the *Pichia pastoris* protein composition has a particle size distribution D10, D50, and D90 of less than 0.1 µm, 1.0 µm and 5 µm, respectively, wherein the *Pichia pastoris* protein composition is least about 80% denatured after about 20 minutes at about 85° C., wherein the *Pichia pastoris* protein composition forms a gel with a storage modulus of at least about 100 Pa when heated at or above about 85° C. for about 20 minutes, wherein the *Pichia pastoris* protein composition forms a gel between about pH 5.5 and about pH 10.0, wherein the *Pichia pastoris* protein composition forms a gel in solutions with ionic strength below about 0.5 M, wherein the ionic strength is calculated based on the concentration of non-protein solutes, and wherein the *Pichia pastoris* protein composition has an emulsion activity index of greater than or equal to about 50 m²/g protein across about pH 4.0 to about pH 8.0.

Embodiment 195 is the *Pichia pastoris* protein composition of any one of embodiments 188-194, wherein the protein composition comprises at least about 40%, on a dry weight basis, of compounds larger than 5 kDa.

Embodiment 196 is the *Pichia pastoris* protein composition of any one of embodiments 188-194, wherein the protein composition comprises at least about 50%, on a dry weight basis, of compounds larger than 5 kDa.

Embodiment 197 is the *Pichia pastoris* protein composition of any one of embodiments 188-194, wherein the protein composition comprises at least about 60%, on a dry weight basis, of compounds larger than 5 kDa.

Embodiment 198 is the *Pichia pastoris* protein composition of any one of embodiments 188-194, wherein the protein composition comprises at least about 70%, on a dry weight basis, of compounds larger than 5 kDa.

Embodiment 199 is the *Pichia pastoris* protein composition of any one of embodiments 188-194, wherein the protein composition comprises at least about 80%, on a dry weight basis, of compounds larger than 5 kDa.

Embodiment 200 is the *Pichia pastoris* protein composition of any one of embodiments 188-199, wherein the compounds larger than 5 kDa are compounds larger than 10 kDa.

Embodiment 201 is the *Pichia pastoris* protein composition of any one of embodiments 188-199, wherein the compounds larger than 5 kDa are compounds larger than 15 kDa.

Embodiment 202 is the *Pichia pastoris* protein composition of any one of embodiments 188-199, wherein the compounds larger than 5 kDa are compounds larger than 20 kDa.

Embodiment 203 is the *Pichia pastoris* protein composition of any one of embodiments 188-199, wherein the compounds larger than 5 kDa are compounds larger than 25 kDa.

Embodiment 204 is the *Pichia pastoris* protein composition of any one of embodiments 188-203, wherein the protein composition does not comprise one or more compounds selected from the group consisting of cysteine, 1-hexanol, 2-butylfuran, 2-methyl-2-pentenal, 3-octanone, ethyl acetate, 2-ethyl-furan, 2-pentylfuran, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment 205 is the *Pichia pastoris* protein composition of any one of embodiments 188-204, wherein at least about 50% of the protein in the protein composition falls between about 10 kDa and about 200 kDa.

Embodiment 206 is an *Escherichia coli* protein composition comprising:
a plurality of functional *Escherichia coli* proteins,
wherein the *Escherichia coli* protein composition comprises at least about 35%, on a dry weight basis, compounds larger than 5 kDa, and wherein the *Escherichia coli* protein composition exhibits two or more characteristics selected from the group consisting of: $H_2S$ is detectable in an amount of less than about 0.1 ppm when L-cysteine is not added to the *Escherichia coli* protein composition, and $H_2S$ is detectable in an amount of at least about 0.2 ppm in the headspace about 24 hours at 25° C. after about 25 mM L-cysteine is added to the *Escherichia coli* protein composition; the *Escherichia coli* protein composition forms a gel upon heating to 65° C.; the *Escherichia coli* protein composition has a particle size distribution D10, D50, and D90 of less than 0.1 μm, 1.0 μm and 5 μm, respectively; the *Escherichia coli* protein composition is least about 80% denatured after about 20 minutes at about 85° C.; the *Escherichia coli* protein composition forms a gel with a storage modulus of at least about 100 Pa when heated at or above about 85° C. for about 20 minutes; the *Escherichia coli* protein composition forms a gel between about pH 5.5 and about pH 10.0; the *Escherichia coli* protein composition forms a gel in solutions with ionic strength below about 0.5 M, wherein the ionic strength is calculated based on the concentration of non-protein solutes; and the *Escherichia coli* protein composition has an emulsion activity index of greater than or equal to about 50 m²/g protein across about pH 4.0 to about pH 8.0.

Embodiment 207 is the *Escherichia coli* protein composition of embodiment 206, wherein the *Escherichia coli* protein composition exhibits three or more characteristics selected from the group consisting of: $H_2S$ is detectable in an amount of less than about 0.1 ppm when L-cysteine is not added to the *Escherichia coli* protein composition, and $H_2S$ is detectable in an amount of at least about 0.2 ppm in the headspace about 24 hours at 25° C. after about 25 mM L-cysteine is added to the *Escherichia coli* protein composition; the *Escherichia coli* protein composition forms a gel upon heating to 65° C.; the *Escherichia coli* protein composition has a particle size distribution D10, D50, and D90 of less than 0.1 μm, 1.0 μm and 5 μm, respectively; the *Escherichia coli* protein composition is least about 80% denatured after about 20 minutes at about 85° C.; the *Escherichia coli* protein composition forms a gel with a storage modulus of at least about 100 Pa when heated at or above about 85° C. for about 20 minutes; the *Escherichia coli* protein composition forms a gel between about pH 5.5 and about pH 10.0; the *Escherichia coli* protein composition forms a gel in solutions with ionic strength below about 0.5 M, wherein the ionic strength is calculated based on the concentration of non-protein solutes; and the *Escherichia coli* protein composition has an emulsion activity index of greater than or equal to about 50 m²/g protein across about pH 4.0 to about pH 8.0.

Embodiment 208 is the *Escherichia coli* protein composition of embodiment 206, wherein the *Escherichia coli* protein composition exhibits four or more characteristics selected from the group consisting of: $H_2S$ is detectable in an amount of less than about 0.1 ppm when L-cysteine is not added to the *Escherichia coli* protein composition, and $H_2S$ is detectable in an amount of at least about 0.2 ppm in the headspace about 24 hours at 25° C. after about 25 mM L-cysteine is added to the *Escherichia coli* protein composition; the *Escherichia coli* protein composition forms a gel upon heating to 65° C.; the *Escherichia coli* protein composition has a particle size distribution D10, D50, and D90 of less than 0.1 μm, 1.0 μm and 5 μm, respectively; the *Escherichia coli* protein composition is least about 80% denatured after about 20 minutes at about 85° C.; the *Escherichia coli* protein composition forms a gel with a storage modulus of at least about 100 Pa when heated at or above about 85° C. for about 20 minutes; the *Escherichia coli* protein composition forms a gel between about pH 5.5 and about pH 10.0; the *Escherichia coli* protein composition forms a gel in solutions with ionic strength below about 0.5 M, wherein the ionic strength is calculated based on the concentration of non-protein solutes; and the *Escherichia coli* protein composition has an emulsion activity index of greater than or equal to about 50 m²/g protein across about pH 4.0 to about pH 8.0.

Embodiment 209 is the *Escherichia coli* protein composition of embodiment 206, wherein the *Escherichia coli* protein composition exhibits five or more characteristics selected from the group consisting of: $H_2S$ is detectable in an amount of less than about 0.1 ppm when L-cysteine is not added to the *Escherichia coli* protein composition, and $H_2S$ is detectable in an amount of at least about 0.2 ppm in the headspace about 24 hours at 25° C after about 25 mM L-cysteine is added to the *Escherichia coli* protein composition; the *Escherichia coli* protein composition forms a gel upon heating to 65° C.; the *Escherichia coli* protein composition has a particle size distribution D10, D50, and D90 of less than 0.1 µm, 1.0 µm and 5 µm, respectively; the *Escherichia coli* protein composition is least about 80% denatured after about 20 minutes at about 85° C.; the *Escherichia coli* protein composition forms a gel with a storage modulus of at least about 100 Pa when heated at or above about 85° C. for about 20 minutes; the *Escherichia coli* protein composition forms a gel between about pH 5.5 and about pH 10.0; the *Escherichia coli* protein composition forms a gel in solutions with ionic strength below about 0.5 M, wherein the ionic strength is calculated based on the concentration of non-protein solutes; and the *Escherichia coli* protein composition has an emulsion activity index of greater than or equal to about 50 $m^2$/g protein across about pH 4.0 to about pH 8.0.

Embodiment 210 is the *Escherichia coli* protein composition of embodiment 206, wherein the *Escherichia coli* protein composition exhibits six or more characteristics selected from the group consisting of: $H_2S$ is detectable in an amount of less than about 0.1 ppm when L-cysteine is not added to the *Escherichia coli* protein composition, and $H_2S$ is detectable in an amount of at least about 0.2 ppm in the headspace about 24 hours at 25° C. after about 25 mM L-cysteine is added to the *Escherichia coli* protein composition; the *Escherichia coli* protein composition forms a gel upon heating to 65° C.; the *Escherichia coli* protein composition has a particle size distribution D10, D50, and D90 of less than 0.1 µm, 1.0 µm and 5 µm, respectively; the *Escherichia coli* protein composition is least about 80% denatured after about 20 minutes at about 85° C.; the *Escherichia coli* protein composition forms a gel with a storage modulus of at least about 100 Pa when heated at or above about 85° C. for about 20 minutes; the *Escherichia coli* protein composition forms a gel between about pH 5.5 and about pH 10.0; the *Escherichia coli* protein composition forms a gel in solutions with ionic strength below about 0.5 M, wherein the ionic strength is calculated based on the concentration of non-protein solutes; and the *Escherichia coli* protein composition has an emulsion activity index of greater than or equal to about 50 $m^2$/g protein across about pH 4.0 to about pH 8.0.

Embodiment 211 is the *Escherichia coli* protein composition of embodiment 206, wherein the *Escherichia coli* protein composition exhibits seven or more characteristics selected from the group consisting of: $H_2S$ is detectable in an amount of less than about 0.1 ppm when L-cysteine is not added to the *Escherichia coli* protein composition, and $H_2S$ is detectable in an amount of at least about 0.2 ppm in the headspace about 24 hours at 25° C. after about 25 mM L-cysteine is added to the *Escherichia coli* protein composition; the *Escherichia coli* protein composition forms a gel upon heating to 65° C.; the *Escherichia coli* protein composition has a particle size distribution D10, D50, and D90 of less than 0.1 µm, 1.0 µm and 5 µm, respectively; the *Escherichia coli* protein composition is least about 80% denatured after about 20 minutes at about 85° C.; the *Escherichia coli* protein composition forms a gel with a storage modulus of at least about 100 Pa when heated at or above about 85° C. for about 20 minutes; the *Escherichia coli* protein composition forms a gel between about pH 5.5 and about pH 10.0; the *Escherichia coli* protein composition forms a gel in solutions with ionic strength below about 0.5 M, wherein the ionic strength is calculated based on the concentration of non-protein solutes; and the *Escherichia coli* protein composition has an emulsion activity index of greater than or equal to about 50 $m^2$/g protein across about pH 4.0 to about pH 8.0.

Embodiment 212 is the *Escherichia coli* protein composition of embodiment 206, wherein the *Escherichia coli* protein composition exhibits the characteristics:
$H_2S$ is detectable in an amount of less than about 0.1 ppm when L-cysteine is not added to the *Escherichia coli* protein composition, and $H_2S$ is detectable in an amount of at least about 0.2 ppm in the headspace about 24 hours at 25° C. after about 25 mM L-cysteine is added to the *Escherichia coli* protein composition, wherein the *Escherichia coli* protein composition forms a gel upon heating to 65° C.,
wherein the *Escherichia coli* protein composition has a particle size distribution D10, D50, and D90 of less than 0.1 µm, 1.0 µm and 5 µm, respectively,
wherein the *Escherichia coli* protein composition is least about 80% denatured after about 20 minutes at about 85° C.,
wherein the *Escherichia coli* protein composition forms a gel with a storage modulus of at least about 100 Pa when heated at or above about 85° C. for about 20 minutes,
wherein the *Escherichia coli* protein composition forms a gel between about pH 5.5 and about pH 10.0,
wherein the *Escherichia coli* protein composition forms a gel in solutions with ionic strength below about 0.5 M, wherein the ionic strength is calculated based on the concentration of non-protein solutes, and
wherein the *Escherichia coli* protein composition has an emulsion activity index of greater than or equal to about 50 $m^2$/g protein across about pH 4.0 to about pH 8.0.

Embodiment 213 is the *Escherichia coli* protein composition of any one of embodiments 206-212, wherein the protein composition comprises at least about 40%, on a dry weight basis, of compounds larger than 5 kDa.

Embodiment 214 is the *Escherichia coli* protein composition of any one of embodiments 206-212, wherein the protein composition comprises at least about 50%, on a dry weight basis, of compounds larger than 5 kDa.

Embodiment 215 is the *Escherichia coli* protein composition of any one of embodiments 206-212, wherein the protein composition comprises at least about 60%, on a dry weight basis, of compounds larger than 5 kDa.

Embodiment 216 is the *Escherichia coli* protein composition of any one of embodiments 206-212, wherein the protein composition comprises at least about 70%, on a dry weight basis, of compounds larger than 5 kDa.

Embodiment 217 is the *Escherichia coli* protein composition of any one of embodiments 206-216, wherein the protein composition comprises at least about 80%, on a dry weight basis, of compounds larger than 5 kDa.

Embodiment 218 is the *Escherichia coli* protein composition of any one of embodiments 206-216, wherein the compounds larger than 5 kDa are compounds larger than 10 kDa.
Embodiment 219 is the *Escherichia coli* protein composition of any one of embodiments 206-216, wherein the compounds larger than 5 kDa are compounds larger than 15 kDa.
Embodiment 220 is the *Escherichia coli* protein composition of any one of embodiments 206-216, wherein the compounds larger than 5 kDa are compounds larger than 20 kDa.
Embodiment 221 is the *Escherichia coli* protein composition of any one of embodiments 206-216, wherein the compounds larger than 5 kDa are compounds larger than 25 kDa.
Embodiment 222 is the *Escherichia coli* protein composition of any one of embodiments 206-221, wherein the protein composition does not comprise one or more compounds selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.
Embodiment 223 is the *Escherichia coli* protein composition of any one of embodiments 206-222, wherein at least about 50% of the protein in the protein composition falls between about 10 kDa and about 200 kDa.
Embodiment 224 is a protein composition produced by a method comprising:
  a) lysing an aqueous suspension of the plurality of cells to obtain a cell lysate;
  b) clarifying the cell lysate, optionally in the presence of one or more flocculants, to obtain a clarified lysate;
  c) filtering the clarified lysate to obtain a filtered lysate;
  d) concentrating the filtered lysate to obtain a protein composition; and
  e) optionally pasteurizing the protein composition of protein to obtain a pasteurized protein composition,
  wherein steps a), b), c), d), and e) independently, are performed at a pH between about 8.5 and about 12.0.
Embodiment 225 is a protein composition produced by a method comprising:
  a) lysing an aqueous suspension of the plurality of cells to obtain a cell lysate;
  b) clarifying the cell lysate, optionally in the presence of one or more flocculants, to obtain a clarified lysate;
  c) concentrating the clarified lysate to obtain a protein composition; and
  d) optionally pasteurizing the protein composition of protein to obtain a pasteurized protein composition,
  wherein steps a), b), c), and d) independently, are performed at a pH between about 8.5 and about 12.0.
Embodiment 226 is a protein composition produced by a method comprising:
  a) lysing an aqueous suspension of the plurality of cells to obtain a cell lysate;
  b) clarifying the cell lysate, optionally in the presence of one or more flocculants, to obtain a clarified lysate;
  c) filtering the clarified lysate to obtain a protein composition; and
  d) optionally pasteurizing the protein composition, to obtain a pasteurized protein composition,
  wherein steps a), b), c), and d) independently, are performed at a pH between about 8.5 and about 12.0.
Embodiment 227 is a protein composition produced by a method comprising:
  a) lysing an aqueous suspension of the plurality of cells to obtain a cell lysate;
  b) clarifying the cell lysate, optionally in the presence of one or more flocculants, to obtain a clarified lysate;
  c) filtering the clarified lysate using microfiltration to obtain a first filtered lysate;
  d) filtering the first filtered lysate using diafiltration to obtain a second filtered lysate;
  e) filtering the second filtered lysate using ultrafiltration obtain a third filtered lysate;
  f) filtering the third filtered lysate using diafiltration to obtain a protein composition; and
  g) optionally pasteurizing the protein composition to obtain a pasteurized protein composition,
  wherein steps a), b), c), d), e), f), and g) independently, are performed at a pH between about 8.5 and about 12.0.
Embodiment 228 is a protein composition produced by a method comprising:
  a) lysing an aqueous suspension of the plurality of cells to obtain a cell lysate;
  b) clarifying the cell lysate, optionally in the presence of one or more flocculants, to obtain a clarified lysate;
  c) filtering the clarified lysate using ultrafiltration to obtain a first filtered lysate;
  d) filtering the first filtered lysate using diafiltration to obtain a protein composition; and
  e) optionally pasteurizing the protein composition to obtain a pasteurized protein composition,
  wherein steps a), b), c), d), and e) independently, are performed at a pH between about 8.5 and about 12.0.
Embodiment 229 is a protein composition produced by a method comprising:
  a) lysing an aqueous suspension of the plurality of cells to obtain a cell lysate;
  b) filtering the cell lysate to obtain a protein composition; and
  c) optionally pasteurizing the protein composition to obtain a pasteurized protein composition,
  wherein steps a), b), and c) independently, are performed at a pH between about 8.5 and about 12.0.
Embodiment 230 is a protein composition produced by a method comprising:
  a) lysing an aqueous suspension of the plurality of cells to obtain a cell lysate;
  b) filtering the cell lysate using ultrafiltration obtain a first filtered lysate;
  c) filtering the first filtered lysate using diafiltration to obtain a protein composition; and
  d) optionally pasteurizing the protein composition to obtain a pasteurized protein composition,
  wherein steps a) b), c), and d) independently, are performed at a pH between about 8.5 and about 12.0.
Embodiment 231 is a protein composition produced by a method comprising:
  a) lysing an aqueous suspension of the plurality of cells to obtain a cell lysate;
  b) filtering the cell lysate using ultrafiltration to obtain a protein composition; and c) optionally pasteurizing the protein composition to obtain a pasteurized protein composition,
   wherein steps a), b), and c) independently, are performed at a pH between about 8.5 and about 12.0.

Embodiment 232 is the protein composition of any one of embodiments 224-228 wherein the clarifying step is performed, optionally in the presence of one or more flocculants, at a pH between about 9.0 and about 12.0.

Embodiment 233 is the protein composition of embodiment 232, wherein the clarifying step is performed at a pH between about 9.0 and about 10.0.

Embodiment 234 is the protein composition of embodiment 232, wherein the clarifying step is performed at a pH between about 10.0 and about 11.0.

Embodiment 235 is the protein composition of embodiment 232, wherein the clarifying step is performed at a pH between about 11.0 and about 12.0.

Embodiment 236 is the protein composition of any one of embodiments 224-228 or 232-235, wherein clarifying step is performed by centrifugation to less than about 20% dry solids.

Embodiment 237 is the protein composition of any one of embodiments 224-228 or 232-236, wherein the clarifying step is performed by gravity settling to less than about 20% dry solids.

Embodiment 238 is the protein composition of any one of embodiments 224-228 or 232-237, wherein the clarifying step is performed by diatomaceous earth filtration to less than about 20% dry solids.

Embodiment 239 is the protein composition of any one of embodiments 224-228 or 232-238, wherein the lysate is diluted 1:1 with water or aqueous solution of salt or buffer before clarifying, wherein the pH is between about 8.5 and about 12.0.

Embodiment 240 is the protein composition of any one of embodiments 224-228 or 232-239, wherein the cell lysate from step a) is clarified in the presence of one or more flocculants.

Embodiment 241 is the protein composition of embodiment 240, wherein the one or more flocculants comprise one or more of alkylamine epichlorohydrin, polydimethyldiallylammonium chloride, a polyamine, lime, hydrated lime, ferric chloride, ferric sulfate, ferrous sulfate, aluminum sulfate, sodium aluminate, aluminum chloride, magnesium carbonate hydroxide, calcium carbonate, calcium hydroxide, an activated silicate, a guar gum, a starch, a tannin, sodium alginate, polyaluminum sulfate, polyaluminum hydroxy chloride, BIO-FLOCK®, and a synthetic polyelectrolyte.

Embodiment 242 is the protein composition of embodiment 240, wherein the one or more flocculants are selected from the group consisting of alkylamine epichlorohydrin, polydimethyldiallylammonium chloride, a polyamine, lime, hydrated lime, ferric chloride, ferric sulfate, ferrous sulfate, aluminum sulfate, sodium aluminate, aluminum chloride, magnesium carbonate hydroxide, calcium carbonate, calcium hydroxide, an activated silicate, a guar gum, a starch, a tannin, sodium alginate, polyaluminum sulfate, polyaluminum hydroxy chloride, BIO-FLOCK®, and a synthetic polyelectrolyte.

Embodiment 243 is the method of any one of embodiments 224-242, wherein filtering comprises microfiltration.

Embodiment 244 is the method of any one of embodiments 224-243, wherein filtering comprises ultrafiltration.

Embodiment 245 is the method of any one of embodiments 224-244, wherein filtering comprises diafiltration.

Embodiment 246 is the method of embodiment 245, where diafiltration is performed for at least two diavolumes.

Embodiment 247 is the protein composition of any one of embodiments 224-246, wherein the plurality of cells comprises microbial cells.

Embodiment 248 is the protein composition of any one of embodiments 224-247, wherein the plurality of cells comprises fungal cells.

Embodiment 249 is the protein composition of embodiment 248, wherein the fungal cells are selected from the group consisting of *Saccharomyces, Pichia, Candida, Hansenula, Torulopsis, Kluyveromyces, Yarrowia*, and *Fasarium* cells.

Embodiment 250 is the protein composition of embodiment 248, wherein the fungal cells are selected from the group consisting of *Saccharomyces cerevisiae, Pichia pastoris, Candida boidinii, Hansenula polymorpha, Kluyveromyces lactis, Yarrowia lipolytica*, and *Fusarium venenatum*.

Embodiment 251 is the protein composition of any one of embodiments 224-250, wherein the plurality of cells comprises bacterial cells.

Embodiment 252 is the protein composition of embodiment 251, wherein the bacterial cells are selected from the group consisting of *Bacillus, Escherichia, Lactobacillus, Corynebacterium, Pseudomonas*, and *Methanococcus*.

Embodiment 253 is the protein composition of embodiment 251, wherein the bacterial cells are selected from the group consisting of *Escherichia coli, Bacillus subtilis, Lactobacillus lactis, Corynebacterium glutamicum, Pseudomonas fluorescens*, and *Methanococcus maripaludis*.

Embodiment 254 is the protein composition of any one of embodiments 224-253, wherein the aqueous suspension of the plurality of cells comprises from about 2% to about 25% dry solids.

Embodiment 255 is the protein composition of any one of embodiments 224-254, further comprising washing the aqueous suspension of the plurality of cells at a pH between about 8.5 and about 12.0 before step a).

Embodiment 256 is the protein composition of any one of embodiments 224-255, wherein the lysing step is performed at a temperature between about 4° C. and about 15° C.

Embodiment 257 is the protein composition of any one of embodiments 224-256, wherein the lysing step is performed biochemically.

Embodiment 258 is the protein composition of any one of embodiments 224-257, wherein the lysing step is performed chemically.

Embodiment 259 is the protein composition of any one of embodiments 224-258, wherein the lysing step is performed mechanically.

Embodiment 260 is the protein composition of any one of embodiments 224-259, wherein the lysing step is performed at a pH between about 9.0 and about 12.0.

Embodiment 261 is the protein composition of embodiment 260, wherein the lysing step is performed at a pH between about 9.0 and about 10.0.

Embodiment 262 is the protein composition of embodiment 260, wherein the lysing step is performed at a pH between about 10.0 and about 11.0.

Embodiment 263 is the protein composition of embodiment 260, wherein the lysing step is performed at a pH between about 11.0 and about 12.0.

Embodiment 264 is the protein composition of any one of embodiments 224-263, wherein the lysate is diluted 1:1 with water or aqueous solution of salt or buffer before filtering, wherein the pH is between about 8.5 and about 12.0.

Embodiment 265 is the protein composition of any one of embodiments 224-264, wherein the protein composition has a protein content of about 2 mg/mL to about 250 mg/mL.

Embodiment 266 is the protein composition of any one of embodiments 224-265, wherein the protein composition exhibits one or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 267 is the protein composition of any one of embodiments 224-265, wherein the protein composition exhibits two or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 268 is the protein composition of any one of embodiments 224-265, wherein the protein composition exhibits three or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 269 is the protein composition of any one of embodiments 224-265, wherein the protein composition exhibits four or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m$^2$/g protein across about pH 4.0 to about pH 8.0.

Embodiment 270 is the protein composition of any one of embodiments 224-265, wherein the protein composition exhibits five or more characteristics selected from the group consisting of: $H_2S$ is detectable in an amount of less than about 0.1 ppm when L-cysteine is not added to the protein composition, and $H_2S$ is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 µm, 1.0 µm and 5 µm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 271 is the protein composition of any one of embodiments 224-265, wherein the protein composition exhibits six or more characteristics selected from the group consisting of: H₂S is detectable in an amount of less than about 0.1 ppm when L-cysteine is not added to the protein composition, and H₂S is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 272 is the protein composition of any one of embodiments 224-265, wherein the protein composition exhibits seven or more characteristics selected from the group consisting of: H₂S is detectable in an amount of less than about 0.1 ppm when L-cysteine is not added to the protein composition, and H₂S is detectable in an amount of at least about 0.2 ppm in the headspace about 24 hours at 25° C. after about 25 mM L-cysteine is added to the protein composition; the protein composition forms a gel upon heating to 65° C.; the protein composition has a particle size distribution D10, D50, and D90 of less than 0.1 μm, 1.0 μm and 5 μm, respectively; the protein composition is least about 80% denatured after about 20 minutes at about 85° C.; the protein composition forms a gel with a storage modulus of at least about 100 Pa when heated at or above about 85° C. for about 20 minutes; the protein composition forms a gel between about pH 5.5 and about pH 10.0; the protein composition forms a gel in solutions with ionic strength below about 0.5 M, wherein the ionic strength is calculated based on the concentration of non-protein solutes; and the protein composition has an emulsion activity index of greater than or equal to about 50 m²/g protein across about pH 4.0 to about pH 8.0.

Embodiment 273 is the protein composition of any one of embodiments 224-265, wherein the protein composition exhibits the characteristics:
H₂S is detectable in an amount of less than about 0.1 ppm when L-cysteine is not added to the protein composition, and H₂S is detectable in an amount of at least about 0.2 ppm in the headspace about 24 hours at 25° C. after about 25 mM L-cysteine is added to the protein composition,
the protein composition forms a gel upon heating to 65° C.,
the protein composition has a particle size distribution D10, D50, and D90 of less than 0.1 μm, 1.0 μm and 5 μm, respectively,
the protein composition is least about 80% denatured after about 20 minutes at about 85° C.,
the protein composition forms a gel with a storage modulus of at least about 100 Pa when heated at or above about 85° C. for about 20 minutes, wherein the protein composition forms a gel between about pH 5.5 and about pH 10.0,
the protein composition forms a gel in solutions with ionic strength below about 0.5 M, wherein the ionic strength is calculated based on the concentration of non-protein solutes, and
the protein composition has an emulsion activity index of greater than or equal to about 50 m²/g protein across about pH 4.0 to about pH 8.0.

Embodiment 274 is the protein composition of any one of embodiments 224-273, wherein the protein composition comprises at least about 35%, on a dry weight basis, of compounds larger than 5 kDa.

Embodiment 275 is the protein composition of any one of embodiments 224-273, wherein the protein composition comprises at least about 40%, on a dry weight basis, of compounds larger than 5 kDa.

Embodiment 276 is the protein composition of any one of embodiments 224-273, wherein the protein composition comprises at least about 50%, on a dry weight basis, of compounds larger than 5 kDa.

Embodiment 277 is the protein composition of any one of embodiments 224-273, wherein the protein composition comprises at least about 60%, on a dry weight basis, of compounds larger than 5 kDa.

Embodiment 278 is the protein composition of any one of embodiments 224-273, wherein the protein composition comprises at least about 70%, on a dry weight basis, of compounds larger than 5 kDa.

Embodiment 279 is the protein composition of any one of embodiments 274-278, wherein the compounds larger than 5 kDa are compounds larger than 10 kDa.

Embodiment 280 is the protein composition of any one of embodiments 274-278, wherein the compounds larger than 5 kDa are compounds larger than 15 kDa.

Embodiment 281 is the protein composition of any one of embodiments 274-278, wherein the compounds larger than 5 kDa are compounds larger than 20 kDa.

Embodiment 282 is the protein composition of any one of embodiments 274-278, wherein the compounds larger than 5 kDa are compounds larger than 25 kDa.

Embodiment 283 is the protein composition of any one of embodiments 224-282, further comprising drying the protein composition.

Embodiment 284 is the protein composition of embodiment 283, wherein the protein composition is spray dried.

Embodiment 285 is the protein composition of embodiment 283, wherein the protein composition is freeze dried.

Embodiment 286 is the protein composition of any one of embodiments 224-282, further comprising pasteurizing the protein composition to obtain a pasteurized protein composition.

Embodiment 287 is the protein composition of embodiment 286, wherein the protein composition is pasteurized by microfiltration.

Embodiment 288 is the protein composition of embodiment 286, wherein protein composition is pasteurized by high temperature short time pasteurization.

Embodiment 289 is the protein composition of embodiment 286, wherein the protein composition is pasteurized by adding one or more antimicrobials.

Embodiment 290 is the protein composition of any one of embodiments 286-289, further comprising drying the pasteurized protein composition.

Embodiment 291 is the protein composition of embodiment 290, wherein the pasteurized protein composition is spray dried.

Embodiment 292 is the protein composition of embodiment 290, wherein the pasteurized protein composition is freeze dried.

Embodiment 293 is the protein composition of any one of embodiments 224-292, wherein the amount of one or more volatile compounds is reduced by at least about 1.05-fold compared to a corresponding method in which one or more of the lysing, clarifying, or filtering steps are not performed at a pH between about 8.5 and about 12.0, wherein the volatile compound is selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment 294 is the protein composition of any one of embodiments 224-293, wherein the protein composition does not comprise one or more compounds selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, and pentanal.

Embodiment 295 is the protein composition of any one of embodiments 224-294, wherein at least about 50% of the protein in the protein composition falls between about 10 kDa and about 200 kDa Embodiment 296 is a food product comprising:
a protein composition of any one of embodiments 129-169.

Embodiment 297 is a food product comprising:
a *Saccharomyces cerevisiae* protein composition of any one of embodiments 170-187.

Embodiment 298 is a food product comprising:
a *Pichia pastoris* protein composition of any one of embodiments 188-205.

Embodiment 299 is a food product comprising:
an *Escherichia coli* protein composition of any one of embodiments 206-223.

Embodiment 300 is the food product of any one of embodiments 296-290, wherein the food product is a dairy replica.

Embodiment 301 is the food product of embodiment 300, wherein the food product is a milk replica.

Embodiment 302 is the food product of embodiment 300, wherein the food product is a cheese replica.

Embodiment 303 is the food product of any one of embodiments 300-302, wherein the food product further comprises one or more microbes.

Embodiment 304 is the food product of embodiment 303, wherein the one or more microbes are selected from the group consisting of a *Lactococcus* species, a *Lactobacillus* species, a *Leuconostocaceae* species, a *Streptococcus* species, a *Pediococcus* species, a *Clostridium* species, a *Staphylococcus* species, a *Brevibacterium* species, a *Propioniibacteria* species, a *Penicillium* species, a *Debaryomyces*, a *Geotrichum* species, a *Corynebacteria* species, a *Verticillium* species, a *Kluyveromyces* species, a *Saccharomyces* species, a *Candida* species, a *Rhodosporidum* species, a *Micrococcus* species, a *Halomonas* species, a *Psychrobacter* species, or a combination thereof.

Embodiment 305 is the food product of embodiment 303, wherein the one or more microbes are selected from the group consisting of *Lactococcus lactis lactis*, *Lactococcus lactis cremoris*, *Lactococcus lactis biovar diacetylactis*, *Lactobacillus delbrueckii lactis*, *Lactobacillus delbrueckii bulgaricus*, *Lactobacillus helveticus*, *Lactobacillus plantarum*, *Lactobacillus casei*, *Lactobacillus rhamnosus*, *Leuconostoc mesenteroides cremoris*, *Streptococcus thermophiles*, *Pediococcus pentosaceus*, *Clostridium butyricum*, *Staphylococcus xylosus*, *Brevibacterium linens*, *Penicillium candidum*, *Penicillium camemberti*, *Penicillium roqueforti*, *Debaryomyces hansenii*, *Geotrichum candidum*, *Verticillium lecanii*, *Kluyveromyces lactis*, *Saccharomyces cerevisiae*, *Candida jefer*, *Candida utilis*, *Rhodosporidum infirmominiatum*, Embodiment 306 is the food product of any one of embodiments 296-299, wherein the food product is a meat replica.

Embodiment 307 is the food product of embodiment 306, further comprising a heme.

Embodiment 308 is the food product of embodiment 308, wherein the heme is provided in the form of a heme-containing protein.

Embodiment 309 is the food product of any one of embodiments 306-308, further comprising one or more flavor precursors.

Embodiment 310 is the food product of embodiment 309 wherein the one or more flavor precursors comprise a compound selected from the group consisting of a sugar, a sugar alcohol, a sugar acid, a sugar derivative, a sulfur-containing compound, an amino acids or derivative thereof, a nucleotide, a nucleoside, a vitamin, an acid, a peptides, a protein hydrolysate, an extract, and combinations thereof.

Embodiment 311 is the food product of embodiment 309, wherein the flavor precursors comprise a sugar and a sulfur-containing compound.

Embodiment 312 is the food product of any one of embodiments 310-311, wherein the sulfur-containing compound is selected from the group consisting of cysteine, cystine, a cysteine sulfoxide, allicin, selenocysteine, methionine, thiamine, and combinations thereof.

Embodiment 313 is the food product of any one of embodiments 310-312, wherein the sugar is selected from the group consisting of glucose, fructose, ribose, sucrose, arabinose, glucose-6-phosphate, fructose-6-phosphate, fructose 1,6-diphosphate, inositol, maltose, molasses, maltodextrin, glycogen, galactose, lactose, ribitol, gluconic acid and glucuronic acid, amylose, amylopectin, xylose, and combinations thereof.

Embodiment 314 is the food product of any one of embodiments 306-313, further comprising an oil.

Embodiment 315 is the food product of embodiment 314, wherein the oil is selected from the group consisting of coconut oil, mango oil, sunflower oil, cottonseed oil, safflower oil, rice bran oil, cocoa butter, palm fruit oil, palm oil, soybean oil, canola oil, corn oil, sesame oil, walnut oil, flaxseed, jojoba oil, castor, grapeseed oil, peanut oil, olive oil, algal oil, oil from bacteria or fungi, and combinations thereof.

Embodiment 316 is the food product of any one of embodiments 296-299, wherein the food product is a protein supplement.

Embodiment 317 is the food product of any one of embodiments 296-316, wherein the food product contains less than 10% (by weight of the food product) animal products.

Embodiment 318 is the food product of any one of embodiments 296-316, wherein the food product contains less than 5% (by weight of the food product) animal products.

Embodiment 319 is the food product of any one of embodiments 296-316, wherein the food product contains less than 1% (by weight of the food product) animal products.

Embodiment 320 is the food product of any one of embodiments 296-316, wherein the food product contains no animal products.

Embodiment 321 is the food product of any one of embodiments 296-316, wherein the food product contains less than 10% (by weight of the food product) animal-derived products.

Embodiment 322 is the food product of any one of embodiments 296-316, wherein the food product contains less than 5% (by weight of the food product) animal-derived products.

Embodiment 323 is the food product of any one of embodiments 296-316, wherein the food product contains less than 1% (by weight of the food product) animal-derived products.

Embodiment 324 is the food product of any one of embodiments 296-316, wherein the food product contains no animal-derived products.

Embodiment 325 is the food product of any one of embodiments 296-316, wherein the food product contains less than 10% (by weight of the food product) animal meat.

Embodiment 326 is the food product of any one of embodiments 296-316, wherein the food product contains less than 5% (by weight of the food product) animal meat.

Embodiment 327 is the food product of any one of embodiments 296-316, wherein the food product contains less than 1% (by weight of the food product) animal meat.

Embodiment 328 is the food product of any one of embodiments 296-316, wherein the food product contains no animal meat.

Embodiment 329 is a method for purifying proteins from a plurality of cells having cell walls, the method comprising:
 a) perforating the cell walls of the plurality of cells;
 b) separating an aqueous suspension of the plurality of cells to form a solids portion and a liquid portion;
 c) filtering the liquid portion to form a filtrate and a retentate;
 d) concentrating the retentate to form a protein composition; and
 e) optionally pasteurizing the protein composition,
 wherein each of a)-d), independently, are performed at a pH of about 8.5 and about 12.0, and/or wherein the method results in the liquid portion comprising at least about 50% by weight of the cytoplasmic proteins of the plurality of cells.

Embodiment 330 is a method for purifying proteins from a plurality of cells, the method comprising:
 a) treating an aqueous suspension of the plurality of cells with a base until the pH of the aqueous suspension is about 8.5 to about 12.0;
 b) separating the aqueous suspension of the plurality of cells to form a solids portion and a liquid portion;
 c) filtering the liquid portion to form a filtrate and a retentate;
 d) concentrating the retentate to form a protein composition; and
 e) optionally pasteurizing the protein composition,
 wherein each of a)-d), independently, are performed at a pH of about 8.5 and about 12.0, and/or wherein the method results in the liquid portion comprising at least about 10% by weight of the cytoplasmic proteins of the plurality of cells.

Embodiment 331 is a method for purifying proteins from a plurality of cells having cell walls, the method comprising:
 a) treating an aqueous suspension of the plurality of cells with a base until the pH of the aqueous suspension is about 8.5 to about 12.0;
 b) perforating the cell walls of the plurality of cells;
 c) separating the aqueous suspension of the plurality of cells to form a solids portion and a liquid portion;
 d) filtering the liquid portion to form a filtrate and a retentate;
 e) concentrating the retentate to form a protein composition; and
 f) optionally pasteurizing the protein composition,
 wherein each of a)-e), independently, are performed at a pH of about 8.5 and about 12.0, and/or wherein the method results in the liquid portion comprising at least about 50% by weight of the cytoplasmic proteins of the plurality of cells.

Embodiment 332 is a method for purifying proteins from a plurality of cells having cell walls, the method comprising:
 a) perforating the cell walls of the plurality of cells;
 b) treating an aqueous suspension of the plurality of cells with a base until the pH of the aqueous suspension is about 8.5 to about 12.0;
 c) separating the aqueous suspension of the plurality of cells to form a solids portion and a liquid portion;
 d) filtering the liquid portion to form a filtrate and a retentate;
 e) concentrating the retentate to form a protein composition; and
 f) optionally pasteurizing the protein composition,
 wherein each of a)-e), independently, are performed at a pH of about 8.5 and about 12.0, and/or wherein the method results in the liquid portion comprising at least about 50% by weight of the cytoplasmic proteins of the plurality of cells.

Embodiment 333 is a method for purifying proteins from a plurality of cells, the method comprising:
 a) heating the plurality of cells to a temperature of about 50° C. to about 85° C.;
 b) separating an aqueous suspension of the plurality of cells to form a solids portion and a liquid portion;
 c) filtering the liquid portion to form a filtrate and a retentate;
 d) concentrating the retentate to form a protein composition; and e) optionally pasteurizing the protein composition,
wherein each of a)-d), independently, are performed at a pH of about 8.5 and about 12.0, and/or wherein the method results in the liquid portion comprising at least about 50% by weight of the cytoplasmic proteins of the plurality of cells.

Embodiment 334 is a method for preparing a cytosolic protein-enriched protein composition from a plurality of cells having cell walls, the method comprising:
a) perforating the cell walls of the plurality of cells;
b) separating an aqueous suspension of the plurality of cells to form a solids portion and a liquid portion;
c) filtering the liquid portion to form a filtrate and a retentate;
d) concentrating the retentate to form a cytosolic protein-enriched protein composition; and
e) optionally pasteurizing the cytosolic protein-enriched protein composition,
wherein each of a)-d), independently, are performed at a pH of about 8.5 and about 12.0, and/or wherein the method results in the liquid portion comprising at least about 50% by weight of the cytoplasmic proteins of the plurality of cells.

Embodiment 335 is a method for preparing a cytosolic protein-enriched protein composition from a plurality of cells, the method comprising:
a) treating an aqueous suspension of the plurality of cells with a base until the pH of the aqueous suspension is about 8.5 to about 12.0;
b) separating the aqueous suspension of the plurality of cells to form a solids portion and a liquid portion;
c) filtering the liquid portion to form a filtrate and a retentate;
d) concentrating the retentate to form a cytosolic protein-enriched protein composition; and
e) optionally pasteurizing the cytosolic protein-enriched protein composition,
wherein each of a)-d), independently, are performed at a pH of about 8.5 and about 12.0, and/or wherein the method results in the liquid portion comprising at least about 10% by weight of the cytoplasmic proteins of the plurality of cells.

Embodiment 336 is a method for preparing a cytosolic protein-enriched protein composition from a plurality of cells having cell walls, the method comprising:
a) treating an aqueous suspension of the plurality of cells with a base until the pH of the aqueous suspension is about 8.5 to about 12.0;
b) perforating the cell walls of the plurality of cells;
c) separating the aqueous suspension of the plurality of cells to form a solids portion and a liquid portion;
d) filtering the liquid portion to form a filtrate and a retentate;
e) concentrating the retentate to form a cytosolic protein-enriched protein composition; and
f) optionally pasteurizing the cytosolic protein-enriched protein composition,
wherein each of a)-e), independently, are performed at a pH of about 8.5 and about 12.0, and/or wherein the method results in the liquid portion comprising at least about 50% by weight of the cytoplasmic proteins of the plurality of cells.

Embodiment 337 is a method for preparing a cytosolic protein-enriched protein composition from a plurality of cells having cell walls, the method comprising:
a) perforating the cell walls of the plurality of cells;
b) treating an aqueous suspension of the plurality of cells with a base until the pH of the aqueous suspension is about 8.5 to about 12.0;
c) separating the aqueous suspension of the plurality of cells to form a solids portion and a liquid portion;
d) filtering the liquid portion to form a filtrate and a retentate;
e) concentrating the retentate to form a cytosolic protein-enriched protein composition; and
f) optionally pasteurizing the cytosolic protein-enriched protein composition,
wherein each of a)-e), independently, are performed at a pH of about 8.5 and about 12.0, and/or wherein the method results in the liquid portion comprising at least about 50% by weight of the cytoplasmic proteins of the plurality of cells.

Embodiment 338 is a method for preparing a cytosolic protein-enriched protein composition from a plurality of cells, the method comprising:
a) heating the plurality of cells to a temperature of about 50° C. to about 85° C.;
b) separating an aqueous suspension of the plurality of cells to form a solids portion and a liquid portion;
c) filtering the liquid portion to form a filtrate and a retentate;
d) concentrating the retentate to form a cytosolic protein-enriched protein composition; and
e) optionally pasteurizing the cytosolic protein-enriched protein composition,
wherein each of a)-d), independently, are performed at a pH of about 8.5 and about 12.0, and/or wherein the method results in the liquid portion comprising at least about 50% by weight of the cytoplasmic proteins of the plurality of cells.

Embodiment 339 is a method for preparing a membrane-bound and/or subcellular compartment protein-enriched protein composition from a plurality of cells having cell walls, the method comprising:
a) perforating the cell walls of the plurality of cells;
b) separating an aqueous suspension of the plurality of cells to form a solids portion and a liquid portion;
c) extracting protein from the solids portion to form a membrane-bound and/or subcellular compartment protein-enriched protein composition; and
d) optionally pasteurizing the membrane-bound and/or subcellular compartment protein-enriched protein composition,
wherein each of a)-b), independently, are performed at a pH of about 8.5 and about 12.0, and/or wherein the method results in the liquid portion comprising at least about 50% by weight of the cytoplasmic proteins of the plurality of cells.

Embodiment 340 is a method for preparing a membrane-bound and/or subcellular compartment protein-enriched protein composition from a plurality of cells, the method comprising:
a) treating an aqueous suspension of the plurality of cells with a base until the pH of the aqueous suspension is about 8.5 to about 12.0;
b) separating the aqueous suspension of the plurality of cells to form a solids portion and a liquid portion;
c) extracting protein from the solids portion to form a membrane-bound and/or subcellular compartment protein-enriched protein composition; and
d) optionally pasteurizing the membrane-bound and/or subcellular compartment protein-enriched protein composition, wherein each of a)-b), independently, are performed at a pH of about 8.5 and about 12.0, and/or wherein the method results in the liquid portion comprising at least about 10% by weight of the cytoplasmic proteins of the plurality of cells.

Embodiment 341 is a method for preparing a membrane-bound and/or subcellular compartment protein-enriched protein composition from a plurality of cells having cell walls, the method comprising:
a) treating an aqueous suspension of the plurality of cells with a base until the pH of the aqueous suspension is about 8.5 to about 12.0;
b) perforating the cell walls of the plurality of cells;
c) separating the aqueous suspension of the plurality of cells to form a solids portion and a liquid portion;
d) extracting protein from the solids portion to form a membrane-bound and/or subcellular compartment protein-enriched protein composition; and
e) optionally pasteurizing the membrane-bound and/or subcellular compartment protein-enriched protein composition,
wherein each of a)-c), independently, are performed at a pH of about 8.5 and about 12.0, and/or wherein the method results in the liquid portion comprising at least about 50% by weight of the cytoplasmic proteins of the plurality of cells.

Embodiment 342 is a method for preparing a membrane-bound and/or subcellular compartment protein-enriched protein composition from a plurality of cells having cell walls, the method comprising:
a) perforating the cell walls of the plurality of cells;
b) treating an aqueous suspension of the plurality of cells with a base until the pH of the aqueous suspension is about 8.5 to about 12.0;
c) separating the aqueous suspension of the plurality of cells to form a solids portion and a liquid portion;
d) extracting protein from the solids portion to form a membrane-bound and/or subcellular compartment protein-enriched protein composition; and
e) optionally pasteurizing the membrane-bound and/or subcellular compartment protein-enriched protein composition,
wherein each of a)-c), independently, are performed at a pH of about 8.5 and about 12.0, and/or wherein the method results in the liquid portion comprising at least about 50% by weight of the cytoplasmic proteins of the plurality of cells.

Embodiment 343 is a method for preparing a membrane-bound and/or subcellular compartment protein-enriched protein composition from a plurality of cells, the method comprising:
a) heating the plurality of cells to a temperature of about 50° C. to about 85° C.;
b) separating an aqueous suspension of the plurality of cells to form a solids portion and a liquid portion;
d) extracting protein from the solids portion to form a membrane-bound and/or subcellular compartment protein-enriched protein composition; and
e) optionally pasteurizing the membrane-bound and/or subcellular compartment protein-enriched protein composition,
wherein each of a)-d), independently, are performed at a pH of about 8.5 and about 12.0, and/or wherein the method results in the liquid portion comprising at least about 50% by weight of the cytoplasmic proteins of the plurality of cells.

Embodiment 344 is the method of any one of embodiments 339-343, wherein the extracting protein from the solids portion comprises mechanical lysis of the solids portion.

Embodiment 345 is a method for purifying a soluble protein from a plurality of cells having cell walls, the method comprising:
a) perforating the cell walls of the plurality of cells;
b) separating an aqueous suspension of the plurality of cells to form a solids portion and a liquid portion;
c) filtering the liquid portion to form a filtrate and a retentate;
d) concentrating the retentate to form a protein composition comprising the soluble protein; and
e) optionally pasteurizing the protein composition,
wherein each of a)-d), independently, are performed at a pH of about 8.5 and about 12.0, and/or wherein the method results in the liquid portion comprising at least about 50% by weight of the cytoplasmic proteins of the plurality of cells.

Embodiment 346 is a method for purifying a soluble protein from a plurality of cells, the method comprising:
a) treating an aqueous suspension of the plurality of cells expressing the soluble protein with a base until the pH of the aqueous suspension is about 8.5 to about 12.0;
b) separating the aqueous suspension of the plurality of cells to form a solids portion and a liquid portion;
c) filtering the liquid portion to form a filtrate and a retentate;
d) concentrating the retentate to form a protein composition comprising the soluble protein; and
e) optionally pasteurizing the protein composition,
wherein each of a)-d), independently, are performed at a pH of about 8.5 and about 12.0, and/or wherein the method results in the liquid portion comprising at least about 10% by weight of the cytoplasmic proteins of the plurality of cells.

Embodiment 347 is a method for purifying a soluble protein from a plurality of cells having cell walls, the method comprising:
a) treating an aqueous suspension of the plurality of cells expressing the soluble protein with a base until the pH of the aqueous suspension is about 8.5 to about 12.0;
b) perforating the cell walls of the plurality of cells;
c) separating the aqueous suspension of the plurality of cells to form a solids portion and a liquid portion;
d) filtering the liquid portion to form a filtrate and a retentate;
e) concentrating the retentate to form a protein composition comprising the soluble protein; and
f) optionally pasteurizing the protein composition,
wherein each of a)-e), independently, are performed at a pH of about 8.5 and about 12.0, and/or wherein the method results in the liquid portion comprising at least about 50% by weight of the cytoplasmic proteins of the plurality of cells.

Embodiment 348 is a method for purifying a soluble protein from a plurality of cells having cell walls, the method comprising:
a) perforating the cell walls of the plurality of cells;
b) treating an aqueous suspension of the plurality of cells with a base until the pH of the aqueous suspension is about 8.5 to about 12.0;

c) separating the aqueous suspension of the plurality of cells to form a solids portion and a liquid portion;
d) filtering the liquid portion to form a filtrate and a retentate;
e) concentrating the retentate to form a protein composition comprising the soluble protein; and
f) optionally pasteurizing the protein composition,
wherein each of a)-e), independently, are performed at a pH of about 8.5 and about 12.0, and/or wherein the method results in the liquid portion comprising at least about 50% by weight of the cytoplasmic proteins of the plurality of cells.

Embodiment 349 is a method for purifying a soluble protein from a plurality of cells, the method comprising:
a) heating the plurality of cells expressing the soluble protein to a temperature of about 50° C. to about 85° C.;
b) separating an aqueous suspension of the plurality of cells to form a solids portion and a liquid portion;
c) filtering the liquid portion to form a filtrate and a retentate;
d) concentrating the retentate to form a protein composition comprising the soluble protein; and
e) optionally pasteurizing the protein composition,
wherein each of a)-d), independently, are performed at a pH of about 8.5 and about 12.0, and/or wherein the method results in the liquid portion comprising at least about 50% by weight of the cytoplasmic proteins of the plurality of cells.

Embodiment 350 is the method of any one of embodiments 345-349, wherein the soluble protein is a heme-containing protein.

Embodiment 351 is the method of embodiment 350, wherein the method comprises treating the plurality of cells with about 5 mM to about 500 mM reducing equivalents of a reductant.

Embodiment 352 is the method of embodiment 351, wherein treatment with the reductant comprises treatment with about 20 mM to about 80 mM reducing equivalents of the reductant.

Embodiment 353 is the method of any one of embodiments 351-352, wherein the reductant is selected from the group consisting of cysteine, glutathione, bisulfite, and a combination thereof.

Embodiment 354 is the method of any one of embodiments 351-353, wherein the reductant is a food safe reductant.

Embodiment 355 is the method of any one of embodiments 345-354, wherein the soluble protein has a melting point, and method further comprises, before a), heating the plurality of cells to a temperature of about 10° C. or about 5° C. below the melting point of the soluble protein.

Embodiment 356 is the method of embodiment 355, wherein the soluble protein has a melting point of at least about 60° C.

Embodiment 357 is the method of any one of embodiments 345-356, wherein the soluble protein is heterologous to the plurality of cells.

Embodiment 358 is the method of any one of embodiments 345-357, wherein the soluble protein makes up at least about 30% by dry weight of the protein in the protein composition.

Embodiment 359 is the method of any one of embodiments 345-357, wherein the soluble protein makes up at least about 50% by dry weight of the protein in the protein composition.

Embodiment 360 is the method of any one of embodiments 345-357, wherein the soluble protein makes up at least about 70% by dry weight of the protein in the protein composition.

Embodiment 361 is the method of any one of embodiments 345-357, wherein the soluble protein makes up at least about 90% by dry weight of the protein in the protein composition.

Embodiment 362 is the method of embodiment 339 or embodiment 340, wherein each of a) and b), independently, are performed at a pH of about 8.5 to about 12.0.

Embodiment 363 is the method of embodiment 341 or embodiment 342, wherein each of a)-c), independently, are performed at a pH of about 8.5 to about 12.0.

Embodiment 364 is the method of any one of embodiments 329, 330, 333, 334, 335, 338, 343, 345, 346, or 349, wherein each of a)-d), independently, are performed at a pH of about 8.5 to about 12.0.

Embodiment 365 is the method of any one of embodiments 331, 332, 336, 337, 347, or 348, wherein each of a)-e), independently, are performed at a pH of about 8.5 to about 12.0.

Embodiment 366 is the method of embodiment 339 or embodiment 340, wherein each of a) and b), independently, are performed at a pH of about 9.0 to about 12.0.

Embodiment 367 is the method of embodiment 341 or embodiment 342, wherein each of a)-c), independently, are performed at a pH of about 9.0 to about 12.0.

Embodiment 368 is the method of any one of embodiments 329, 330, 333, 334, 335, 338, 343, 345, 346, or 349, wherein each of a)-d), independently, are performed at a pH of about 9.0 to about 12.0.

Embodiment 369 is the method of any one of embodiments 331, 332, 336, 337, 347, or 348, wherein each of a)-e), independently, are performed at a pH of about 9.0 to about 12.0.

Embodiment 370 is the method of embodiment 339 or embodiment 340, wherein each of a) and b), independently, are performed at a pH of about 9.0 to about 10.0.

Embodiment 371 is the method of embodiment 341 or embodiment 342, wherein each of a)-c), independently, are performed at a pH of about 9.0 to about 10.0.

Embodiment 372 is the method of any one of embodiments 329, 330, 333, 334, 335, 338, 343, 345, 346, or 349, wherein each of a)-d), independently, are performed at a pH of about 9.0 to about 10.0.

Embodiment 373 is the method of any one of embodiment 331, 332, 336, 337, 347, or 348, wherein each of a)-e), independently, are performed at a pH of about 9.0 to about 10.0.

Embodiment 374 is the method of embodiment 339 or embodiment 340, wherein each of a) and b), independently, are performed at a pH of about 10.0 to about 11.0.

Embodiment 375 is the method of embodiment 341 or embodiment 342, wherein each of a)-c), independently, are performed at a pH of about 10.0 to about 11.0.

Embodiment 376 is the method of any one of embodiments 329, 330, 333, 334, 335, 338, 343, 345, 346, or 349, wherein each of a)-d), independently, are performed at a pH of about 10.0 to about 11.0.

Embodiment 377 is the method of any one of embodiment 331, 332, 336, 337, 347, or 348, wherein each of a)-e), independently, are performed at a pH of about 10.0 to about 11.0.

Embodiment 378 is the method of embodiment 339 or embodiment 340, wherein each of a) and b), independently, are performed at a pH of about 11.0 to about 12.0.

Embodiment 379 is the method of embodiment 341 or embodiment 342, wherein each of a)-c), independently, are performed at a pH of about 11.0 to about 12.0.

Embodiment 380 is the method of any one of embodiments 329, 330, 333, 334, 335, 338, 343, 345, 346, or 349, wherein each of a)-d), independently, are performed at a pH of about 11.0 to about 12.0.

Embodiment 381 is the method of any one of embodiment 331, 332, 336, 337, 347, or 348, wherein each of a)-e), independently, are performed at a pH of about 11.0 to about 12.0.

Embodiment 382 is the method of embodiment 339 or embodiment 340, wherein each of a) and b), independently, are performed at a temperature of less than or equal to about 12° C.

Embodiment 383 is the method of embodiment 341 or embodiment 342, wherein each of a)-c), independently, are performed at a temperature of less than or equal to about 12° C.

Embodiment 384 is the method of any one of embodiments 329, 330, 333, 334, 335, 338, 343, 345, 346, or 349, wherein each of a)-d), independently, are performed at a temperature of less than or equal to about 12° C.

Embodiment 385 is the method of any one of embodiments 331, 332, 336, 337, 347, or 348, wherein each of a)-e), independently, are performed at a temperature of less than or equal to about 12° C.

Embodiment 386 is the method of any one of embodiments 333, 338, 343, or 349, further comprising, between heating the plurality of cells and separating an aqueous suspension of the plurality of cells to form a solids portion and a liquid portion, treating the aqueous suspension of the plurality of cells with a base until the pH of the aqueous suspension is about 8.5 to about 12.0.

Embodiment 387 is the method of any one of embodiments 333, 338, 343, or 349, wherein when the plurality of cells has cell walls, the method further comprises, between heating the plurality of cells and separating an aqueous suspension of the plurality of cells to form a solids portion and a liquid portion, perforating the cell walls of the plurality of cells.

Embodiment 388 is the method of any one of embodiments 330-332, 335-337, 340-342, or 346-348, wherein treating the aqueous suspension of the plurality of cells with a base until the pH of the aqueous suspension is about 8.5 to about 12.0 comprises treating the aqueous suspension of the plurality of cells with a base until the pH of the aqueous suspension is between about 8.5 and 12.0 for at least about 3 minutes.

Embodiment 389 is the method of any one of embodiments 330-332, 335-337, 340-342, or 346-348, wherein treating the aqueous suspension of the plurality of cells with a base until the pH of the aqueous suspension is between about 8.5 and 12.0 comprises treating the aqueous suspension of the plurality of cells with a base until the pH of the aqueous suspension is between about 8.5 and 12.0 for at least about 5 minutes.

Embodiment 390 is the method of any one of embodiments 330-332, 335-337, 340-342, or 346-348, wherein treating the aqueous suspension of the plurality of cells with a base until the pH of the aqueous suspension is between about 8.5 and 12.0 comprises wherein treating the aqueous suspension of the plurality of cells with a base until the pH of the aqueous suspension is between about 8.5 and 12.0 for at least about 10 minutes.

Embodiment 391 is the method of any one of embodiments 330-332, 335-337, 340-342, or 346-348, wherein treating an aqueous suspension of the plurality of cells with a base is performed at a temperature of less than or equal to about 12° C.

Embodiment 392 is the method of any one of embodiments 329-332, 334-337, 339-342, or 345-348, wherein the method further comprises, prior to separating the aqueous suspension of the plurality of cells to form a solids portion and a liquid portion, heating the plurality of cells to at least about 60° C.

Embodiment 393 is the method of any one of embodiments 329, 331, 332, 334, 336, 337, 339, 341, 342, 345, 347, or 348, wherein the perforating is performed at a temperature of less than or equal to about 12° C.

Embodiment 394 is the method of any one of embodiments 329, 331, 332, 334, 336, 337, 339, 341, 342, 345, 347, or 348, wherein perforating comprises treatment with a reductant, treatment with an enzyme, electroporation, or a combination thereof.

Embodiment 395 is the method of embodiment 394, wherein treatment with the reductant comprises treatment with about 10 mM to about 500 mM reducing equivalents of the reductant.

Embodiment 396 is the method of embodiment 394, wherein treatment with the reductant comprises treatment with about 20 mM to about 80 mM reducing equivalents of the reductant.

Embodiment 397 is the method of embodiment 394, wherein treatment with the reductant comprises treatment with about 50 mM reducing equivalents of the reductant.

Embodiment 398 is the method of any one of embodiments 394-397, wherein the reductant is selected from the group consisting of cysteine, glutathione, bisulfite, and a combination thereof.

Embodiment 399 is the method of any one of embodiments 394-398, wherein the reductant is a food safe reductant.

Embodiment 400 is the method of any one of embodiments 329-399, wherein dry solids from the liquid portion, following desalting, have an $A_{260}/A_{280}$ ratio of less than about 1.5.

Embodiment 401 is the method of any one of embodiments 329-400, wherein dry solids from the solids portion, following desalting, have an A260/A280 ratio of greater than about 1.5.

Embodiment 402 is the method of any one of embodiments 329-401, wherein the method results in the liquid portion comprising at least about 50% by weight of the cytoplasmic proteins of the plurality of cells.

Embodiment 403 is the method of any one of embodiments 329-402, wherein the method results in the liquid portion comprising at least about 60% by weight of the cytoplasmic proteins of the plurality of cells.

Embodiment 404 is the method of any one of embodiments 329-403, wherein the method results in the liquid portion comprising at least about 70% by weight of the cytoplasmic proteins of the plurality of cells.

Embodiment 405 is the method of any one of embodiments 329-404, wherein the method results in the liquid portion comprising at least about 80% by weight of the cytoplasmic proteins of the plurality of cells.

Embodiment 406 is the method of any one of embodiments 329-402, wherein the method results in the liquid portion comprising at least about 50% by weight of the hexokinase of the plurality of cells.

Embodiment 407 is the method of any one of embodiments 329-406, wherein the method results in the liquid portion comprising at least about 70% by weight of the hexokinase of the plurality of cells.

Embodiment 408 is the method of any one of embodiments 329-407, wherein the method results in the liquid portion comprising at least about 90% by weight of the hexokinase of the plurality of cells.

Embodiment 409 is the method of any one of embodiments 329-408, wherein the method results in the liquid portion comprising at least about 50% by weight of the non-membrane-bound cell wall proteins of the plurality of cells.

Embodiment 410 is the method of any one of embodiments 329-409, wherein the method results in the liquid portion comprising at least about 70% by weight of the non-membrane-bound cell wall proteins of the plurality of cells.

Embodiment 411 is the method of any one of embodiments 329-410, wherein the method results in the liquid portion comprising at least about 90% by weight of the non-membrane-bound cell wall proteins of the plurality of cells.

Embodiment 412 is the method of any one of embodiments 329-411, wherein the method results in protein in the liquid portion comprising less than 40% by weight of membrane-bound and subcellular compartment protein of the plurality of cells.

Embodiment 413 is the method of any one of embodiments 329-412, wherein the method results in protein in the liquid portion comprising less than 35% by weight of membrane-bound and subcellular compartment protein of the plurality of cells Embodiment 414 is the method of any one of embodiments 329-413, wherein the method results in protein in the liquid portion comprising less than 33% by weight of membrane-bound and subcellular compartment protein of the plurality of cells.

Embodiment 415 is the method of any one of embodiments 329-414, wherein the method results in the liquid portion comprising less than 50% by weight of the total histone protein of the plurality of cells.

Embodiment 416 is the method of any one of embodiments 329-415, wherein the method results in the liquid portion comprising less than 70% by weight of the total histone protein of the plurality of cells.

Embodiment 417 is the method of any one of embodiments 329-416, wherein the method results in the liquid portion comprising less than 90% by weight of the total histone protein of the plurality of cells.

Embodiment 418 is the method of any one of embodiments 329-417, wherein the method results in the liquid portion comprising less than 50% by weight of the total ferrochelatase of the plurality of cells.

Embodiment 419 is the method of any one of embodiments 329-418, wherein the method results in the liquid portion comprising less than 70% by weight of the total ferrochelatase of the plurality of cells.

Embodiment 420 is the method of any one of embodiments 329-419, wherein the method results in the liquid portion comprising less than 90% by weight of the total ferrochelatase of the plurality of cells.

Embodiment 421 is the method of any one of embodiments 329-420, wherein the method results in at least about 25% by weight of the cells of the plurality of cells remaining intact.

Embodiment 422 is the method of any one of embodiments 329-421, wherein the method results in at least about 50% by weight of the cells of the plurality of cells remaining intact.

Embodiment 423 is the method of any one of embodiments 329-422, wherein the method results in at least about 75% by weight of the cells of the plurality of cells remaining intact.

Embodiment 424 is the method of any one of embodiments 329-423, wherein prior to separating an aqueous suspension of the plurality of cells to form a solids portion and a liquid portion, the plurality of cells has a particle size distribution median of about 2 μm to about 4 μm.

Embodiment 425 is the method of any one of embodiments 329-343 or 345-424, wherein the method does not comprise mechanical lysis of the plurality of cells.

Embodiment 426 is the method of embodiment 425, wherein the protein composition comprises a higher proportion of cytosolic protein as compared to a similar method comprising mechanical lysis.

Embodiment 427 is the method of any one of embodiments 329-424, wherein the method further comprises mechanical lysis of the plurality of cells.

Embodiment 428 is the method of any one of embodiments 329-427, wherein the separating of the aqueous suspension of the plurality of cells to form a solids portion and a liquid portion is performed at a temperature of less than or equal to about 12° C.

Embodiment 429 is the method of any one of embodiments 329-428, wherein the filtering of the liquid portion to form a filtrate and a retentate is performed at a temperature of less than or equal to about 12° C.

Embodiment 430 is the method of any one of embodiments 329-429, wherein the separating comprises centrifugation, gravity settling, depth filtration, microfiltration, or a combination thereof.

Embodiment 431 is the method of embodiment 430, wherein the centrifugation comprises centrifugation of at least about 3,000×g.

Embodiment 432 is the method of any one of embodiments 329-431, wherein the protein composition comprises at least about 10-fold fewer esters as compared to a similar method wherein each step was carried out at a pH of about 6.5.

Embodiment 433 is the method of any one of embodiments 329-432, wherein the protein composition is a low-flavor protein composition.

Embodiment 434 is the method of any one of embodiments 329-433, wherein the filtering comprises microfiltration, ultrafiltration, diafiltration, or a combination thereof.

Embodiment 435 is the method of any one of embodiments 329-434, wherein the filtering is performed until the amount of sodium hydroxide required to adjust the pH of a 2% (w/v) suspension of the protein composition from pH 3 to pH 12 is less than or equal to 3 mmol.

Embodiment 436 is the method of any one of embodiments 329-435, wherein the plurality of cells comprises microbial cells.

Embodiment 437 is the method of any one of embodiments 329-436, wherein the plurality of cells comprises eukaryotic cells.

Embodiment 438 is the method of any one of embodiments 329-437, wherein the plurality of cells comprises fungal cells.

Embodiment 439 is the method of embodiment 438, wherein the fungal cells are selected from the group consisting of *Saccharomyces* cells, *Pichia* cells, *Candida* cells, *Hansenula* cells, *Torulopsis* cells, *Kluyveromyces* cells, *Yarrowia* cells, *Fusarium* cells, and a combination thereof.

Embodiment 440 is the method of embodiment 438, wherein the fungal cells are selected from the group consisting of *Saccharomyces cerevisiae* cells, *Pichia pastoris* cells, *Candida boidinii* cells, *Hansenula polymorpha* cells, *Kluyveromyces lactis* cells, *Yarrowia lipolytica* cells, *Fusarium venenatum* cells, and a combination thereof.

Embodiment 441 is the method of any one of embodiments 329-440, wherein the plurality of cells comprises bacterial cells.

Embodiment 442 is the method of embodiment 441, wherein the bacterial cells are selected from the group consisting of *Bacillus* cells, *Escherichia* cells, *Lactobacillus* cells, *Corynebacterium* cells, *Pseudomonas* cells, *Methanococcus* cells, and a combination thereof.

Embodiment 443 is the method of embodiment 441, wherein the bacterial cells are selected from the group consisting of *Escherichia coli* cells, *Bacillus subtilis* cells, *Lactobacillus lactis* cells, *Corynebacterium glutamicum* cells, *Pseudomonas fluorescens* cells, *Methanococcus maripaludis* cells, and a combination thereof.

Embodiment 444 is the method of any one of embodiments 329-443, wherein the aqueous suspension of the plurality of cells comprises from about 2% to about 25% dry solids.

Embodiment 445 is the method of any one of embodiments 329-444, further comprising washing the plurality of cells at a pH of about 8.5 to about 12.0 before step a).

Embodiment 446 is the method of any one of embodiments 329-445, wherein the protein composition has a protein content of about 2 mg/mL to about 250 mg/mL.

Embodiment 447 is the method of any one of embodiments 329-446, wherein $H_2S$ is detectable in an amount of less than about 0.1 ppm in the headspace when L-cysteine is not added to the protein composition.

Embodiment 448 is the method of any one of embodiments 329-447, wherein $H_2S$ is detectable in an amount of at least about 0.2 ppm in the headspace about 24 hours at 25° C. after about 25 mM L-cysteine is added to the protein composition.

Embodiment 449 is the method of any one of embodiments 329-448, wherein the protein composition forms a gel upon heating to 65° C.

Embodiment 450 is the method of any one of embodiments 329-449, wherein the protein composition has a particle size distribution D10, D50, and D90 of less than 0.1 µm, 1.0 µm and 5 µm, respectively.

Embodiment 451 is the method of any one of embodiments 329-450, wherein the protein composition is at least about 80% denatured after about 20 minutes at about 85° C.

Embodiment 452 is the method of any one of embodiments 329-451, wherein a 10% (w/v) suspension of the protein composition forms a gel with a storage modulus of at least about 100 Pa when heated at or above about 85° C. for about 20 minutes.

Embodiment 453 is the method of any one of embodiments 329-452, wherein the protein composition forms a gel at a pH of about 5.5 to about pH 10.0.

Embodiment 454 is the method of any one of embodiments 329-453, wherein the protein composition forms a gel in solutions with ionic strength below about 0.5 M, wherein the ionic strength is calculated based on the concentration of non-protein solutes.

Embodiment 455 is the method of any one of embodiments 329-454, the protein composition has an emulsion activity index of greater than or equal to about 50 $m^2/g$ protein across about pH 4.0 to about pH 8.0.

Embodiment 456 is the method of any one of embodiments 329-455, wherein the protein composition comprises at least about 35%, on a dry weight basis, of compounds larger than 5 kDa.

Embodiment 457 is the method of any one of embodiments 329-455, wherein the protein composition comprises at least about 40%, on a dry weight basis, of compounds larger than 5 kDa.

Embodiment 458 is the method of any one of embodiments 329-455, wherein the protein composition comprises at least about 50%, on a dry weight basis, of compounds larger than 5 kDa.

Embodiment 459 is the method of any one of embodiments 329-455, wherein the protein composition comprises at least about 60%, on a dry weight basis, of compounds larger than 5 kDa.

Embodiment 460 is the method of any one of embodiments 329-455, wherein the protein composition comprises at least about 70%, on a dry weight basis, of compounds larger than 5 kDa.

Embodiment 461 is the method of any one of embodiments 456-460, wherein the compounds larger than 5 kDa are compounds larger than 10 kDa.

Embodiment 462 is the method of any one of embodiments 456-460, wherein the compounds larger than 5 kDa are compounds larger than 15 kDa.

Embodiment 463 is the method of any one of embodiments 456-460, wherein the compounds larger than 5 kDa are compounds larger than 20 kDa.

Embodiment 464 is the method of any one of embodiments 456-460, wherein the compounds larger than 5 kDa are compounds larger than 25 kDa.

Embodiment 465 is the method of any one of embodiments 329-464, further comprising drying the protein composition.

Embodiment 466 is the method of embodiment 465, wherein the protein composition is spray dried.

Embodiment 467 is the method of embodiment 465, wherein the protein composition is freeze dried.

Embodiment 468 is the method of any one of embodiments 329-464, further comprising pasteurizing the protein composition to obtain a pasteurized protein composition.

Embodiment 469 is the method of embodiment 468, wherein the protein composition is pasteurized by microfiltration.

Embodiment 470 is the method of embodiment 468, wherein the protein composition is pasteurized by high-temperature short time pasteurization.

Embodiment 471 is the method of embodiment 468, wherein the protein composition is pasteurized by adding one or more antimicrobials.

Embodiment 472 is the method of any one of embodiments 468-471, further comprising drying the pasteurized protein composition.

Embodiment 473 is the method of embodiment 472, wherein the pasteurized protein composition is spray dried.

Embodiment 474 is the method of embodiment 472, wherein the pasteurized protein composition is freeze dried.

Embodiment 475 is the method of any one of embodiment 329-474, wherein at least about 50% of the protein in the protein composition falls between about 10 kDa and about 200 kDa.

Embodiment 476 is a protein composition prepared by the method of any one of embodiments 329-475.

Embodiment 477 is use of a protein composition prepared by the method of any one of embodiments 329-475 in a food, a beverage, or a supplement.

Embodiment 478 is use of a protein composition prepared by the method of any one of embodiments 329-475 in a meat replica.

Embodiment 479 is a protein composition comprising:
a plurality of functional proteins,
wherein the protein composition can stabilize an oil-in-water emulsion.

Embodiment 480 is a protein composition comprising:
a plurality of functional proteins,
wherein the protein composition can stabilize an air-in-water emulsion.

Embodiment 481 is a protein composition comprising:
a plurality of functional proteins,
wherein the plurality of functional proteins comprises at least about 50% by dry weight cytosolic proteins.

Embodiment 482 is a protein composition comprising:
a plurality of functional proteins,
wherein a suspension or solution of dry solids from the protein composition has an $A_{260}/A_{280}$ ratio of less than about 1.5.

Embodiment 483 is a protein composition comprising:
a plurality of functional proteins,
wherein the protein composition is a low-flavor protein composition.

Embodiment 484 is a protein composition comprising:
a plurality of functional proteins,
wherein at least about 35%, on a dry weight basis, of the protein composition comprises compounds larger than 5 kDa.

Embodiment 485 is a protein composition comprising:
a plurality of functional proteins,
wherein the protein composition has a buffering capacity of less than about 3.0 mmol NaOH per gram dry solids.

Embodiment 486 is a protein composition comprising:
a plurality of functional proteins,
wherein heating a 10% (w/v) suspension of the protein composition to at least about 95° C. results in a gel with a storage modulus of at least about 100 Pa.

Embodiment 487 is the protein composition of any one of embodiments 479-100,
wherein $H_2S$ is detectable in an amount of less than about 0.1 ppm in the headspace after about 24 hours at 25° C. when L-cysteine is not added to 5 mL of a 2% (w/v) suspension of the protein composition at pH 7.0.

Embodiment 488 is the protein composition of any one of embodiments 479-101,
wherein after about 25 mM L-cysteine is added to 5 mL of a 2% (w/v) suspension of the protein composition at pH 7.0 and subsequent incubation for about 24 hours at 25° C., $H_2S$ is detectable in an amount of at least about 0.2 ppm in the headspace.

Embodiment 489 is a protein composition comprising:
a plurality of functional proteins,
wherein $H_2S$ is detectable in an amount of less than about 0.1 ppm in the headspace after about 24 hours at 25° C. when L-cysteine is not added to 5 mL of a 2% (w/v) suspension of the protein composition at pH 7.0.

Embodiment 490 is the protein composition of embodiment 103, wherein $H_2S$ is detectable in an amount of at least about 0.2 ppm in the headspace after about 24 hours at 25° C. and after about 25 mM L-cysteine is added to 5 mL of a 2% (w/v) suspension of the protein composition at pH 7.0.

Embodiment 491 is the protein composition of any one of embodiments 479-481 or 483-490, wherein a suspension or solution of dry solids from the protein composition has an A260/A280 ratio of less than about 1.5.

Embodiment 492 is the protein composition of any one of embodiments 479-491, wherein the protein composition is a low-flavor protein composition.

Embodiment 493 is the protein composition of any one of embodiments 479-492, wherein the plurality of functional proteins comprises at least about 50% by dry weight cytosolic protein.

Embodiment 494 is the protein composition of any one of embodiments 480-493, wherein the protein composition can stabilize an oil-in-water emulsion.

Embodiment 495 is the protein composition of any one of embodiments 479 or 481-494, wherein the protein composition can stabilize an air-in-water emulsion.

Embodiment 496 is the protein composition of any one of embodiments 479-495, wherein at least about 30% by dry weight of the protein composition comprises an abundant protein.

Embodiment 497 is the protein composition of any one of embodiments 479-495, wherein at least about 40% by dry weight of the protein composition comprises an abundant protein.

Embodiment 498 is the protein composition of any one of embodiments 479-494, wherein at least about 50% by dry weight of the protein composition comprises an abundant protein.

Embodiment 499 is the protein composition of any one of embodiments 496-498, wherein the abundant protein is a heme-containing protein.

Embodiment 500 is the protein composition of any one of embodiments 479-499, wherein the plurality of functional proteins comprises at least one protein heterologous to a source organism of the plurality of functional proteins.

Embodiment 501 is the protein composition of embodiment 500, wherein the at least one protein heterologous to the source organism of the plurality of functional proteins comprises a heme-containing protein.

Embodiment 502 is the protein composition of embodiment 500 or embodiment 501, wherein the at least one protein heterologous to the source organism of the plurality of functional proteins does not comprise a secretion signal.

Embodiment 503 is the protein composition of any one of embodiments 500-502, wherein at least about 30% by dry weight of the protein composition comprises the at least one protein heterologous to the source organism of the plurality of functional proteins.

Embodiment 504 is the protein composition of any one of embodiments 500-502, wherein at least about 40% by dry weight of the protein composition comprises the at least one protein heterologous to the source organism of the plurality of functional proteins.

Embodiment 505 is the protein composition of any one of embodiments 500-502, wherein at least about 50% by dry weight of the protein composition comprises the at least one protein heterologous to the source organism of the plurality of functional proteins.

Embodiment 506 is the protein composition of any one of embodiments 479-505, wherein at least about 35%, on a dry weight basis, of the protein composition comprises compounds larger than 5 kDa.

Embodiment 507 is the protein composition of any one of embodiments 479-506, wherein the protein composition transitions to a gel upon heating to 65° C.

Embodiment 508 is the protein composition of any one of embodiments 479-507, wherein the protein composition is at least about 80% denatured after about 20 minutes at about 85° C.

Embodiment 509 is the protein composition of any one of embodiments 479-508, wherein the protein composition forms a gel with a storage modulus of at least about 100 Pa when heated at or above about 85° C. for about 20 minutes.

Embodiment 510 is the protein composition of any one of embodiments 479-509, wherein the protein composition can form a gel at a pH of about pH 5.5 to about pH 10.0.

Embodiment 511 is the protein composition of any one of embodiments 479-510, wherein the protein composition can form a gel in solutions with ionic strength below about 0.5 M, wherein the ionic strength is calculated based on the concentration of non-protein solutes.

Embodiment 512 is the protein composition of any one of embodiments 479-511, wherein the protein composition has a particle size distribution D10 of less than about 0.1 μm.

Embodiment 513 is the protein composition of any one of embodiments 479-512, wherein the protein composition has a particle size distribution D50 of less than about 1.0 μm.

Embodiment 514 is the protein composition of any one of embodiments 479-513, wherein the protein composition has a particle size distribution D90 of less than about 5 μm.

Embodiment 515 is the protein composition of any one of embodiments 479-514, wherein the protein composition has an emulsion activity index of greater than or equal to about 50 m²/g protein across about pH 4.0 to about pH 8.0.

Embodiment 516 is the protein composition of any one of embodiments 479-484 or 486-515, wherein the protein composition has a buffering capacity of less than about 3.0 mmol NaOH per gram dry solids.

Embodiment 517 is the protein composition of any one of embodiments 479-516, wherein the protein composition displays activity in one or more multi-step metabolic pathways.

Embodiment 518 is the protein composition of any one of embodiments 479-517, wherein the plurality of functional proteins comprises at least 10 different functional proteins.

Embodiment 519 is the protein composition of any one of embodiments 479-518, wherein the plurality of functional proteins comprises at least 20 different functional proteins.

Embodiment 520 is the protein composition of any one of embodiments 479-519, wherein the plurality of functional proteins comprises at least 50 different functional proteins.

Embodiment 521 is the protein composition of any one of embodiments 479-520, wherein the plurality of functional proteins comprises functional microbial proteins.

Embodiment 522 is the protein composition of any one of embodiments 479-521, wherein the plurality of functional proteins comprises functional fungal proteins.

Embodiment 523 is the protein composition of any one of embodiments 479-522, wherein the plurality of functional proteins comprises functional bacterial proteins.

Embodiment 524 is the protein composition of any one of embodiments 479-523, wherein the plurality of functional proteins comprises functional proteins from *Saccharomyces, Pichia, Candida, Hansenula, Torulopsis, Kluyveromyces, Yarrowia, Aspergillus, Trichoderma, Fusarium*, or a combination thereof.

Embodiment 525 is the protein composition of any one of embodiments 479-524, wherein the plurality of functional proteins comprises functional proteins from *Saccharomyces cerevisiae, Pichia pastoris, Candida boidinii, Hansenula polymorpha, Kluyveromyces lactis, Yarrowia lipolytica, Fusarium venenatum*, or a combination thereof.

Embodiment 526 is the protein composition of any one of embodiments 479-525, wherein the plurality of functional proteins comprises functional proteins from *Bacillus, Escherichia, Lactobacillus, Corynebacterium, Pseudomonas, Methanococcus*, or a combination thereof.

Embodiment 527 is the protein composition of any one of embodiments 479-526, wherein the plurality of functional proteins comprises functional proteins from *E. coli, Bacillus subtilis, Lactobacillus lactis, Corynebacterium glutamicum, Pseudomonas fluorescens, Methanococcus maripaludis*, or a combination thereof.

Embodiment 528 is the protein composition of any one of embodiments 479-527, wherein the plurality of functional proteins comprises one or more heterologous functional proteins.

Embodiment 529 is the protein composition of any one of embodiments 479-528, wherein at least about 40%, on a dry weight basis, of the protein composition comprises compounds larger than 5 kDa.

Embodiment 530 is the protein composition of any one of embodiments 479-529, wherein at least about 50%, on a dry weight basis, of the protein composition comprises compounds larger than 5 kDa.

Embodiment 531 is the protein composition of any one of embodiments 479-529, wherein at least about 60%, on a dry weight basis, of the protein composition comprises compounds larger than 5 kDa.

Embodiment 532 is the protein composition of any one of embodiments 479-529, wherein at least about 70%, on a dry weight basis, of the protein composition comprises compounds larger than 5 kDa.

Embodiment 533 is the protein composition of any one of embodiments 479-529, wherein at least about 80%, on a dry weight basis, of the protein composition comprises compounds larger than 5 kDa.

Embodiment 534 is the protein composition of any one of embodiments 484 or 529-533, wherein the compounds larger than 5 kDa are compounds larger than 10 kDa.

Embodiment 535 is the protein composition of any one of embodiments 484 or 529-533, wherein the compounds larger than 5 kDa are compounds larger than 15 kDa.

Embodiment 536 is the protein composition of any one of embodiments 484 or 529-533, wherein the compounds larger than 5 kDa are compounds larger than 20 kDa.

Embodiment 537 is the protein composition of any one of embodiments 484 or 529-533, wherein the compounds larger than 5 kDa are compounds larger than 25 kDa.

Embodiment 538 is the protein composition of any one of embodiments 479-537, wherein the protein composition does not comprise one or more compounds selected from the group consisting of cysteine, 1-hexanol, 2-butylfuran, 2-methyl-2-pentenal, 3-octanone, ethyl acetate, 2-ethyl-furan, 2-pentyl-furan, pyrazine, 1-decanol, acetophenone, 1-nonanol, 2,5-dimethyl-pyrazine, dodecanal, benzeneacetaldehyde, nonanal, butyrolactone, octanal, 2-decanone, hexanal, 2-nonanone, benzaldehyde, heptanal, 2-octanone, furfural, 2-heptanone, pentanal, 3-methyl butanal, and 3-methylbutanoic acid.

Embodiment 539 is the protein composition of any one of embodiments 479-538, wherein at least about 50% of the protein in the protein composition falls between about 10 kDa and about 200 kDa.

Embodiment 540 is a food, a beverage, or a supplement comprising the protein composition of any one of embodiments 479-539.

Embodiment 541 is a meat substitute comprising the protein composition of any one of embodiments 479-539.

Embodiment 542 is a method for treating a plurality of cells having cell walls, the method comprising:
perforating the cell walls of the plurality of cells,
wherein treatment of a supernatant of the plurality of cells with a mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids.

Embodiment 543 is a method for treating a plurality of cells, the method comprising: treating an aqueous suspension of the plurality of cells with a base until the pH of the aqueous suspension is about 8.5 to about 12.0;
wherein treatment of a supernatant of the plurality of cells with a mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids.

Embodiment 544 is a method for treating a plurality of cells having cell walls, the method comprising:
a) treating an aqueous suspension of the plurality of cells with a base until the pH of the aqueous suspension is about 8.5 to about 12.0;
b) perforating the cell walls of the plurality of cells;
wherein treatment of a supernatant of the plurality of cells with a mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids.

Embodiment 545 is a method for treating a plurality of cells having cell walls, the method comprising:
a) perforating the cell walls of the plurality of cells;
b) treating an aqueous suspension of the plurality of cells with a base until the pH of the aqueous suspension is about 8.5 to about 12.0;
wherein treatment of a supernatant of the plurality of cells with a mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids.

Embodiment 546 is a method for treating a plurality of cells, the method comprising:
heating the plurality of cells to a temperature of about 50° C. to about 85° C.; wherein treatment of a supernatant of the plurality of cells with a mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids.

Embodiment 547 is the method of any one of embodiments 542-546, wherein less than about 200 µg/mL beta glucan is detectable in a soluble phase, wherein the soluble phase is prepared using a 10% (w/v) suspension of the plurality of cells, after being incubated at 50° C. for 10 minutes at pH 12.0.

Embodiment 548 is a method for treating a plurality of cells having cell walls, the method comprising:
perforating the cell walls of the plurality of cells,
wherein less than about 200 µg/mL beta glucan is detectable in a soluble phase,
wherein the soluble phase is prepared using a 10% (w/v) suspension of the plurality of cells, after being incubated at 50° C. for 10 minutes at pH 12.0.

Embodiment 549 is a method for treating a plurality of cells, the method comprising:
treating an aqueous suspension of the plurality of cells with a base until the pH of the aqueous suspension is about 8.5 to about 12.0;
wherein less than about 200 µg/mL beta glucan is detectable in a soluble phase,
wherein the soluble phase is prepared using a 10% (w/v) suspension of the plurality of cells, after being incubated at 50° C. for 10 minutes at pH 12.0.

Embodiment 550 is a method for treating a plurality of cells having cell walls, the method comprising:
a) treating an aqueous suspension of the plurality of cells with a base until the pH of the aqueous suspension is about 8.5 to about 12.0;
b) perforating the cell walls of the plurality of cells;
wherein less than about 200 µg/mL beta glucan is detectable in a soluble phase,
wherein the soluble phase is prepared using a 10% (w/v) suspension of the plurality of cells, after being incubated at 50° C. for 10 minutes at pH 12.0.

Embodiment 551 is a method for treating a plurality of cells having cell walls, the method comprising:

a) perforating the cell walls of the plurality of cells;
b) treating an aqueous suspension of the plurality of cells with a base until the pH of the aqueous suspension is about 8.5 to about 12.0;
wherein less than about 200 μg/mL beta glucan is detectable in a soluble phase,
wherein the soluble phase is prepared using a 10% (w/v) suspension of the plurality of cells, after being incubated at 50° C. for 10 minutes at pH 12.0.

Embodiment 552 is a method for treating a plurality of cells, the method comprising:
heating the plurality of cells to a temperature of about 50° C. to about 85° C.;
wherein less than about 200 μg/mL beta glucan is detectable in a soluble phase,
wherein the soluble phase is prepared using a 10% (w/v) suspension of the plurality of cells, after being incubated at 50° C. for 10 minutes at pH 12.0.

Embodiment 553 is the method of any one of embodiments 542, 544, 545, 548, 550, or 551, wherein the perforating is performed at a pH of about 8.5 to about 12.0.

Embodiment 554 is the method of embodiment 546 or embodiment 552, wherein the heating is performed at a pH of about 8.5 to about 12.0.

Embodiment 555 is the method of any one of embodiments 542, 544, 545, 548, 550, or 551, wherein the perforating is performed at a pH of about 9.0 to about 12.0.

Embodiment 556 is the method of embodiment 546 or embodiment 552, wherein the heating is performed at a pH of about 9.0 to about 12.0.

Embodiment 557 is the method of any one of embodiments 543-545 or 549-551, wherein the treating comprises treating the aqueous suspension of the plurality of cells with the base until the pH of the aqueous suspension is about a pH of about 9.0 to about 12.0.

Embodiment 558 is the method of any one of embodiments 542, 544, 545, 548, 550, or 551, wherein the perforating is performed at a pH of about 9.0 to about 10.0.

Embodiment 559 is the method of embodiment 546 or embodiment 552, wherein the heating is performed at a pH of about 9.0 to about 10.0.

Embodiment 560 is the method of any one of embodiments 543-545 or 549-551, wherein the treating comprises treating the aqueous suspension of the plurality of cells with the base until the pH of the aqueous suspension is about a pH of about 9.0 to about 10.0.

Embodiment 561 is the method of any one of embodiments 542, 544, 545, 548, 550, or 551, wherein the perforating is performed at a pH of about 10.0 to about 11.0.

Embodiment 562 is the method of embodiment 546 or embodiment 552, wherein the heating is performed at a pH of about 10.0 to about 11.0.

Embodiment 563 is the method of any one of embodiments 543-545 or 549-551, wherein the treating comprises treating the aqueous suspension of the plurality of cells with the base until the pH of the aqueous suspension is about a pH of about 10.0 to about 11.0.

Embodiment 564 is the method of any one of embodiments 542, 544, 545, 548, 550, or 551, wherein the perforating is performed at a pH of about 11.0 to about 12.0.

Embodiment 565 is the method of embodiment 546 or embodiment 552, wherein the heating is performed at a pH of about 11.0 to about 12.0.

Embodiment 566 is the method of any one of embodiments 543-545 or 549-551, wherein the treating comprises treating the aqueous suspension of the plurality of cells with the base until the pH of the aqueous suspension is about a pH of about 11.0 to about 12.0.

Embodiment 567 is the method of any one of 544, 545, 550, or 551, wherein each of a) and b), independently, are performed at a temperature of less than or equal to about 12° C.

Embodiment 568 is the method of any one of embodiments 544, 545, 550, or 551, wherein each of a)-c), independently, are performed at a temperature of less than or equal to about 10° C.

Embodiment 569 is the method of any one of embodiments 542, 544, 545, 548, 550, or 551, wherein the perforating is performed at a temperature of less than or equal to about 12° C.

Embodiment 570 is the method of any one of embodiments 543-545 or 549-551, wherein the treating is performed at a temperature of less than or equal to about 12° C.

Embodiment 571 is the method of embodiment 546 or embodiment 552, further comprising after heating the plurality of cells, treating the aqueous suspension of the plurality of cells with a base until the pH of the aqueous suspension is about 8.5 to about 12.0.

Embodiment 572 is the method of embodiment 546 or embodiment 552, wherein when the plurality of cells has cell walls, the method further comprises, after heating the plurality of cells, perforating the cell walls of the plurality of cells.

Embodiment 573 is the method of any one of 543-545 or 549-551, wherein treating the aqueous suspension of the plurality of cells with a base until the pH of the aqueous suspension is about 8.5 to about 12.0 comprises treating the aqueous suspension of the plurality of cells with a base until the pH of the aqueous suspension is between about 8.5 and 12.0 for at least about 3 minutes.

Embodiment 574 is the method of any one of 543-545 or 549-551, wherein treating the aqueous suspension of the plurality of cells with a base until the pH of the aqueous suspension is between about 8.5 and 12.0 comprises treating the aqueous suspension of the plurality of cells with a base until the pH of the aqueous suspension is between about 8.5 and 12.0 for at least about 5 minutes.

Embodiment 575 is the method of any one of 543-545 or 549-551, wherein treating the aqueous suspension of the plurality of cells with a base until the pH of the aqueous suspension is between about 8.5 and 12.0 comprises wherein treating the aqueous suspension of the plurality of cells with a base until the pH of the aqueous suspension is between about 8.5 and 12.0 for at least about 10 minutes.

Embodiment 576 is the method of any one of embodiments 542, 544, 545, 548, 550, or 551, wherein the method further comprises, after the perforating, heating the plurality of cells to at least about 60° C.

Embodiment 577 is the method of any one of embodiments 543-545 or 549-551, wherein the method further comprises, after the treating, heating the plurality of cells to at least about 60° C.

Embodiment 578 is the method of any one of embodiments 542, 544, 545, 548, 550, or 551, wherein perforating comprises treatment with a reductant, treatment with an enzyme, electroporation, or a combination thereof.

Embodiment 579 is the method of embodiment 578, wherein treatment with the reductant comprises treatment with about 10 mM to about 500 mM reducing equivalents of the reductant.

Embodiment 580 is the method of embodiment 578, wherein treatment with the reductant comprises treatment with about 20 mM to about 80 mM reducing equivalents of the reductant.

Embodiment 581 is the method of embodiment 578, wherein treatment with the reductant comprises treatment with about 50 mM reducing equivalents of the reductant.

Embodiment 582 is the method of any one of embodiments 578-581, wherein the reductant is selected from the group consisting of cysteine, glutathione, bisulfite, and a combination thereof.

Embodiment 583 is the method of any one of embodiments 578-582, wherein the reductant is a food safe reductant.

Embodiment 584 is a composition prepared by the method of any one of embodiments 542-583.

Embodiment 585 is a composition comprising:
a plurality of cells,
wherein treatment of a supernatant of the plurality of cells with a mannosidase yields less than about 30 µg/mL detectable mannose in the supernatant, wherein the supernatant is prepared using a 10% (w/v) suspension of the plurality of cells, after being incubated at 50° C. for 10 minutes at pH 10.5 and centrifuged to remove solids.

Embodiment 586 is the composition of embodiment as, wherein less than about 200 µg/mL beta glucan is detectable in a soluble phase, wherein the soluble phase is prepared using a 10% (w/v) suspension of the plurality of cells, after being incubated at 50° C. for 10 minutes at pH 12.0.

Embodiment 587 is a composition comprising:
a plurality of cells,
wherein less than about 200 µg/mL beta glucan is detectable in a soluble phase,
wherein the soluble phase is prepared using a 10% (w/v) suspension of the plurality of cells, after being incubated at 50° C. for 10 minutes at pH 12.0.

Embodiment 588 is the composition of any one of embodiments 585-587, wherein the composition further comprises a reductant.

Embodiment 589 is the composition of embodiment 588, the reductant is present in the composition in an amount of about 10 mM to about 500 mM reducing equivalents of the reductant.

Embodiment 590 is the composition of embodiment 588, the reductant is present in the composition in an amount of about 20 mM to about 80 mM reducing equivalents of the reductant.

Embodiment 591 is the composition of embodiment 588, the reductant is present in the composition in an amount of about 50 mM reducing equivalents of the reductant.

Embodiment 592 is the composition of any one of embodiments 588-591, wherein the reductant is selected from the group consisting of cysteine, glutathione, bisulfite, and a combination thereof.

Embodiment 593 is the composition of any one of embodiments 588-592, wherein the reductant is a food safe reductant.

Embodiment 594 is the composition of any one of embodiments 585-593, wherein at least about 25% by weight of the cells of the plurality of cells are intact.

Embodiment 595 is the composition of any one of embodiments 585-593, wherein at least about 50% by weight of the cells of the plurality of cells are intact.

Embodiment 596 is the composition of any one of embodiments 585-593, wherein at least about 75% by weight of the cells of the plurality of cells are intact.

Embodiment 597 is the composition of any one of embodiments 585-593, wherein the plurality of cells has a particle size distribution median of about 2 µm to about 4 µm.

The invention will be further described in the following examples, which do not limit the scope of the invention described in the claims.

EXAMPLES

Example 1

Lysis of Yeast Cells at pH 6.0 or 9.0

Aqueous cell suspensions (CS) of *S. cerevisiae* were prepared using yeast crumble or yeast cream at 15-21% dry solids final, as provided by the manufacturer. In the case of yeast crumble, a 1:1 suspension was prepared using milliQ water. The CS were maintained at either pH 6.0 or pH 9.0. Yeast cells in the CS were lysed using bead milling while maintaining a pH or either 6.0 or 9.0, as appropriate. The lysed cells were clarified by centrifuging at 8,000×g for 3 minutes using a small-scale model of a pilot scale disc-stack centrifuge. The clarified lysate was microfiltered using a membrane with 0.2 µm nominal pore size.

Figure 10:
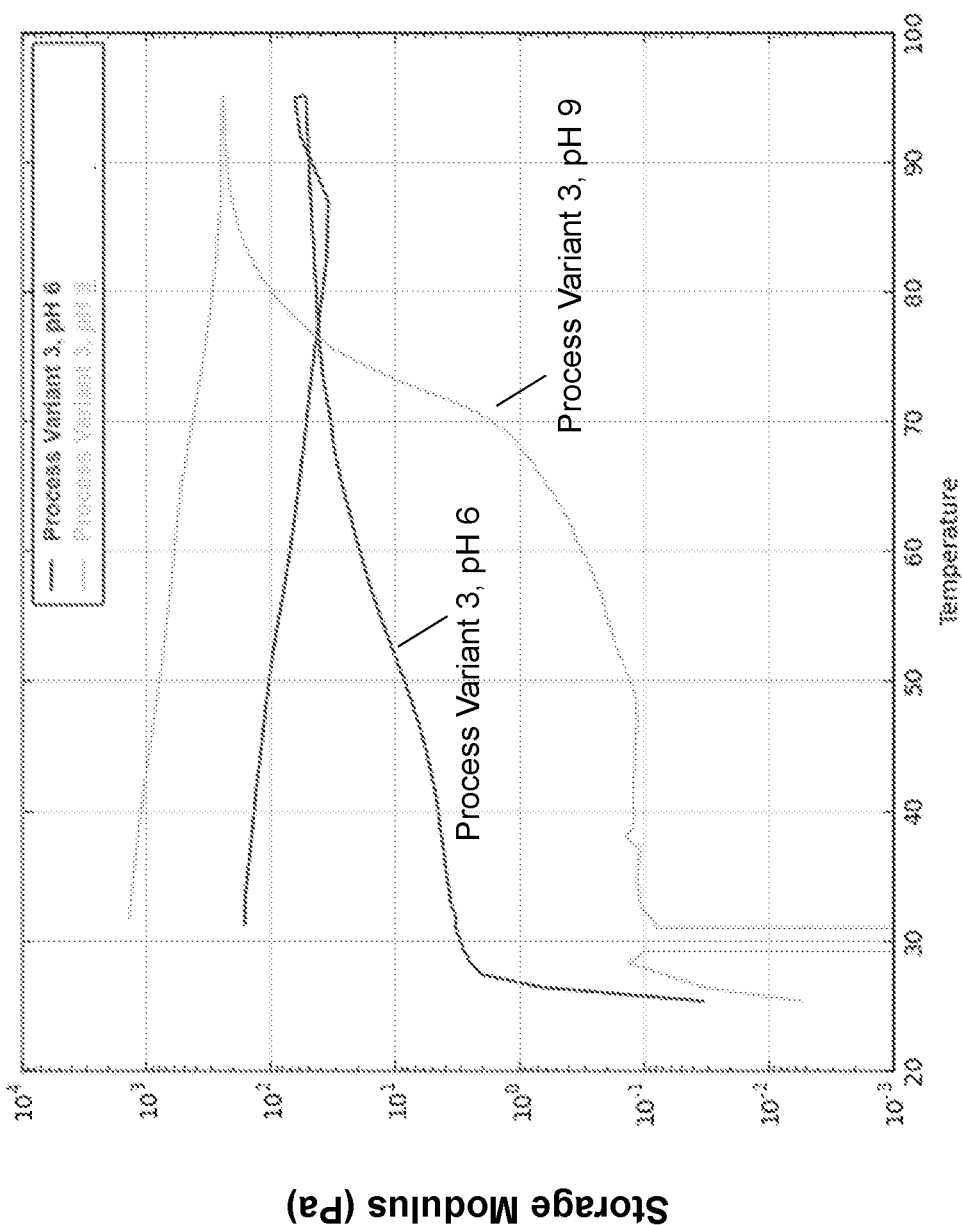
FIG. 10 is a plot of the rheology of protein compositions produced by Process Variant 3 (see FIG. 9B) was conducted at pH 6.5 or at pH 9.5. Rheology of the resulting material was measured using a hybrid rheometer. Vertical axis shows storage modulus (Pa) in log scale. Horizontal axis shows incubation temperature.
Figure 11A:
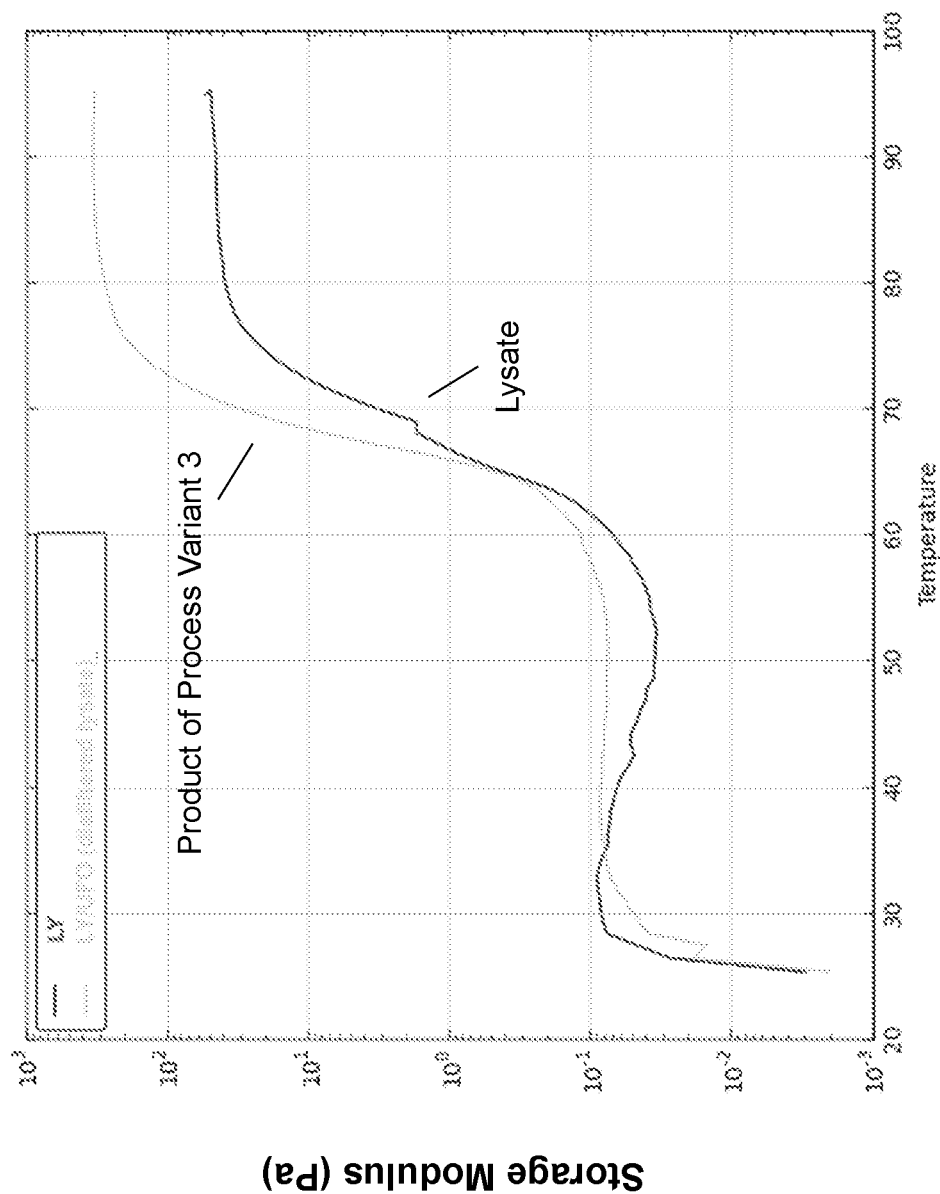
FIG. 11A is a plot of the rheology of protein compositions produced by Process Variant 3 (see FIG. 9B) conducted at pH 9.3. In-process samples were taken of lysate ("LY") and the final product of Process Variant 3 ("LY/UFO"). Each sample was freeze dried, then suspended to 10% (w/v) in milliQ water. Suspensions were assayed at pH 7.5.
Figure 11B:
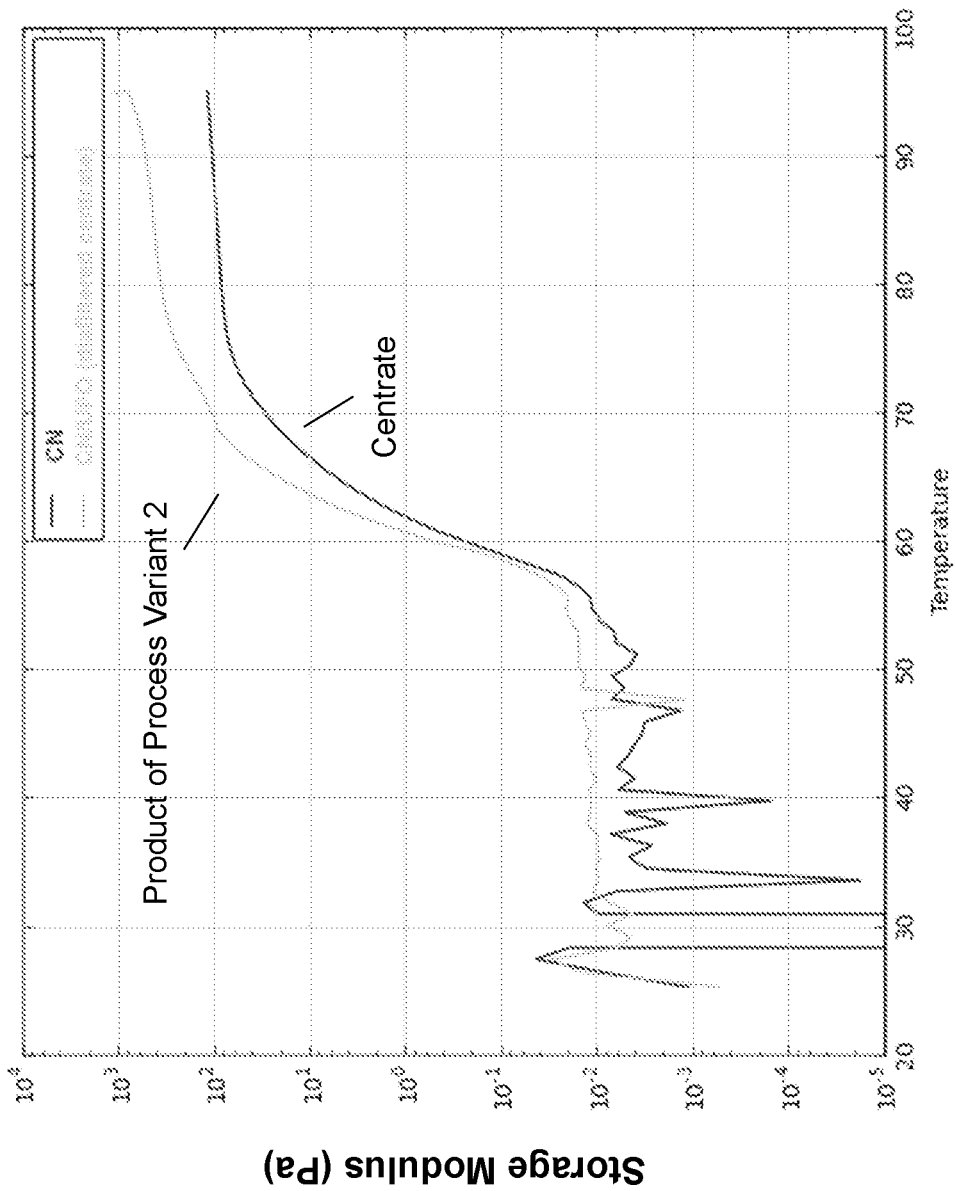
FIG. 11B is a plot of the rheology of protein compositions produced by Process Variant 2 (see FIG. 9B) conducted at pH 9.3. In-process samples were taken of centrate ("CN") and the final product of Process Variant 2 ("CN/UFO"). Each sample was freeze dried, then suspended to 10% (w/v) in milliQ water. Suspensions were assayed at pH 7.5.

The use of pH 9.0 versus 6.0 had several desirable results. During centrifugation, solids were removed far more effectively. After centrifugation, the clarified lysate maintained at pH 9.0 had a 25-50% increase in yield relative to the lysate maintained at pH 6.0 (e.g., in one experiment, pH 6.0 gave 10% dry-basis (DB) yield vs. 15% DB yield at pH 9.0) and a 30% decrease in protein loss during microfiltration (0.2 µm membrane). Protein obtained from an alkaline process was more functional as determined by hybrid rheometer (FIG. 10). At the sensory level, the development of undesirable off-flavors in supernatant/centrate were significantly reduced, such that a panel of experienced sniffers were immediately able to sort blinded samples. Analytical results support these findings and are consistent with internal sensory panel comments.

Example 2

Lysis of Yeast Cells at pH 6.0 or 9.0

Aqueous suspensions of *P. pastoris* expressing soybean leghemoglobin were prepared using broth fermented by Impossible Foods. Whole cells were isolated by centrifugation using a pilot-scale disk stack centrifuge (Alfa Laval BRPX 810 SGV-34CG; feed rate: 10 LPM; initial discharge timer: 5 min; feed % SS: 10-13; centrate solids % SS: 55-60; 2-10° C.). Cells were resuspended at 1:1 ratio using deionized water (2-10° C.). Cell suspension pH was adjusted to pH 6.0 or 9.0 using 5M HCl or 5M NaOH until cell suspension pH was stable for 30 minutes. Cell suspensions were lysed using a small-scale homogenizer (Gaulin 30CD; 13,000-15,000 psi; 3 passes) with cooling to 2-10° C. and pH adjustment between passes. The lysed cells were clarified by centrifuging at 12,000×g for 20 minutes using a small-scale model of a pilot scale disc-stack centrifuge. Clarified lysate ("centrate") was applied directly to a hollow-fiber ultrafiltration membrane (Koch Romicon part #0721039; 30 kDa molecular weight cutoff (MWCO), 1.1 mm diameter fibers), concentrated to ~10% dry solids (DS) and diafiltered using deionized water at either pH 6.0 or pH 9.0. Final product was obtained after drying in a lyophilizer. After drying, 10% (w/v) suspensions using each final product were prepared at a final pH of approximately 7.0 and analyzed using a hybrid rheometer (TA Instruments, DHR series; 4 C/min steps).

The use of pH 9.0 versus 6.0 had several desirable results. After centrifugation, the clarified lysate maintained at pH 9.0 had a 35% increase in protein yield relative to the lysate maintained at pH 6.0. When heated to 95° C. at 10% (w/v) DS, thermally-set gels using the pH 9.0 final product were about 10-fold stronger (i.e., higher storage modulus) than those obtained from final product from the pH 6.0 process.

Example 3

Lysis of Bacterial Cells at pH 6.0 or 9.0

Cultures of E. coli cells (DH5alpha, 8 liters total) were prepared by growth in lysogeny broth (LSB media) at 37° C. in shake flasks. Whole cells were isolated by centrifugation at 15,000×g for 20 minutes using a floor model laboratory centrifuge.

Cells were resuspended at 1:5 ratio (grams cell pellet:mL water) using MILLI-Q® water (2-10° C.). Cell suspension was split into two halves, with pH was adjusted to pH 6.0 or 9.0 using 5M HCl or 5M NaOH until cell suspension pH was stable for 30 minutes. Cell suspensions were lysed using a small-scale homogenizer (Gaulin 30CD; 13,000-15,000 psi; 3 passes) with cooling to 2-10° C. and pH adjustment between passes. The lysed cells were dialyzed directly on 30 kDa dialysis membranes (Pierce Slide-a-Lyzer)

The use of pH 9.0 versus 6.0 had several desirable results: 1) protein released after cell lysis increased by 30%; 2) storage modulus (firmness) increase of thermally-set gels improved by about 6-fold (final product of Process Variant C, pH 9 vs. pH 6; 10% w/v suspensions prepared in MILLI-Q® water to pH 7.0; assayed by rheometer as described previously); key odor-active volatiles from a range of classes were decreased by 30-75% (e.g., 3-octanone, ethyl acetate, pyrazine, nonanal, acetaldehyde).

Example 4

Purification of Protein at pH 6.5 or 9.5

Total cellular protein was purified from cultures of S. cerevisiae in two different experiments using the same methods and materials, except the pH of the solutions throughout the purification were at either pH 6.5 or pH 9.5. Aqueous cell suspensions (CS) of S. cerevisiae were prepared using yeast crumble or yeast cream at 15-21% dry solids final, as provided by the manufacturer. In the case of yeast crumble, a 1:1 suspension was prepared using milliQ water. The yeast cells were lysed using bead milling while maintaining a pH of or either 6.5 or 9.5, as appropriate, to make cell lysates. The lysates were clarified by centrifuging at 8,000×g for 3 minutes using a small-scale model of a pilot scale disc-stack centrifuge. The clarified lysates ("centrates") were incubated at 4° C. overnight. A panel of trained tasters and smellers then tested the resulting product after cold storage. The panel was able to correctly sort the pH 6.5 from the pH 9.5 process samples by scoring off-odors in the absence of other visual cues.

Example 5

Filtration, Concentration and/or Desalting of Protein Concentration or Isolate at pH 9.5

Lysis of yeast cells was performed as indicated in previous examples. The material may be optionally microfiltered to remove in-process microbial counts (e.g., using a WaterSep Mini-BioProducer41, HF 0.2 µm microfilter, cat WA 920 10MPR41 SG), yielding the improved protein passage of 30%. With or without microfiltration, the material may be concentrated, diafiltered and depleted of small molecules using ultrafiltration. For example, the material has been applied to both WaterSep (cat: BC 030 20GRA43 1L) and Koch (cat: HF,6043-97-43-PM30) using 4-10 diavolumes prior to a final concentration down to 10-16% dry solids. The alkaline processing method described produced a superior ingredient that demonstrates improved food activities: firmer gels upon cooking (FIGS. 3-5, 10, and 11A-B) with lower off-odor and off-flavor (See, e.g., Table 4). Table 2 lists some exemplary specifications of protein produced by this process. Table 3 lists some exemplary benefits of the pH 9.5 technique compared to the pH 6.5 technique. Table 4 lists some exemplary compounds that can be depleted by a pH 9.5 technique.

TABLE 2

| Material Specifications | | |
|---|---|---|
| Property | Assay | Specification |
| Protein Denaturation | Differential Scanning Fluorimetry | >80% detectable hydrophobic exposure is complete between 50° C. and 85° C.; maximal hydrophobic exposure occurs between 50° C. and 75° C.; pH 5.5-10.0; non-protein ionic strength 0-0.5M |
| Gelation | Hybrid Rheometer | 10% (w/v) suspension gels to 100 Pa storage modulus when heated to 95° C. and cooled back to 25° C. |
| Particle Size Distribution | Laser diffraction (Mastersizer, Malvern) | D10 < 0.1 µm; D50 < 1.0 µm; D90 < 5 µm |
| Polypeptide | Reducing, denaturing SDS- | Greater than 50% of |

TABLE 2-continued

Material Specifications

| Property | Assay | Specification |
|---|---|---|
| Integrity | PAGE | Coommassie-stained polypeptides fall between 10 kDa and 200 kDa (e.g., 20 kDa and 200 kDa) as measured by densitometry |
| $H_2S$ release | Hach Hydrogen Sulfide Test Kit (Cat. No. 25379-00). Test 45 mL head space in 50 mL Falcon tube with 5 mL product, 2% (w/v, aqueous), pH 7.0 at RT x 24 hours. Filters fitted under cap. No effervescent tablet added | Three-fold or greater increase in released H2S upon addition of L-cysteine; and/or No added cysteine: $H_2S$ < 0.1 ppm 25 mM added cysteine: $H_2S$ > 0.2 ppm (e.g., >0.3 ppm) |
| Buffer Capacity | Buffer capacity measured by titration with NaOH or HCl between pH 3 and pH 12 | less than 3.0 mmol (e.g., less than 2.5 mmol) NaOH per gram dry solids |
| Volatile Ester content | GCMS on pH- and volume-matched sample | >10X reduction in ester content vs. matched sample processed at pH 6.5 |
| Volatile Aroma Compounds | GCMS on pH- and volume-matched sample when headspace of a 2 mL of a 10% (w/v) suspension is assayed in a 20 mL glass vial at 50° C. by adsorption onto SPME fiber, followed by GCMS | >2.5X reduction in the following volatile compounds: 3-Octanone; Acetophenone; 1-Nonanol; Benzeneacetaldehyde; Nonanal, |
| Emulsion Activity Index | Mechanical homogenization of aqueous protein solution with canola oil; EAI = (2T)/(c*vol_fx_oil) where T = ln(10)*$A_{600}$/path_length | >50 $m^2$/g protein across pH 4.0-8.0 |

TABLE 3

Process and composition benefits obtained using alkaline process technique combined with filtration

| Process or composition feature | Benefit (pH 9.5 vs. pH 6.5) |
|---|---|
| Protein Released | 25-50% increase |
| Microfiltration performance | 30% increase in permeated protein |
| Solids removal (e.g., by centrifugation) | >20% recovery of aqueous phase volume |
| Gel strength at 10% (w/v) | ≥10-fold increase in storage modulus at 95° C. |
| Buffer capacity of isolate/concentrate | Decreased by about 30%. Stable pH after addition to meat replica as dry ingredient, and/or less than or equal to the equivalent of 2.5 mmol NaOH per gram dry solids required to shift pH from pH 3.0-pH 12.0 of material at 2% dry solids (w/v) in MILLI-Q ® water. |
| Gelation capacity after pasteurization; assayed at 10% (w/v) dry solids | ≥2-fold increase in storage modulus at 95° C. PZ at 65° C. x 30 sec |

TABLE 4

Small Molecules depleted using alkaline processing technique

| Compound | Pichia processed without alkaline process | Pichia processed with alkaline process | Pichia Factor Change | Saccharomyces processed without alkaline process | Saccharomyces processed with alkaline process | Saccharomyces factor change | Odor Descriptor |
|---|---|---|---|---|---|---|---|
| 3-Octanone | 1,661,170.00 | 169,881 | 9.78 | Not Detected | Not Detected | Not Detected | Musty, mushroom, ketonic, moldy and cheesy fermented with a green, vegetative nuance |
| Ethyl Acetate | 15,927,040.00 | 5,408,039 | 2.95 | Not Detected | Not Detected | Not Detected | Etherial, fruity, sweet, with a grape and cherry nuance |
| Pyrazine | 2,592,053 | 1,656,755 | 1.56 | Not Detected | Not Detected | Not Detected | pungent sweet corn like roasted hazelnut barly |
| Acetophenone | 9,416,779 | 321,953 | 29.25 | 120,697,700 | 9,104,363 | 13.25 | Powdery, bitter almond cherry pit-like with coumarinic and fruity nuances |
| 1-Nonanol | 831,649 | Not Detected | INF | 92,858,790 | 9,737,588 | 9.53 | fresh clean fatty floral rose orange dusty wet oily |
| 2,5-dimethyl-Pyrazine | Not Detected | Not Detected | Not Detected | 3,615,044 | 405,892 | 8.90 | Nutty, peanut, musty, earthy, powdery and slightly roasted with a cocoa powder nuance |
| Nonanal | 2,819,845 | 456,452 | 6.18 | 467,067,300 | 186,830,400 | 2.49 | waxy aldehydic rose fresh orris orange peel fatty peely |
| 2-Decanone | 592,550 | Not Detected | INF | 2,333,218 | 2,163,738 | 1.07 | orange floral fatty peach |

Listed values correspond to peak integration areas as described in the data processing in example 4.
Factor change = (compound area of non alkaline process/compound area of alkaline process)
INF = factor change unable to be determined Example 6

Measurement of Polypeptide Integrity in Protein Compositions

Dried protein compositions from using Process Variants B or C (FIG. 2), from S. cerevisiae, P. pastoris or E. coli, were brought to 10% (w/v) final suspension of material in MILLI-Q® water. The pH was adjusted to pH 9.0 using NaOH or HCl and protein concentration was measured using the Pierce 660 nm Protein Assay Reagent (cat #22660), following the manufacturer's instructions. Suspensions were then adjusted to final protein concentration of 0.1 mg/mL in 1× final concentration SDS-PAGE loading buffer (4× Laemmli Sample Buffer Bio-Rad #1610747) with 0.1 mM DTT final added freshly. Samples were incubated as 50-500 uL aliquots in tightly sealed container (1.7 mL Eppendorf tube) at 95° C. for 10 minutes to denature protein. Heated samples were clarified at 20,000×g, 25° C. for 5 minutes prior to resolving on a gradient (e.g., 4-10% polyacrylamide) SDS-PAGE gel (Bio-Rad Criterion gel, cat #5671091) according to the manufacturer's instructions. Between 100 ng-5 ug protein was loaded per gel lane depending on staining method. In adjacent lanes, molecular weight markers covering range 10-200 kDa (Bio-Rad Precision Plus markers, cat #1610373) were loaded according to the manufacturer's recommendations. In one example, protein bands were visualized using Bio-Rad QC Colloidal Coomassie Stain (cat #1610803) according to the manufacturer's instructions.

Destained gels were scanned before measuring band intensity using the Bio-Rad Gel Doc system equipped with Image Lab (cat #1708270EDU). Bands were detected, quantified and sized using automated band detection and molecular weight calibration against the standard loaded. Data was exported to Microsoft Excel. Individual band intensity was summed to demonstrate that more than 50% of individual band intensities resided between 10 kDa and 200 kDa.

Example 7

Measurement of Change in Buffering Capacity Before and After Process Variant

Two independent pilot-scale process replicates of protein compositions derived from the beginning ("Lysate") and end ("Final Product") Process Variant C (FIG. 2) using *S. cerevisiae* cells as starting material were obtained as freeze-dried powders. Suspensions (500 mL) were made of each replicate to 2% (w/v) final suspension, transferring 200 mL to a glass beaker equipped with a magnetic stir bar. The suspension was mixed well (200 rpm-700 rpm). Suspension pH was measured using a pH meter equipped with pH probe (ThermoFisher Orion module cat #VSTAR82) calibrated against standardized buffer solutions (ThermoFisher cat #810199).

In 0.2 mL increments, 5M NaOH was added until pH=12.0+/−0.1 unit. Total volume of NaOH solution added was recorded, then the sample was discarded. The process was repeated with a fresh aliquot of 200 mL suspension, except increments of 5M HCl were added in 0.2 mL increments until pH=3.0+/−0.1 unit. Total volume of HCl solution added was recorded, then the sample was discarded.

To compute buffering capacity of each suspension, total volumes of HCl and NaOH added during titration were summed and expressed in milliliters (mL). This number was multiplied by 5 to obtain total millimoles (mmol) NaOH required to adjust 200 mL of the 2% (w/v) solution (4 grams dry solids) from a starting pH of 3.0 to a final pH of 12.0. Using this method, a protein composition (Final Product) required only 2.5 mmol per gram dry solids, whereas the starting material (Lysate) required about 50% more NaOH to achieve the same shift in pH.

Example 8

Measure of Hydrogen Sulfide Release Capacity of Protein Composition

Freeze-dried final product of Process Variants B or C (FIG. 2), from *S. cerevisiae*, *P. pastoris* or *E. coli*, were suspended to 2% (w/v) in MILLIQ® water and adjusted to a final pH of about 7.0 using HCl, using the method as described above for measuring buffer capacity. A volume of 5 mL of the pH-adjusted sample was transferred to a 50 mL Falcon conical tube (Corning cat #352070). Triplicate samples were made, either with 25 mM final concentration of L-cysteine (Acros cat #173600250) or with an equivalent volume of water added (control). Into the cap of each tube was fitted a single filter from the Hach kit for detecting hydrogen sulfide (Hach HS-C cat #2537900). Capped tubes were left at room temperature (25° C.) for about 24 hours to detect released hydrogen sulfide.

Figure 6:
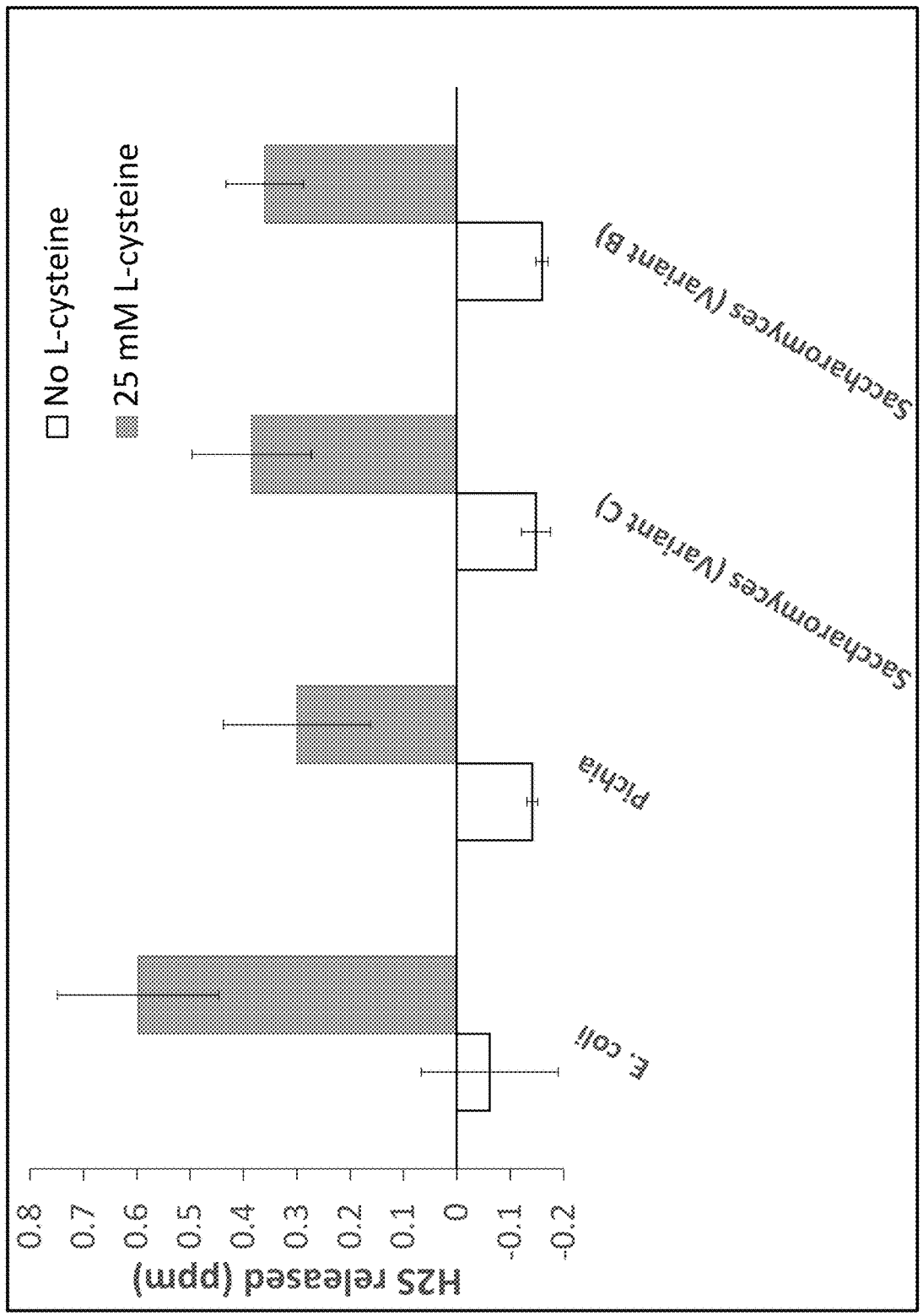
FIG. 6 is a plot showing the absence of detectable hydrogen sulfide ($H_2S$) in the headspace and the appearance of >0.1 ppm hydrogen sulfide ($H_2S$) after addition of 25 mM L-cysteine to microbial protein compositions prepared using Process Variants C or Process Variant D. Microbes used to prepare the protein compositions are representatives of either Bacteria (*Escherichia coli*) or Eukarya (*Pichia pastoris* or *Saccharomyces cerevisiae*).
Figure 7:
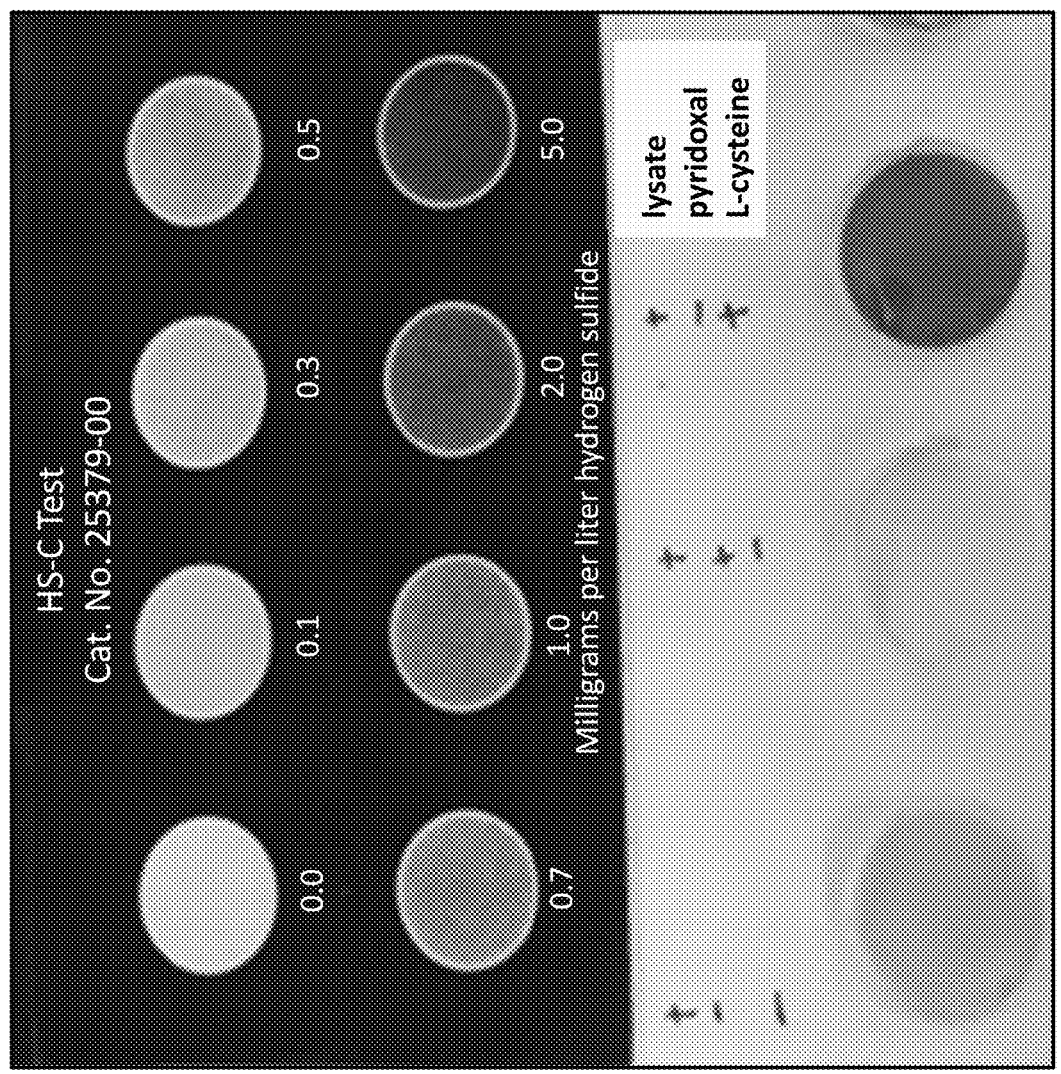
FIG. 7 is a photograph of the results of assaying for $H_2S$ in the headspace of lysates from *Saccharomyces* cells were prepared at about 2% (w/v) final by taking an in-process sample after homogenizer lysis during Process Variant C. The upper half shows standards, and the lower half shows the results of the lysate with no added cysteine (left), Process Variant C with added pyridoxal hydrochloride (center), and Process Variant C with added L-cysteine (right).

A standard curve was used to determine hydrogen sulfide released, as follows. The Hach detection kit used provides a reference set of images for use in determining hydrogen sulfide (expressed as ppm). The colorimetric intensity of these images was measured using a Konica Minolta Chroma Meter CR-5 E350, with each reference image measured against a black background. This produced a standard curve linear in the "b" channel (yellow) between 0 and 1 ppm hydrogen sulfide. To determine hydrogen sulfide release in the four unknown samples (*E. coli* (Variant C), *Pichia* (Variant B), *Saccharomyces* (Variant C), and *Saccharomyces* (Variant B)), filter colors were measured with same device, and the "b" (yellow) intensity compared to the standard curve. Results of this assay, given in FIG. 6, show cysteine-dependent increase in hydrogen sulfide release. Control experiments (FIGS. 6 and 7) demonstrated that this activity: 1) decreased from high (>1 ppm) in starting lysates of *S. cerevisiae* with no added L-cysteine to undetectable in final products of Process Variants B or C; 2) was inhibited by pyridoxal hydrochloride, consistent with this being a characterized sulfhydrylase enzyme (Yamagata and Takeshima (1976) J. Biochem 80: 777). In the experiment shown in FIG. 7, lysates from *Saccharomyces* cells were prepared at about 2% (w/v) final by taking an in-process sample after homogenizer lysis during Process Variant C, quantifying dry solids, then supplementing with water (control), or to 50 mM final pyridoxal hydrochloride (pH 7) or 50 mM final cysteine (pH 7). Sulfide release was measured as described, using HS-C sulfide detection filters and comparing to the kit standard given (shown in FIG. 7). Note that pyridoxal inhibits sulfide release, while non-diafiltered lysate yields a strong sulfide signal that is further increased upon addition of L-cysteine.

Example 9

Measure Rheology of Lysates, Centrates and Final Product Protein Compositions During Heating Freeze-dried lysates, centrates or final products of Process Variants B or C, from *S. cerevisiae* or *P. pastoris*, were suspended to 10% (w/v) in MILLI-Q® water and adjusted to a final pH of about 7.0 using NaOH or HCl, using the method as described above for measuring buffer capacity. A volume of 1.25 mL of pH-adjusted sample was transferred to a steel (Peltier) plate in a hybrid rheometer (TA instruments, DHR unit). Storage modulus was measured following manufacturer's recommendations while temperature was increased at a ramp rate of 3° C. per minute from 25° C. to 95° C. Resulting storage modulus data was plotted in log scale against corresponding temperature in linear scale to yield FIGS. 3, 4 and 5.

Example 10

Measure Thermal Exposure of Hydrophobic Amino Acids

Freeze-dried lysates, centrates or final products of Process Variants B or C were prepared as suspensions at various pH (e.g., pH 6, 7, 8, 9) and concentrations (e.g. 0.5%, 1%, 2% w/v). The relative and total fluorescent signal increase during thermal denaturation was measured using the "Thermal Shift" method as described in Lo et al (2004) Anal. Biochem. 332(1):153. Samples were run on a Bio-Rad CFX96 (C1000 Touch) device using factory calibrations. Data from Channel 2 (HEX) were plotted as relative fluorescence intensity (RFI) vs. temperature. Fluorescence was read once per minute during a 1° C. per minute ramp rate from 25° C. to 100° C. After subtracting baseline and dye-only signal, maximal fluorescence was assigned as maximum peak height to calculate hydrophobic exposure). Maximal peak height was taken as '100% denaturation' of a sample.

Example 11

Measurement of Particle Size Distribution (PSD)

Suspensions of *S. cerevisiae* or *P. pastoris* lysates or final product (Process Variant B or C) (FIG. 2) were prepared at 10% (w/v). These were dispersed in a Malvern Mastersizer 3000 unit equipped with a Hydro MV unit until obscuration reached about 15%. Distributions were measured using the following instrument parameters. Material properties: refractive index 1.45; Absorbance index 0.001; density 1 g/cm$^3$; Disperant: water; refractive index 1.33; non-spherical particles; background measurement time 10 seconds; sample measurement time 10 seconds; obscuration limits 0.1%-50%; ultrasound power, 50%; stirrer, 2000 rpm. Using these values and Process Variants B and C, PSD values were observed as given in the Table 2: D10<0.1 μm; D50<1.0 μm; D90<5 μm. Characteristic PSD values were considerably larger when pH 6 process was used, presumably due to electrostatic-mediated aggregation.

Example 12

Sampling and Characterization of Headspace Profile for Microbial Protein Samples In-process samples prepared from microbial extracts of *S. cerevisiae*, *P. pastoris* and *E. coli* (LY, CN, MF retentate, MF permeate, UF retentate, UF permeate, final product) prepared at process pH of 6.0-6.5 (control) or pH 9.0-9.5 (test) were all made to 10% solutions (wt/wt) with MILLI-Q® water. All samples were adjusted to pH 6.5 (or pH 9.5) with 10M NaOH or 3 M HCl. Three mL of each sample were measured into 20 mL GCMS vials. To evaluate the production of volatile compounds, an Agilent 7890A GC coupled with a Leco Pegasus HT-C High Throughput TOFMS was used along with a Gerstel MultiPurpose Sampler for autosampling. The Gerstel auto-sampler was used perform HS-SPME on each of the samples. Each sample was incubated at 50° C. for 15 mins with 250 rpm agitation before being extracted for 20 minutes at 50° C. with 250 rpm agitation using a 2 cm 50/30 μm Divinylbenzene/Carboxen/Polydimethylsiloxane (DVB/CAR/PDMS), Stable flex, 23 Ga, Autosampler (Supleco, Cat #57299-U) SPME fiber.

Extracted samples were run on the GCMS by desorbing the SPME fiber into a Gerstel septum-less head with a PTV inlet set to 240° C. for 60 seconds and cryofocused at −50° C. with a Gerstel Cooled Injection System (CIS). The CIS was held at −50° C. for 0.1 min, temperature was ramped at +12° C./second to 240° C., and held for the remainder of the run. The desorbed sample was separated on a 60-meter wax column (Agilent, VF-WAXms 60 m×0.25 mm×0.25 mm, Part #CP9207) using a 50 minute GC method (35° C. for 2 minutes, ramp of 5° C./min until 255° C., hold at 255° C. for 4 minutes) and 1.5 mL/min helium flow rate in splitless mode. Separated compounds were analyzed by the mass spectrometer, and all data was collected over a 20-500μ mass range, with an acquisition rate of 10 spectra/sec, and a detector voltage off-set of 200.

Samples were then analyzed using Leco ChromaTOF optimized for Pegasus 4D (Version 4.71.0.0) coupled with the NIST MS Search 2.2. The identity of each peak in each sample was identified in a two-step process. First, the mass spectrum of each peak with a signal to noise greater than 30 was matched to a mass spectrum in the NIST library using a similarity threshold of 650. Additionally, an internally developed calibration method was applied to the data set to confirm the identity of the compounds of interest. In the second step, the Statistical Compare function of ChromaTOF was used to align the named analyses across all samples in a set. The criteria for aligning a single peak across all samples were a match score (similarity between the peak spectra across all samples) of 700, a maximum retention time difference of 10 seconds, and the peak must have been present in at least two samples.

Table 4 includes compounds assayed using this technique.

Example 13

Additional Process Variants

Additional process variants are performed. FIG. 9A shows exemplary process variants for treating cells suspensions (CS), either staring with alkaline exhaustion (AE) or reduction (e.g., with 50 mM L-cysteine) (RD). In some cases, cells suspensions undergo upfront pasteurization (PZ1), either as a first step (e.g., alone, or combined with RD or AE in any order), or as a step following RD or AE as a first step. FIG. 9B shows exemplary process variants for treading "feed" input cells, such as those from the processes of FIG. 9A; some process variants use mechanical lysis, and some rely on perforation of the cells, such as that resulting from the treatments in FIG. 9A.

Example 14

Figure 12A:
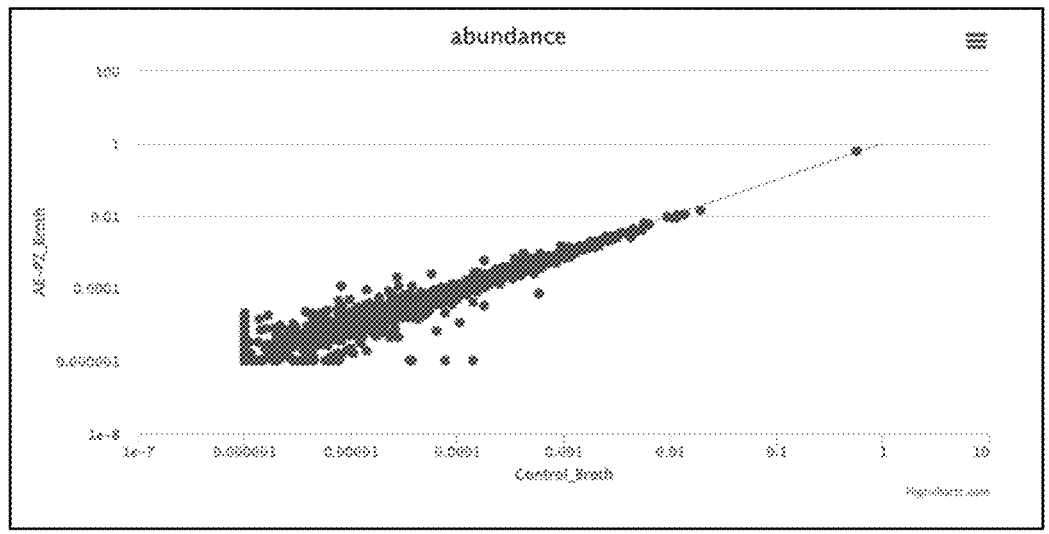
FIG. 12A is a plot of the relative abundance correlation for all proteins identified by shotgun mass spectrometry (MS) in total protein extracted from *Pichia* cells washed in water ("Control", horizontal axis) or treated with alkali and heat ("AE_PZ", vertical axis) as described in Examples. All axes are logarithmic scale.
Figure 12B:
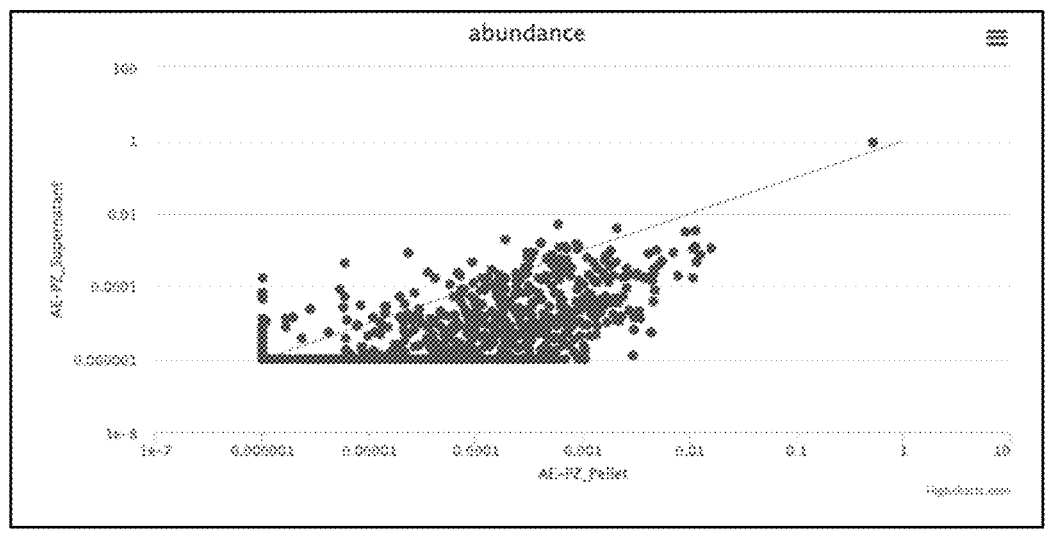
FIG. 12B is a plot of relative abundance correlation for all proteins identified by shotgun mass spectrometry (MS) in the solids from *Pichia* cells expressing a target protein (horizontal axis, "AE_PZ_Pellet") vs the clarified centrate prepared from this lysate (vertical axis, "AE_PZ_Supernatant").
Figure 12C:
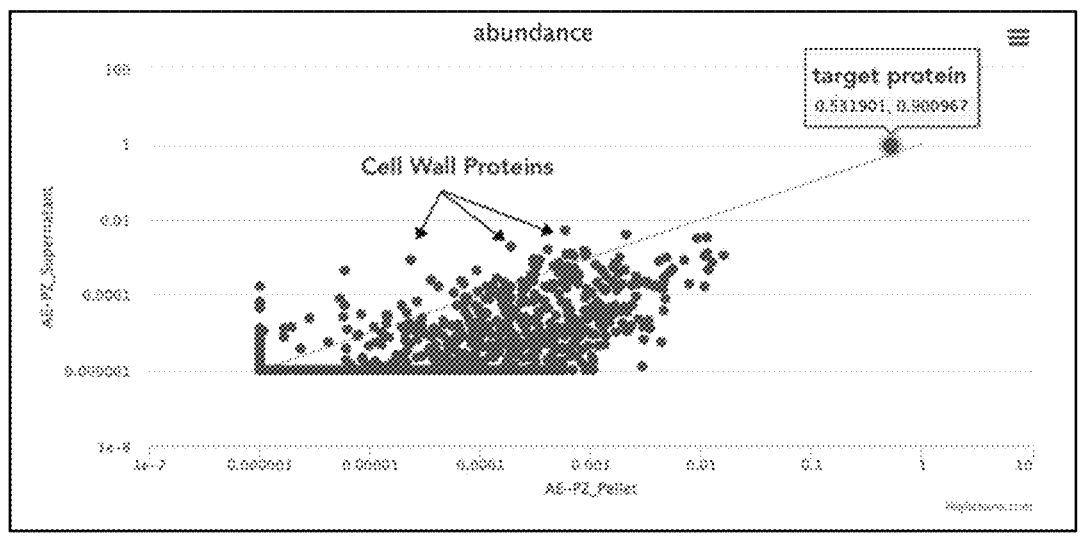
FIG. 12C is an annotated version of FIG. 12B, to show that centrifugation alone results in twofold enrichment of the target protein, from 53% to 90% of protein in the fraction. Note that other proteins annotated as cell wall components are released/enriched in clarified centrate, consistent with cell wall damage by alkali and heat treatments.
Figure 12D:
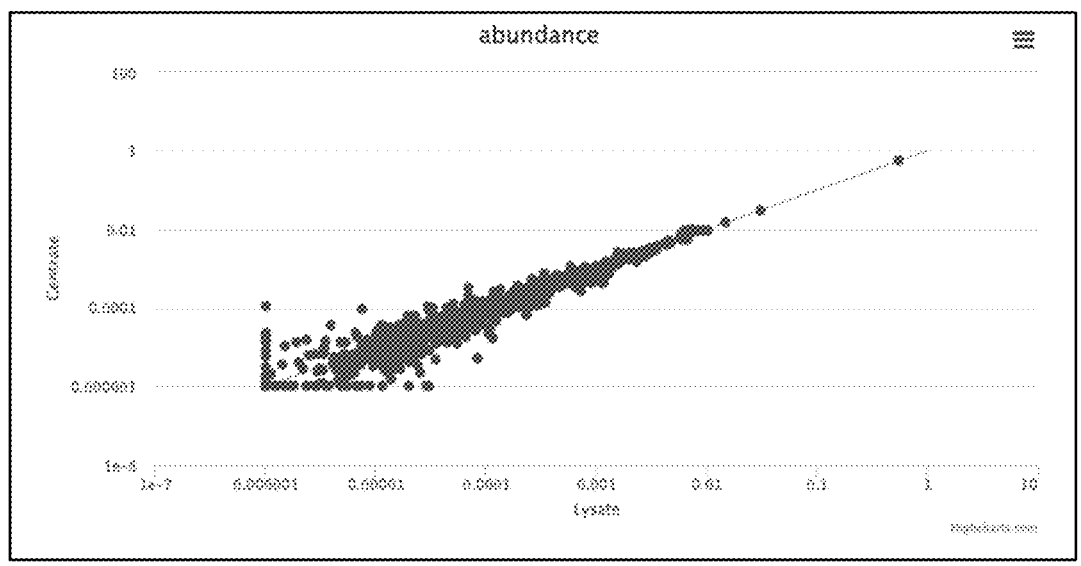
FIG. 12D is a plot relative abundance correlation for all proteins identified by shotgun mass spectrometry (MS) in a mechanical lysate of *Pichia* cells expressing a target protein (horizontal axis) vs a clarified centrate prepared from this lysate (vertical axis).

Chemical and Thermal Treatment of Microbial Cells Enables Substantial Target Enrichment by Simply Clarifying the Mixture Microbial cells (here, a strain of *Pichia pastoris* expressing an abundant target protein) did not affect the relative abundance of all detectable proteins (FIG. 12A), but did permit substantial purification of cytoplasmic targets by centrifugation (FIG. 12B, 12C). In FIG. 12A, the relative abundance of total protein content (measured by shotgun mass spectrometry after stringent mechanical and chemical release) is shown for *Pichia* cells washed in water ("Control Broth") and treated with alkali and heat ("AE_PZ"). This demonstrates that total protein content is not substantially changed by "AE_PZ" treatment. In FIGS. 12B and C, the relative abundance of proteins (by shotgun mass spectrometry) is shown for *Pichia* cells treated with alkali and heat then separated into a solids portion ("AE_PZ_Pellet") and a liquid portion ("AE_PZ_Superantant"). FIG. 12B annotates some of the proteins enriched in the liquid portion including the abundant target protein and cell wall associated proteins. Mechanically lysed cells, however, showed no such shift in relative protein abundance (FIG. 12D) upon clarification.

Example 15

Figure 13:
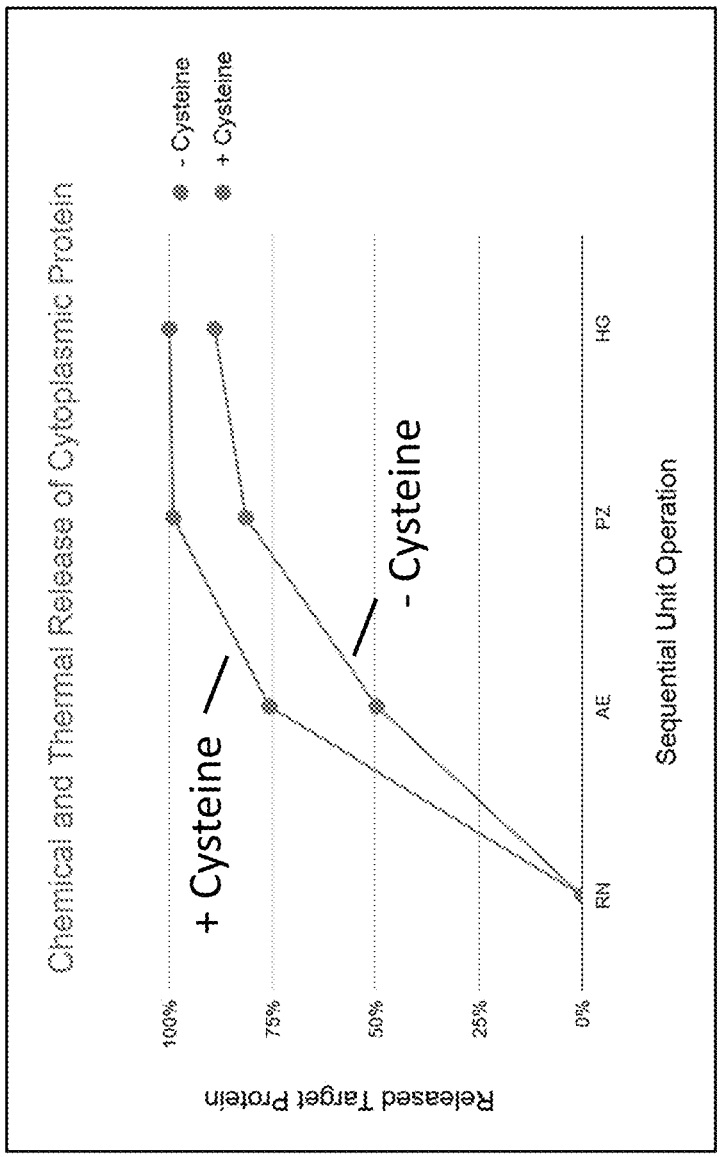
FIG. 13 is a plot of the relative amount of released target protein over several unit operations, having been treated or not treated with cysteine.

Chemical and Thermal Treatments can Completely Release Target Cytoplasmic Protein Simply by Perforating Cells and Removing Solids Microbial cells from a *Pichia pastoris* fermentation were washed in cold water (RN). Sodium hydroxide (NaOH) was added until the stirred suspension pH was stable about pH 9 for at least 10 minutes (alkaline exhaustion, or "AE"). The AE suspension was heated to 60° C. (PZ), then cooled to 4° C. The material was subsequently passed through a homogenizer (HG) at 12-15 kpsi while chilled to test whether additional protein was extracted. At each stage, samples were withdrawn, centrifuged and then analyzed for the release of a target protein into the supernatant. FIG. 13 shows that cysteine (50 mM, added prior to NaOH) treatment improved release of the target cytoplasmic protein, and even without cysteine, more than 75% of the target cytoplasmic protein was released without homogenization.

Example 16

Chemical and Thermal Treatments can be Selected to Control Particle Size

Figure 14A:
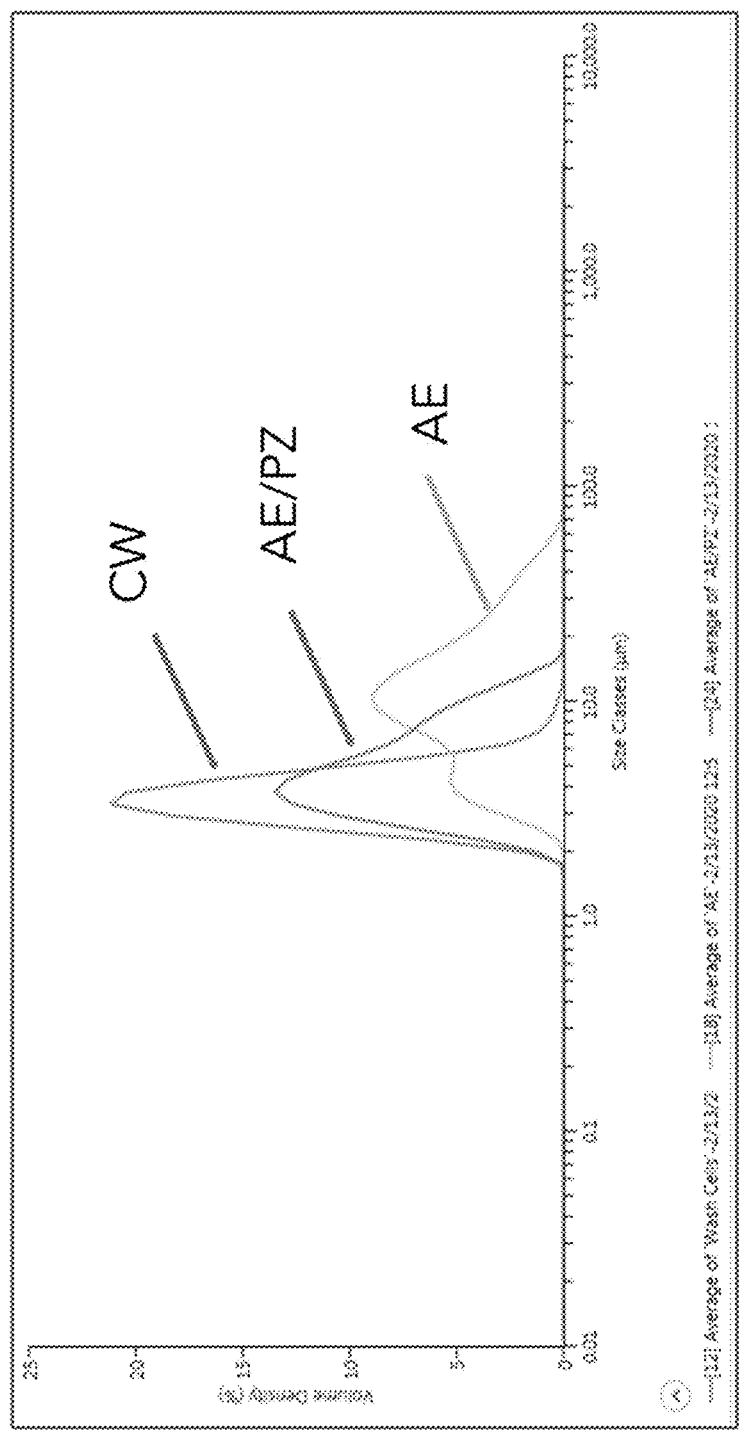
FIG. 14A is a plot of the particle size distribution of washed *Pichia* cells ("CW") without reductant added; cells were treated with alkaline exhaustion at pH 10.5 ("AE") and subsequent heating at 60° C. ("AE/PZ"). Volume fraction (vertical axis) is plotted against size in micrometers (horizontal axis, logarithmic scale).
Figure 14B:
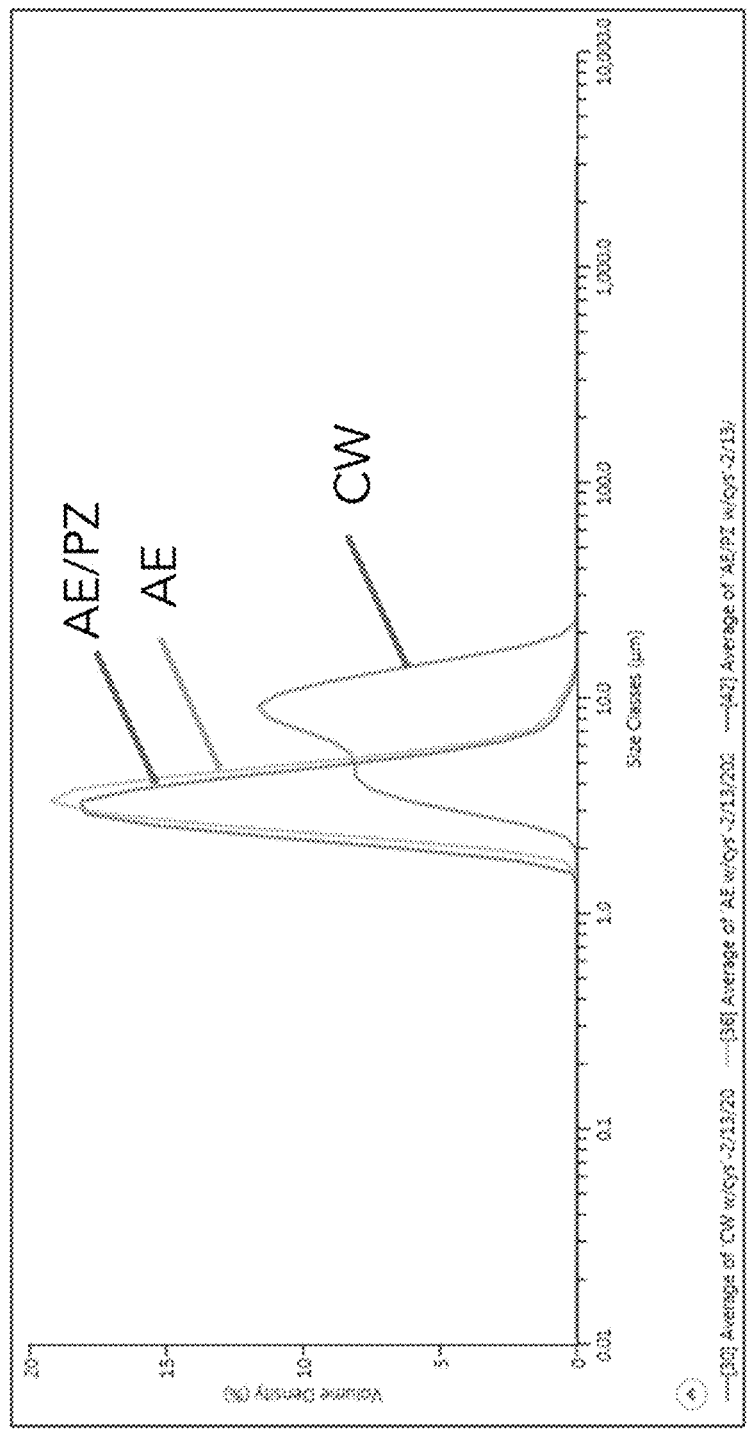
FIG. 14B is a plot of the particle size distribution of washed *Pichia* cells ("CW") with food-safe reductant added (L-cysteine, 50 mM); cells were subsequently alkaline exhausted at pH 10.5 ("AE"), then heated to 60° C. ("AE/PZ"). Axes as in FIG. 14A.
Figure 14C:
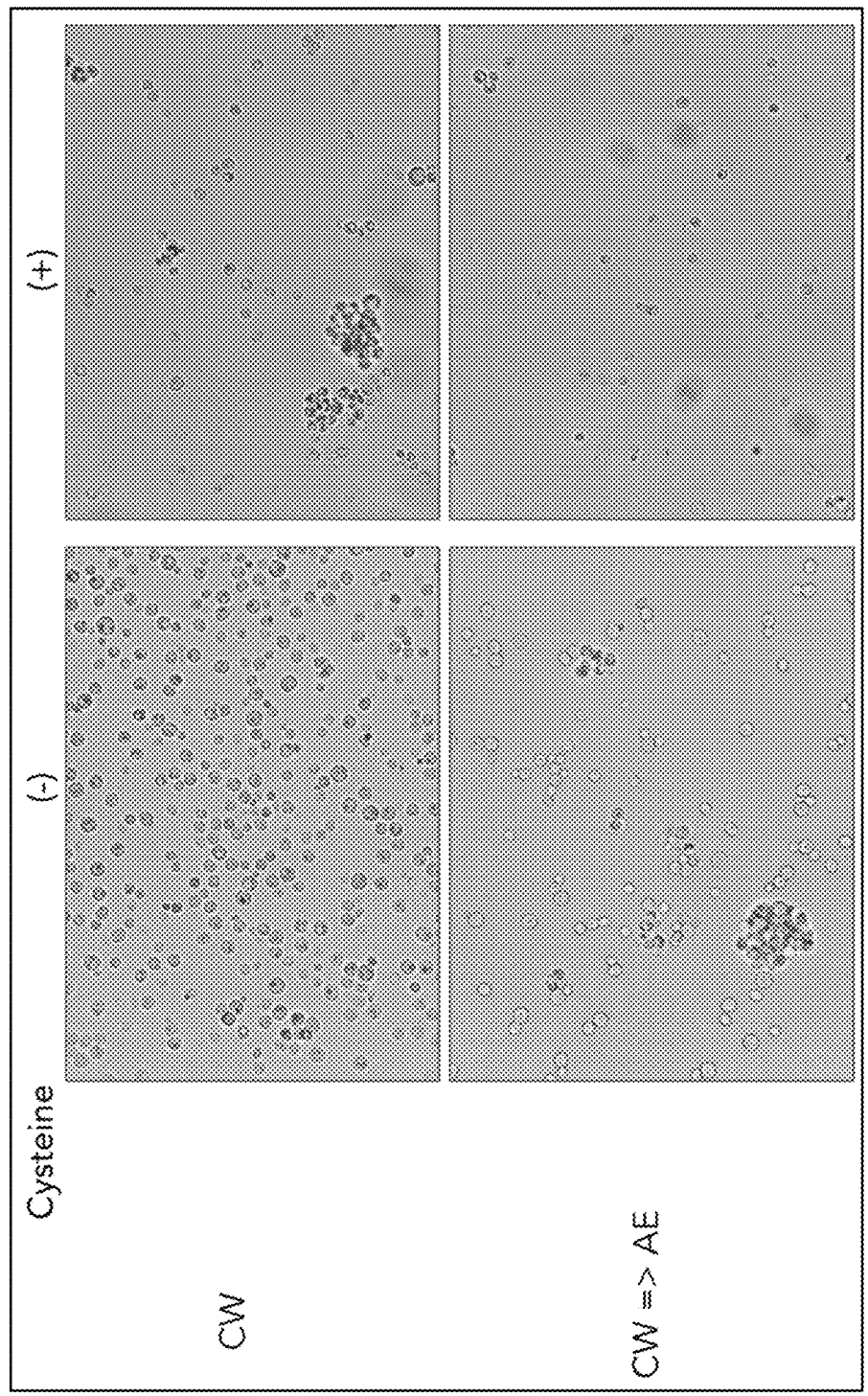
FIG. 14C is images of light microscopy of *Pichia* cells treated as indicated, showing clumping or dispersal consistent with the particle size distribution data shown in FIGS. 14A and 14B. Cells were diluted 100× in cold water, then visualized at 100× under visible light.

Cell flocculation was tuned by process treatments as described to promote solids removal and remodel adherence of the cell wall surface. FIG. 14A shows that particle size distribution of washed Pichia cells ("CW") without reductant added; cells were treated with alkaline exhaustion at pH 10.5 ("AE") and subsequent heating at 60° C. ("AE/PZ"). Volume fraction (vertical axis) is plotted against size in micrometers (horizontal axis, logarithmic scale). FIG. 14B shows that particle size distribution of washed cells ("CW") with food-safe reductant added (L-cysteine, 50 mM); cells were subsequently alkaline exhausted at pH 10.5 ("AE"), then heated to 60 C ("AE/PZ") (axes as in FIG. 14A). FIG. 14C shows images of light microscopy of Pichia cells treated as indicated, showing clumping or dispersal consistent with the particle size data shown in FIGS. 14A and 14B. Cells were diluted 100× in cold water, then visualized at 100× under visible light.

Example 17

Properties of Protein Compositions I

Figure 15:
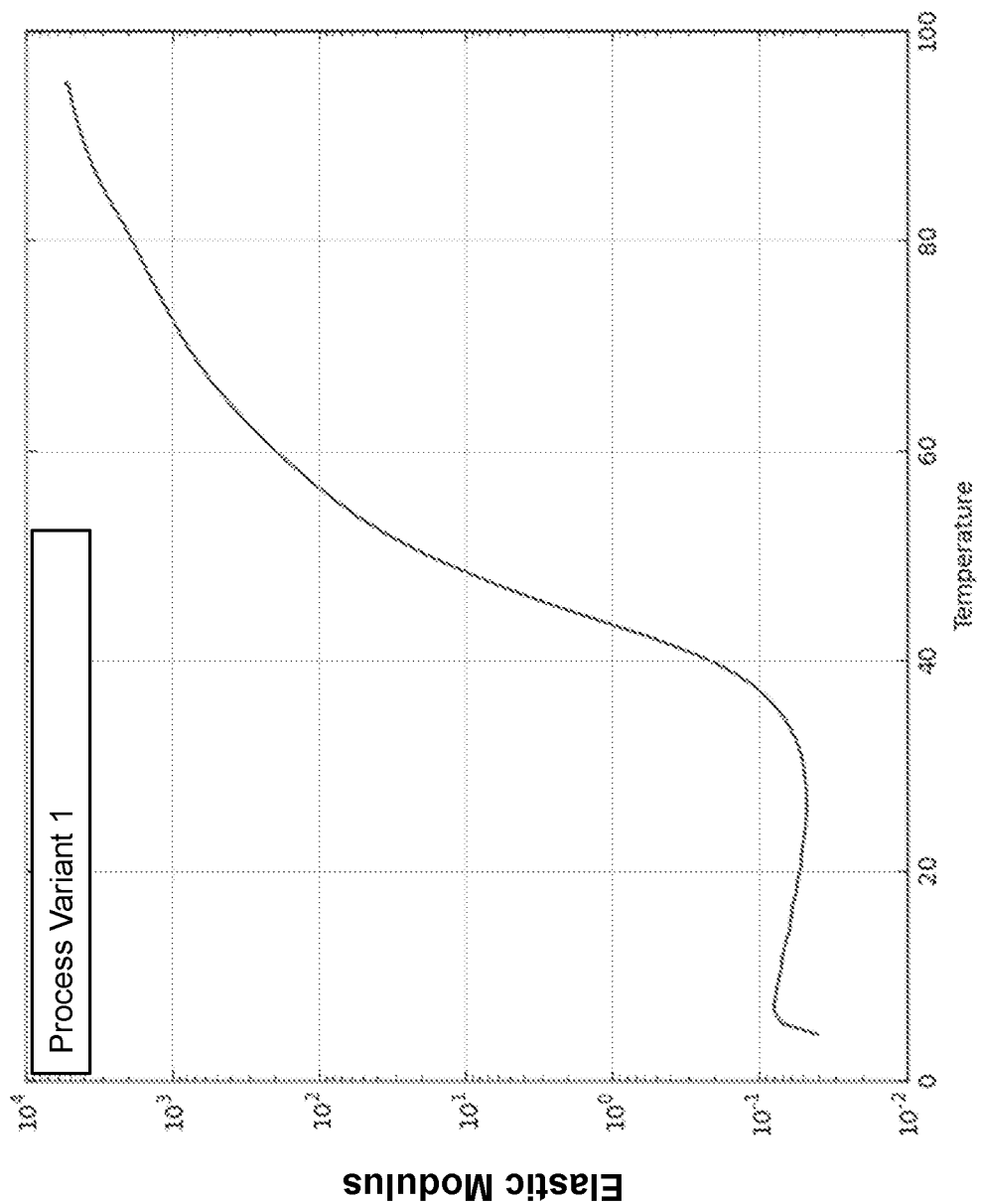
FIG. 15 is a plot of the elastic modulus of a 10% (w/v) suspension of the product of Process Variant 1 (FIG. 9B).

A 10% (w/v) suspension of the product of Process Variant 1 (see FIG. 9B) was made in water at neutral, then assayed as described in Table 2. Upon heating to 375° C., the suspension formed a gel with high elastic modulus (FIG. 15) and formed an elastic, shiny gel.

Example 18

Properties of Protein Compositions II

An oil-in water emulsion was formed by combining vegetable oil with a 10% (w/v) suspension of the product of process variant 1 at a volume ratio of 1:1, then mixed with a handheld homogenizer at room temperature. Upon heating at 375° C., the emulsion was stable. Emulsions prepared this way were stable to centrifugation at up to 20,000×g and to storage over several days at 4° C.

Example 19

Figure 16A:
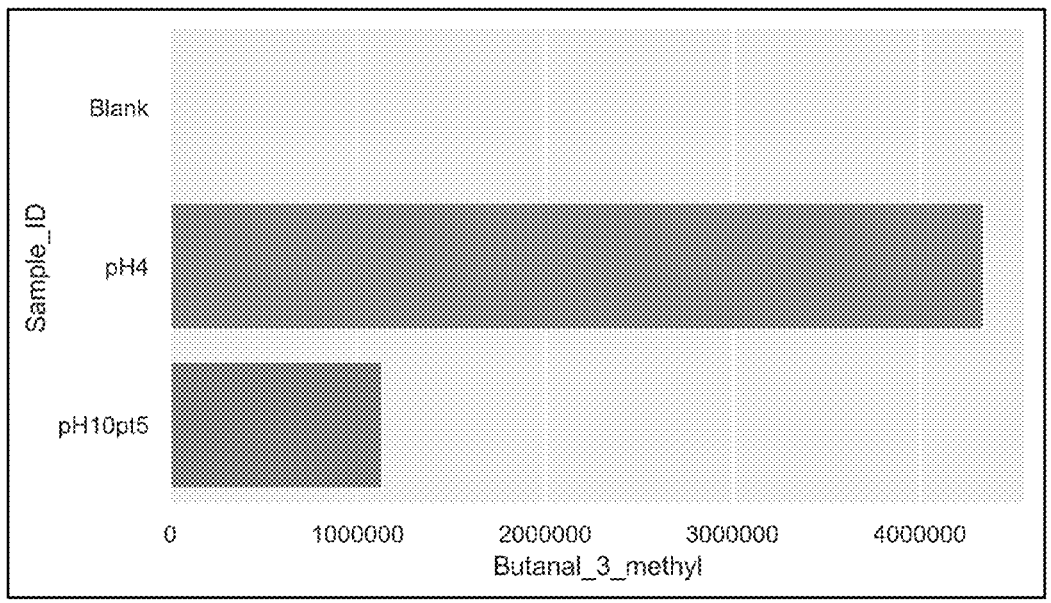
FIG. 16A is a plot of the amount of 3-methyl-butanal detected in protein compositions at pH 4 and pH 10.5.
Figure 16B:
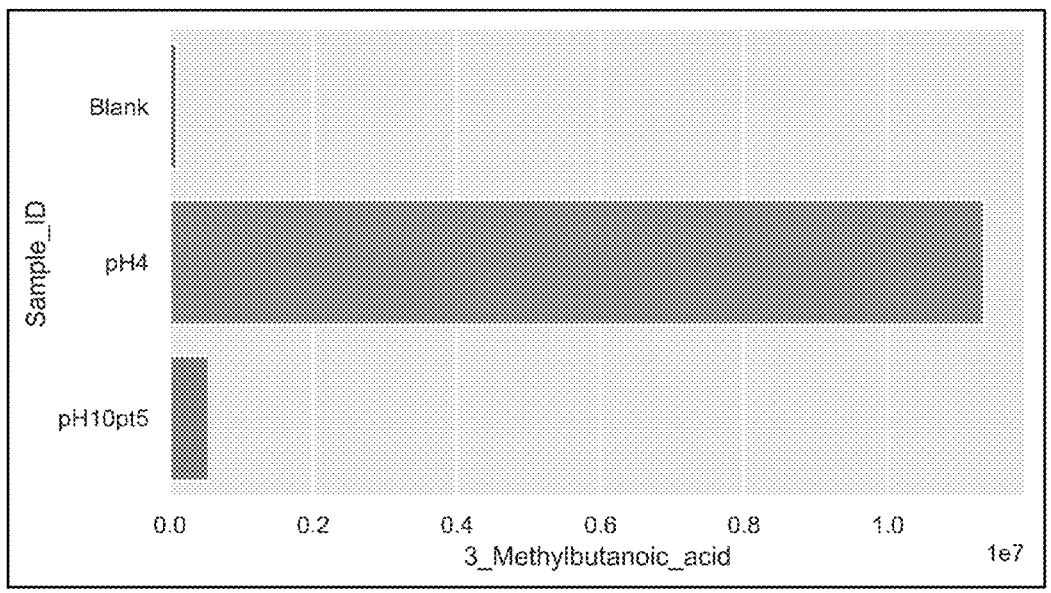
FIG. 16B is a plot of the amount of 3-methyl-butanoic acid detected in protein compositions at pH 4 and pH 10.5.

Alkaline Processing Deflavors Yeast (Pichia pastoris) Cells when Compared to Unadjusted pH Illustration of the influence of pH on chemical species which may be undesirable in some applications. Microbial compositions were adjusted to pH adjusted to pH 4.0 and 10.5, centrifuged 5,000×g for 10 minutes, the supernatant was decanted, cells were reconstituted to the starting volume with water and thoroughly mixed. Samples were analyzed through gas chromatography mass spectrometry as indicated in Table 2. An example of "AE" deflavoring, elevated pH (10.5) at the AE stage leads to increased removal of flavor compounds relative to pH 4.0 process (FIGS. 16A and 16B). Samples were assayed as summarized in Table 2.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for purifying proteins from a plurality of cells having cell walls, the method comprising:
   a) perforating the cell walls of the plurality of cells;
   b) separating an aqueous suspension of the perforated plurality of cells of a) to form a solids portion and a liquid portion;
   c) filtering the liquid portion to form a filtrate and a retentate; and
   d) concentrating the retentate to form a protein composition;
   wherein each of a)-d), independently, is performed at a pH between about 8.5 and about 12.0, inclusive; and
   wherein the perforating comprises treating with a reductant, treating with an enzyme, electroporation, or a combination thereof.

2. The method of claim 1, wherein each of a)-d), independently, is performed at a pH between about 9.0 and about 10.0, inclusive.

3. The method of claim 1, wherein the perforating comprises treating with a reductant, and wherein the reductant is selected from the group consisting of cysteine, glutathione, bisulfite, and a combination thereof.

4. The method of claim 1, wherein the method does not comprise mechanical lysis of the plurality of cells.

5. The method of claim 1, wherein the filtering is performed until the amount of sodium hydroxide required to adjust the pH of a 200 mL of a 2% (w/v) suspension of the protein composition from a starting pH of 3 to a final pH of 12 is less than or equal to 3 mmol of sodium hydroxide per gram of the protein composition.

6. The method of claim 1, wherein $H_2S$ is detectable in an amount of less than about 0.1 ppm in a 45 mL headspace when L-cysteine is not added to 5 mL of a 2% (w/v) suspension of the protein composition at pH 7.0.

7. The method of claim 1, wherein $H_2S$ is detectable in an amount of at least about 0.2 ppm in a 45 mL headspace about 24 hours at 25° C. after 5 mL of a 2% (w/v) suspension of the protein composition at pH 7.0 is brought to about 25 mM final concentration of L-cysteine.

8. The method of claim 1, wherein the protein composition comprises at least about 35%, on a dry weight basis, of compounds larger than 5 kDa.

9. A protein composition prepared by the method of claim 1.

10. A method of preparing a food, a beverage, or a supplement, the method comprising including the protein composition of claim 9 in the food, the beverage, or the supplement.

11. The method of claim 1, wherein the method comprises pasteurizing the protein composition.

12. The method of claim 1, wherein the liquid portion comprises at least about 50% by weight of cytoplasmic proteins from the plurality of cells.

13. The method of claim 1, wherein the liquid portion comprises less than about 40% by weight of membrane-bound and subcellular compartment protein from the plurality of cells, and/or wherein the solids portion comprises at least about 30% by weight of membrane-bound and/or subcellular compartment protein from the plurality of cells.

14. The method of claim 1, wherein the plurality of cells comprises microbial cells.

15. The method of claim 1, wherein the plurality of cells comprises eukaryotic cells.

16. The method of claim 1, wherein the plurality of cells comprises fungal cells, algal cells, archaeal cells, or bacterial cells.

17. The method of claim 1, wherein less than about 200 μg/mL beta glucan is detectable in a soluble phase, wherein the soluble phase is prepared using a 10% (w/v) suspension of the perforated plurality of cells, after being incubated at 50° C. for 10 minutes at pH 12.0.

18. The method of claim 1, wherein treatment of a supernatant of the perforated plurality of cells with a mannosidase yields less than about 30 μg/mL detectable mannose in the supernatant, wherein the supernatant is prepared using a 10% (w/v) suspension of the perforated plurality of cells, after being incubated at 50° C. for 10 minutes at pH 10.5 and centrifuged to remove solids.

19. The method of claim 1, wherein the perforating comprises treating with a reductant, and wherein treating with the reductant comprises treating with about 10 mM to about 500 mM reducing equivalents of the reductant.

20. The method of claim 1, wherein the perforating is performed at a temperature between about 4° C. and about 12° C.

21. The method of claim 1, wherein the method further comprises, after the perforating, heating the plurality of cells to at least about 60° C.

22. The method of claim 1, wherein the method further comprises, prior to separating the aqueous suspension of the plurality of cells to form a solids portion and a liquid portion, heating the plurality of cells to at least about 60° C.

23. The method of claim 1, wherein the liquid portion comprises at least about 30% by weight of hexokinase of the plurality of cells.

24. The method of claim 1, wherein the solids portion comprises at least about 30% by weight of total histone protein of the plurality of cells.

25. The method of claim 1, wherein the solids portion comprises at least about 30% by weight of ferrochelatase protein of the plurality of cells.

26. The method of claim 1, wherein dry solids from the liquid portion, following desalting, have an A260/A280 ratio of less than about 1.5, wherein dry solids from the solids portion, following desalting, have an A260/A280 ratio of greater than about 1.5, or a combination thereof.

27. The method of claim 1, wherein the method further comprises drying the protein composition.

\* \* \* \* \*

SEQUENCE LISTING

<160> NUMBER OF SEQ ID NOS: 27

<210> SEQ ID NO 1
<211> LENGTH: 161
<212> TYPE: PRT
<213> ORGANISM: Vigna radiata

<400> SEQUENCE: 1

Met Thr Thr Thr Leu Glu Arg Gly Phe Thr Glu Glu Gln Ala Leu
1               5                   10                  15

Val Val Lys Ser Trp Asn Val Met Lys Lys Asn Ser Gly Glu Leu Gly
            20                  25                  30

```
Leu Lys Phe Phe Leu Lys Ile Phe Glu Ile Ala Pro Ser Ala Gln Lys
            35                  40                  45

Leu Phe Ser Phe Leu Arg Asp Ser Thr Val Pro Leu Glu Gln Asn Pro
 50                  55                  60

Lys Leu Lys Pro His Ala Val Ser Val Phe Val Met Thr Cys Asp Ser
 65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Arg Thr Gly Val Ala Asn Glu
            100                 105                 110

His Phe Glu Val Thr Lys Phe Ala Leu Leu Glu Thr Ile Lys Glu Ala
            115                 120                 125

Val Pro Glu Met Trp Ser Pro Ala Met Lys Asn Ala Trp Gly Glu Ala
        130                 135                 140

Tyr Asp Gln Leu Val Asp Ala Ile Lys Tyr Glu Met Lys Pro Pro Ser
145                 150                 155                 160

Ser

<210> SEQ ID NO 2
<211> LENGTH: 133
<212> TYPE: PRT
<213> ORGANISM: Methylacidiphilum infernorum

<400> SEQUENCE: 2

Met Ile Asp Gln Lys Glu Lys Glu Leu Ile Lys Glu Ser Trp Lys Arg
1               5                   10                  15

Ile Glu Pro Asn Lys Asn Glu Ile Gly Leu Leu Phe Tyr Ala Asn Leu
            20                  25                  30

Phe Lys Glu Glu Pro Thr Val Ser Val Leu Phe Gln Asn Pro Ile Ser
        35                  40                  45

Ser Gln Ser Arg Lys Leu Met Gln Val Leu Gly Ile Leu Val Gln Gly
    50                  55                  60

Ile Asp Asn Leu Glu Gly Leu Ile Pro Thr Leu Gln Asp Leu Gly Arg
65                  70                  75                  80

Arg His Lys Gln Tyr Gly Val Val Asp Ser His Tyr Pro Leu Val Gly
                85                  90                  95

Asp Cys Leu Leu Lys Ser Ile Gln Glu Tyr Leu Gly Gln Gly Phe Thr
            100                 105                 110

Glu Glu Ala Lys Ala Ala Trp Thr Lys Val Tyr Gly Ile Ala Ala Gln
        115                 120                 125

Val Met Thr Ala Glu
    130

<210> SEQ ID NO 3
<211> LENGTH: 139
<212> TYPE: PRT
<213> ORGANISM: Aquifex aeolicus

<400> SEQUENCE: 3

Met Leu Ser Glu Glu Thr Ile Arg Val Ile Lys Ser Thr Val Pro Leu
1               5                   10                  15

Leu Lys Glu His Gly Thr Glu Ile Thr Ala Arg Met Tyr Glu Leu Leu
            20                  25                  30

Phe Ser Lys Tyr Pro Lys Thr Lys Glu Leu Phe Ala Gly Ala Ser Glu
        35                  40                  45

Glu Gln Pro Lys Lys Leu Ala Asn Ala Ile Ile Ala Tyr Ala Thr Tyr
```

```
                50                  55                  60
Ile Asp Arg Leu Glu Glu Leu Asp Asn Ala Ile Ser Thr Ile Ala Arg
 65                  70                  75                  80

Ser His Val Arg Arg Asn Val Lys Pro Glu His Tyr Pro Leu Val Lys
                 85                  90                  95

Glu Cys Leu Leu Gln Ala Ile Glu Glu Val Leu Asn Pro Gly Glu Glu
                100                 105                 110

Val Leu Lys Ala Trp Glu Glu Ala Tyr Asp Phe Leu Ala Lys Thr Leu
            115                 120                 125

Ile Thr Leu Glu Lys Lys Leu Tyr Ser Gln Pro
        130                 135

<210> SEQ ID NO 4
<211> LENGTH: 145
<212> TYPE: PRT
<213> ORGANISM: Glycine max

<400> SEQUENCE: 4

Met Gly Ala Phe Thr Glu Lys Gln Glu Ala Leu Val Ser Ser Ser Phe
  1               5                  10                  15

Glu Ala Phe Lys Ala Asn Ile Pro Gln Tyr Ser Val Val Phe Tyr Thr
                 20                  25                  30

Ser Ile Leu Glu Lys Ala Pro Ala Ala Lys Asp Leu Phe Ser Phe Leu
             35                  40                  45

Ser Asn Gly Val Asp Pro Ser Asn Pro Lys Leu Thr Gly His Ala Glu
         50                  55                  60

Lys Leu Phe Gly Leu Val Arg Asp Ser Ala Gly Gln Leu Lys Ala Asn
 65                  70                  75                  80

Gly Thr Val Val Ala Asp Ala Ala Leu Gly Ser Ile His Ala Gln Lys
                 85                  90                  95

Ala Ile Thr Asp Pro Gln Phe Val Val Lys Glu Ala Leu Leu Lys
                100                 105                 110

Thr Ile Lys Glu Ala Val Gly Asp Lys Trp Ser Asp Glu Leu Ser Ser
            115                 120                 125

Ala Trp Glu Val Ala Tyr Asp Glu Leu Ala Ala Ala Ile Lys Lys Ala
        130                 135                 140

Phe
145

<210> SEQ ID NO 5
<211> LENGTH: 162
<212> TYPE: PRT
<213> ORGANISM: Hordeum vulgare

<400> SEQUENCE: 5

Met Ser Ala Ala Glu Gly Ala Val Val Phe Ser Glu Glu Lys Glu Ala
  1               5                  10                  15

Leu Val Leu Lys Ser Trp Ala Ile Met Lys Lys Asp Ser Ala Asn Leu
                 20                  25                  30

Gly Leu Arg Phe Phe Leu Lys Ile Phe Glu Ile Ala Pro Ser Ala Arg
             35                  40                  45

Gln Met Phe Pro Phe Leu Arg Asp Ser Asp Val Pro Leu Glu Thr Asn
         50                  55                  60

Pro Lys Leu Lys Thr His Ala Val Ser Val Phe Val Met Thr Cys Glu
 65                  70                  75                  80

Ala Ala Ala Gln Leu Arg Lys Ala Gly Lys Ile Thr Val Arg Glu Thr
```

```
                    85                  90                  95
Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
            115                 120                 125

Ala Leu Pro Ala Asp Met Trp Gly Pro Glu Met Arg Asn Ala Trp Gly
            130                 135                 140

Glu Ala Tyr Asp Gln Leu Val Ala Ala Ile Lys Gln Glu Met Lys Pro
145                 150                 155                 160

Ala Glu

<210> SEQ ID NO 6
<211> LENGTH: 1153
<212> TYPE: PRT
<213> ORGANISM: Magnaporthe oryzae

<400> SEQUENCE: 6

Met Asp Gly Ala Val Arg Leu Asp Trp Thr Gly Leu Asp Leu Thr Gly
1               5                   10                  15

His Glu Ile His Asp Gly Val Pro Ile Ala Ser Arg Val Gln Val Met
            20                  25                  30

Val Ser Phe Pro Leu Phe Lys Asp Gln His Ile Ile Met Ser Ser Lys
        35                  40                  45

Glu Ser Pro Ser Arg Lys Ser Ser Thr Ile Gly Gln Ser Thr Arg Asn
    50                  55                  60

Gly Ser Cys Gln Ala Asp Thr Gln Lys Gly Gln Leu Pro Pro Val Gly
65                  70                  75                  80

Glu Lys Pro Lys Pro Val Lys Glu Asn Pro Met Lys Lys Leu Lys Glu
                85                  90                  95

Met Ser Gln Arg Pro Leu Pro Thr Gln His Gly Asp Gly Thr Tyr Pro
            100                 105                 110

Thr Glu Lys Lys Leu Thr Gly Ile Gly Glu Asp Leu Lys His Ile Arg
            115                 120                 125

Gly Tyr Asp Val Lys Thr Leu Leu Ala Met Val Lys Ser Lys Leu Lys
        130                 135                 140

Gly Glu Lys Leu Lys Asp Asp Lys Thr Met Leu Met Glu Arg Val Met
145                 150                 155                 160

Gln Leu Val Ala Arg Leu Pro Thr Glu Ser Lys Lys Arg Ala Glu Leu
                165                 170                 175

Thr Asp Ser Leu Ile Asn Glu Leu Trp Glu Ser Leu Asp His Pro Pro
            180                 185                 190

Leu Asn Tyr Leu Gly Pro Glu His Ser Tyr Arg Thr Pro Asp Gly Ser
            195                 200                 205

Tyr Asn His Pro Phe Asn Pro Gln Leu Gly Ala Ala Gly Ser Arg Tyr
        210                 215                 220

Ala Arg Ser Val Ile Pro Thr Val Thr Pro Pro Gly Ala Leu Pro Asp
225                 230                 235                 240

Pro Gly Leu Ile Phe Asp Ser Ile Met Gly Arg Thr Pro Asn Ser Tyr
                245                 250                 255

Arg Lys His Pro Asn Asn Val Ser Ser Ile Leu Trp Tyr Trp Ala Thr
            260                 265                 270

Ile Ile Ile His Asp Ile Phe Trp Thr Asp Pro Arg Asp Ile Asn Thr
            275                 280                 285

Asn Lys Ser Ser Ser Tyr Leu Asp Leu Ala Pro Leu Tyr Gly Asn Ser
```

```
                290                 295                 300
Gln Glu Met Gln Asp Ser Ile Arg Thr Phe Lys Asp Gly Arg Met Lys
305                 310                 315                 320

Pro Asp Cys Tyr Ala Asp Lys Arg Leu Ala Gly Met Pro Pro Gly Val
                325                 330                 335

Ser Val Leu Leu Ile Met Phe Asn Arg Phe His Asn His Val Ala Glu
                340                 345                 350

Asn Leu Ala Leu Ile Asn Glu Gly Gly Arg Phe Asn Lys Pro Ser Asp
                355                 360                 365

Leu Leu Glu Gly Glu Ala Arg Glu Ala Ala Trp Lys Lys Tyr Asp Asn
370                 375                 380

Asp Leu Phe Gln Val Ala Arg Leu Val Thr Ser Gly Leu Tyr Ile Asn
385                 390                 395                 400

Ile Thr Leu Val Asp Tyr Val Arg Asn Ile Val Asn Leu Asn Arg Val
                405                 410                 415

Asp Thr Thr Trp Thr Leu Asp Pro Arg Gln Asp Ala Gly Ala His Val
                420                 425                 430

Gly Thr Ala Asp Gly Ala Glu Arg Gly Thr Gly Asn Ala Val Ser Ala
                435                 440                 445

Glu Phe Asn Leu Cys Tyr Arg Trp His Ser Cys Ile Ser Glu Lys Asp
                450                 455                 460

Ser Lys Phe Val Glu Ala Gln Phe Gln Asn Ile Phe Gly Lys Pro Ala
465                 470                 475                 480

Ser Glu Val Arg Pro Asp Glu Met Trp Lys Gly Phe Ala Lys Met Glu
                485                 490                 495

Gln Asn Thr Pro Ala Asp Pro Gly Gln Arg Thr Phe Gly Gly Phe Lys
                500                 505                 510

Arg Gly Pro Asp Gly Lys Phe Asp Asp Asp Leu Val Arg Cys Ile
                515                 520                 525

Ser Glu Ala Val Glu Asp Val Ala Gly Ala Phe Gly Ala Arg Asn Val
                530                 535                 540

Pro Gln Ala Met Lys Val Val Glu Thr Met Gly Ile Ile Gln Gly Arg
545                 550                 555                 560

Lys Trp Asn Val Ala Gly Leu Asn Glu Phe Arg Lys His Phe His Leu
                565                 570                 575

Lys Pro Tyr Ser Thr Phe Glu Asp Ile Asn Ser Asp Pro Gly Val Ala
                580                 585                 590

Glu Ala Leu Arg Arg Leu Tyr Asp His Pro Asp Asn Val Glu Leu Tyr
                595                 600                 605

Pro Gly Leu Val Ala Glu Asp Lys Gln Pro Met Val Pro Gly Val
610                 615                 620

Gly Ile Ala Pro Thr Tyr Thr Ile Ser Arg Val Leu Ser Asp Ala
625                 630                 635                 640

Val Cys Leu Val Arg Gly Asp Arg Phe Tyr Thr Thr Asp Phe Thr Pro
                645                 650                 655

Arg Asn Leu Thr Asn Trp Gly Tyr Lys Glu Val Asp Tyr Asp Leu Ser
                660                 665                 670

Val Asn His Gly Cys Val Phe Tyr Lys Leu Phe Ile Arg Ala Phe Pro
                675                 680                 685

Asn His Phe Lys Gln Asn Ser Val Tyr Ala His Tyr Pro Met Val Val
                690                 695                 700

Pro Ser Glu Asn Lys Arg Ile Leu Glu Ala Leu Gly Arg Ala Asp Leu
705                 710                 715                 720
```

```
Phe Asp Phe Glu Ala Pro Lys Tyr Ile Pro Pro Arg Val Asn Ile Thr
                725                 730                 735

Ser Tyr Gly Gly Ala Glu Tyr Ile Leu Glu Thr Gln Glu Lys Tyr Lys
                740                 745                 750

Val Thr Trp His Glu Gly Leu Gly Phe Leu Met Gly Gly Gly Leu
            755                 760                 765

Lys Phe Met Leu Ser Gly Asp Asp Pro Leu His Ala Gln Gln Arg Lys
770                 775                 780

Cys Met Ala Ala Gln Leu Tyr Lys Asp Gly Trp Thr Glu Ala Val Lys
785                 790                 795                 800

Ala Phe Tyr Ala Gly Met Met Glu Glu Leu Leu Val Ser Lys Ser Tyr
                805                 810                 815

Phe Leu Gly Asn Asn Lys His Arg His Val Asp Ile Ile Arg Asp Val
                820                 825                 830

Gly Asn Met Val His Val His Phe Ala Ser Gln Val Phe Gly Leu Pro
                835                 840                 845

Leu Lys Thr Ala Lys Asn Pro Thr Gly Val Phe Thr Glu Gln Glu Met
            850                 855                 860

Tyr Gly Ile Leu Ala Ala Ile Phe Thr Thr Ile Phe Phe Asp Leu Asp
865                 870                 875                 880

Pro Ser Lys Ser Phe Pro Leu Arg Thr Lys Thr Arg Glu Val Cys Gln
                885                 890                 895

Lys Leu Ala Lys Leu Val Glu Ala Asn Val Lys Leu Ile Asn Lys Ile
            900                 905                 910

Pro Trp Ser Arg Gly Met Phe Val Gly Lys Pro Ala Lys Asp Glu Pro
            915                 920                 925

Leu Ser Ile Tyr Gly Lys Thr Met Ile Lys Gly Leu Lys Ala His Gly
            930                 935                 940

Leu Ser Asp Tyr Asp Ile Ala Trp Ser His Val Val Pro Thr Ser Gly
945                 950                 955                 960

Ala Met Val Pro Asn Gln Ala Gln Val Phe Ala Gln Ala Val Asp Tyr
                965                 970                 975

Tyr Leu Ser Pro Ala Gly Met His Tyr Ile Pro Glu Ile His Met Val
                980                 985                 990

Ala Leu Gln Pro Ser Thr Pro Glu  Thr Asp Ala Leu Leu  Leu Gly Tyr
                995                 1000                1005

Ala Met  Glu Gly Ile Arg Leu  Ala Gly Thr Phe Gly   Ser Tyr Arg
    1010             1015                1020

Glu Ala  Ala Val Asp Asp Val  Val Lys Glu Asp Asn  Gly Arg Gln
    1025             1030                1035

Val Pro  Val Lys Ala Gly Asp  Arg Val Phe Val Ser  Phe Val Asp
    1040             1045                1050

Ala Ala  Arg Asp Pro Lys His  Phe Pro Asp Pro Glu  Val Val Asn
    1055             1060                1065

Pro Arg  Arg Pro Ala Lys Lys  Tyr Ile His Tyr Gly  Val Gly Pro
    1070             1075                1080

His Ala  Cys Leu Gly Arg Asp  Ala Ser Gln Ile Ala  Ile Thr Glu
    1085             1090                1095

Met Phe  Arg Cys Leu Phe Arg  Arg Asn Val Arg    Arg Val Pro
    1100             1105                1110

Gly Pro  Gln Gly Glu Leu Lys  Lys Val Pro Arg Pro  Gly Gly Phe
    1115             1120                1125
```

Tyr Val Tyr Met Arg Glu Asp Trp Gly Gly Leu Phe Pro Phe Pro
    1130                1135                1140

Val Thr Met Arg Val Met Trp Asp Asp Glu
    1145                1150

<210> SEQ ID NO 7
<211> LENGTH: 530
<212> TYPE: PRT
<213> ORGANISM: Fusarium oxysporum

<400> SEQUENCE: 7

Met Lys Gly Ser Ala Thr Leu Ala Phe Ala Leu Val Gln Phe Ser Ala
1               5                   10                  15

Ala Ser Gln Leu Val Trp Pro Ser Lys Trp Asp Glu Val Glu Asp Leu
            20                  25                  30

Leu Tyr Met Gln Gly Gly Phe Asn Lys Arg Gly Phe Ala Asp Ala Leu
        35                  40                  45

Arg Thr Cys Glu Phe Gly Ser Asn Val Pro Gly Thr Gln Asn Thr Ala
    50                  55                  60

Glu Trp Leu Arg Thr Ala Phe His Asp Ala Ile Thr His Asp Ala Lys
65                  70                  75                  80

Ala Gly Thr Gly Gly Leu Asp Ala Ser Ile Tyr Trp Glu Ser Ser Arg
                85                  90                  95

Pro Glu Asn Pro Gly Lys Ala Phe Asn Asn Thr Phe Gly Phe Phe Ser
            100                 105                 110

Gly Phe His Asn Pro Arg Ala Thr Ala Ser Asp Leu Thr Ala Leu Gly
        115                 120                 125

Thr Val Leu Ala Val Gly Ala Cys Asn Gly Pro Arg Ile Pro Phe Arg
    130                 135                 140

Ala Gly Arg Ile Asp Ala Tyr Lys Ala Gly Pro Ala Gly Val Pro Glu
145                 150                 155                 160

Pro Ser Thr Asn Leu Lys Asp Thr Phe Ala Ala Phe Thr Lys Ala Gly
                165                 170                 175

Phe Thr Lys Glu Glu Met Thr Ala Met Val Ala Cys Gly His Ala Ile
            180                 185                 190

Gly Gly Val His Ser Val Asp Phe Pro Glu Ile Val Gly Ile Lys Ala
        195                 200                 205

Asp Pro Asn Asn Asp Thr Asn Val Pro Phe Gln Lys Asp Val Ser Ser
    210                 215                 220

Phe His Asn Gly Ile Val Thr Glu Tyr Leu Ala Gly Thr Ser Lys Asn
225                 230                 235                 240

Pro Leu Val Ala Ser Lys Asn Ala Thr Phe His Ser Asp Lys Arg Ile
                245                 250                 255

Phe Asp Asn Asp Lys Ala Thr Met Lys Lys Leu Ser Thr Lys Ala Gly
            260                 265                 270

Phe Asn Ser Met Cys Ala Asp Ile Leu Thr Arg Met Ile Asp Thr Val
        275                 280                 285

Pro Lys Ser Val Gln Leu Thr Pro Val Leu Glu Ala Tyr Asp Val Arg
    290                 295                 300

Pro Tyr Ile Thr Glu Leu Ser Leu Asn Lys Asn Lys Ile His Phe
305                 310                 315                 320

Thr Gly Ser Val Arg Val Arg Ile Thr Asn Asn Ile Arg Asp Asn Asn
                325                 330                 335

Asp Leu Ala Ile Asn Leu Ile Tyr Val Gly Arg Asp Gly Lys Lys Val
            340                 345                 350

```
Thr Val Pro Thr Gln Val Thr Phe Gln Gly Gly Thr Ser Phe Gly
        355                 360                 365

Ala Gly Glu Val Phe Ala Asn Phe Glu Phe Asp Thr Thr Met Asp Ala
        370                 375                 380

Lys Asn Gly Ile Thr Lys Phe Phe Ile Gln Glu Val Lys Pro Ser Thr
385                 390                 395                 400

Lys Ala Thr Val Thr His Asp Asn Gln Lys Thr Gly Gly Tyr Lys Val
                405                 410                 415

Asp Asp Thr Val Leu Tyr Gln Leu Gln Gln Ser Cys Ala Val Leu Glu
                420                 425                 430

Lys Leu Pro Asn Ala Pro Leu Val Val Thr Ala Met Val Arg Asp Ala
                435                 440                 445

Arg Ala Lys Asp Ala Leu Thr Leu Arg Val Ala His Lys Lys Pro Val
        450                 455                 460

Lys Gly Ser Ile Val Pro Arg Phe Gln Thr Ala Ile Thr Asn Phe Lys
465                 470                 475                 480

Ala Thr Gly Lys Lys Ser Ser Gly Tyr Thr Gly Phe Gln Ala Lys Thr
                485                 490                 495

Met Phe Glu Glu Gln Ser Thr Tyr Phe Asp Ile Val Leu Gly Gly Ser
                500                 505                 510

Pro Ala Ser Gly Val Gln Phe Leu Thr Ser Gln Ala Met Pro Ser Gln
        515                 520                 525

Cys Ser
    530

<210> SEQ ID NO 8
<211> LENGTH: 358
<212> TYPE: PRT
<213> ORGANISM: Fusarium graminearum

<400> SEQUENCE: 8

Met Ala Ser Ala Thr Arg Gln Phe Ala Arg Ala Ala Thr Arg Ala Thr
1               5                   10                  15

Arg Asn Gly Phe Ala Ile Ala Pro Arg Gln Val Ile Arg Gln Gln Gly
            20                  25                  30

Arg Arg Tyr Tyr Ser Ser Glu Pro Ala Gln Lys Ser Ser Ser Ala Trp
        35                  40                  45

Ile Trp Leu Thr Gly Ala Ala Val Ala Gly Ala Gly Tyr Tyr Phe
    50                  55                  60

Tyr Gly Asn Ser Ala Ser Ser Thr Ala Lys Val Phe Asn Pro Ser
65                  70                  75                  80

Lys Glu Asp Tyr Gln Lys Val Tyr Asn Glu Ile Ala Ala Arg Leu Glu
                85                  90                  95

Glu Lys Asp Asp Tyr Asp Asp Gly Ser Tyr Gly Pro Val Leu Val Arg
            100                 105                 110

Leu Ala Trp His Ala Ser Gly Thr Tyr Asp Lys Glu Thr Gly Thr Gly
        115                 120                 125

Gly Ser Asn Gly Ala Thr Met Arg Phe Ala Pro Glu Ser Asp His Gly
    130                 135                 140

Ala Asn Ala Gly Leu Ala Ala Arg Asp Phe Leu Gln Pro Val Lys
145                 150                 155                 160

Glu Lys Phe Pro Trp Ile Thr Tyr Ser Asp Leu Trp Ile Leu Ala Gly
                165                 170                 175

Val Cys Ala Ile Gln Glu Met Leu Gly Pro Ala Ile Pro Tyr Arg Pro
```

```
                  180                 185                 190
Gly Arg Ser Asp Arg Asp Val Ser Gly Cys Thr Pro Asp Gly Arg Leu
            195                 200                 205
Pro Asp Ala Ser Lys Arg Gln Asp His Leu Arg Gly Ile Phe Gly Arg
        210                 215                 220
Met Gly Phe Asn Asp Gln Glu Ile Val Ala Leu Ser Gly Ala His Ala
225                 230                 235                 240
Leu Gly Arg Cys His Thr Asp Arg Ser Gly Tyr Ser Gly Pro Trp Thr
                245                 250                 255
Phe Ser Pro Thr Val Leu Thr Asn Asp Tyr Phe Arg Leu Leu Val Glu
            260                 265                 270
Glu Lys Trp Gln Trp Lys Lys Trp Asn Gly Pro Ala Gln Tyr Glu Asp
        275                 280                 285
Lys Ser Thr Lys Ser Leu Met Met Leu Pro Ser Asp Ile Ala Leu Ile
    290                 295                 300
Glu Asp Lys Lys Phe Lys Pro Trp Val Glu Lys Tyr Ala Lys Asp Asn
305                 310                 315                 320
Asp Ala Phe Phe Lys Asp Phe Ser Asn Val Val Leu Arg Leu Phe Glu
                325                 330                 335
Leu Gly Val Pro Phe Ala Gln Gly Thr Glu Asn Gln Arg Trp Thr Phe
            340                 345                 350
Lys Pro Thr His Gln Glu
        355

<210> SEQ ID NO 9
<211> LENGTH: 122
<212> TYPE: PRT
<213> ORGANISM: Chlamydomonas eugametos

<400> SEQUENCE: 9

Met Ser Leu Phe Ala Lys Leu Gly Gly Arg Glu Ala Val Glu Ala Ala
1               5                   10                  15
Val Asp Lys Phe Tyr Asn Lys Ile Val Ala Asp Pro Thr Val Ser Thr
            20                  25                  30
Tyr Phe Ser Asn Thr Asp Met Lys Val Gln Arg Ser Lys Gln Phe Ala
        35                  40                  45
Phe Leu Ala Tyr Ala Leu Gly Gly Ala Ser Glu Trp Lys Gly Lys Asp
    50                  55                  60
Met Arg Thr Ala His Lys Asp Leu Val Pro His Leu Ser Asp Val His
65                  70                  75                  80
Phe Gln Ala Val Ala Arg His Leu Ser Asp Thr Leu Thr Glu Leu Gly
                85                  90                  95
Val Pro Pro Glu Asp Ile Thr Asp Ala Met Ala Val Val Ala Ser Thr
            100                 105                 110
Arg Thr Glu Val Leu Asn Met Pro Gln Gln
        115                 120

<210> SEQ ID NO 10
<211> LENGTH: 121
<212> TYPE: PRT
<213> ORGANISM: Tetrahymena pyriformis

<400> SEQUENCE: 10

Met Asn Lys Pro Gln Thr Ile Tyr Glu Lys Leu Gly Gly Glu Asn Ala
1               5                   10                  15
Met Lys Ala Ala Val Pro Leu Phe Tyr Lys Lys Val Leu Ala Asp Glu
```

```
            20                  25                  30
Arg Val Lys His Phe Lys Asn Thr Asp Met Asp His Gln Thr Lys
            35                  40                  45

Gln Gln Thr Asp Phe Leu Thr Met Leu Leu Gly Gly Pro Asn His Tyr
        50                  55                  60

Lys Gly Lys Asn Met Thr Glu Ala His Lys Gly Met Asn Leu Gln Asn
65                  70                  75                  80

Leu His Phe Asp Ala Ile Ile Glu Asn Leu Ala Thr Leu Lys Glu
                85                  90                  95

Leu Gly Val Thr Asp Ala Val Ile Asn Glu Ala Ala Lys Val Ile Glu
                100                 105                 110

His Thr Arg Lys Asp Met Leu Gly Lys
            115                 120

<210> SEQ ID NO 11
<211> LENGTH: 117
<212> TYPE: PRT
<213> ORGANISM: Paramecium caudatum

<400> SEQUENCE: 11

Met Ser Leu Phe Glu Gln Leu Gly Gly Gln Ala Val Gln Ala Val
1               5                   10                  15

Thr Ala Gln Phe Tyr Ala Asn Ile Gln Ala Asp Ala Thr Val Ala Thr
                20                  25                  30

Phe Phe Asn Gly Ile Asp Met Pro Asn Gln Thr Asn Lys Thr Ala Ala
            35                  40                  45

Phe Leu Cys Ala Ala Leu Gly Gly Pro Asn Ala Trp Thr Gly Arg Asn
        50                  55                  60

Leu Lys Glu Val His Ala Asn Met Gly Val Ser Asn Ala Gln Phe Thr
65                  70                  75                  80

Thr Val Ile Gly His Leu Arg Ser Ala Leu Thr Gly Ala Gly Val Ala
                85                  90                  95

Ala Ala Leu Val Glu Gln Thr Val Ala Val Glu Thr Val Arg Gly
            100                 105                 110

Asp Val Val Thr Val
            115

<210> SEQ ID NO 12
<211> LENGTH: 147
<212> TYPE: PRT
<213> ORGANISM: Aspergillus niger

<400> SEQUENCE: 12

Met Pro Leu Thr Pro Glu Gln Ile Lys Ile Lys Ala Thr Val Pro
1               5                   10                  15

Val Leu Gln Glu Tyr Gly Thr Lys Ile Thr Thr Ala Phe Tyr Met Asn
                20                  25                  30

Met Ser Thr Val His Pro Glu Leu Asn Ala Val Phe Asn Thr Ala Asn
            35                  40                  45

Gln Val Lys Gly His Gln Ala Arg Ala Leu Ala Gly Ala Leu Phe Ala
        50                  55                  60

Tyr Ala Ser His Ile Asp Asp Leu Gly Ala Leu Gly Pro Ala Val Glu
65                  70                  75                  80

Leu Ile Cys Asn Lys His Ala Ser Leu Tyr Ile Gln Ala Asp Glu Tyr
                85                  90                  95

Lys Ile Val Gly Lys Tyr Leu Leu Glu Ala Met Lys Glu Val Leu Gly
```

```
                100                 105                 110
Asp Ala Cys Thr Asp Asp Ile Leu Asp Ala Trp Gly Ala Ala Tyr Trp
            115                 120                 125

Ala Leu Ala Asp Ile Met Ile Asn Arg Glu Ala Ala Leu Tyr Lys Gln
        130                 135                 140

Ser Gln Gly
145

<210> SEQ ID NO 13
<211> LENGTH: 165
<212> TYPE: PRT
<213> ORGANISM: Zea mays

<400> SEQUENCE: 13

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Glu Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
        115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
                165

<210> SEQ ID NO 14
<211> LENGTH: 169
<212> TYPE: PRT
<213> ORGANISM: Oryza sativa subsp. japonica

<400> SEQUENCE: 14

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met Thr Cys Glu Ala Ala Ala Gln Leu Arg Lys Ala Gly
                85                  90                  95

Lys Val Thr Val Arg Asp Thr Thr Leu Lys Arg Leu Gly Ala Thr His
```

```
                    100                 105                 110
Phe Lys Tyr Gly Val Gly Asp Ala His Phe Glu Val Thr Arg Phe Ala
            115                 120                 125

Leu Leu Glu Thr Ile Lys Glu Ala Val Pro Val Asp Met Trp Ser Pro
130                 135                 140

Ala Met Lys Ser Ala Trp Ser Glu Ala Tyr Asn Gln Leu Val Ala Ala
145                 150                 155                 160

Ile Lys Gln Glu Met Lys Pro Ala Glu
                165

<210> SEQ ID NO 15
<211> LENGTH: 160
<212> TYPE: PRT
<213> ORGANISM: Arabidopsis thaliana

<400> SEQUENCE: 15

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
                20                  25                  30

Leu Lys Leu Phe Ile Lys Ile Phe Glu Ile Ala Pro Thr Thr Lys Lys
            35                  40                  45

Met Phe Ser Phe Leu Arg Asp Ser Pro Ile Pro Ala Glu Gln Asn Pro
        50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160

<210> SEQ ID NO 16
<211> LENGTH: 147
<212> TYPE: PRT
<213> ORGANISM: Pisum sativum

<400> SEQUENCE: 16

Met Gly Phe Thr Asp Lys Gln Glu Ala Leu Val Asn Ser Ser Trp Glu
1               5                   10                  15

Ser Phe Lys Gln Asn Leu Ser Gly Asn Ser Ile Leu Phe Tyr Thr Ile
                20                  25                  30

Ile Leu Glu Lys Ala Pro Ala Ala Lys Gly Leu Phe Ser Phe Leu Lys
            35                  40                  45

Asp Thr Ala Gly Val Glu Asp Ser Pro Lys Leu Gln Ala His Ala Glu
        50                  55                  60

Gln Val Phe Gly Leu Val Arg Asp Ser Ala Ala Gln Leu Arg Thr Lys
65                  70                  75                  80

Gly Glu Val Val Leu Gly Asn Ala Thr Leu Gly Ala Ile His Val Gln
                85                  90                  95

Arg Gly Val Thr Asp Pro His Phe Val Val Val Lys Glu Ala Leu Leu
```

```
            100                 105                 110
Gln Thr Ile Lys Lys Ala Ser Gly Asn Asn Trp Ser Glu Glu Leu Asn
        115                 120                 125

Thr Ala Trp Glu Val Ala Tyr Asp Gly Leu Ala Thr Ile Lys Lys
    130                 135                 140

Ala Met Thr
145

<210> SEQ ID NO 17
<211> LENGTH: 145
<212> TYPE: PRT
<213> ORGANISM: Vigna unguiculata

<400> SEQUENCE: 17

Met Val Ala Phe Ser Asp Lys Gln Glu Ala Leu Val Asn Gly Ala Tyr
1               5                   10                  15

Glu Ala Phe Lys Ala Asn Ile Pro Lys Tyr Ser Val Val Phe Tyr Thr
            20                  25                  30

Thr Ile Leu Glu Lys Ala Pro Ala Ala Lys Asn Leu Phe Ser Phe Leu
        35                  40                  45

Ala Asn Gly Val Asp Ala Thr Asn Pro Lys Leu Thr Gly His Ala Glu
    50                  55                  60

Lys Leu Phe Gly Leu Val Arg Asp Ser Ala Ala Gln Leu Arg Ala Ser
65                  70                  75                  80

Gly Gly Val Val Ala Asp Ala Ala Leu Gly Ala Val His Ser Gln Lys
                85                  90                  95

Ala Val Asn Asp Ala Gln Phe Val Val Lys Glu Ala Leu Val Lys
            100                 105                 110

Thr Leu Lys Glu Ala Val Gly Asp Lys Trp Ser Asp Glu Leu Gly Thr
        115                 120                 125

Ala Val Glu Leu Ala Tyr Asp Glu Leu Ala Ala Ile Lys Lys Ala
    130                 135                 140

Tyr
145

<210> SEQ ID NO 18
<211> LENGTH: 154
<212> TYPE: PRT
<213> ORGANISM: Bos taurus

<400> SEQUENCE: 18

Met Gly Leu Ser Asp Gly Glu Trp Gln Leu Val Leu Asn Ala Trp Gly
1               5                   10                  15

Lys Val Glu Ala Asp Val Ala Gly His Gly Gln Glu Val Leu Ile Arg
            20                  25                  30

Leu Phe Thr Gly His Pro Glu Thr Leu Glu Lys Phe Asp Lys Phe Lys
        35                  40                  45

His Leu Lys Thr Glu Ala Glu Met Lys Ala Ser Glu Asp Leu Lys Lys
    50                  55                  60

His Gly Asn Thr Val Leu Thr Ala Leu Gly Gly Ile Leu Lys Lys Lys
65                  70                  75                  80

Gly His His Glu Ala Glu Val Lys His Leu Ala Glu Ser His Ala Asn
                85                  90                  95

Lys His Lys Ile Pro Val Lys Tyr Leu Glu Phe Ile Ser Asp Ala Ile
            100                 105                 110

Ile His Val Leu His Ala Lys His Pro Ser Asp Phe Gly Ala Asp Ala
```

```
                    115                 120                 125

Gln Ala Ala Met Ser Lys Ala Leu Glu Leu Phe Arg Asn Asp Met Ala
        130                 135                 140

Ala Gln Tyr Lys Val Leu Gly Phe His Gly
145                 150

<210> SEQ ID NO 19
<211> LENGTH: 154
<212> TYPE: PRT
<213> ORGANISM: Sus scrofa

<400> SEQUENCE: 19

Met Gly Leu Ser Asp Gly Glu Trp Gln Leu Val Leu Asn Val Trp Gly
1               5                   10                  15

Lys Val Glu Ala Asp Val Ala Gly His Gly Gln Glu Val Leu Ile Arg
            20                  25                  30

Leu Phe Lys Gly His Pro Glu Thr Leu Glu Lys Phe Asp Lys Phe Lys
        35                  40                  45

His Leu Lys Ser Glu Asp Glu Met Lys Ala Ser Glu Asp Leu Lys Lys
    50                  55                  60

His Gly Asn Thr Val Leu Thr Ala Leu Gly Gly Ile Leu Lys Lys Lys
65                  70                  75                  80

Gly His His Glu Ala Glu Leu Thr Pro Leu Ala Gln Ser His Ala Thr
                85                  90                  95

Lys His Lys Ile Pro Val Lys Tyr Leu Glu Phe Ile Ser Glu Ala Ile
            100                 105                 110

Ile Gln Val Leu Gln Ser Lys His Pro Gly Asp Phe Gly Ala Asp Ala
        115                 120                 125

Gln Gly Ala Met Ser Lys Ala Leu Glu Leu Phe Arg Asn Asp Met Ala
    130                 135                 140

Ala Lys Tyr Lys Glu Leu Gly Phe Gln Gly
145                 150

<210> SEQ ID NO 20
<211> LENGTH: 154
<212> TYPE: PRT
<213> ORGANISM: Equus caballus

<400> SEQUENCE: 20

Met Gly Leu Ser Asp Gly Glu Trp Gln Gln Val Leu Asn Val Trp Gly
1               5                   10                  15

Lys Val Glu Ala Asp Ile Ala Gly His Gly Gln Glu Val Leu Ile Arg
            20                  25                  30

Leu Phe Thr Gly His Pro Glu Thr Leu Glu Lys Phe Asp Lys Phe Lys
        35                  40                  45

His Leu Lys Thr Glu Ala Glu Met Lys Ala Ser Glu Asp Leu Lys Lys
    50                  55                  60

His Gly Thr Val Val Leu Thr Ala Leu Gly Gly Ile Leu Lys Lys Lys
65                  70                  75                  80

Gly His His Glu Ala Glu Leu Lys Pro Leu Ala Gln Ser His Ala Thr
                85                  90                  95

Lys His Lys Ile Pro Ile Lys Tyr Leu Glu Phe Ile Ser Asp Ala Ile
            100                 105                 110

Ile His Val Leu His Ser Lys His Pro Gly Asp Phe Gly Ala Asp Ala
        115                 120                 125

Gln Gly Ala Met Thr Lys Ala Leu Glu Leu Phe Arg Asn Asp Ile Ala
```

```
                130                 135                 140
Ala Lys Tyr Lys Glu Leu Gly Phe Gln Gly
145                 150

<210> SEQ ID NO 21
<211> LENGTH: 152
<212> TYPE: PRT
<213> ORGANISM: Nicotiana benthamiana

<400> SEQUENCE: 21

Met Ser Ser Phe Thr Glu Glu Gln Glu Ala Leu Val Val Lys Ser Trp
1               5                   10                  15

Asp Ser Met Lys Lys Asn Ala Gly Glu Trp Gly Leu Lys Leu Phe Leu
            20                  25                  30

Lys Ile Phe Glu Ile Ala Pro Ser Ala Lys Lys Leu Phe Ser Phe Leu
        35                  40                  45

Lys Asp Ser Asn Val Pro Leu Glu Gln Asn Ala Lys Leu Lys Pro His
50                  55                  60

Ser Lys Ser Val Phe Val Met Thr Cys Glu Ala Ala Val Gln Leu Arg
65                  70                  75                  80

Lys Ala Gly Lys Val Val Arg Asp Ser Thr Leu Lys Lys Leu Gly
                85                  90                  95

Ala Thr His Phe Lys Tyr Gly Val Ala Asp Glu His Phe Glu Val Thr
            100                 105                 110

Lys Phe Ala Leu Leu Glu Thr Ile Lys Glu Ala Val Pro Glu Met Trp
        115                 120                 125

Ser Val Asp Met Lys Asn Ala Trp Gly Glu Ala Phe Asp Gln Leu Val
    130                 135                 140

Asn Ala Ile Lys Thr Glu Met Lys
145                 150

<210> SEQ ID NO 22
<211> LENGTH: 132
<212> TYPE: PRT
<213> ORGANISM: Bacillus subtilis

<400> SEQUENCE: 22

Met Gly Gln Ser Phe Asn Ala Pro Tyr Glu Ala Ile Gly Glu Glu Leu
1               5                   10                  15

Leu Ser Gln Leu Val Asp Thr Phe Tyr Glu Arg Val Ala Ser His Pro
            20                  25                  30

Leu Leu Lys Pro Ile Phe Pro Ser Asp Leu Thr Glu Thr Ala Arg Lys
        35                  40                  45

Gln Lys Gln Phe Leu Thr Gln Tyr Leu Gly Gly Pro Pro Leu Tyr Thr
50                  55                  60

Glu Glu His Gly His Pro Met Leu Arg Ala Arg His Leu Pro Phe Pro
65                  70                  75                  80

Ile Thr Asn Glu Arg Ala Asp Ala Trp Leu Ser Cys Met Lys Asp Ala
                85                  90                  95

Met Asp His Val Gly Leu Glu Gly Glu Ile Arg Glu Phe Leu Phe Gly
            100                 105                 110

Arg Leu Glu Leu Thr Ala Arg His Met Val Asn Gln Thr Glu Ala Glu
        115                 120                 125

Asp Arg Ser Ser
    130
```

-continued

```
<210> SEQ ID NO 23
<211> LENGTH: 131
<212> TYPE: PRT
<213> ORGANISM: Corynebacterium glutamicum

<400> SEQUENCE: 23

Met Thr Thr Ser Glu Asn Phe Tyr Asp Ser Val Gly Gly Glu Thr
1               5                   10                  15

Phe Ser Leu Ile Val His Arg Phe Tyr Glu Gln Val Pro Asn Asp Asp
            20                  25                  30

Ile Leu Gly Pro Met Tyr Pro Pro Asp Asp Phe Glu Gly Ala Glu Gln
        35                  40                  45

Arg Leu Lys Met Phe Leu Ser Gln Tyr Trp Gly Gly Pro Lys Asp Tyr
    50                  55                  60

Gln Glu Gln Arg Gly His Pro Arg Leu Arg Met Arg His Val Asn Tyr
65                  70                  75                  80

Pro Ile Gly Val Thr Ala Ala Glu Arg Trp Leu Gln Leu Met Ser Asn
                85                  90                  95

Ala Leu Asp Gly Val Asp Leu Thr Ala Glu Gln Arg Glu Ala Ile Trp
            100                 105                 110

Glu His Met Val Arg Ala Ala Asp Met Leu Ile Asn Ser Asn Pro Asp
        115                 120                 125

Pro His Ala
    130

<210> SEQ ID NO 24
<211> LENGTH: 124
<212> TYPE: PRT
<213> ORGANISM: Synechocystis sp.

<400> SEQUENCE: 24

Met Ser Thr Leu Tyr Glu Lys Leu Gly Gly Thr Thr Ala Val Asp Leu
1               5                   10                  15

Ala Val Asp Lys Phe Tyr Glu Arg Val Leu Gln Asp Asp Arg Ile Lys
            20                  25                  30

His Phe Phe Ala Asp Val Asp Met Ala Lys Gln Arg Ala His Gln Lys
        35                  40                  45

Ala Phe Leu Thr Tyr Ala Phe Gly Gly Thr Asp Lys Tyr Asp Gly Arg
    50                  55                  60

Tyr Met Arg Glu Ala His Lys Glu Leu Val Glu Asn His Gly Leu Asn
65                  70                  75                  80

Gly Glu His Phe Asp Ala Val Ala Glu Asp Leu Leu Ala Thr Leu Lys
                85                  90                  95

Glu Met Gly Val Pro Glu Asp Leu Ile Ala Glu Val Ala Ala Val Ala
            100                 105                 110

Gly Ala Pro Ala His Lys Arg Asp Val Leu Asn Gln
        115                 120

<210> SEQ ID NO 25
<211> LENGTH: 183
<212> TYPE: PRT
<213> ORGANISM: Synechococcus sp.

<400> SEQUENCE: 25

Met Asp Val Ala Leu Leu Glu Lys Ser Phe Glu Gln Ile Ser Pro Arg
1               5                   10                  15

Ala Ile Glu Phe Ser Ala Ser Phe Tyr Gln Asn Leu Phe His His His
            20                  25                  30
```

```
Pro Glu Leu Lys Pro Leu Phe Ala Glu Thr Ser Gln Thr Ile Gln Glu
            35                  40                  45

Lys Lys Leu Ile Phe Ser Leu Ala Ala Ile Ile Glu Asn Leu Arg Asn
 50                  55                  60

Pro Asp Ile Leu Gln Pro Ala Leu Lys Ser Leu Gly Ala Arg His Ala
 65                  70                  75                  80

Glu Val Gly Thr Ile Lys Ser His Tyr Pro Leu Val Gly Gln Ala Leu
                85                  90                  95

Ile Glu Thr Phe Ala Glu Tyr Leu Ala Ala Asp Trp Thr Glu Gln Leu
            100                 105                 110

Ala Thr Ala Trp Val Glu Ala Tyr Asp Val Ile Ala Ser Thr Met Ile
            115                 120                 125

Glu Gly Ala Asp Asn Pro Ala Ala Tyr Leu Glu Pro Glu Leu Thr Phe
        130                 135                 140

Tyr Glu Trp Leu Asp Leu Tyr Gly Glu Glu Ser Pro Lys Val Arg Asn
145                 150                 155                 160

Ala Ile Ala Thr Leu Thr His Phe His Tyr Gly Glu Asp Pro Gln Asp
                165                 170                 175

Val Gln Arg Asp Ser Arg Gly
            180

<210> SEQ ID NO 26
<211> LENGTH: 118
<212> TYPE: PRT
<213> ORGANISM: Nostoc commune

<400> SEQUENCE: 26

Met Ser Thr Leu Tyr Asp Asn Ile Gly Gly Gln Pro Ala Ile Glu Gln
1               5                   10                  15

Val Val Asp Glu Leu His Lys Arg Ile Ala Thr Asp Ser Leu Leu Ala
            20                  25                  30

Pro Val Phe Ala Gly Thr Asp Met Val Lys Gln Arg Asn His Leu Val
        35                  40                  45

Ala Phe Leu Ala Gln Ile Phe Glu Gly Pro Lys Gln Tyr Gly Gly Arg
    50                  55                  60

Pro Met Asp Lys Thr His Ala Gly Leu Asn Leu Gln Gln Pro His Phe
65                  70                  75                  80

Asp Ala Ile Ala Lys His Leu Gly Glu Arg Met Ala Val Arg Gly Val
                85                  90                  95

Ser Ala Glu Asn Thr Lys Ala Ala Leu Asp Arg Val Thr Asn Met Lys
            100                 105                 110

Gly Ala Ile Leu Asn Lys
        115

<210> SEQ ID NO 27
<211> LENGTH: 136
<212> TYPE: PRT
<213> ORGANISM: Bacillus megaterium

<400> SEQUENCE: 27

Met Arg Glu Lys Ile His Ser Pro Tyr Glu Leu Leu Gly Gly Glu His
1               5                   10                  15

Thr Ile Ser Lys Leu Val Asp Ala Phe Tyr Thr Arg Val Gly Gln His
            20                  25                  30

Pro Glu Leu Ala Pro Ile Phe Pro Asp Asn Leu Thr Glu Thr Ala Arg
        35                  40                  45
```

```
Lys Gln Lys Gln Phe Leu Thr Gln Tyr Leu Gly Gly Pro Ser Leu Tyr
    50                  55                  60

Thr Glu Glu His Gly His Pro Met Leu Arg Ala Arg His Leu Pro Phe
 65              70                  75                      80

Glu Ile Thr Pro Ser Arg Ala Lys Ala Trp Leu Thr Cys Met His Glu
                 85                  90              95

Ala Met Asp Glu Ile Asn Leu Glu Gly Pro Glu Arg Asp Glu Leu Tyr
            100                 105             110

His Arg Leu Ile Leu Thr Ala Gln His Met Ile Asn Ser Pro Glu Gln
        115                 120                 125

Thr Asp Glu Lys Gly Phe Ser His
130                 135
```